US011230574B2

(12) United States Patent
Bonaldo et al.

(10) Patent No.: US 11,230,574 B2
(45) Date of Patent: Jan. 25, 2022

(54) HETEROLOGOUS EXPRESSION CASSETTE, DNA CONSTRUCT AND VACCINE COMPOSITION TO IMMUNIZE AGAINST FLAVIVIRUS AND/OR OTHER PATHOGENS

(71) Applicant: FUNDAÇÃO OSWALDO CRUZ, Rio de Janeiro (BR)

(72) Inventors: Myrna Cristina Bonaldo, Rio de Janeiro (BR); Noemia Santana Lima, Rio de Janeiro (BR)

(73) Assignee: FUNDAÇÃO OSWALDO CRUZ, Rio de Janeiro (BR)

( * ) Notice: Subject to any disclaimer, the term of this patent is extended or adjusted under 35 U.S.C. 154(b) by 0 days.

(21) Appl. No.: 16/324,510

(22) PCT Filed: Aug. 4, 2017

(86) PCT No.: PCT/BR2017/050221
§ 371 (c)(1),
(2) Date: Feb. 8, 2019

(87) PCT Pub. No.: WO2018/027290
PCT Pub. Date: Feb. 15, 2018

(65) Prior Publication Data
US 2019/0276500 A1    Sep. 12, 2019

(30) Foreign Application Priority Data

Aug. 10, 2016   (BR) ......................... 102016018430-4

(51) Int. Cl.
| | |
|---|---|
| *C07K 14/18* | (2006.01) |
| *A61K 39/12* | (2006.01) |
| *C12N 15/66* | (2006.01) |
| *C12N 15/86* | (2006.01) |
| *A61K 39/00* | (2006.01) |

(52) U.S. Cl.
CPC .............. *C07K 14/18* (2013.01); *A61K 39/12* (2013.01); *C12N 15/66* (2013.01); *C12N 15/86* (2013.01); *A61K 2039/525* (2013.01); *A61K 2039/53* (2013.01); *Y02A 50/30* (2018.01)

(58) Field of Classification Search
None
See application file for complete search history.

(56) References Cited

U.S. PATENT DOCUMENTS

| 8,828,687 | B2 | 9/2014 | Bonaldo et al. | |
|---|---|---|---|---|
| 2003/0194801 | A1* | 10/2003 | Bonaldo .................. | C12N 7/00 435/320.1 |
| 2010/0297167 | A1 | 11/2010 | Bonaldo et al. | |
| 2011/0003884 | A1 | 1/2011 | Pugachev et al. | |
| 2012/0321655 | A1 | 12/2012 | Bonaldo et al. | |

FOREIGN PATENT DOCUMENTS

| BR | 05049458 A | 8/2007 |
|---|---|---|
| WO | 2007/051267 A2 | 5/2007 |

OTHER PUBLICATIONS

Despres et al., Characterization of yellow fever virus proteins E and NS1 expressed in Vero and Spodoptera frugiperda cells, 1991, Journal of General Virology, vol. 72, pp. 1331-1342.*
Co, Mary Dawn T., et al., "Human Cytotoxic T Lymphocyte Responses to Live Attenuated 17D Yellow Fever Vaccine Identification of HLA-B35-Restricted CTL Epitopes on Nonstructural Proteins NS1, NS2b, NS3, and the Structural Protein E," Virology, vol. 293, 2002, pp. 151-163 (13 p.).
Duckert, Peter, et al., "Prediction of Proprotein Convertase Cleavage Sites," Protein Engineering, Design, & Selection, vol. 17, No. 1, 2004, pp. 107-112 (6 p.).
Franco, David, et al., "Evaluation of Yellow Fever Virus 17D Strain as a New Vector for HIV-1 Vaccine Development," Vaccine, vol. 28, 2010, pp. 5676-5685 (10 p.).
Galler, Ricardo, et al., "Genetic Variability Among Yellow Fever Virus 17D Substrains," Vaccine, vol. 16, No. 9/10, 1998, pp. 1024-1028 (5 p.).
Gaucher, Denis, et al., "Yellow Fever Vaccine Induces Integrated Multilineage and Polyfunctional Immune Responses," The Journal of Experimental Medicine, vol. 205, Dec. 22, 2008, pp. 3119-3131 (13 p.).
Gillespie, Leah K., et al., "The Endoplasmic Reticulum Provides the Membrane Platform for Biogenesis of the Flavivirus Replication Complex," Journal of Virology, vol. 84, No. 20, Oct. 2010, pp. 10438-10447 (10 p.).
Guirakhoo, F, et al., "Construction, Safety, and Immunogenicity in Nonhuman Primates of a Chimeric Yellow Fever-Dengue Virus Tetravalent Vaccine," Journal of Virology, vol. 75, No. 16, Aug. 2001, pp. 7290-7304 (15 p.).

(Continued)

*Primary Examiner* — Benjamin P Blumel
(74) *Attorney, Agent, or Firm* — Conley Rose, P.C.

(57) ABSTRACT

A heterologous expression cassette, DNA construct and vaccine composition for immunization against flavivirus and/or other pathogens. DNA constructs, recombinant viruses and vaccine compositions containing the recombinant viruses were obtained. This invention also concerns and provide an improved expression vector of the live-attenuated yellow fever 17D virus. Modifications in the expression cassette of heterologous proteins in the intergenic E/NS1 region of the yellow fever 17D vaccine virus, were made. The two new functional domains inserted in the expression cassette were (1) a coding sequence for the N-glycosylation motif, located between the NS1 N-terminal motif and the heterologous protein and (2) a sequence which promoted the proteolytic cleavage, or not, of the recombinant protein in such a way as to release it from its C-terminal containing the transmembrane domains and, consequently, from its association with the membrane of the endoplasmatic reticulum—ER.

19 Claims, 4 Drawing Sheets

Specification includes a Sequence Listing.

(56) References Cited

OTHER PUBLICATIONS

Hallenberger, S., et al., "The Role of Eukaryotic Subtilisin-Like Endoproteases for the Activation of Human Immunodeficiency Virus Glycoproteins in Natural Host Cells," Journal of Virology, vol. 71, No. 2, Feb. 1997, pp. 1036-1045 (10 p.).
Helenius, Ari, et al., "Intracellular Functions of N-Linked Glycans," Science, vol. 291, Mar. 23, 2001, pp. 2364-2369 (7 p.).
Hsieh, Szu-Chia, et al., "The Length of and Nonhydrophobic Residues in the Transmembrane Domain of Dengue Virus Envelope Protein Are Critical for Its Retention and Assembly in the Endoplasmic Reticulum," Journal of Virology, vol. 84, No. 9, Apr. 2010, pp. 4782-4797 (16 p.).
Shikawa, Tomohiro, et al., "A Review of Successful Flavivirus Vaccines and the Problems with Those Flaviviruses for Which Vaccines are Not Yet Available," Vaccine, vol. 32, 2014, pp. 1326-1337 (12 p).
James, Eddie A., et al., "Yellow Fever Vaccination Elicits Broad Functional CD4 T Cell Responses That Recognize Structural and Nonstructural Proteins," Journal of Virology, vol. 87, No. 23, Dec. 2013, pp. 12794-12804 (11 p.).
Jonker, Emile F.F., et al., "Advances and Controversies in Yellow Fever Vaccination," Therapeutic Advances in Vaccines, vol. 1, No. 4, 2013, pp. 144-152 (9 p.).
Kim, Jin Hee, et al., "High Cleavage Efficiency of a 2A Peptide Derived from Porcine Teschovirus-1 in Human Cell Lines, Zebrafish and Mice," PLOS One, vol. 6, No. 4, Apr. 2011, pp. 1-8 (8 p.).
Lefeuvre, Anabelle, et al., "Host-Cell Interaction of Attenuated and Wild-Type Strains of Yellow Fever Virus can be Differentiated at Early Stages of Hepatocyte Infection," Microbes and Infection, vol. 8, 2006, pp. 1530-1538 (9 p).
Bonaldo, Myrna C., et al., "Construction and Characterization of Recombinant Flaviviruses Bearing Insertions Between E and NS1 Genes," Virology Journal, vol. 4, No. 115, 2007, pp. 1-16 (16 p.).
Bonaldo, Myrna C., et al., "The Yellow Fever 17D Virus as a Platform for New Live Attenuated Vaccines," Human Vaccines & Immunotherapeutics, vol. 10, No. 5, May 2014, pp. 1256-1265 (10 p.).
Nogueira, Raquel Tayar, et al., "Recombinant Yellow Fever Viruses Elicit CD8+ T Cell Responses and Protective Immunity against Trypanosoma cruzi," PLOS One, vol. 8, No. 3, Mar. 2013, pp. 1-13 (13 p.).
De Santana, Marlon G. Veloso, et al., "Improved Genetic Stability of Recombinant Yellow Fever 17D Virus Expressing a Lentiviral Gag Gene Fragment," Virology, Mar. 2014, pp. 202-211 (22 p.).
Frindade, Gisela Freitas, et al., "Retention of a Recombinant GFP Protein Expressed by the Yellow Fever 17D Virus in the E/NS1 Intergenic Region in the Endoplasmic Reticulum," Mem. Inst. Oswaldo Cruz, Rio de Janeiro, vol. 107, No. 2, pp. 262-272, Mar. 2012 (11 p.).
Li, Long, et al., "The Flavivirus Precursor Membrane-Envelope Protein Complex: Structure and Maturation," Science, vol. 319, No. 5871, pp. 1830-1834, Mar. 28, 2008, www.sciencemag.org (6 p ).
Lorenz, Ivo C., et al., "Intracellular Assembly and Secretion of Recombinant Subviral Particles from Tick-Borne Encephalitis Virus," Journal of Virology, vol. 77, No. 7, pp. 4370-4382, Apr. 2003 (13 p ).
Mackenzie, Jason M., et al., "Immunolocalization of the Dengue Virus Nonstrucural Glycoprotein NS1 Suggests a Role in Viral RNA Replication," Virology, vol. 220, No. 0307, pp. 232-240, 1996 (9 p.).
Mackenzie, Jason M., et al., "Assembly and Maturation of the Flavivirus Kunjin Virus Appear To Occur in the Rough Endoplasmic Reticulum and along the Secretory Pathway, Respectively," Journal of Virology, vol. 75, No. 22, p. 10787-10799, Nov. 2001 (13 p.).
McAllister, Andres, et al., "Recombinant Yellow Fever Viruses Are Effective Therapeutic Vaccines for Treatment of Murine Experimental Solid Tumors and Pulmonary Metastases," Journal of Virology, vol. 74, No. 19, pp. 9197-9205, Oct. 2000 (9 p.).
Miller, Joseph D., et al., "Human Effector and Memory CD8+ T Cell Responses to Smallpox and Yellow Fever Vaccines," Immunity, vol. 28, pp. 710-722, May 2008 (13 p.).
Molinari, Maurizio, "N-glycan Structure Dictates Extension of Protein Folding or Onset of Disposal," Nature Chemical Biology, vol. 3, No. 6, pp. 313-320, Jun. 2007 (8 p).
Mudd, Philip A., et al., "The Live-Attenuated Yellow Fever Vaccine 17D Induces Broad and Potent T Cell Responses Against Several Viral Proteins in Indian Rhesus Macaques—Implications for Recombinant Vaccine Design," mmunogenetics, vol. 62, No. 9, pp. 593-600, Sep. 2010 (14 p.).
Mukhopadhyay, Suchetana, et al., "A Structural Perspective of the Flavivirus Life Cycle," Nature Reviews/Microbiology, vol. 3, Jan. 2005, pp. 13-22 (10 p.).
Neves, Patricia C.C., et al., "CD8+ Gamma-Delta TCR+ and CD4+ T Cells Produce IFN- at 5-7 Days after Yellow Fever Vaccination in Indian Rhesus Macaques, Before the Induction of Classical Antigen-Specific T Cell Responses," Elsevier/Vaccine, vol. 28, Oct. 2010, pp. 8183-8188 (6 p.).
Neves, Patricia C.C., et al., Early IFN-Gamma Production after YF 17D Vaccine Virus Immunization in Mice and Its Association with Adaptive Immune Responses, Plos One, vol. 8, Issue 12, Dec. 2013, pp. 1-16 (16 p.).
Nogueira, Raquel T., et al., "Biological and Immunological Characterization of Recombinant Yellow Fever 17D Viruses Expressing a Trypanosoma Cruzi Amastigote Surface Protein-2 CD8+ T cell Epitope at Two Distinct Regions of the Genome," Virology Journal, vol. 8, No. 127, 2011, pp. 1-13 (13 p.).
Op De Beeck, Anne, et al., "The Transmembrane Domains of the prM and E Proteins of Yellow Fever Virus Are Endoplasmic Reticulum Localization Signals," Journal of Virology, vol. 78, No. 22, Nov. 2004, pp. 12591-12602 (12 p.).
Poland, J.D., et al., "Persistence of Neutralizing Antibody 30-35 Years After Immunization with 17D Yellow Fever Vaccine," Bulletin of the World Health Organization, vol. 59, No. 6, 1981, pp. 895-900 (6 p.).
Pulendran, Bali, "Learning Immunology from the Yellow Fever Vaccine: Innate Immunity to Systems Vaccinology," Nature Reviews/Immunology, vol. 9, Oct. 2009, pp. 741-747 (7 p.).
Pulendran, Bail, et al., "Immunity to Viruses: Learning from Successful Human Vaccines," Immunol Rev., Sep. 2013, vol. 255 (1), pp. 243-255 (20 p.).
Querec, Troy, et al., "Yellow Fever Vaccine YF-17D Activates Multiple Dendritic Cell Subsets via TLR2, 7, 8, and 9 to Stimulate Polyvalent Immunity," JEM, vol. 203, No. 2, Feb. 20, 2006, pp. 413-424 (12 p.).
Ryan, Martin D., et al., "Cleavage of Foot-and-Mouth Disease Virus Polyprotein is Mediated by Residues Located within a 19 Amino Acid Sequence," Journal of General Virology, 1991, vol. 72, pp. 2727-2732 (6 p).
Schaack, Jerome, "Adenovirus Vectors Deleted for Genes Essential for Viral DNA Replication," Frontiers in Bioscience, vol. 10, May 1, 2005, pp. 1146-1155 (10 p.).
Silva, Maria Luiza, et al., "Characterization of Main Cytokine Sources from the Innate and Adaptive Immune Responses Following Primary 17DD Yellow Fever Vaccination in Adults," Vaccine, vol. 29, 2011, pp. 583-592 (10 p.).
Stieneke-Grober, Andrea, et al., "Influenza Virus Hemagglutinin with Multibasic Cleavage Site is Activated by Furin, a Subtilisin-like Endoprotease," The EMBO Journal, vol. 11, No. 7, pp. 2407-2414, 1992 (8 p.).
Szczesna-Skorupa, Elzbieta, et al., "Endoplasmic Reticulum Retention Determinants in the Transmembrane and Linker Domains of Cytochrome P450 2C1," The Journal of Biological Chemistry, vol. 275, No. 25, Jun. 22, 2000, pp. 19409-19415 (8 p.).
Theiler, Max, et al., "The Use of Yellow Fever Virus Modified by In Vitro Cultivation for Human Immunization," Laboratories of the International Health Division, Immunization Against Yellow Fever, Mar. 18, 1937, pp. 787-800 (14 p.).
Theiler, Max, et al., "The Effect of Prolonged Cultivation in Vido Upon the Pathogenicity of Yellow Fever Virus," Laboratories of the

(56) References Cited

OTHER PUBLICATIONS

International Health Division, The Cultivation of Yellow Fever Virus, Mar. 18, 1937, pp. 767-786 (20 p.).
Tian, Sun, et al., "FurinDB: A Database of 20-Residue Furin Cleavage Site Motifs, Substrates and Their Associated Drugs," International Journal of Molecular Sciences, vol. 12, 2011, pp. 1060-1065 (6 p).
Van Der Most, Robbert G., et al., "Yellow Fever Virus 17D Envelope and NS3 Proteins Are Major Targets of the Antiviral T Cell Response in Mice," Virology, vol. 296, 2002, pp. 117-124 (8 p.).
Villar, Luis A., et al., "Safety and Immunogenicity of a Recombinant Tetravalent Dengue Vaccine in 9-16 Year Olds," The Pediatric Infectious Disease Journal, vol. 32, No. 10, Oct. 2013, pp. 1102-1109 (8 p.).
Welsch, Sonja, et al., "Composition and Three-Dimensional Architecture of the Dengue Virus Replication and Assembly Sites," Cell Host & Microbe, vol. 5, pp. 365-375, Apr. 23, 2009 (11 p.).
Wojczyk, Boguslaw S., et al., "N-glycosylation at One Rabies Virus Glycoprotein Sequon Influences N-glycan Processing at a Distant Sequon on the Same Molecule," Glycobiology, vol. 5, No. 6, pp. 655-666, 2005 (12 p).
Yang, Mei, et al., "The Transmembrane Domain of a Carboxyl-terminal Anchored Protein Determines Localization to the Endoplasmic Reticulum," The Journal of Biological Chemistry, vol. 272, No. 3, pp. 1970-1975, Jan. 17, 1997 (7 p.).
Yu, Chia-Yi, et al., "Flavivirus Infection Activates the XBP1 Pathway of the Unfolded Protein Response To Cope with Endoplasmic Reticulum Stress," Journal of Virology, vol. 80, No. 23, Dec. 2006, pp. 11868-11880 (13 p ).
Yu, I-Mei, et al., "Structure of the Immature Dengue Virus at Low pH Primes Proteolytic Maturation," Science, vol. 319, No. 5871, Mar. 28, 2008, pp. 1834-1837 (5 p.).
Aebi, Markus, et al., "N-Glycan Structures: Recognition and Processing in the ER," Trends in Biochemical Sciences, vol. 35, No. 2, Oct. 21, 2009, pp. 74-82 (9 p).
Allison, Seven L., et al., "Mapping of Functional Elements in the Stem-Anchor Region of Tick-Borne Encephalitis Virus Envelope Protein E," Journal of Virology, vol. 73, No. 7, Jul. 1999, pp. 5605-5612 (8 p.).
Arroyo, Juan, et al., "ChimeriVax-West Nile Virus Live-Attenuated Vaccine: Preclinical Evaluation of Safety, Immunogenicity, and Efficacy," Journal of Virology, vol. 78, No. 22, Nov. 2004, p. 12497-12507 (11 p.).
Barba-Spaeth, Giovanna, et al., "Live Attenuated Yellow Fever 17D Infects Human DCs and Allows for Presentation of Endogenous and Recombinant T Cell Epitopes," The Journal of Experimental Medicine, vol. 202, No. 9, Nov. 7, 2005, pp. 1179-1184 (6 p.).
Bassi, Maria R., et al., "CD8+ T Cells Complement Antibodies in Protecting Against YF Virus," The Journal of mmunology, vol. 194, No. 3, Feb. 1, 2015, pp. 1141-1153 (32 pages).
Benyair, Ron, et al., "Glycan Regulation of ER-Associated Degradation Through Compartmentalization," Seminars in Cell & Developmental Biology, vol. 41, 2015, pp. 99-1090 (11 p.).
Blom, Kim, et al., "Temporal Dynamics of the Primary Human T Cell Response to Yellow Fever Virus 17D Memory-Type Response," The Journal of Immunology, vol. 190, Jan. 21, 2013, pp. 2150-2158 (10 p.).

Bonaldo, Myrna C., et al., "Surface Expression of an Immunodominant Malaria Protein B Cell Epitope by Yellow Fever Virus," The Journal of Molecular Biology, vol. 315, 2002, pp. 873-885 (13 p.).
Bonaldo, Myrna C., et al., "Attenuation of Recombinant Yellow Fever 17D Viruses Expressing Foreign Protein Epitopes at the Surface," Journal of Virology, vol. 79, No. 13, Jul. 2005, pp. 8602-8613 (12 p.).
Bonaldo, Myrna C., et al., "Expression of Foreign Protein Epitopes at the Surface of Recombinant Yellow Fever 17D Viruses Based on Three-Dimensional Modeling of Its Envelope Protein," Cell Biochemistry and Biophysics, vol. 44, 2006, pp. 313-324 (12 p.).
Bonaldo, Myrna C., et al., "Recombinant Yellow Fever Vaccine Virus 17D Expressing Simian Immunodeficiency Virus SIVmac239 Gag Induces SIV-Specific CD8 T-Cell Responses in Rhesus Macaques," Journal of Virology, vol. 34, No. 7, Apr. 2010, pp. 3699-3706 (8 p.).
Burger, S.R., et al., "Stable Expression of Rabies Virus Glycoprotein in Chinese Hamster Ovary Cells," Journal of General Virology, vol. 72, 1991, pp. 359-367 (9 p.).
Cao, Weiping, et al., "Toll-like Receptor-Mediated Induction of Type 1 Interferon in Plasmacytoid Dendritic Cells Requires the Rapamycin-Sensitive PI(3)K-mTOR-p70S6K Pathway," Nature Immunology, vol. 9, No. 10, Oct. 2008, pp. 1157-1164 (8 p.).
Capeding, Rosario Z., et al., "Live-Attenuated, Tetravalent Dengue Vaccine in Children, Adolescents and Adults in a Dengue Endemic Country: Randomized Controlled Phase I Trial in the Philippines," Vaccine, vol. 29, 2011, pp. 3863-3872 (10 p.).
Caufour, P.S., et al., "Construction, Characterization and Immunogenicity of Recombinant Yellow Fever 17D-Dengue type 2 Viruses," Virus Research, vol. 79, 2001, pp. 1-14 (14 p.).
Cherepanova, Natalia A., et al., "Oxidoreductase Activity is Necessary for N-Glycosylation of Cysteine-Proximal Acceptor Sites in Glycoproteins," Journal of Cell Biology, vol. 206, No. 4, 2014, pp. 525-539 (15 p.).
Ciczora, Yann, et al., "Identification of a Dominant Endoplasmic Reticulumretention Signal in Yellow Fever Virus Pre-Membrane Protein, " Journal of General Virology, vol. 91, 2010, pp. 404-414 (12 p.).
Monath, Thomas P. et al., "Yellow fever vaccine," Vaccines (Sixth Edition), Section Two: Licensed Vaccines Chapter 38; 2013, pp. 870-968.
Oliveira, M.F., Aprimoramento da platform de expressão na região intergênica E/NS1 do virus da febre amrela 17D, in Michelli Faria de Oliveira. 2008, Fiocruz: Pós-Graduação em Biologia Parasitária (29 pages).
Monath, Thomas P., "Yellow fever vaccine," Expert Rev. Vaccines 4(4), 2005, pp. 553-574.
Reinhardt, Barbara et al., "Development of Viremia and Humoral and Cellular Parameters of Immune Activation After Vaccination with Yellow Fever Virus Strain 17D: A Model of Human Flavivirus Infection," J. Med. Virol., 1998, 56, pp. 159-167.
Rice, Charles M. et al., "Transcription of Infectious Yellow Fever RNA From Full-Length cDNA Templates Produced by In Vitro Ligation," New Biologist, Dec. 1989, vol. 1, No. 3, pp. 285-296.
Chambers, Thomas J. et al., "Yellow Fever/Japanese Encephalitis Chimeric Viruses: Construction and Biological Properties," J. Virol., 1999, vol. 73, No. 4, pp. 3095-3101.

\* cited by examiner

FIGURE 1

Sites of insertion of the YF genome

FIGURE 2

SEQUENCE LISTING

<160> NUMBER OF SEQ ID NOS: 77

<210> SEQ ID NO 1
<211> LENGTH: 11800
<212> TYPE: DNA
<213> ORGANISM: Yellow fever virus

<400> SEQUENCE: 1

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tctttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgaccggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaacccctt ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg aggggtgca    1020 tggaggaact tgggtttcag ctaccctgga gcaagacaag tgtgtcactg ttatggcccc    1080
tgacaagcct tcattggaca tctcactaga gacagtagcc attgatagac tgctgaggc    1140 gaggaaagtg tgttacaatg cagttctcac tcatgtgaag attaatgaca gtgcccag     1200 cactggagag gcccacctag ctgaagagaa cgaaggggac aatgcgtgca agcgcactta    1260
```

```
ttctgataga ggctggggca atggctgtgg cctatttggg aaagggagca ttgtggcatg      1320
cgccaaattc acttgtgcca aatccatgag tttgtttgag gttgatcaga ccaaaattca      1380
gtatgtcatc agagcacaat tgcatgtagg ggccaagcag gaaaattgga ataccagcat      1440
taagactctc aagtttgatg ccctgtcagg ctcccaggaa gtcgagttca ttgggtatgg      1500
aaaagctaca ctggaatgcc aggtgcaaac tgcggtggac tttggtaaca gttacatcgc      1560
tgagatggaa acagagagct ggatagtgga cagacagtgg gcccaggact tgaccctgcc      1620
atggcagagt ggaagtggcg gggtgtggag agagatgcat catcttgtcg aatttgaacc      1680
tccgcatgcc gccactatca gagtactggc cctgggaaac caggaaggct ccttgaaaac      1740
agctcttact ggcgcaatga gggttacaaa ggacacaaat gacaacaacc tttacaaact      1800
acatggtgga catgtttctt gcagagtgaa attgtcagct ttgacactca aggggacatc      1860
ctacaaaata tgcactgaca aaatgttttt tgtcaagaac ccaactgaca ctggccatgg      1920
cactgttgtg atgcaggtga aagtgtcaaa aggagccccc tgcaggattc cagtgatagt      1980
agctgatgat cttacagcgg caatcaataa aggcattttg gttacagtta accccatcgc      2040
ctcaaccaat gatgatgaag tgctgattga ggtgaaccca cctttggag acagctacat      2100 tatcgttggg agaggagatt cacgtctcac ttaccagtgg cacaaagagg gaagctcaat      2160
aggaaagttg ttcactcaga ccatgaaagg cgtggaacgc ctggccgtca tgggagacac      2220
cgcctgggat ttcagctccg ctggagggtt cttcacttcg gttgggaaag gaattcatac      2280
ggtgtttggc tctgcctttc aggggctatt tggcggcttg aactggataa caaaggtcat      2340
catgggggcg gtacttatat gggttggcat caacacaaga aacatgacaa tgtccatgag      2400
catgatcttg gtaggagtga tcatgatgtt tttgtctcta ggagttgggg cggatcaagg      2460
atgcgccatc aactttggcg tgagcaaggg cgaggagctg ttcaccgggg tggtgcccat      2520
cctggtcgag ctggacggcg acgtaaacgg ccacaagttc agcgtgtccg gcgagggcga      2580
gggcgatgcc acctacggca agctgaccct gaagttcatc tgcaccaccg gcaagctgcc      2640
cgtgccctgg cccaccctcg tgaccaccct gacctacggc gtgcagtgct tcagccgcta      2700
ccccgaccac atgaagcagc acgacttctt caagtccgcc atgcccgaag gctacgtcca      2760
ggagcgcacc atcttcttca aggacgacgg caactacaag acccgcgccg aggtgaagtt      2820
cgagggcgac accctggtga accgcatcga gctgaagggc atcgacttca aggaggacgg      2880
caacatcctg gggcacaagc tggagtacaa ctacaacagc cacaacgtct atatcatggc      2940
cgacaagcag aagaacggca tcaaggtgaa cttcaagatc cgccacaaca tcgaggacgg      3000
cagcgtgcag ctcgccgacc actaccagca gaacaccccc atcggcgacg gccccgtgct      3060
gctgcccgac aaccactacc tgagcaccca gtccgccctg agcaaagacc ccaacgagaa      3120
gcgcgatcac atggtcctgc tggagttcgt gaccgccgcc gggatcactc tcggcatgga      3180
cgagctgtac aagacatcat gggaaaggc tgtgcaccag ttttttggaa gtgtgtatac      3240
aaccatgttt ggaggagtct catggatgat tagaatccta attgggttct tagtgttgtg      3300
gattggcacg aactcgagga acacttcaat ggctatgacg tgcatagctg ttggaggaat      3360
cactctgttt ctgggcttca cagttggcgc cgatcaagga tgcgccatca actttggcaa      3420
gagagagctc aagtgcggag atggtatctt catatttaga gactctgatg actggctgaa      3480
caagtactca tactatccag aagatcctgt gaagcttgca tcaatagtga aagcctcttt      3540
tgaagaaggg aagtgtggcc taaattcagt tgactcccct tgagcatgaga tgtggagaag      3600
```

```
cagggcagat gagatcaatg ccattttga ggaaaacgag gtggacattt ctgttgtcgt     3660
gcaggatcca agaatgttt accagagagg aactcatcca ttttccagaa ttcgggatgg     3720
tctgcagtat ggttggaaga cttggggtaa gaaccttgtg ttctccccag ggaggaagaa     3780
tggaagcttc atcatagatg gaaagtccag gaaagaatgc ccgttttcaa accgggtctg     3840
gaattctttc cagatagagg agtttgggac gggagtgttc accacacgcg tgtacatgga     3900
cgcagtcttt gaatacacca tagactgcga tggatctatc ttgggtgcag cggtgaacgg     3960
aaaaaagagt gcccatggct ctccaacatt ttggatggga agtcatgaag taaatgggac     4020
atggatgatc cacaccttgg aggcattaga ttacaaggag tgtgagtggc cactgacaca     4080
tacgattgga acatcagttg aagagagtga aatgttcatg ccgagatcaa tcggaggccc     4140
agttagctct cacaatcata tccctggata caaggttcag acgaacggac cttggatgca     4200
ggtaccacta gaagtgaaga gagaagcttg cccagggact agcgtgatca ttgatggcaa     4260
ctgtgatgga cggggaaaat caaccagatc caccacggat agcggaaag ttattcctga      4320 atggtgttgc cgctcctgca caatgccgcc tgtgagcttc catggtagtg atgggtgttg     4380
gtatcccatg gaaattaggc caaggaaaac gcatgaaagc catctggtgc gctcctgggt     4440
tacagctgga gaaatacatg ctgtcccttt tggtttggtg agcatgatga tagcaatgga     4500
agtggtccta aggaaaagac agggaccaaa gcaaatgttg gttggaggag tagtgctctt     4560
gggagcaatg ctggtcgggc aagtaactct ccttgatttg ctgaaactca cagtggctgt     4620
gggattgcat ttccatgaga tgaacaatgg aggagacgcc atgtatatgg cgttgattgc     4680
tgccttttca atcagaccag ggctgctcat cggctttggg ctcaggaccc tatggagccc     4740
tcgggaacgc cttgtgctga ccctaggagc agccatggtg gagattgcct gggtggcgt      4800 gatgggcggc ctgtggaagt atctaaatgc agtttctctc tgcatcctga caataaatgc     4860
tgttgcttct aggaaagcat caaataccat cttgccccctc atggctctgt tgacacctgt     4920
cactatggct gaggtgagac ttgccgcaat gttctttgt gccatggtta tcataggggt      4980
ccttcaccag aatttcaagg acacctccat gcagaagact ataccctctgg tggccctcac     5040 actcacatct tacctgggct tgacacaacc ttttttgggc ctgtgtgcat ttctggcaac     5100
ccgcatattt gggcgaagga gtatcccagt gaatgaggca ctcgcagcag ctggtctagt     5160
gggagtgctg gcaggactgg cttttcagga gatggagaac ttccttggtc cgattgcagt     5220
tggaggactc ctgatgatgc tggttagcgt ggctggggag gtggatgggc tagagctcaa     5280
gaagcttggt gaagtttcat gggaagagga ggcggagatc agcggagtt ccgcccgcta      5340 tgatgtggca ctcagtgaac aaggggagtt caagctgctt tctgaagaga agtgccatg      5400 ggaccaggtt gtgatgacct cgctggcctt ggttggggct gccctccatc catttgctct     5460
tctgctggtc cttgctgggt ggctgtttca tgtcagggga gctaggagaa gtgggatgt      5520 cttgtgggat attcccactc ctaagatcat cgaggaatgt gaacatctgg aggatgggat     5580
ttatggcata ttccagtcaa ccttcttggg ggcctcccag cgaggagtgg gagtggcaca     5640
gggaggggtg ttccacacaa tgtggcatgt cacaagagga gctttccttg tcaggaatgg     5700
caagaagttg attccatctt gggcttcagt aaaggaagac cttgtcgcct atggtggctc     5760
atggaagttg gaaggcagat gggatggaga ggaagaggtc cagttgatcg cggctgttcc     5820
aggaaagaac gtggtcaacg tccagacaaa accgagcttg ttcaaagtga ggaatggggg     5880
agaaatcggg gctgtcgctc ttgactatcc gagtggcact tcaggatctc ctattgttaa     5940
caggaacgga gaggtgattg gctgtacgg caatggcatc cttgtcggtg acaactccctt     6000
```

```
cgtgtccgcc atatcccaga ctgaggtgaa ggaagaagga aaggaggagc tccaagagat   6060
cccgacaatg ctaaagaaag gaatgacaac tgtccttgat tttcatcctg gagctgggaa   6120
gacaagacgt ttcctcccac agatcttggc cgagtgcgca cggagacgct tgcgcactct   6180
tgtgttggcc cccaccaggg ttgttctttc tgaaatgaag gaggcttttc acggcctgga   6240
cgtgaaattc cacacacagg cttttccgc tcacggcagc gggagagaag tcattgatgc    6300
catgtgccat gccaccctaa cttacaggat gttggaacca actagggttg ttaactggga   6360
agtgatcatt atggatgaag cccattttt ggatccagct agcatagccg ctagaggttg    6420
ggcagcgcac agagctaggg caaatgaaag tgcaacaatc ttgatgacag ccacaccgcc   6480
tgggactagt gatgaatttc cacattcaaa tggtgaaata aagatgttc aaacggacat    6540 acccagtgag ccctggaaca cagggcatga ctggatcctg gctgacaaaa ggcccacggc   6600
atggttcctt ccatccatca gagctgcaaa tgtcatggct gcctctttgc gtaaggctgg   6660
aaagagtgtg gtggtcctga acaggaaaac ctttgagaga gaatacccca cgataaagca   6720
gaagaaacct gactttatat tggccactga catagctgaa atgggagcca acctttgcgt   6780
ggagcgagtg ctggattgca ggacggcttt taagcctgtg cttgtggatg aagggaggaa   6840
ggtggcaata aaagggccac ttcgtatctc cgcatcctct gctgctcaaa ggaggggcg    6900 cattgggaga aatcccaaca gagatggaga ctcatactac tattctgagc ctacaagtga   6960
aaataatgcc caccacgtct gctggttgga ggcctcaatg ctcttggaca catggaggt    7020 gaggggtgga atggtcgccc cactctatgg cgttgaagga actaaaacac cagtttcccc   7080
tggtgaaatg agactgaggg atgaccagag gaaagtcttc agagaactag tgaggaattg   7140
tgacctgccc gtttggcttt cgtggcaagt ggccaaggct ggtttgaaga cgaatgatcg   7200
taagtggtgt tttgaaggcc ctgaggaaca tgagatcttg aatgacagcg gtgaaacagt   7260
gaagtgcagg gctcctggag gagcaaagaa gcctctgcgc ccaaggtggt gtgatgaaag   7320
ggtgtcatct gaccagagtg cgctgtctga atttattaag tttgctgaag gtaggagggg   7380
agctgctgaa gtgctagttg tgctgagtga actccctgat ttcctggcta aaaaaggtgg   7440
agaggcaatg gataccatca gtgtgttcct ccactctgag gaaggctcta gggcttaccg   7500
caatgcacta tcaatgatgc ctgaggcaat gacaatagtc atgctgttta tactggctgg   7560
actactgaca tcgggaatgg tcatcttttt catgtctccc aaaggcatca gtagaatgtc   7620
tatggcgatg ggcacaatgg ccggctgtgg atatctcatg ttccttggag gcgtcaaacc   7680
cactcacatc tcctatgtca tgctcatatt cttgtcctg atggtggttg tgatccccga    7740
gccagggcaa caaaggtcca tccaagacaa ccaagtggca tacctcatta ttggcatcct   7800
gacgctggtt tcagcggtgg cagccaacga gctaggcatg ctgagaaaaa ccaaagagga   7860
cctctttggg aagaagaact taattccatc tagtgcttca ccctggagtt ggccggatct   7920
tgacctgaag ccaggagctg cctggacagt gtacgttggc attgttacaa tgctctctcc   7980
aatgttgcac cactggatca aagtcgaata tggcaacctg tctctgtctg aatagcccca   8040
gtcagcctca gtcctttctt tcatggacaa ggggatacca ttcatgaaga tgaatatctc   8100
ggtcataatg ctgctggtca gtggctgaa ttcaataaca gtgatgcctc tgctctgtgg    8160 cataggtgc gccatgctcc actggtctct cattttacct ggaatcaaag cgcagcagtc    8220
aaagcttgca cagagaaggg tgttccatgg cgttgccaag aaccctgtgg ttgatgggaa   8280
tccaacagtt gacattgagg aagctcctga aatgcctgcc ctttatgaga agaaactggc   8340
```

-continued

```
tctatatctc cttcttgctc tcagcctagc ttctgttgcc atgtgcagaa cgccctttc     8400
attggctgaa ggcattgtcc tagcatcagc tgccttaggg ccgctcatag agggaaacac    8460
cagccttctt tggaatggac ccatggctgt ctccatgaca ggagtcatga ggggaatca     8520
ctatgctttt gtgggagtca tgtacaatct atggaagatg aaaactggac gccggggag     8580
cgcgaatgga aaactttggg gtgaagtctg gaagagggaa ctgaatctgt tggacaagcg    8640
acagtttgag ttgtataaaa ggaccgacat tgtggaggtg gatcgtgata cggcacgcag    8700
gcatttggcc gaagggaagg tggacaccgg ggtggcggtc tccaggggga ccgcaaagtt    8760
aaggtggttc catgagcgtg gctatgtcaa gctggaaggt aggtgattg acctggggtg     8820
tggccgcgga ggctggtgtt actacgctgc tgcgcaaaag gaagtgagtg gggtcaaagg    8880
atttactctt ggaagagacg gccatgaaga acccatgaat gtgcaaagtc tgggatggaa    8940
catcatcacc ttcaaggaca aaactgatat ccaccgccta gaaccagtga atgtgacac     9000
cctttttgtgt gacattggag agtcatcatc gtcatcggtc acagaggggg aaaggaccgt    9060
gagagttctt gatactgtag aaaaatggct ggcttgtggg gttgacaact tctgtgtgaa    9120
ggtgttagct ccatacatgc cagatgttct tgagaaactg gaattgctcc aaaggaggtt    9180
tggcggaaca gtgatcagga accctctctc caggaattcc actcatgaaa tgtactacgt    9240
gtctggagcc cgcagcaatg tcacatttac tgtgaaccaa acatcccgcc tcctgatgag    9300
gagaatgagg cgtccaactg gaaaagtgac cctggaggct gacgtcatcc tcccaattgg    9360
gacacgcagt gttgagacag acaagggacc cctggacaaa gaggccatag aagaagggt     9420
tgagaggata aaatctgagt acatgacctc ttggttttat gacaatgaca cccctacag     9480
gacctggcac tactgtggct cctatgtcac aaaaacctca ggaagtgcgg cgagcatggt    9540
aaatggtgtt attaaaattc tgacatatcc atgggacagg atagaggagg tcaccagaat    9600
ggcaatgact gacacaaccc cttttggaca gcaaagagtg tttaaagaaa agttgacac     9660
cagagcaaag gatccaccag cgggaactag gaagatcatg aaagttgtca acaggtggct    9720
gttccgccac ctggccagag aaaagagccc cagactgtgc acaaaggaag aatttattgc    9780
aaaagtccga agtcatgcag ccattggagc ttacctggaa gaacaagaac agtgaaagac    9840
tgccaatgag gctgtccaag acccaaagtt ctgggaactg gtggatgaag aaaggaagct    9900
gcaccaacaa gcaggtgtc ggacttgtgt gtacaacatg atggggaaaa gagagaagaa    9960
gctgtcagag tttgggaaag caagggaag ccgtgccata tggtatatgt ggctgggagc    10020
gcggtatctt gagtttgagg ccctgggatt cctgaatgag gaccattggg cttccaggga    10080
aaactcagga ggaggagtgg aaggcattgg cttacaatac ctaggatatg tgatcagaga    10140
cctggctgca atggatggtg gtggattcta cgcggatgac accgctggat gggacacgcg    10200
catcacagag gcagaccttg atgatgaaca ggagatcttg aactacatga gcccacatca    10260
caaaaaactg gcacaagcag tgatggaaat gacatacaag aacaaagtgg tgaaagtgtt    10320
gagaccagcc ccaggaggga agcctacat ggatgtcata agtcgacgag accagagagg    10380
atccgggcag gtagtgactt atgctctgaa caccatcacc aacttgaaag tccaattgat    10440
cagaatggca gaagcagaga tgtgatacat caccaacat gttcaagatt gtgatgaatc    10500
agttctgacc aggctggagg catggctcac tgagcacgga gtgtaacagac tgaagaggat    10560
ggcggtgagt ggagacgact gtgtggtccg gccatcgat gacaggttcg gcctggccct    10620
gtcccatctc aacgccatgt ccaaggttag aaaggacata tctgaatggc agccatcaaa    10680
agggtggaat gattgggaga atgtgccctt ctgttccac cacttccatg aactacagct    10740
```

```
gaaggatggc aggaggattg tggtgccttg ccgagaacag gacgagctca ttgggagagg   10800
aagggtgtct ccaggaaacg gctggatgat caaggaaaca gcttgcctca gcaaagccta   10860
tgccaacatg tggtcactga tgtattttca caaagggac atgaggctac tgtcattggc    10920
tgtttcctca gctgttccca cctcatgggt tccacaagga cgcacaacat ggtcgattca   10980
tgggaagggg gagtggatga ccacggaaga catgcttgag gtgtggaaca gagtatggat   11040
aaccaacaac ccacacatgc aggacaagac aatggtgaaa aaatggagag atgtccctta   11100
tctaaccaag agacaagaca agctgtgcgg atcactgatt ggaatgacca ataggggccac  11160
ctgggcctcc cacatccatt tagtcatcca tcgtatccga acgctgattg gacaggagaa   11220
atacactgac tacctaacag tcatggacag gtattctgtg gatgctgacc tgcaactggg   11280
tgagcttatc tgaaacacca tctaacagga ataaccggga tacaaaccac gggtggaaaa   11340
ccggactccc cacaacctga aaccgggata taaaccacgg ctggagaacc gggctccgca   11400
cttaaaatga aacagaaacc gggataaaaaa ctacggatgg agaaccggac tccacacatt   11460
gagacagaag aagttgtcag cccagaaccc cacacgagtt ttgccactgc taagctgtga   11520
ggcagtgcag gctgggacag ccgacctcca ggttgcgaaa aacctggttt ctgggacctc   11580
ccaccccaga gtaaaaagaa cggagcctcc gctaccaccc tcccacgtgg tggtagaaag   11640
acggggtcta gaggttagag gagacccctcc agggaacaaa tagtgggacc atattgacgc   11700
cagggaaaga ccggagtggt tctctgcttt tcctccagag gtctgtgagc acagtttgct   11760
caagaataag cagacctttg gatgacaaac acaaaaccac                         11800
```

\<210\> SEQ ID NO 2
\<211\> LENGTH: 3724
\<212\> TYPE: PRT
\<213\> ORGANISM: Yellow fever virus

\<400\> SEQUENCE: 2

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
```

-continued

```
            180                 185                 190
Arg Val Ala Tyr Gly Lys Cys Asp Ser Ala Gly Arg Ser Arg Arg Ser
            195                 200                 205
Arg Arg Ala Ile Asp Leu Pro Thr His Glu Asn His Gly Leu Lys Thr
            210                 215                 220
Arg Gln Glu Lys Trp Met Thr Gly Arg Met Gly Glu Arg Gln Leu Gln
225                 230                 235                 240
Lys Ile Glu Arg Trp Phe Val Arg Asn Pro Phe Phe Ala Val Thr Ala
                    245                 250                 255
Leu Thr Ile Ala Tyr Leu Val Gly Ser Asn Met Thr Gln Arg Val Val
                    260                 265                 270
Ile Ala Leu Leu Val Leu Ala Val Gly Pro Ala Tyr Ser Ala His Cys
                    275                 280                 285
Ile Gly Ile Thr Asp Arg Asp Phe Ile Glu Gly Val His Gly Gly Thr
                    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                    325                 330                 335
Arg Pro Ala Glu Ala Arg Lys Val Cys Tyr Asn Ala Val Leu Thr His
                    340                 345                 350
Val Lys Ile Asn Asp Lys Cys Pro Ser Thr Gly Glu Ala His Leu Ala
                    355                 360                 365
Glu Glu Asn Glu Gly Asp Asn Ala Cys Lys Arg Thr Tyr Ser Asp Arg
            370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                    405                 410                 415
Gln Thr Lys Ile Gln Tyr Val Ile Arg Ala Gln Leu His Val Gly Ala
                    420                 425                 430
Lys Gln Glu Asn Trp Asn Thr Ser Ile Lys Thr Leu Lys Phe Asp Ala
            435                 440                 445
Leu Ser Gly Ser Gln Glu Val Glu Phe Ile Gly Tyr Gly Lys Ala Thr
450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                    485                 490                 495
Asp Leu Thr Leu Pro Trp Gln Ser Gly Ser Gly Val Trp Arg Glu
            500                 505                 510
Met His His Leu Val Glu Phe Glu Pro Pro His Ala Ala Thr Ile Arg
            515                 520                 525
Val Leu Ala Leu Gly Asn Gln Glu Gly Ser Leu Lys Thr Ala Leu Thr
            530                 535                 540
Gly Ala Met Arg Val Thr Lys Asp Thr Asn Asp Asn Leu Tyr Lys
545                 550                 555                 560
Leu His Gly Gly His Val Ser Cys Arg Val Lys Leu Ser Ala Leu Thr
                    565                 570                 575
Leu Lys Gly Thr Ser Tyr Lys Ile Cys Thr Asp Lys Met Phe Phe Val
                    580                 585                 590
Lys Asn Pro Thr Asp Thr Gly His Gly Thr Val Val Met Gln Val Lys
                    595                 600                 605
```

```
Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
            675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
            755                 760                 765

Met Met Phe Leu Ser Leu Gly Val Gly Ala Asp Gln Gly Cys Ala Ile
770                 775                 780

Asn Phe Gly Val Ser Lys Gly Glu Glu Leu Phe Thr Gly Val Val Pro
785                 790                 795                 800

Ile Leu Val Glu Leu Asp Gly Asp Val Asn Gly His Lys Phe Ser Val
                805                 810                 815

Ser Gly Glu Gly Glu Gly Asp Ala Thr Tyr Gly Lys Leu Thr Leu Lys
                820                 825                 830

Phe Ile Cys Thr Thr Gly Lys Leu Pro Val Pro Trp Pro Thr Leu Val
            835                 840                 845

Thr Thr Leu Thr Tyr Gly Val Gln Cys Phe Ser Arg Tyr Pro Asp His
850                 855                 860

Met Lys Gln His Asp Phe Phe Lys Ser Ala Met Pro Glu Gly Tyr Val
865                 870                 875                 880

Gln Glu Arg Thr Ile Phe Phe Lys Asp Asp Gly Asn Tyr Lys Thr Arg
                885                 890                 895

Ala Glu Val Lys Phe Glu Gly Asp Thr Leu Val Asn Arg Ile Glu Leu
                900                 905                 910

Lys Gly Ile Asp Phe Lys Glu Asp Gly Asn Ile Leu Gly His Lys Leu
            915                 920                 925

Glu Tyr Asn Tyr Asn Ser His Asn Val Tyr Ile Met Ala Asp Lys Gln
930                 935                 940

Lys Asn Gly Ile Lys Val Asn Phe Lys Ile Arg His Asn Ile Glu Asp
945                 950                 955                 960

Gly Ser Val Gln Leu Ala Asp His Tyr Gln Gln Asn Thr Pro Ile Gly
                965                 970                 975

Asp Gly Pro Val Leu Leu Pro Asp Asn His Tyr Leu Ser Thr Gln Ser
                980                 985                 990

Ala Leu Ser Lys Asp Pro Asn Glu Lys Arg Asp His Met Val Leu Leu
            995                 1000                1005

Glu Phe Val Thr Ala Ala Gly Ile Thr Leu Gly Met Asp Glu Leu
    1010                1015                1020
```

-continued

Tyr Lys Thr Ser Leu Gly Lys Ala Val His Gln Val Phe Gly Ser
    1025                1030                1035

Val Tyr Thr Thr Met Phe Gly Gly Val Ser Trp Met Ile Arg Ile
    1040                1045                1050

Leu Ile Gly Phe Leu Val Leu Trp Ile Gly Thr Asn Ser Arg Asn
    1055                1060                1065

Thr Ser Met Ala Met Thr Cys Ile Ala Val Gly Gly Ile Thr Leu
    1070                1075                1080

Phe Leu Gly Phe Thr Val Gly Ala Asp Gln Gly Cys Ala Ile Asn
    1085                1090                1095

Phe Gly Lys Arg Glu Leu Lys Cys Gly Asp Gly Ile Phe Ile Phe
    1100                1105                1110

Arg Asp Ser Asp Asp Trp Leu Asn Lys Tyr Ser Tyr Tyr Pro Glu
    1115                1120                1125

Asp Pro Val Lys Leu Ala Ser Ile Val Lys Ala Ser Phe Glu Glu
    1130                1135                1140

Gly Lys Cys Gly Leu Asn Ser Val Asp Ser Leu Glu His Glu Met
    1145                1150                1155

Trp Arg Ser Arg Ala Asp Glu Ile Asn Ala Ile Phe Glu Glu Asn
    1160                1165                1170

Glu Val Asp Ile Ser Val Val Val Gln Asp Pro Lys Asn Val Tyr
    1175                1180                1185

Gln Arg Gly Thr His Pro Phe Ser Arg Ile Arg Asp Gly Leu Gln
    1190                1195                1200

Tyr Gly Trp Lys Thr Trp Gly Lys Asn Leu Val Phe Ser Pro Gly
    1205                1210                1215

Arg Lys Asn Gly Ser Phe Ile Ile Asp Gly Lys Ser Arg Lys Glu
    1220                1225                1230

Cys Pro Phe Ser Asn Arg Val Trp Asn Ser Phe Gln Ile Glu Glu
    1235                1240                1245

Phe Gly Thr Gly Val Phe Thr Thr Arg Val Tyr Met Asp Ala Val
    1250                1255                1260

Phe Glu Tyr Thr Ile Asp Cys Asp Gly Ser Ile Leu Gly Ala Ala
    1265                1270                1275

Val Asn Gly Lys Lys Ser Ala His Gly Ser Pro Thr Phe Trp Met
    1280                1285                1290

Gly Ser His Glu Val Asn Gly Thr Trp Met Ile His Thr Leu Glu
    1295                1300                1305

Ala Leu Asp Tyr Lys Glu Cys Glu Trp Pro Leu Thr His Thr Ile
    1310                1315                1320

Gly Thr Ser Val Glu Glu Ser Glu Met Phe Met Pro Arg Ser Ile
    1325                1330                1335

Gly Gly Pro Val Ser Ser His Asn His Ile Pro Gly Tyr Lys Val
    1340                1345                1350

Gln Thr Asn Gly Pro Trp Met Gln Val Pro Leu Glu Val Lys Arg
    1355                1360                1365

Glu Ala Cys Pro Gly Thr Ser Val Ile Ile Asp Gly Asn Cys Asp
    1370                1375                1380

Gly Arg Gly Lys Ser Thr Arg Ser Thr Thr Asp Ser Gly Lys Val
    1385                1390                1395

Ile Pro Glu Trp Cys Cys Arg Ser Cys Thr Met Pro Pro Val Ser
    1400                1405                1410

Phe His Gly Ser Asp Gly Cys Trp Tyr Pro Met Glu Ile Arg Pro

-continued

```
            1415                1420                1425
Arg Lys Thr His Glu Ser His Leu Val Arg Ser Trp Val Thr Ala
        1430                1435                1440
Gly Glu Ile His Ala Val Pro Phe Gly Leu Val Ser Met Met Ile
        1445                1450                1455
Ala Met Glu Val Val Leu Arg Lys Arg Gln Gly Pro Lys Gln Met
        1460                1465                1470
Leu Val Gly Gly Val Val Leu Leu Gly Ala Met Leu Val Gly Gln
        1475                1480                1485
Val Thr Leu Leu Asp Leu Leu Lys Leu Thr Val Ala Val Gly Leu
        1490                1495                1500
His Phe His Glu Met Asn Asn Gly Gly Asp Ala Met Tyr Met Ala
        1505                1510                1515
Leu Ile Ala Ala Phe Ser Ile Arg Pro Gly Leu Leu Ile Gly Phe
        1520                1525                1530
Gly Leu Arg Thr Leu Trp Ser Pro Arg Glu Arg Leu Val Leu Thr
        1535                1540                1545
Leu Gly Ala Ala Met Val Glu Ile Ala Leu Gly Gly Val Met Gly
        1550                1555                1560
Gly Leu Trp Lys Tyr Leu Asn Ala Val Ser Leu Cys Ile Leu Thr
        1565                1570                1575
Ile Asn Ala Val Ala Ser Arg Lys Ala Ser Asn Thr Ile Leu Pro
        1580                1585                1590
Leu Met Ala Leu Leu Thr Pro Val Thr Met Ala Glu Val Arg Leu
        1595                1600                1605
Ala Ala Met Phe Phe Cys Ala Met Val Ile Ile Gly Val Leu His
        1610                1615                1620
Gln Asn Phe Lys Asp Thr Ser Met Gln Lys Thr Ile Pro Leu Val
        1625                1630                1635
Ala Leu Thr Leu Thr Ser Tyr Leu Gly Leu Thr Gln Pro Phe Leu
        1640                1645                1650
Gly Leu Cys Ala Phe Leu Ala Thr Arg Ile Phe Gly Arg Arg Ser
        1655                1660                1665
Ile Pro Val Asn Glu Ala Leu Ala Ala Ala Gly Leu Val Gly Val
        1670                1675                1680
Leu Ala Gly Leu Ala Phe Gln Glu Met Glu Asn Phe Leu Gly Pro
        1685                1690                1695
Ile Ala Val Gly Gly Leu Leu Met Met Leu Val Ser Val Ala Gly
        1700                1705                1710
Arg Val Asp Gly Leu Glu Leu Lys Lys Leu Gly Glu Val Ser Trp
        1715                1720                1725
Glu Glu Glu Ala Glu Ile Ser Gly Ser Ser Ala Arg Tyr Asp Val
        1730                1735                1740
Ala Leu Ser Glu Gln Gly Glu Phe Lys Leu Leu Ser Glu Glu Lys
        1745                1750                1755
Val Pro Trp Asp Gln Val Val Met Thr Ser Leu Ala Leu Val Gly
        1760                1765                1770
Ala Ala Leu His Pro Phe Ala Leu Leu Leu Val Leu Ala Gly Trp
        1775                1780                1785
Leu Phe His Val Arg Gly Ala Arg Arg Ser Gly Asp Val Leu Trp
        1790                1795                1800
Asp Ile Pro Thr Pro Lys Ile Ile Glu Glu Cys Glu His Leu Glu
        1805                1810                1815
```

```
Asp Gly Ile Tyr Gly Ile Phe Gln Ser Thr Phe Leu Gly Ala Ser
    1820            1825                1830

Gln Arg Gly Val Gly Val Ala Gln Gly Gly Val Phe His Thr Met
    1835            1840                1845

Trp His Val Thr Arg Gly Ala Phe Leu Val Arg Asn Gly Lys Lys
    1850            1855                1860

Leu Ile Pro Ser Trp Ala Ser Val Lys Glu Asp Leu Val Ala Tyr
    1865            1870                1875

Gly Gly Ser Trp Lys Leu Glu Gly Arg Trp Asp Gly Glu Glu Glu
    1880            1885                1890

Val Gln Leu Ile Ala Ala Val Pro Gly Lys Asn Val Val Asn Val
    1895            1900                1905

Gln Thr Lys Pro Ser Leu Phe Lys Val Arg Asn Gly Gly Glu Ile
    1910            1915                1920

Gly Ala Val Ala Leu Asp Tyr Pro Ser Gly Thr Ser Gly Ser Pro
    1925            1930                1935

Ile Val Asn Arg Asn Gly Glu Val Ile Gly Leu Tyr Gly Asn Gly
    1940            1945                1950

Ile Leu Val Gly Asp Asn Ser Phe Val Ser Ala Ile Ser Gln Thr
    1955            1960                1965

Glu Val Lys Glu Gly Lys Glu Glu Leu Gln Glu Ile Pro Thr
    1970            1975                1980

Met Leu Lys Lys Gly Met Thr Thr Val Leu Asp Phe His Pro Gly
    1985            1990                1995

Ala Gly Lys Thr Arg Arg Phe Leu Pro Gln Ile Leu Ala Glu Cys
    2000            2005                2010

Ala Arg Arg Arg Leu Arg Thr Leu Val Leu Ala Pro Thr Arg Val
    2015            2020                2025

Val Leu Ser Glu Met Lys Glu Ala Phe His Gly Leu Asp Val Lys
    2030            2035                2040

Phe His Thr Gln Ala Phe Ser Ala His Gly Ser Gly Arg Glu Val
    2045            2050                2055

Ile Asp Ala Met Cys His Ala Thr Leu Thr Tyr Arg Met Leu Glu
    2060            2065                2070

Pro Thr Arg Val Val Asn Trp Glu Val Ile Ile Met Asp Glu Ala
    2075            2080                2085

His Phe Leu Asp Pro Ala Ser Ile Ala Ala Arg Gly Trp Ala Ala
    2090            2095                2100

His Arg Ala Arg Ala Asn Glu Ser Ala Thr Ile Leu Met Thr Ala
    2105            2110                2115

Thr Pro Pro Gly Thr Ser Asp Glu Phe Pro His Ser Asn Gly Glu
    2120            2125                2130

Ile Glu Asp Val Gln Thr Asp Ile Pro Ser Glu Pro Trp Asn Thr
    2135            2140                2145

Gly His Asp Trp Ile Leu Ala Asp Lys Arg Pro Thr Ala Trp Phe
    2150            2155                2160

Leu Pro Ser Ile Arg Ala Ala Asn Val Met Ala Ala Ser Leu Arg
    2165            2170                2175

Lys Ala Gly Lys Ser Val Val Val Leu Asn Arg Lys Thr Phe Glu
    2180            2185                2190

Arg Glu Tyr Pro Thr Ile Lys Gln Lys Lys Pro Asp Phe Ile Leu
    2195            2200                2205
```

-continued

```
Ala Thr Asp Ile Ala Glu Met Gly Ala Asn Leu Cys Val Glu Arg
    2210            2215            2220

Val Leu Asp Cys Arg Thr Ala Phe Lys Pro Val Leu Val Asp Glu
    2225            2230            2235

Gly Arg Lys Val Ala Ile Lys Gly Pro Leu Arg Ile Ser Ala Ser
    2240            2245            2250

Ser Ala Ala Gln Arg Arg Gly Arg Ile Gly Arg Asn Pro Asn Arg
    2255            2260            2265

Asp Gly Asp Ser Tyr Tyr Ser Glu Pro Thr Ser Glu Asn Asn
    2270            2275            2280

Ala His His Val Cys Trp Leu Glu Ala Ser Met Leu Leu Asp Asn
    2285            2290            2295

Met Glu Val Arg Gly Gly Met Val Ala Pro Leu Tyr Gly Val Glu
    2300            2305            2310

Gly Thr Lys Thr Pro Val Ser Pro Gly Glu Met Arg Leu Arg Asp
    2315            2320            2325

Asp Gln Arg Lys Val Phe Arg Glu Leu Val Arg Asn Cys Asp Leu
    2330            2335            2340

Pro Val Trp Leu Ser Trp Gln Val Ala Lys Ala Gly Leu Lys Thr
    2345            2350            2355

Asn Asp Arg Lys Trp Cys Phe Glu Gly Pro Glu Glu His Glu Ile
    2360            2365            2370

Leu Asn Asp Ser Gly Glu Thr Val Lys Cys Arg Ala Pro Gly Gly
    2375            2380            2385

Ala Lys Lys Pro Leu Arg Pro Arg Trp Cys Asp Glu Arg Val Ser
    2390            2395            2400

Ser Asp Gln Ser Ala Leu Ser Glu Phe Ile Lys Phe Ala Glu Gly
    2405            2410            2415

Arg Arg Gly Ala Ala Glu Val Leu Val Val Leu Ser Glu Leu Pro
    2420            2425            2430

Asp Phe Leu Ala Lys Lys Gly Gly Glu Ala Met Asp Thr Ile Ser
    2435            2440            2445

Val Phe Leu His Ser Glu Glu Gly Ser Arg Ala Tyr Arg Asn Ala
    2450            2455            2460

Leu Ser Met Met Pro Glu Ala Met Thr Ile Val Met Leu Phe Ile
    2465            2470            2475

Leu Ala Gly Leu Leu Thr Ser Gly Met Val Ile Phe Phe Met Ser
    2480            2485            2490

Pro Lys Gly Ile Ser Arg Met Ser Met Ala Met Gly Thr Met Ala
    2495            2500            2505

Gly Cys Gly Tyr Leu Met Phe Leu Gly Gly Val Lys Pro Thr His
    2510            2515            2520

Ile Ser Tyr Val Met Leu Ile Phe Phe Val Leu Met Val Val Val
    2525            2530            2535

Ile Pro Glu Pro Gly Gln Gln Arg Ser Ile Gln Asp Asn Gln Val
    2540            2545            2550

Ala Tyr Leu Ile Ile Gly Ile Leu Thr Leu Val Ser Ala Val Ala
    2555            2560            2565

Ala Asn Glu Leu Gly Met Leu Glu Lys Thr Lys Glu Asp Leu Phe
    2570            2575            2580

Gly Lys Lys Asn Leu Ile Pro Ser Ser Ala Ser Pro Trp Ser Trp
    2585            2590            2595

Pro Asp Leu Asp Leu Lys Pro Gly Ala Ala Trp Thr Val Tyr Val
```

-continued

```
            2600                2605               2610
Gly Ile Val Thr Met Leu Ser Pro Met Leu His His Trp Ile Lys
            2615                2620               2625
Val Glu Tyr Gly Asn Leu Ser Leu Ser Gly Ile Ala Gln Ser Ala
            2630                2635               2640
Ser Val Leu Ser Phe Met Asp Lys Gly Ile Pro Phe Met Lys Met
            2645                2650               2655
Asn Ile Ser Val Ile Met Leu Leu Val Ser Gly Trp Asn Ser Ile
            2660                2665               2670
Thr Val Met Pro Leu Leu Cys Gly Ile Gly Cys Ala Met Leu His
            2675                2680               2685
Trp Ser Leu Ile Leu Pro Gly Ile Lys Ala Gln Gln Ser Lys Leu
            2690                2695               2700
Ala Gln Arg Arg Val Phe His Gly Val Ala Lys Asn Pro Val Val
            2705                2710               2715
Asp Gly Asn Pro Thr Val Asp Ile Glu Glu Ala Pro Glu Met Pro
            2720                2725               2730
Ala Leu Tyr Glu Lys Lys Leu Ala Leu Tyr Leu Leu Leu Ala Leu
            2735                2740               2745
Ser Leu Ala Ser Val Ala Met Cys Arg Thr Pro Phe Ser Leu Ala
            2750                2755               2760
Glu Gly Ile Val Leu Ala Ser Ala Ala Leu Gly Pro Leu Ile Glu
            2765                2770               2775
Gly Asn Thr Ser Leu Leu Trp Asn Gly Pro Met Ala Val Ser Met
            2780                2785               2790
Thr Gly Val Met Arg Gly Asn His Tyr Ala Phe Val Gly Val Met
            2795                2800               2805
Tyr Asn Leu Trp Lys Met Lys Thr Gly Arg Arg Gly Ser Ala Asn
            2810                2815               2820
Gly Lys Thr Leu Gly Glu Val Trp Lys Arg Glu Leu Asn Leu Leu
            2825                2830               2835
Asp Lys Arg Gln Phe Glu Leu Tyr Lys Arg Thr Asp Ile Val Glu
            2840                2845               2850
Val Asp Arg Asp Thr Ala Arg Arg His Leu Ala Glu Gly Lys Val
            2855                2860               2865
Asp Thr Gly Val Ala Val Ser Arg Gly Thr Ala Lys Leu Arg Trp
            2870                2875               2880
Phe His Glu Arg Gly Tyr Val Lys Leu Glu Gly Arg Val Ile Asp
            2885                2890               2895
Leu Gly Cys Gly Arg Gly Gly Trp Cys Tyr Tyr Ala Ala Ala Gln
            2900                2905               2910
Lys Glu Val Ser Gly Val Lys Gly Phe Thr Leu Gly Arg Asp Gly
            2915                2920               2925
His Glu Lys Pro Met Asn Val Gln Ser Leu Gly Trp Asn Ile Ile
            2930                2935               2940
Thr Phe Lys Asp Lys Thr Asp Ile His Arg Leu Glu Pro Val Lys
            2945                2950               2955
Cys Asp Thr Leu Leu Cys Asp Ile Gly Glu Ser Ser Ser Ser Ser
            2960                2965               2970
Val Thr Glu Gly Glu Arg Thr Val Arg Val Leu Asp Thr Val Glu
            2975                2980               2985
Lys Trp Leu Ala Cys Gly Val Asp Asn Phe Cys Val Lys Val Leu
            2990                2995               3000
```

```
Ala Pro Tyr Met Pro Asp Val Leu Glu Lys Leu Glu Leu Leu Gln
    3005              3010                3015

Arg Arg Phe Gly Gly Thr Val Ile Arg Asn Pro Leu Ser Arg Asn
    3020              3025                3030

Ser Thr His Glu Met Tyr Tyr Val Ser Gly Ala Arg Ser Asn Val
    3035              3040                3045

Thr Phe Thr Val Asn Gln Thr Ser Arg Leu Leu Met Arg Arg Met
    3050              3055                3060

Arg Arg Pro Thr Gly Lys Val Thr Leu Glu Ala Asp Val Ile Leu
    3065              3070                3075

Pro Ile Gly Thr Arg Ser Val Glu Thr Asp Lys Gly Pro Leu Asp
    3080              3085                3090

Lys Glu Ala Ile Glu Glu Arg Val Glu Arg Ile Lys Ser Glu Tyr
    3095              3100                3105

Met Thr Ser Trp Phe Tyr Asp Asn Asp Asn Pro Tyr Arg Thr Trp
    3110              3115                3120

His Tyr Cys Gly Ser Tyr Val Thr Lys Thr Ser Gly Ser Ala Ala
    3125              3130                3135

Ser Met Val Asn Gly Val Ile Lys Ile Leu Thr Tyr Pro Trp Asp
    3140              3145                3150

Arg Ile Glu Glu Val Thr Arg Met Ala Met Thr Asp Thr Thr Pro
    3155              3160                3165

Phe Gly Gln Gln Arg Val Phe Lys Glu Lys Val Asp Thr Arg Ala
    3170              3175                3180

Lys Asp Pro Pro Ala Gly Thr Arg Lys Ile Met Lys Val Val Asn
    3185              3190                3195

Arg Trp Leu Phe Arg His Leu Ala Arg Glu Lys Ser Pro Arg Leu
    3200              3205                3210

Cys Thr Lys Glu Glu Phe Ile Ala Lys Val Arg Ser His Ala Ala
    3215              3220                3225

Ile Gly Ala Tyr Leu Glu Glu Gln Glu Gln Trp Lys Thr Ala Asn
    3230              3235                3240

Glu Ala Val Gln Asp Pro Lys Phe Trp Glu Leu Val Asp Glu Glu
    3245              3250                3255

Arg Lys Leu His Gln Gln Gly Arg Cys Arg Thr Cys Val Tyr Asn
    3260              3265                3270

Met Met Gly Lys Arg Glu Lys Lys Leu Ser Glu Phe Gly Lys Ala
    3275              3280                3285

Lys Gly Ser Arg Ala Ile Trp Tyr Met Trp Leu Gly Ala Arg Tyr
    3290              3295                3300

Leu Glu Phe Glu Ala Leu Gly Phe Leu Asn Glu Asp His Trp Ala
    3305              3310                3315

Ser Arg Glu Asn Ser Gly Gly Gly Val Glu Gly Ile Gly Leu Gln
    3320              3325                3330

Tyr Leu Gly Tyr Val Ile Arg Asp Leu Ala Ala Met Asp Gly Gly
    3335              3340                3345

Gly Phe Tyr Ala Asp Asp Thr Ala Gly Trp Asp Thr Arg Ile Thr
    3350              3355                3360

Glu Ala Asp Leu Asp Asp Glu Gln Glu Ile Leu Asn Tyr Met Ser
    3365              3370                3375

Pro His His Lys Lys Leu Ala Gln Ala Val Met Glu Met Thr Tyr
    3380              3385                3390
```

-continued

```
Lys Asn  Lys Val Val Lys Val  Leu Arg Pro Ala Pro  Gly Gly Lys
    3395                 3400                 3405

Ala Tyr  Met Asp Val Ile Ser  Arg Arg Asp Gln Arg  Gly Ser Gly
    3410                 3415                 3420

Gln Val  Val Thr Tyr Ala Leu  Asn Thr Ile Thr Asn  Leu Lys Val
    3425                 3430                 3435

Gln Leu  Ile Arg Met Ala Glu  Ala Glu Met Val Ile  His His Gln
    3440                 3445                 3450

His Val  Gln Asp Cys Asp Glu  Ser Val Leu Thr Arg  Leu Glu Ala
    3455                 3460                 3465

Trp Leu  Thr Glu His Gly Cys  Asn Arg Leu Lys Arg  Met Ala Val
    3470                 3475                 3480

Ser Gly  Asp Asp Cys Val Val  Arg Pro Ile Asp Asp  Arg Phe Gly
    3485                 3490                 3495

Leu Ala  Leu Ser His Leu Asn  Ala Met Ser Lys Val  Arg Lys Asp
    3500                 3505                 3510

Ile Ser  Glu Trp Gln Pro Ser  Lys Gly Trp Asn Asp  Trp Glu Asn
    3515                 3520                 3525

Val Pro  Phe Cys Ser His His  Phe His Glu Leu Gln  Leu Lys Asp
    3530                 3535                 3540

Gly Arg  Arg Ile Val Val Pro  Cys Arg Glu Gln Asp  Glu Leu Ile
    3545                 3550                 3555

Gly Arg  Gly Arg Val Ser Pro  Gly Asn Gly Trp Met  Ile Lys Glu
    3560                 3565                 3570

Thr Ala  Cys Leu Ser Lys Ala  Tyr Ala Asn Met Trp  Ser Leu Met
    3575                 3580                 3585

Tyr Phe  His Lys Arg Asp Met  Arg Leu Leu Ser Leu  Ala Val Ser
    3590                 3595                 3600

Ser Ala  Val Pro Thr Ser Trp  Val Pro Gln Gly Arg  Thr Thr Trp
    3605                 3610                 3615

Ser Ile  His Gly Lys Gly Glu  Trp Met Thr Thr Glu  Asp Met Leu
    3620                 3625                 3630

Glu Val  Trp Asn Arg Val Trp  Ile Thr Asn Asn Pro  His Met Gln
    3635                 3640                 3645

Asp Lys  Thr Met Val Lys Lys  Trp Arg Asp Val Pro  Tyr Leu Thr
    3650                 3655                 3660

Lys Arg  Gln Asp Lys Leu Cys  Gly Ser Leu Ile Gly  Met Thr Asn
    3665                 3670                 3675

Arg Ala  Thr Trp Ala Ser His  Ile His Leu Val Ile  His Arg Ile
    3680                 3685                 3690

Arg Thr  Leu Ile Gly Gln Glu  Lys Tyr Thr Asp Tyr  Leu Thr Val
    3695                 3700                 3705

Met Asp  Arg Tyr Ser Val Asp  Ala Asp Leu Gln Leu  Gly Glu Leu
    3710                 3715                 3720

Ile

<210> SEQ ID NO 3
<211> LENGTH: 11890
<212> TYPE: DNA
<213> ORGANISM: Yellow fever virus

<400> SEQUENCE: 3
agtaaatcct gtgtgctaat tgaggtgcat tggtctgcaa atcgagttgc taggcaataa     60
acacatttgg attaatttta atcgttcgtt gagcgattag cagagaactg accagaacat    120
```

```
gtctggtcgt aaagctcagg gaaaaaccct gggcgtcaat atggtacgac gaggagttcg      180
ctccttgtca aacaaaataa aacaaaaaac aaaacaaatt ggaaacagac ctggaccttc      240
aagaggtgtt caaggattta tcttttctt  tttgttcaac attttgactg gaaaaaagat     300
cacagcccac ctaaagaggt tgtggaaaat gctggaccca agacaaggct tggctgttct      360
aaggaaagtc aagagagtgg tggccagttt gatgagagga ttgtcctcaa ggaaacgccg      420
ttcccatgat gttctgactg tgcaattcct aattttggga atgctgttga tgaccggtgg      480
agtgaccttg gtgcggaaaa acagatggtt gctcctaaat gtgacatctg aggacctcgg      540
gaaaacattc tctgtgggca caggcaactg cacaacaaac attttggaag ccaagtactg      600
gtgcccagac tcaatggaat acaactgtcc caatctcagt ccaagagagg agccagatga      660
cattgattgc tggtgctatg gggtggaaaa cgttagagtc gcatatggta agtgtgactc      720
agcaggcagg tctaggaggt caagaagggc cattgacttg cctacgcatg aaaaccatgg      780
tttgaagacc cggcaagaaa aatggatgac tggaagaatg ggtgaaaggc aactccaaaa      840
gattgagaga tggttcgtga ggaaccccct ttttgcagtg acggctctga ccattgccta      900
ccttgtggga agcaacatga cgcaacgagt cgtgattgcc ctactggtct tggctgttgg      960
tccggcctac tcagctcact gcattggaat tactgacagg gatttcattg aggggtgca     1020 tggaggaact tgggtttcag ctaccctgga gcaagacaag tgtgtcactg ttatggcccc     1080
tgacaagcct tcattggaca tctcactaga gacagtagcc attgatagac ctgctgaggc     1140
gaggaaagtg tgttacaatg cagttctcac tcatgtgaag attaatgaca agtgccccag     1200
cactggagag gcccacctag ctgaagagaa cgaagggac  aatgcgtgca agcgcactta     1260
ttctgataga ggctggggca atggctgtgg cctatttggg aaaggagca  ttgtggcatg     1320 cgccaaattc acttgtgcca aatccatgag ttttgtgag  gttgatcaga ccaaaattca     1380
gtatgtcatc agagcacaat tgcatgtagg ggccaagcag gaaaattgga taccagcat      1440 taagactctc aagtttgatg ccctgtcagg ctcccaggaa gtcgagttca ttgggtatgg     1500
aaaagctaca ctggaatgcc aggtgcaaac tgccggtgga ctttggtaaca gttacatcgc     1560 tgagatggaa acagagagct ggatagtgga cagacagtgg gcccaggact tgaccctgcc     1620
atggcagagt ggaagtggcg gggtgtggag agagatgcat catcttgtcg aatttgaacc     1680
tccgcatgcc gccactatca gagtactggc cctgggaaac caggaaggct ccttgaaaac     1740
agctcttact ggcgcaatga gggttacaaa ggacacaaat gacaacaacc tttacaaact     1800
acatggtgga catgtttctt gcagagtgaa attgtcagct ttgacactca aggggacatc     1860
ctacaaaata tgcactgaca aaatgttttt tgtcaagaac ccaactgaca ctggccatgg     1920
cactgttgtg atgcaggtga aagtgtcaaa aggagccccc tgcaggattc cagtgatagt     1980
agctgatgat cttacagcgg caatcaataa aggcatttg  gttacagtta accccatcgc     2040
ctcaaccaat gatgatgaag tgctgattga ggtgaaccca cctttggag  acagctacat      2100 tatcgttggg agaggagatt cacgtctcac ttaccagtgg cacaaagagg gaagctcaat     2160
aggaaagttg ttcactcaga ccatgaaagg cgtggaacgc ctggccgtca tgggagacac     2220
cgcctgggat ttcagctccg ctgagggggt ctccacttcg gttgggaaag gaattcatac     2280 ggtgttggc tctgcctttc aggggctatt tggcggcttg aactggataa caaaggtcat     2340 catggggcg gtacttatat gggttggcat caacacaaga aacatgacaa tgtccatgag     2400
catgatcttg gtaggagtga tcatgatgtt tttgtctcta ggagttgggg cggatcaagg     2460
```

```
atgcgccatc aactttggcg tgagcaaggg cgaggagctg ttcaccgggg tggtgcccat    2520
cctggtcgag ctggacggcg acgtaaacgg ccacaagttc agcgtgtccg gcgagggcga    2580
gggcgatgcc acctacggca agctgaccct gaagttcatc tgcaccaccg gcaagctgcc    2640
cgtgccctgg cccaccctcg tgaccaccct gacctacggc gtgcagtgct tcagccgcta    2700
ccccgaccac atgaagcagc acgacttctt caagtccgcc atgcccgaag gctacgtcca    2760
ggagcgcacc atcttcttca aggacgacgg caactacaag acccgcgccg aggtgaagtt    2820
cgagggcgac accctggtga accgcatcga gctgaagggc atcgacttca aggaggacgg    2880
caacatcctg gggcacaagc tggagtacaa ctacaacagc cacaacgtct atatcatggc    2940
cgacaagcag aagaacggca tcaaggtgaa cttcaagatc cgccacaaca tcgaggacgg    3000
cagcgtgcag ctcgccgacc actaccagca gaacaccccc atcggcgacg gccccgtgct    3060
gctgcccgac aaccactacc tgagcaccca gtccgccctg agcaaagacc ccaacgagaa    3120
gcgcgatcac atggtcctgc tggagttcgt gaccgccgcc gggatcactc tcggcatgga    3180
cgagctgtac aagaagatgt tgagtccac atacagaggt gcaaaacgaa tggccattct    3240
aggtgaaaca gcttgggatt ttggttccgt tggtggactg ttcacatcat tgggaaaggc    3300
tgtgcaccag gttttggaa gtgtgtatac aaccatgttt ggaggagtct catggatgat    3360
tagaatccta attgggttct tagtgttgtg gattggcacg aactccagga acacttcaat    3420
ggctatgacg tgcatagctg ttggaggaat cactctgttt ctgggcttca cagttggcgc    3480
cgatcaagga tgcgccatca actttggcaa agagagagctc aagtgcggag atggtatctt    3540
catatttaga gactctgatg actggctgaa caagtactca tactatccag aagatcctgt    3600
gaagcttgca tcaatagtga aagcctcttt tgaagaaggg aagtgtggcc taaattcagt    3660
tgactccctt gagcatgaga tgtggagaag cagggcagat gagatcaatg ccattttga    3720
ggaaaacgag gtggacattt ctgttgtcgt gcaggatcca aagaatgttt accagagagg    3780
aactcatcca ttttccagaa ttcgggatgg tctgcagtat ggttggaaga cttggggtaa    3840
gaaccttgtg ttctccccag ggaggaagaa tggaagcttc atcatagatg gaaagtccag    3900
gaaagaatgc ccgttttcaa accgggtctg gaattctttc cagatagagg agtttgggac    3960
gggagtgttc accacacgcg tgtacatgga cgcagtcttt gaatacacca tagactgcga    4020
tggatcatac ttgggtgcag cggtgaacgg aaaaaagagt gcccatggct ctccaacatt    4080
ttggatggga agtcatgaag taaatgggac atggatgatc cacaccttgg aggcattaga    4140
ttacaaggag tgtgagtggc cactgacaca tacgattgga acatcagttg aagagagtga    4200
aatgttcatg ccgagatcaa tcggaggccc agttagctct cacaatcata tccctggata    4260
caaggttcag acgaacggac cttggatgca ggtaccacta gaagtgaaga gagaagcttg    4320
cccagggact agcgtgatca ttgatggcaa ctgtgatgga cggggaaaat caaccagatc    4380
caccacggat agcgggaaag ttattcctga atggtgttgc cgctcctgca caatgccgcc    4440
tgtgagcttc catggtagtg atgggtgttg gtatcccatg gaaattaggc caaggaaaac    4500
gcatgaaagc catctggtgc gctcctgggt tacagctgga gaaatacatg ctgtcccttt    4560
tggtttggtg agcatgatga tagcaatgga agtggtccta aggaaaagac agggaccaaa    4620
gcaaatgttg gttggaggag tagtgctctt gggagcaatg ctggtcgggc aagtaactct    4680
ccttgatttg ctgaaactca cagtggctgt gggattgcat ttccatgaga tgaacaatgg    4740
aggagacgcc atgtatatgg cgttgattgc tgccttttca atcagaccag gctgctcat    4800
cggcttgggg ctcaggacc tatggagccc tcgggaacgc cttgtgctga ccctaggagc    4860
```

```
agccatggtg gagattgcct tgggtggcgt gatgggcggc ctgtggaagt atctaaatgc    4920
agtttctctc tgcatcctga caataaatgc tgttgcttct aggaaagcat caaataccat    4980
cttgcccctc atggctctgt tgacacctgt cactatggct gaggtgagac ttgccgcaat    5040
gttcttttgt gccatggtta tcataggggt ccttcaccag aatttcaagg cacctccat    5100 gcagaagact atacctctgg tggccctcac actcacatct tacctgggct tgacacaacc    5160 tttttttgggc ctgtgtgcat ttctggcaac ccgcatattt gggcgaagga gtatcccagt    5220
gaatgaggca ctcgcagcag ctggtctagt gggagtgctg gcaggactgg cttttcagga    5280
gatggagaac ttccttggtc cgattgcagt tggaggactc ctgatgatgc tggttagcgt    5340
ggctgggagg gtggatgggc tagagctcaa aaagcttggt gaagtttcat gggaagagga    5400
ggcggagatc agcgggagtt ccgcccgcta tgatgtggca ctcagtgaac aaggggagtt    5460
caagctgctt tctgaagaga aagtgccatg ggaccaggtt gtgatgacct cgctggcctt    5520 ggttgggggct gccctccatc catttgctct tctgctggtc cttgctgggt ggctgttttca    5580 tgtcagggga gctaggagaa gtggggatgt cttgtgggat attcccactc ctaagatcat    5640
cgaggaatgt gaacatctgg aggatgggat ttatggcata ttccagtcaa ccttcttggg    5700
ggcctcccag cgaggagtgg gagtggcaca gggagggtg ttccacacaa tgtggcatgt    5760
cacaagagga gctttccttg tcaggaatgg caagaagttg attccatctt gggcttcagt    5820
aaaggaagac cttgtcgcct atggtggctc atggaagttg aaggcagat gggatggaga    5880 ggaagaggtc cagttgatcg cggctgttcc aggaaagaac gtggtcaacg tccagacaaa    5940
accgagcttg ttcaaagtga ggaatggggg agaaatcggg gctgtcgctc ttgactatcc    6000
gagtggcact tcaggatctc ctattgttaa caggaacgga gaggtgattg gctgtacgg    6060 caatggcatc cttgtcggtg acaactcctt cgtgtccgcc atatcccaga ctgaggtgaa    6120
ggaagaagga aaggaggagc tccaagagat cccgacaatg ctaaagaaag gaatgacaac    6180
tgtccttgat tttcatcctg gagctgggaa gacaagacgt ttcctcccac agatcttggc    6240
cgagtgcgca cggagacgct tgcgcactct tgtgttggcc cccaccaggg ttgttctttc    6300
tgaaatgaag gaggcttttc acggcctgga cgtgaaattc cacacacagg cttttttccgc    6360 tcacggcagc gggagagaag tcattgatgc catgtgccat gccacccta acttacaggat    6420 gttggaacca actagggttg ttaactggga agtgatcatt atggatgaag cccattttttt    6480 ggatccagct agcatagccg ctagaggttg ggcagcgcac agagctaggg caaatgaaag    6540
tgcaacaatc ttgatgacag ccacaccgcc tgggactagt gatgaatttc cacattcaaa    6600
tggtgaaata aagatgttc aaacggacat acccagtgag ccctggaaca cagggcatga    6660
ctggatcctg gctgacaaaa ggcccacggc atggttcctt ccatccatca gagctgcaaa    6720
tgtcatggct gcctctttgc gtaaggctgg aaagagtgtg gtggtcctga acaggaaaac    6780
ctttgagaga gaataccccca cgataaagca gaagaaacct gactttatat tggccactga    6840
catagctgaa atgggagcca acctttgcgt ggagcgagtg ctggattgca ggacggcttt    6900
taagcctgtg cttgtggatg aagggaggaa ggtggcaata aagggccac ttcgtatctc    6960 cgcatcctct gctgctcaaa gggaggggcg cattgggaga atcccaaca gagatggaga    7020 ctcatactac tattctgagc ctacaagtga aaataatgcc caccacgtct gctggttgga    7080
ggcctcaatg ctcttggaca acatggaggt gaggggtgga atggtcgccc cactctatgg    7140
cgttgaagga actaaaacac cagtttcccc tggtgaaatg agactgaggg atgaccagag    7200
```

-continued

```
gaaagtcttc agagaactag tgaggaattg tgacctgccc gtttggcttt cgtggcaagt    7260
ggccaaggct ggtttgaaga cgaatgatcg taagtggtgt tttgaaggcc ctgaggaaca    7320
tgagatcttg aatgacagcg gtgaaacagt gaagtgcagg gctcctggag gagcaaagaa    7380
gcctctgcgc ccaaggtggt gtgatgaaag ggtgtcatct gaccagagtg cgctgtctga    7440
atttattaag tttgctgaag gtaggagggg agctgctgaa gtgctagttg tgctgagtga    7500
actccctgat ttcctggcta aaaaggtgg agaggcaatg gataccatca gtgtgttcct    7560
ccactctgag gaaggctcta gggcttaccg caatgcacta tcaatgatgc ctgaggcaat    7620
gacaatagtc atgctgttta tactggctgg actactgaca tcgggaatgg tcatcttttt    7680
catgtctccc aaaggcatca gtagaatgtc tatggcgatg ggcacaatgg ccggctgtgg    7740
atatctcatg ttccttggag gcgtcaaacc cactcacatc tcctatgtca tgctcatatt    7800 cttgtcctg atggtggttg tgatccccga gccagggcaa caaaggtcca tccaagacaa    7860
ccaagtggca tacctcatta ttggcatcct gacgctggtt tcagcggtgg cagccaacga    7920
gctaggcatg ctggagaaaa ccaaagagga cctctttggg aagaagaact taattccatc    7980
tagtgcttca ccctggagtt ggccggatct tgacctgaag ccaggagctg cctggacagt    8040
gtacgttggc attgttacaa tgctctctcc aatgttgcac cactggatca aagtcgaata    8100
tggcaacctg tctctgtctg aatagcccca gtcagcctca gtcctttctt tcatggacaa    8160
ggggatacca ttcatgaaga tgaatatctc ggtcataatg ctgctggtca gtggctggaa    8220
ttcaataaca gtgatgcctc tgctctgtgg catagggtgc gccatgctcc actggtctct    8280
cattttacct ggaatcaaag cgcagcagtc aaagcttgca cagagaaggg tgttccatgg    8340
cgttgccaag aaccctgtgg ttgatgggaa tccaacagtt gacattgagg aagctcctga    8400
aatgcctgcc ctttatgaga gaaactggc tctatatctc cttcttgctc tcagcctagc    8460
ttctgttgcc atgtgcagaa cgcccttttc attggctgaa ggcattgtcc tagcatcagc    8520
tgccttaggg ccgctcatag agggaaacac cagccttctt tggaatggac ccatggctgt    8580
ctccatgaca ggagtcatga gggggaatca ctatgctttt gtgggagtca tgtacaatct    8640
atggaagatg aaaactggac gccgggggag cgcgaatgga aaaactttgg gtgaagtctg    8700
gaagagggaa ctgaatctgt tggacaagcg acagtttgag ttgtataaaa ggaccgacat    8760 tgtgaggtg gatcgtgata cggcacgcag gcatttggcc gaagggaagg tggacaccgg    8820
ggtggcggtc tccagggga ccgcaaagtt aaggtggttc catgagcgtg gctatgtcaa    8880
gctggaaggt agggtgattg acctggggtg tggccgcgga ggctggtgtt actacgctgc    8940
tgcgcaaaag gaagtgagtg gggtcaaagg atttactctt ggaagagacg gccatgagaa    9000
acccatgaat gtgcaaagtc tgggatggaa catcatcacc ttcaaggaca aaactgatat    9060
ccaccgccta gaaccagtga atgtgacac cctttgtgt gacattggag agtcatcatc    9120
gtcatcggtc acagagggg aaaggaccgt gagagttctt gatactgtag aaaaatggct    9180
ggcttgtggg gttgacaact tctgtgtgaa ggtgttagct ccatacatgc cagatgttct    9240
tgagaaactg gaattgctcc aaaggaggtt tggcggaaca gtgatcagga accctctctc    9300
caggaattcc actcatgaaa tgtactacgt gtctggagcc cgcagcaatg tcacatttac    9360
tgtgaaccaa acatcccgcc tcctgatgag gagaatgagg cgtccaactg gaaaagtgac    9420
cctggaggct gacgtcatcc tcccaattgg gacacgcagt gttgagacag acaagggacc    9480 cctgacaaa gaggccatag aagaaggggt tgagaggata aaatctgagt acatgacctc    9540
ttggttttat gacaatgaca accctacag gacctggcac tactgtggct cctatgtcac    9600
```

```
aaaaacctca ggaagtgcgg cgagcatggt aaatggtgtt attaaaattc tgacatatcc    9660
atgggacagg atagaggagg tcaccagaat ggcaatgact gacacaaccc cttttggaca    9720
gcaaagagtg tttaaagaaa aagttgacac cagagcaaag gatccaccag cgggaactag    9780
gaagatcatg aaagttgtca acaggtggct gttccgccac ctggccagag aaaagagccc    9840
cagactgtgc acaaaggaag aatttattgc aaaagtccga agtcatgcag ccattggagc    9900
ttacctggaa gaacaagaac agtggaagac tgccaatgag gctgtccaag acccaaagtt    9960
ctgggaactg gtggatgaag aaaggaagct gcaccaacaa ggcaggtgtc ggacttgtgt   10020
gtacaacatg atggggaaaa gagagaagaa gctgtcagag tttgggaaag caagggaag   10080 ccgtgccata tggtatatgt ggctgggagc gcggtatctt gagtttgagg ccctgggatt   10140
cctgaatgag gaccattggg cttccaggga aaactcagga ggaggagtgg aaggcattgg   10200
cttacaatac ctaggatatg tgatcagaga cctggctgca atggatggtg gtggattcta   10260
cgcggatgac accgctggat gggacacgcg catcacagag gcagaccttg atgatgaaca   10320
ggagatcttg aactacatga gcccacatca caaaaaactg gcacaagcag tgatggaaat   10380
gacatacaag aacaaagtgg tgaaagtgtt gagaccagcc ccaggaggga aagcctacat   10440
ggatgtcata agtcgacgag accagagagg atccgggcag gtagtgactt atgctctgaa   10500
caccatcacc aacttgaaag tccaattgat cagaatggca gaagcagaga tggtgataca   10560
tcaccaacat gttcaagatt gtgatgaatc agttctgacc aggctggagg catggctcac   10620
tgagcacgga tgtaacagac tgaagaggat ggcggtgagt ggagacgact gtgtggtccg   10680
gcccatcgat gacaggttcg gcctggccct gtcccatctc aacgccatgt ccaaggttag   10740 aaaggcata tctgaatggc agccatcaaa agggtggaat gattgggaga atgtgccctt   10800
ctgttcccac cacttccatg aactacagct gaaggatggc aggaggattg tggtgccttg   10860
ccgagaacag gacgagctca ttgggagagg aagggtgtct ccaggaaacg gctggatgat   10920
caaggaaaca gcttgcctca gcaaagccta tgccaacatg tggtcactga tgtattttca   10980
caaaagggac atgaggctac tgtcattggc tgtttcctca gctgttccca cctcatgggt   11040
tccacaagga cgcacaacat ggtcgattca tgggaaaggg gagtggatga ccacggaaga   11100
catgcttgag gtgtggaaca gagtatggat aaccaacaac ccacacatgc aggacaagac   11160
aatggtgaaa aaatgagag atgtccctta tctaaccaag agacaagaca agctgtgcgg   11220
atcactgatt ggaatgacca atagggccac ctgggcctcc cacatccatt agtcatcca   11280 tcgtatccga acgctgattg gacaggagaa atacactgac tacctaacag tcatggacag   11340
gtattctgtg gatgctgacc tgcaactggg tgagcttatc tgaaacacca tctaacagga   11400
ataacgggga tacaaaccac gggtggagaa ccggactccc cacaacctga accgggata   11460 taaaccacgg ctggagaacc gggctccgca cttaaaatga acagaaacc gggataaaaa   11520 ctacggatgg agaaccggac tccacacatt gagacagaag aagttgtcag cccagaaccc   11580
cacacgagtt ttgccactgc taagctgtga ggcagtgcag gctgggacag ccgacctcca   11640
ggttgcgaaa aacctggttt ctgggaccte ccaccccaga gtaaaaagaa cggagcctcc   11700
gctaccaccc tccacgtgg tggtagaaag acggggtcta gaggttagag agacccctcc   11760
agggaacaaa tagtgggacc atattgacgc cagggaaaga ccggagtggt tctctgcttt   11820
tcctccagag gtctgtgagc acagtttgct caagaataag cagaccttg gatgacaaac   11880 acaaaaccac                                                         11890
```

<210> SEQ ID NO 4
<211> LENGTH: 3754
<212> TYPE: PRT
<213> ORGANISM: Yellow fever virus

<400> SEQUENCE: 4

```
Met Ser Gly Arg Lys Ala Gln Gly Lys Thr Leu Gly Val Asn Met Val
1               5                   10                  15
Arg Arg Gly Val Arg Ser Leu Ser Asn Lys Ile Lys Gln Lys Thr Lys
            20                  25                  30
Gln Ile Gly Asn Arg Pro Gly Pro Ser Arg Gly Val Gln Gly Phe Ile
        35                  40                  45
Phe Phe Phe Leu Phe Asn Ile Leu Thr Gly Lys Lys Ile Thr Ala His
    50                  55                  60
Leu Lys Arg Leu Trp Lys Met Leu Asp Pro Arg Gln Gly Leu Ala Val
65                  70                  75                  80
Leu Arg Lys Val Lys Arg Val Val Ala Ser Leu Met Arg Gly Leu Ser
                85                  90                  95
Ser Arg Lys Arg Arg Ser His Asp Val Leu Thr Val Gln Phe Leu Ile
            100                 105                 110
Leu Gly Met Leu Leu Met Thr Gly Gly Val Thr Leu Val Arg Lys Asn
        115                 120                 125
Arg Trp Leu Leu Leu Asn Val Thr Ser Glu Asp Leu Gly Lys Thr Phe
    130                 135                 140
Ser Val Gly Thr Gly Asn Cys Thr Thr Asn Ile Leu Glu Ala Lys Tyr
145                 150                 155                 160
Trp Cys Pro Asp Ser Met Glu Tyr Asn Cys Pro Asn Leu Ser Pro Arg
                165                 170                 175
Glu Glu Pro Asp Asp Ile Asp Cys Trp Cys Tyr Gly Val Glu Asn Val
            180                 185                 190
Arg Val Ala Tyr Gly Lys Cys Asp Ser Ala Gly Arg Ser Arg Arg Ser
        195                 200                 205
Arg Arg Ala Ile Asp Leu Pro Thr His Glu Asn His Gly Leu Lys Thr
    210                 215                 220
Arg Gln Glu Lys Trp Met Thr Gly Arg Met Gly Glu Arg Gln Leu Gln
225                 230                 235                 240
Lys Ile Glu Arg Trp Phe Val Arg Asn Pro Phe Phe Ala Val Thr Ala
                245                 250                 255
Leu Thr Ile Ala Tyr Leu Val Gly Ser Asn Met Thr Gln Arg Val Val
            260                 265                 270
Ile Ala Leu Leu Val Leu Ala Val Gly Pro Ala Tyr Ser Ala His Cys
        275                 280                 285
Ile Gly Ile Thr Asp Arg Asp Phe Ile Glu Gly Val His Gly Gly Thr
    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                325                 330                 335
Arg Pro Ala Glu Ala Arg Lys Val Cys Tyr Asn Ala Val Leu Thr His
            340                 345                 350
Val Lys Ile Asn Asp Lys Cys Pro Ser Thr Gly Glu Ala His Leu Ala
        355                 360                 365
Glu Glu Asn Glu Gly Asp Asn Ala Cys Lys Arg Thr Tyr Ser Asp Arg
    370                 375                 380
```

-continued

```
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
            420                 425                 430
Lys Gln Glu Asn Trp Asn Thr Ser Ile Lys Thr Leu Lys Phe Asp Ala
        435                 440                 445
Leu Ser Gly Ser Gln Glu Val Glu Phe Ile Gly Tyr Gly Lys Ala Thr
450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                485                 490                 495
Asp Leu Thr Leu Pro Trp Gln Ser Gly Ser Gly Val Trp Arg Glu
            500                 505                 510
Met His His Leu Val Glu Phe Glu Pro Pro His Ala Ala Thr Ile Arg
        515                 520                 525
Val Leu Ala Leu Gly Asn Gln Glu Gly Ser Leu Lys Thr Ala Leu Thr
530                 535                 540
Gly Ala Met Arg Val Thr Lys Asp Thr Asn Asp Asn Leu Tyr Lys
545                 550                 555                 560
Leu His Gly Gly His Val Ser Cys Arg Val Lys Leu Ser Ala Leu Thr
                565                 570                 575
Leu Lys Gly Thr Ser Tyr Lys Ile Cys Thr Asp Lys Met Phe Phe Val
            580                 585                 590
Lys Asn Pro Thr Asp Thr Gly His Gly Thr Val Val Met Gln Val Lys
        595                 600                 605
Val Ser Lys Gly Ala Pro Cys Arg Ile Pro Val Ile Val Ala Asp Asp
610                 615                 620
Leu Thr Ala Ala Ile Asn Lys Gly Ile Leu Val Thr Val Asn Pro Ile
625                 630                 635                 640
Ala Ser Thr Asn Asp Asp Glu Val Leu Ile Glu Val Asn Pro Pro Phe
                645                 650                 655
Gly Asp Ser Tyr Ile Ile Val Gly Arg Gly Asp Ser Arg Leu Thr Tyr
            660                 665                 670
Gln Trp His Lys Glu Gly Ser Ser Ile Gly Lys Leu Phe Thr Gln Thr
        675                 680                 685
Met Lys Gly Val Glu Arg Leu Ala Val Met Gly Asp Thr Ala Trp Asp
690                 695                 700
Phe Ser Ser Ala Gly Gly Phe Phe Thr Ser Val Gly Lys Gly Ile His
705                 710                 715                 720
Thr Val Phe Gly Ser Ala Phe Gln Gly Leu Phe Gly Gly Leu Asn Trp
                725                 730                 735
Ile Thr Lys Val Ile Met Gly Ala Val Leu Ile Trp Val Gly Ile Asn
            740                 745                 750
Thr Arg Asn Met Thr Met Ser Met Ser Met Ile Leu Val Gly Val Ile
        755                 760                 765
Met Met Phe Leu Ser Leu Gly Val Gly Ala Asp Gln Gly Cys Ala Ile
770                 775                 780
Asn Phe Gly Val Ser Lys Gly Glu Glu Leu Phe Thr Gly Val Val Pro
785                 790                 795                 800
```

```
Ile Leu Val Glu Leu Asp Gly Asp Val Asn Gly His Lys Phe Ser Val
                805                 810                 815

Ser Gly Glu Gly Glu Gly Asp Ala Thr Tyr Gly Lys Leu Thr Leu Lys
            820                 825                 830

Phe Ile Cys Thr Thr Gly Lys Leu Pro Val Pro Trp Pro Thr Leu Val
            835                 840                 845

Thr Thr Leu Thr Tyr Gly Val Gln Cys Phe Ser Arg Tyr Pro Asp His
        850                 855                 860

Met Lys Gln His Asp Phe Phe Lys Ser Ala Met Pro Glu Gly Tyr Val
865                 870                 875                 880

Gln Glu Arg Thr Ile Phe Phe Lys Asp Asp Gly Asn Tyr Lys Thr Arg
                885                 890                 895

Ala Glu Val Lys Phe Glu Gly Asp Thr Leu Val Asn Arg Ile Glu Leu
            900                 905                 910

Lys Gly Ile Asp Phe Lys Glu Asp Gly Asn Ile Leu Gly His Lys Leu
        915                 920                 925

Glu Tyr Asn Tyr Asn Ser His Asn Val Tyr Ile Met Ala Asp Lys Gln
    930                 935                 940

Lys Asn Gly Ile Lys Val Asn Phe Lys Ile Arg His Asn Ile Glu Asp
945                 950                 955                 960

Gly Ser Val Gln Leu Ala Asp His Tyr Gln Gln Asn Thr Pro Ile Gly
                965                 970                 975

Asp Gly Pro Val Leu Leu Pro Asp Asn His Tyr Leu Ser Thr Gln Ser
            980                 985                 990

Ala Leu Ser Lys Asp Pro Asn Glu Lys Arg Asp His Met Val Leu Leu
        995                 1000                1005

Glu Phe Val Thr Ala Ala Gly Ile Thr Leu Gly Met Asp Glu Leu
    1010                1015                1020

Tyr Lys Lys Met Phe Glu Ser Thr Tyr Arg Gly Ala Lys Arg Met
    1025                1030                1035

Ala Ile Leu Gly Glu Thr Ala Trp Asp Phe Gly Ser Val Gly Gly
    1040                1045                1050

Leu Phe Thr Ser Leu Gly Lys Ala Val His Gln Val Phe Gly Ser
    1055                1060                1065

Val Tyr Thr Thr Met Phe Gly Gly Val Ser Trp Met Ile Arg Ile
    1070                1075                1080

Leu Ile Gly Phe Leu Val Leu Trp Ile Gly Thr Asn Ser Arg Asn
    1085                1090                1095

Thr Ser Met Ala Met Thr Cys Ile Ala Val Gly Gly Ile Thr Leu
    1100                1105                1110

Phe Leu Gly Phe Thr Val Gly Ala Asp Gln Gly Cys Ala Ile Asn
    1115                1120                1125

Phe Gly Lys Arg Glu Leu Lys Cys Gly Asp Gly Ile Phe Ile Phe
    1130                1135                1140

Arg Asp Ser Asp Asp Trp Leu Asn Lys Tyr Ser Tyr Tyr Pro Glu
    1145                1150                1155

Asp Pro Val Lys Leu Ala Ser Ile Val Lys Ala Ser Phe Glu Glu
    1160                1165                1170

Gly Lys Cys Gly Leu Asn Ser Val Asp Ser Leu Glu His Glu Met
    1175                1180                1185

Trp Arg Ser Arg Ala Asp Glu Ile Asn Ala Ile Phe Glu Glu Asn
    1190                1195                1200

Glu Val Asp Ile Ser Val Val Val Gln Asp Pro Lys Asn Val Tyr
```

-continued

```
            1205                1210                1215
Gln Arg Gly Thr His Pro Phe Ser Arg Ile Arg Asp Gly Leu Gln
            1220                1225                1230
Tyr Gly Trp Lys Thr Trp Gly Lys Asn Leu Val Phe Ser Pro Gly
            1235                1240                1245
Arg Lys Asn Gly Ser Phe Ile Ile Asp Gly Lys Ser Arg Lys Glu
            1250                1255                1260
Cys Pro Phe Ser Asn Arg Val Trp Asn Ser Phe Gln Ile Glu Glu
            1265                1270                1275
Phe Gly Thr Gly Val Phe Thr Thr Arg Val Tyr Met Asp Ala Val
            1280                1285                1290
Phe Glu Tyr Thr Ile Asp Cys Asp Gly Ser Ile Leu Gly Ala Ala
            1295                1300                1305
Val Asn Gly Lys Lys Ser Ala His Gly Ser Pro Thr Phe Trp Met
            1310                1315                1320
Gly Ser His Glu Val Asn Gly Thr Trp Met Ile His Thr Leu Glu
            1325                1330                1335
Ala Leu Asp Tyr Lys Glu Cys Glu Trp Pro Leu Thr His Thr Ile
            1340                1345                1350
Gly Thr Ser Val Glu Glu Ser Glu Met Phe Met Pro Arg Ser Ile
            1355                1360                1365
Gly Gly Pro Val Ser Ser His Asn His Ile Pro Gly Tyr Lys Val
            1370                1375                1380
Gln Thr Asn Gly Pro Trp Met Gln Val Pro Leu Glu Val Lys Arg
            1385                1390                1395
Glu Ala Cys Pro Gly Thr Ser Val Ile Ile Asp Gly Asn Cys Asp
            1400                1405                1410
Gly Arg Gly Lys Ser Thr Arg Ser Thr Thr Asp Ser Gly Lys Val
            1415                1420                1425
Ile Pro Glu Trp Cys Cys Arg Ser Cys Thr Met Pro Pro Val Ser
            1430                1435                1440
Phe His Gly Ser Asp Gly Cys Trp Tyr Pro Met Glu Ile Arg Pro
            1445                1450                1455
Arg Lys Thr His Glu Ser His Leu Val Arg Ser Trp Val Thr Ala
            1460                1465                1470
Gly Glu Ile His Ala Val Pro Phe Gly Leu Val Ser Met Met Ile
            1475                1480                1485
Ala Met Glu Val Val Leu Arg Lys Arg Gln Gly Pro Lys Gln Met
            1490                1495                1500
Leu Val Gly Gly Val Val Leu Leu Gly Ala Met Leu Val Gly Gln
            1505                1510                1515
Val Thr Leu Leu Asp Leu Leu Lys Leu Thr Val Ala Val Gly Leu
            1520                1525                1530
His Phe His Glu Met Asn Asn Gly Gly Asp Ala Met Tyr Met Ala
            1535                1540                1545
Leu Ile Ala Ala Phe Ser Ile Arg Pro Gly Leu Leu Ile Gly Phe
            1550                1555                1560
Gly Leu Arg Thr Leu Trp Ser Pro Arg Glu Arg Leu Val Leu Thr
            1565                1570                1575
Leu Gly Ala Ala Met Val Glu Ile Ala Leu Gly Gly Val Met Gly
            1580                1585                1590
Gly Leu Trp Lys Tyr Leu Asn Ala Val Ser Leu Cys Ile Leu Thr
            1595                1600                1605
```

-continued

Ile Asn Ala Val Ala Ser Arg Lys Ala Ser Asn Thr Ile Leu Pro
1610                1615                1620

Leu Met Ala Leu Leu Thr Pro Val Thr Met Ala Glu Val Arg Leu
1625                1630                1635

Ala Ala Met Phe Phe Cys Ala Met Val Ile Ile Gly Val Leu His
1640                1645                1650

Gln Asn Phe Lys Asp Thr Ser Met Gln Lys Thr Ile Pro Leu Val
1655                1660                1665

Ala Leu Thr Leu Thr Ser Tyr Leu Gly Leu Thr Gln Pro Phe Leu
1670                1675                1680

Gly Leu Cys Ala Phe Leu Ala Thr Arg Ile Phe Gly Arg Arg Ser
1685                1690                1695

Ile Pro Val Asn Glu Ala Leu Ala Ala Ala Gly Leu Val Gly Val
1700                1705                1710

Leu Ala Gly Leu Ala Phe Gln Glu Met Glu Asn Phe Leu Gly Pro
1715                1720                1725

Ile Ala Val Gly Gly Leu Leu Met Met Leu Val Ser Val Ala Gly
1730                1735                1740

Arg Val Asp Gly Leu Glu Leu Lys Lys Leu Gly Glu Val Ser Trp
1745                1750                1755

Glu Glu Glu Ala Glu Ile Ser Gly Ser Ser Ala Arg Tyr Asp Val
1760                1765                1770

Ala Leu Ser Glu Gln Gly Glu Phe Lys Leu Leu Ser Glu Glu Lys
1775                1780                1785

Val Pro Trp Asp Gln Val Val Met Thr Ser Leu Ala Leu Val Gly
1790                1795                1800

Ala Ala Leu His Pro Phe Ala Leu Leu Leu Val Leu Ala Gly Trp
1805                1810                1815

Leu Phe His Val Arg Gly Ala Arg Arg Ser Gly Asp Val Leu Trp
1820                1825                1830

Asp Ile Pro Thr Pro Lys Ile Ile Glu Glu Cys Glu His Leu Glu
1835                1840                1845

Asp Gly Ile Tyr Gly Ile Phe Gln Ser Thr Phe Leu Gly Ala Ser
1850                1855                1860

Gln Arg Gly Val Gly Val Ala Gln Gly Gly Val Phe His Thr Met
1865                1870                1875

Trp His Val Thr Arg Gly Ala Phe Leu Val Arg Asn Gly Lys Lys
1880                1885                1890

Leu Ile Pro Ser Trp Ala Ser Val Lys Glu Asp Leu Val Ala Tyr
1895                1900                1905

Gly Gly Ser Trp Lys Leu Glu Gly Arg Trp Asp Gly Glu Glu Glu
1910                1915                1920

Val Gln Leu Ile Ala Ala Val Pro Gly Lys Asn Val Val Asn Val
1925                1930                1935

Gln Thr Lys Pro Ser Leu Phe Lys Val Arg Asn Gly Gly Glu Ile
1940                1945                1950

Gly Ala Val Ala Leu Asp Tyr Pro Ser Gly Thr Ser Gly Ser Pro
1955                1960                1965

Ile Val Asn Arg Asn Gly Glu Val Ile Gly Leu Tyr Gly Asn Gly
1970                1975                1980

Ile Leu Val Gly Asp Asn Ser Phe Val Ser Ala Ile Ser Gln Thr
1985                1990                1995

| | | | | | | | | | | | |
|---|---|---|---|---|---|---|---|---|---|---|---|
| Glu | Val | Lys | Glu | Glu | Gly | Lys | Glu | Glu | Leu | Gln | Glu | Ile | Pro | Thr |
| | 2000 | | | | 2005 | | | | 2010 | | |

Met Leu Lys Lys Gly Met Thr  Thr Val Leu Asp Phe  His Pro Gly
    2015                 2020                 2025

Ala Gly Lys Thr Arg Arg Phe  Leu Pro Gln Ile Leu  Ala Glu Cys
    2030                 2035                 2040

Ala Arg Arg Arg Leu Arg Thr  Leu Val Leu Ala Pro  Thr Arg Val
    2045                 2050                 2055

Val Leu Ser Glu Met Lys Glu  Ala Phe His Gly Leu  Asp Val Lys
    2060                 2065                 2070

Phe His Thr Gln Ala Phe Ser  Ala His Gly Ser Gly  Arg Glu Val
    2075                 2080                 2085

Ile Asp Ala Met Cys His Ala  Thr Leu Thr Tyr Arg  Met Leu Glu
    2090                 2095                 2100

Pro Thr Arg Val Val Asn Trp  Glu Val Ile Ile Met  Asp Glu Ala
    2105                 2110                 2115

His Phe Leu Asp Pro Ala Ser  Ile Ala Ala Arg Gly  Trp Ala Ala
    2120                 2125                 2130

His Arg Ala Arg Ala Asn Glu  Ser Ala Thr Ile Leu  Met Thr Ala
    2135                 2140                 2145

Thr Pro Pro Gly Thr Ser Asp  Glu Phe Pro His Ser  Asn Gly Glu
    2150                 2155                 2160

Ile Glu Asp Val Gln Thr Asp  Ile Pro Ser Glu Pro  Trp Asn Thr
    2165                 2170                 2175

Gly His Asp Trp Ile Leu Ala  Asp Lys Arg Pro Thr  Ala Trp Phe
    2180                 2185                 2190

Leu Pro Ser Ile Arg Ala Ala  Asn Val Met Ala Ala  Ser Leu Arg
    2195                 2200                 2205

Lys Ala Gly Lys Ser Val Val  Val Leu Asn Arg Lys  Thr Phe Glu
    2210                 2215                 2220

Arg Glu Tyr Pro Thr Ile Lys  Gln Lys Lys Pro Asp  Phe Ile Leu
    2225                 2230                 2235

Ala Thr Asp Ile Ala Glu Met  Gly Ala Asn Leu Cys  Val Glu Arg
    2240                 2245                 2250

Val Leu Asp Cys Arg Thr Ala  Phe Lys Pro Val Leu  Val Asp Glu
    2255                 2260                 2265

Gly Arg Lys Val Ala Ile Lys  Gly Pro Leu Arg Ile  Ser Ala Ser
    2270                 2275                 2280

Ser Ala Ala Gln Arg Arg Gly  Arg Ile Gly Arg Asn  Pro Asn Arg
    2285                 2290                 2295

Asp Gly Asp Ser Tyr Tyr Tyr  Ser Glu Pro Thr Ser  Glu Asn Asn
    2300                 2305                 2310

Ala His His Val Cys Trp Leu  Glu Ala Ser Met Leu  Leu Asp Asn
    2315                 2320                 2325

Met Glu Val Arg Gly Gly Met  Val Ala Pro Leu Tyr  Gly Val Glu
    2330                 2335                 2340

Gly Thr Lys Thr Pro Val Ser  Pro Gly Glu Met Arg  Leu Arg Asp
    2345                 2350                 2355

Asp Gln Arg Lys Val Phe Arg  Glu Leu Val Arg Asn  Cys Asp Leu
    2360                 2365                 2370

Pro Val Trp Leu Ser Trp Gln  Val Ala Lys Ala Gly  Leu Lys Thr
    2375                 2380                 2385

Asn Asp Arg Lys Trp Cys Phe  Glu Gly Pro Glu Glu  His Glu Ile

```
                2390                2395                2400
Leu Asn Asp Ser Gly Glu Thr Val Lys Cys Arg Ala Pro Gly Gly
    2405                2410                2415

Ala Lys Lys Pro Leu Arg Pro Arg Trp Cys Asp Glu Arg Val Ser
    2420                2425                2430

Ser Asp Gln Ser Ala Leu Ser Glu Phe Ile Lys Phe Ala Glu Gly
    2435                2440                2445

Arg Arg Gly Ala Ala Glu Val Leu Val Val Leu Ser Glu Leu Pro
    2450                2455                2460

Asp Phe Leu Ala Lys Lys Gly Gly Glu Ala Met Asp Thr Ile Ser
    2465                2470                2475

Val Phe Leu His Ser Glu Glu Gly Ser Arg Ala Tyr Arg Asn Ala
    2480                2485                2490

Leu Ser Met Met Pro Glu Ala Met Thr Ile Val Met Leu Phe Ile
    2495                2500                2505

Leu Ala Gly Leu Leu Thr Ser Gly Met Val Ile Phe Phe Met Ser
    2510                2515                2520

Pro Lys Gly Ile Ser Arg Met Ser Met Ala Met Gly Thr Met Ala
    2525                2530                2535

Gly Cys Gly Tyr Leu Met Phe Leu Gly Gly Val Lys Pro Thr His
    2540                2545                2550

Ile Ser Tyr Val Met Leu Ile Phe Phe Val Leu Met Val Val Val
    2555                2560                2565

Ile Pro Glu Pro Gly Gln Gln Arg Ser Ile Gln Asp Asn Gln Val
    2570                2575                2580

Ala Tyr Leu Ile Ile Gly Ile Leu Thr Leu Val Ser Ala Val Ala
    2585                2590                2595

Ala Asn Glu Leu Gly Met Leu Glu Lys Thr Lys Glu Asp Leu Phe
    2600                2605                2610

Gly Lys Lys Asn Leu Ile Pro Ser Ser Ala Ser Pro Trp Ser Trp
    2615                2620                2625

Pro Asp Leu Asp Leu Lys Pro Gly Ala Ala Trp Thr Val Tyr Val
    2630                2635                2640

Gly Ile Val Thr Met Leu Ser Pro Met Leu His His Trp Ile Lys
    2645                2650                2655

Val Glu Tyr Gly Asn Leu Ser Leu Ser Gly Ile Ala Gln Ser Ala
    2660                2665                2670

Ser Val Leu Ser Phe Met Asp Lys Gly Ile Pro Phe Met Lys Met
    2675                2680                2685

Asn Ile Ser Val Ile Met Leu Leu Val Ser Gly Trp Asn Ser Ile
    2690                2695                2700

Thr Val Met Pro Leu Leu Cys Gly Ile Gly Cys Ala Met Leu His
    2705                2710                2715

Trp Ser Leu Ile Leu Pro Gly Ile Lys Ala Gln Gln Ser Lys Leu
    2720                2725                2730

Ala Gln Arg Arg Val Phe His Gly Val Ala Lys Asn Pro Val Val
    2735                2740                2745

Asp Gly Asn Pro Thr Val Asp Ile Glu Glu Ala Pro Glu Met Pro
    2750                2755                2760

Ala Leu Tyr Glu Lys Lys Leu Ala Leu Tyr Leu Leu Leu Ala Leu
    2765                2770                2775

Ser Leu Ala Ser Val Ala Met Cys Arg Thr Pro Phe Ser Leu Ala
    2780                2785                2790
```

-continued

```
Glu Gly Ile Val Leu Ala Ser Ala Ala Leu Gly Pro Leu Ile Glu
    2795                2800                2805

Gly Asn Thr Ser Leu Leu Trp Asn Gly Pro Met Ala Val Ser Met
    2810                2815                2820

Thr Gly Val Met Arg Gly Asn His Tyr Ala Phe Val Gly Val Met
    2825                2830                2835

Tyr Asn Leu Trp Lys Met Lys Thr Gly Arg Arg Gly Ser Ala Asn
    2840                2845                2850

Gly Lys Thr Leu Gly Glu Val Trp Lys Arg Glu Leu Asn Leu Leu
    2855                2860                2865

Asp Lys Arg Gln Phe Glu Leu Tyr Lys Arg Thr Asp Ile Val Glu
    2870                2875                2880

Val Asp Arg Asp Thr Ala Arg Arg His Leu Ala Glu Gly Lys Val
    2885                2890                2895

Asp Thr Gly Val Ala Val Ser Arg Gly Thr Ala Lys Leu Arg Trp
    2900                2905                2910

Phe His Glu Arg Gly Tyr Val Lys Leu Glu Gly Arg Val Ile Asp
    2915                2920                2925

Leu Gly Cys Gly Arg Gly Gly Trp Cys Tyr Tyr Ala Ala Ala Gln
    2930                2935                2940

Lys Glu Val Ser Gly Val Lys Gly Phe Thr Leu Gly Arg Asp Gly
    2945                2950                2955

His Glu Lys Pro Met Asn Val Gln Ser Leu Gly Trp Asn Ile Ile
    2960                2965                2970

Thr Phe Lys Asp Lys Thr Asp Ile His Arg Leu Glu Pro Val Lys
    2975                2980                2985

Cys Asp Thr Leu Leu Cys Asp Ile Gly Glu Ser Ser Ser Ser Ser
    2990                2995                3000

Val Thr Glu Gly Glu Arg Thr Val Arg Val Leu Asp Thr Val Glu
    3005                3010                3015

Lys Trp Leu Ala Cys Gly Val Asp Asn Phe Cys Val Lys Val Leu
    3020                3025                3030

Ala Pro Tyr Met Pro Asp Val Leu Glu Lys Leu Glu Leu Leu Gln
    3035                3040                3045

Arg Arg Phe Gly Gly Thr Val Ile Arg Asn Pro Leu Ser Arg Asn
    3050                3055                3060

Ser Thr His Glu Met Tyr Tyr Val Ser Gly Ala Arg Ser Asn Val
    3065                3070                3075

Thr Phe Thr Val Asn Gln Thr Ser Arg Leu Leu Met Arg Arg Met
    3080                3085                3090

Arg Arg Pro Thr Gly Lys Val Thr Leu Glu Ala Asp Val Ile Leu
    3095                3100                3105

Pro Ile Gly Thr Arg Ser Val Glu Thr Asp Lys Gly Pro Leu Asp
    3110                3115                3120

Lys Glu Ala Ile Glu Glu Arg Val Glu Arg Ile Lys Ser Glu Tyr
    3125                3130                3135

Met Thr Ser Trp Phe Tyr Asp Asn Asp Asn Pro Tyr Arg Thr Trp
    3140                3145                3150

His Tyr Cys Gly Ser Tyr Val Thr Lys Thr Ser Gly Ser Ala Ala
    3155                3160                3165

Ser Met Val Asn Gly Val Ile Lys Ile Leu Thr Tyr Pro Trp Asp
    3170                3175                3180
```

-continued

```
Arg Ile Glu Glu Val Thr Arg Met Ala Met Thr Asp Thr Thr Pro
    3185                3190                3195

Phe Gly Gln Gln Arg Val Phe Lys Glu Lys Val Asp Thr Arg Ala
    3200                3205                3210

Lys Asp Pro Pro Ala Gly Thr Arg Lys Ile Met Lys Val Val Asn
    3215                3220                3225

Arg Trp Leu Phe Arg His Leu Ala Arg Glu Lys Ser Pro Arg Leu
    3230                3235                3240

Cys Thr Lys Glu Glu Phe Ile Ala Lys Val Arg Ser His Ala Ala
    3245                3250                3255

Ile Gly Ala Tyr Leu Glu Glu Gln Glu Gln Trp Lys Thr Ala Asn
    3260                3265                3270

Glu Ala Val Gln Asp Pro Lys Phe Trp Glu Leu Val Asp Glu Glu
    3275                3280                3285

Arg Lys Leu His Gln Gln Gly Arg Cys Arg Thr Cys Val Tyr Asn
    3290                3295                3300

Met Met Gly Lys Arg Glu Lys Lys Leu Ser Glu Phe Gly Lys Ala
    3305                3310                3315

Lys Gly Ser Arg Ala Ile Trp Tyr Met Trp Leu Gly Ala Arg Tyr
    3320                3325                3330

Leu Glu Phe Glu Ala Leu Gly Phe Leu Asn Glu Asp His Trp Ala
    3335                3340                3345

Ser Arg Glu Asn Ser Gly Gly Gly Val Glu Gly Ile Gly Leu Gln
    3350                3355                3360

Tyr Leu Gly Tyr Val Ile Arg Asp Leu Ala Ala Met Asp Gly Gly
    3365                3370                3375

Gly Phe Tyr Ala Asp Asp Thr Ala Gly Trp Asp Thr Arg Ile Thr
    3380                3385                3390

Glu Ala Asp Leu Asp Asp Glu Gln Glu Ile Leu Asn Tyr Met Ser
    3395                3400                3405

Pro His His Lys Lys Leu Ala Gln Ala Val Met Glu Met Thr Tyr
    3410                3415                3420

Lys Asn Lys Val Val Lys Val Leu Arg Pro Ala Pro Gly Gly Lys
    3425                3430                3435

Ala Tyr Met Asp Val Ile Ser Arg Arg Asp Gln Arg Gly Ser Gly
    3440                3445                3450

Gln Val Val Thr Tyr Ala Leu Asn Thr Ile Thr Asn Leu Lys Val
    3455                3460                3465

Gln Leu Ile Arg Met Ala Glu Ala Glu Met Val Ile His His Gln
    3470                3475                3480

His Val Gln Asp Cys Asp Glu Ser Val Leu Thr Arg Leu Glu Ala
    3485                3490                3495

Trp Leu Thr Glu His Gly Cys Asn Arg Leu Lys Arg Met Ala Val
    3500                3505                3510

Ser Gly Asp Asp Cys Val Val Arg Pro Ile Asp Asp Arg Phe Gly
    3515                3520                3525

Leu Ala Leu Ser His Leu Asn Ala Met Ser Lys Val Arg Lys Asp
    3530                3535                3540

Ile Ser Glu Trp Gln Pro Ser Lys Gly Trp Asn Asp Trp Glu Asn
    3545                3550                3555

Val Pro Phe Cys Ser His His Phe His Glu Leu Gln Leu Lys Asp
    3560                3565                3570

Gly Arg Arg Ile Val Val Pro Cys Arg Glu Gln Asp Glu Leu Ile
```

```
                  3575                3580                3585
Gly Arg Gly Arg Val Ser Pro Gly Asn Gly Trp Met Ile Lys Glu
        3590                3595                3600
Thr Ala Cys Leu Ser Lys Ala Tyr Ala Asn Met Trp Ser Leu Met
        3605                3610                3615
Tyr Phe His Lys Arg Asp Met Arg Leu Leu Ser Leu Ala Val Ser
        3620                3625                3630
Ser Ala Val Pro Thr Ser Trp Val Pro Gln Gly Arg Thr Thr Trp
        3635                3640                3645
Ser Ile His Gly Lys Gly Glu Trp Met Thr Thr Glu Asp Met Leu
        3650                3655                3660
Glu Val Trp Asn Arg Val Trp Ile Thr Asn Asn Pro His Met Gln
        3665                3670                3675
Asp Lys Thr Met Val Lys Lys Trp Arg Asp Val Pro Tyr Leu Thr
        3680                3685                3690
Lys Arg Gln Asp Lys Leu Cys Gly Ser Leu Ile Gly Met Thr Asn
        3695                3700                3705
Arg Ala Thr Trp Ala Ser His Ile His Leu Val Ile His Arg Ile
        3710                3715                3720
Arg Thr Leu Ile Gly Gln Glu Lys Tyr Thr Asp Tyr Leu Thr Val
        3725                3730                3735
Met Asp Arg Tyr Ser Val Asp Ala Asp Leu Gln Leu Gly Glu Leu
        3740                3745                3750
Ile

<210> SEQ ID NO 5
<211> LENGTH: 11941
<212> TYPE: DNA
<213> ORGANISM: Yellow fever virus

<400> SEQUENCE: 5
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta ctttttctt tttgttcaac attttgactg aaaaaagat      300 cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgaccggtgg     480
agtgaccttg gtgcggaaaa acagatggtt gctcctaaat gtgacatctg aggacctcgg     540 gaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaaggc cattgacttg cctacgcatg aaaaccatgg     780
tttgaagacc cggcaagaaa aatggatgac tggaagaatg ggtgaaaggc aactccaaaa     840
gattgagaga tggttcgtga ggaacccctt ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg aggggtgca    1020
```

```
tggaggaact tgggtttcag ctaccctgga gcaagacaag tgtgtcactg ttatggcccc    1080
tgacaagcct tcattggaca tctcactaga gacagtagcc attgatagac ctgctgaggc    1140
gaggaaagtg tgttacaatg cagttctcac tcatgtgaag attaatgaca agtgcccag    1200 cactggagag gcccacctag ctgaagagaa cgaaggggac aatgcgtgca agcgcactta    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccagcat    1440
taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta ccccatcgc    2040 ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggaggggtt cttcacttcg gttgggaaag gaattcatac    2280 ggtgttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aacttcggcc gaaagggatc acaaacctcc aacacaacta atgggctcc    2520 tcccggacaa ggaagtccag gtagcaaggg cgaggagctg ttcaccgggg tggtgcccat    2580
cctggtcgag ctggacggcg acgtaaacgg ccacaagttc agcgtgtccg gcgagggcga    2640
gggcgatgcc acctacggca agctgaccct gaagttcatc tgcaccaccg gcaagctgcc    2700
cgtgccctgg cccaccctcg tgaccaccct gacctacggc gtgcagtgct tcagccgcta    2760
ccccgaccac atgaagcagc acgacttctt caagtccgcc atgcccgaag gctacgtcca    2820
ggagcgcacc atcttcttca aggacgacgg caactacaag acccgcgccg aggtgaagtt    2880
cgagggcgac accctggtga accgcatcga gctgaagggc atcgacttca aggaggacgg    2940
caacatcctg gggcacaagc tggagtacaa ctacaacagc cacaacgtct atatcatggc    3000
cgacaagcag aagaacggca tcaaggtgaa cttcaagatc cgccacaaca tcgaggacgg    3060
cagcgtgcag ctcgccgacc actaccagca gaacacccc atcggcgacg gccccgtgct    3120
gctgcccgac aaccactacc tgagcaccca gtccgccctg agcaaagacc ccaacgagaa    3180
gcgcgatcac atggtcctgc tggagttcgt gaccgccgcc gggatcactc tcggcatgga    3240
cgagctgtac aagggtagca gtccactgtc tcatcgcagt aaaaggagcc tatcctgtcg    3300
gccacccatg gtcaaagagg gaagctcaat aggaacatca ttgggaaagg ctgtgcacca    3360 ggttttgga agtgtgtata caaccatgtt tggaggagtc tcatggatga ttagaatcct    3420
```

```
aattgggttc ttagtgttgt ggattggcac gaactcaagg aacacttcaa tggctatgac    3480
gtgcatagct gttggaggaa tcactctgtt tctgggcttc acagttggcg ccgatcaagg    3540
atgcgccatc aactttggca agagagagct caagtgcgga gatggtatct tcatatttag    3600
agactctgat gactggctga acaagtactc atactatcca gaagatcctg tgaagcttgc    3660
atcaatagtg aaagcctctt ttgaagaagg gaagtgtggc ctaaattcag ttgactccct    3720
tgagcatgag atgtgtgagaa gcagggcaga tgagatcaat gccattttg aggaaaacga    3780 ggtggacatt tctgttgtcg tgcaggatcc aaagaatgtt taccagagag gaactcatcc    3840
attttccaga attcgggatg gtctgcagta tggttggaag acttggggta agaaccttgt    3900
gttctcccca gggaggaaga atggaagctt catcatagat ggaaagtcca ggaaagaatg    3960
cccgttttca aaccgggtct ggaattcttt ccagatagag gagtttggga cgggagtgtt    4020
caccacacgc gtgtacatgg acgcagtctt tgaatacacc atagactgcg atggatctat    4080
cttgggtgca gcggtgaacg gaaaaaagag tgcccatggc tctccaacat tttggatggg    4140
aagtcatgaa gtaaatggga catggatgat ccacaccttg gaggcattag attacaagga    4200
gtgtgagtgg ccactgacac atacgattgg aacatcagtt gaagagagtg aaatgttcat    4260
gccgagatca atcggaggcc cagttagctc tcacaatcat atccctggat acaaggttca    4320
gacgaacgga ccttggatgc aggtaccact agaagtgaag agagaagctt gcccagggac    4380
tagcgtgatc attgatggca actgtgatgg acggggaaaa tcaaccagat ccaccacgga    4440
tagcgggaaa gttattcctg aatggtgttg ccgctcctgc acaatgccgc ctgtgagctt    4500
ccatggtagt gatgggtgtt ggtatcccat ggaaattagg ccaaggaaaa cgcatgaaag    4560
ccatctggtg cgctcctggg ttacagctgg agaaatacat gctgtccctt ttggtttggt    4620
gagcatgatg atagcaatgg aagtggtcct aaggaaaaga cagggaccaa agcaaatgtt    4680
ggttggagga gtagtgctct gggagcaat gctggtcggg caagtaactc tccttgattt    4740
gctgaaactc acagtggctg tgggattgca tttccatgag atgaacaatg gaggagacgc    4800
catgtatatg gcgttgattg ctgccttttc aatcagacca gggctgctca tcggctttgg    4860
gctcaggacc ctatggagcc ctcgggaacg ccttgtgctg accctaggag cagccatggt    4920
ggagattgcc ttgggtggcg tgatgggcgg cctgtggaag tatctaaatg cagtttctct    4980
ctgcatcctg acaataaatg ctgttgcttc taggaaagca tcaaatacca tcttgccct    5040 catggctctg ttgacacctg tcactatggc tgaggtgaga cttgccgcaa tgttctttg    5100 tgccatggtt atcataggg tccttcacca gaatttcaag gacacctcca tgcagaagac    5160 tataccctctg gtggccctca cactcacatc ttacctgggc ttgacacaac cttttttggg    5220
cctgtgtgca tttctggcaa cccgcatatt tgggcgaagg agtatcccag tgaatgaggc    5280
actcgcagca gctggtctag tgggagtgct ggcaggactg gcttttcagg agatggagaa    5340
cttccttggt ccgattgcag ttggaggact cctgatgatg ctggttagcg tggctggag    5400 ggtggatggg ctagagctca agaagcttgg tgaagtttca tgggaagagg aggcggagat    5460
cagcgggagt tccgcccgct atgatgtggc actcagtgaa caaggggagt tcaagctgct    5520
ttctgaagag aaagtgccat gggaccaggt tgtgatgacc cgctggcct tggttgggc    5580 tgccctccat ccatttgctc ttctgctggt ccttgctggg tggctgtttc atgtcaggg    5640 agctaggaga agtggggatg tcttgtggga tattcccact cctaagatca tcgaggaatg    5700
tgaacatctg gaggatggga tttatggcat attccagtca accttcttgg gggcctccca    5760
```

```
gcgaggagtg ggagtggcac agggagggt gttccacaca atgtggcatg tcacaagagg    5820
agctttcctt gtcaggaatg gcaagaagtt gattccatct tgggcttcag taaaggaaga    5880
ccttgtcgcc tatggtggct catggaagtt ggaaggcaga tgggatggag aggaagaggt    5940
ccagttgatc gcggctgttc caggaaagaa cgtggtcaac gtccagacaa aaccgagctt    6000
gttcaaagtg aggaatgggg gagaaatcgg ggctgtcgct cttgactatc cgagtggcac    6060
ttcaggatct cctattgtta acaggaacgg agaggtgatt gggctgtacg gcaatggcat    6120
ccttgtcggt gacaactcct tcgtgtccgc catatcccag actgaggtga aggaagaagg    6180
aaaggaggag ctccaagaga tcccgacaat gctaaagaaa ggaatgacaa ctgtccttga    6240
ttttcatcct ggagctggga agacaagacg tttcctccca cagatcttgg ccgagtgcgc    6300
acggagacgc ttgcgcactc ttgtgttggc ccccaccagg gttgttcttt ctgaaatgaa    6360
ggaggctttt cacggcctgg acgtgaaatt ccacacacag gcttttccg ctcacggcag    6420 cgggagagaa gtcattgatg ccatgtgcca tgccacccta acttacagga tgttggaacc    6480
aactagggtt gttaactggg aagtgatcat tatggatgaa gcccatttt tggatccagc    6540 tagcatagcc gctagaggtt gggcagcgca cagagctagg gcaaatgaaa gtgcaacaat    6600
cttgatgaca gccacaccgc ctgggactag tgatgaattt ccacattcaa atggtgaaat    6660
agaagatgtt caaacggaca tacccagtga gccctggaac acagggcatg actggatcct    6720
ggctgacaaa aggcccacgg catggttcct tccatccatc agagctgcaa atgtcatggc    6780
tgcctctttg cgtaaggctg aaagagtgt ggtggtcctg aacaggaaaa cctttgagag    6840 agaataccccc acgataaagc agaagaaacc tgactttata ttggccactg acatagctga    6900
aatgggagcc aaccttttgcg tggagcgagt gctggattgc aggacggctt ttaagcctgt    6960
gcttgtggat gaagggagga aggtggcaat aaaagggcca cttcgtatct ccgcatcctc    7020
tgctgctcaa aggaggggc gcattgggag aaatcccaac agagatggag actcatacta    7080
ctattctgag cctacaagtg aaaataatgc ccaccacgtc tgctggttgg aggcctcaat    7140
gctcttggac aacatggagg tgaggggtgg aatggtcgcc ccactctatg gcgttgaagg    7200
aactaaaaca ccagttttccc ctggtgaaat gagactgagg gatgaccaga ggaaagtctt    7260
cagagaacta gtgaggaatt gtgacctgcc cgtttggctt tcgtggcaag tggccaaggc    7320
tggtttgaag acgaatgatc gtaagtggtg ttttgaaggc cctgaggaac atgagatctt    7380
gaatgacagc ggtgaaacag tgaagtgcag ggctcctgga ggagcaaaga agcctctgcg    7440
cccaaggtgg tgtgatgaaa gggtgtcatc tgaccagagt gcgctgtctg aatttattaa    7500
gtttgctgaa ggtaggaggg gagctgctga agtgctagtt gtgctgagtg aactccctga    7560
tttcctggct aaaaaaggtg gagaggcaat ggataccatc agtgtgttcc tccactctga    7620
ggaaggctct agggcttacc gcaatgcact atcaatgatg cctgaggcaa tgacaatagt    7680
catgctgttt atactggctg gactactgac atcgggaatg gtcatctttt tcatgtctcc    7740
caaaggcatc agtagaatgt ctatggcgat gggcacaatg gccggctgtg atatctcat    7800 gttccttgga ggcgtcaaac ccactcacat ctcctatgtc atgctcatat tctttgtcct    7860 gatggtggt gtgatccccg agccagggca acaaaggtcc atccaagaca accaagtggc    7920
atacctcatt attggcatcc tgacgctggt ttcagcggtg gcagccaacg agctaggcat    7980
gctggagaaa accaaagagg acctctttgg gaagaagaac ttaattccat ctagtgcttc    8040 accctgagt tggccggatc ttgacctgaa gccaggagct gcctgacag tgtacgttgg    8100 cattgttaca atgctctctc caatgttgca ccactggatc aaagtcgaat atggcaacct    8160
```

```
gtctctgtct ggaatagccc agtcagcctc agtcctttct ttcatggaca aggggatacc   8220
attcatgaag atgaatatct cggtcataat gctgctggtc agtggctgga attcaataac   8280
agtgatgcct ctgctctgtg cataggggtg cgccatgctc cactggtctc tcattttacc   8340
tggaatcaaa gcgcagcagt caaagcttgc acagagaagg gtgttccatg gcgttgccaa   8400
gaaccctgtg gttgatggga atccaacagt tgacattgag gaagctcctg aaatgcctgc   8460
cctttatgag aagaaactgg ctctatatct ccttcttgct ctcagcctag cttctgttgc   8520
catgtgcaga acgccctttt cattggctga aggcattgtc ctagcatcag ctgccttagg   8580
gccgctcata gagggaaaca ccagccttct ttggaatgga cccatggctg tctccatgac   8640
aggagtcatg aggggaatc actatgcttt tgtgggagtc atgtacaatc tatggaagat   8700
gaaaactgga cgccggggga gcgcgaatgg aaaaactttg ggtgaagtct ggaagaggga   8760
actgaatctg ttggacaagc gacagtttga gttgtataaa aggaccgaca ttgtggaggt   8820
ggatcgtgat acggcacgca ggcatttggc cgaaggggaag gtggacaccg gggtggcggt   8880
ctccaggggg accgcaaagt taaggtggtt ccatgagcgt ggctatgtca agctggaagg   8940
tagggtgatt gacctggggt gtggccgcgg aggctggtgt tactacgctg ctgcgcaaaa   9000
ggaagtgagt ggggtcaaag gatttactct tggaagagac ggccatgaga acccatgaa   9060 tgtgcaaagt ctgggatgga acatcatcac cttcaaggac aaaactgata tccaccgcct   9120
agaaccagtg aaatgtgaca ccctttttgtg tgacattgga gagtcatcat cgtcatcggt   9180
cacagagggg gaaaggaccg tgagagttct tgatactgta gaaaaatggc tggcttgtgg   9240
ggttgacaac ttctgtgtga aggtgttagc tccatacatg ccagatgttc ttgagaaact   9300
ggaattgctc caaggaggt ttggcggaac agtgatcagg aaccctctct ccaggaattc   9360
cactcatgaa atgtactacg tgtctggagc ccgcagcaat gtcacattta ctgtgaacca   9420
aacatcccgc ctcctgatga ggagaatgag gcgtccaact ggaaaagtga ccctggaggc   9480
tgacgtcatc ctcccaattg ggacacgcag tgttgagaca gacaagggac ccctggacaa   9540
agaggccata aagaaaggg ttgagaggat aaaatctgag tacatgacct cttggttta   9600 tgacaatgac aaccctaca ggacctggca ctactgtggc tcctatgtca aaaaacctc   9660 aggaagtgcg gcgagcatgg taaatggtgt tattaaaatt ctgacatatc catgggacag   9720
gatagaggag gtcaccagaa tggcaatgac tgacacaacc ccttttggac agcaaagagt   9780
gtttaaagaa aaagttgaca ccagagcaaa ggatccacca gcgggaacta ggaagatcat   9840
gaaagttgtc aacaggtggc tgttccgcca cctggccaga aaaagagcc ccagactgtg   9900 cacaaaggaa gaatttattg caaaagtccg aagtcatgca gccattggag cttacctgga   9960
agaacaagaa cagtggaaga ctgccaatga ggctgtccaa gacccaaagt ctgggaact   10020 ggtggatgaa gaaaggaagc tgcaccaaca aggcaggtgt cggacttgtg tgtacaacat   10080 gatgggaaa agagagaaga gctgtcaga gtttgggaaa gcaaagggaa gccgtgccat   10140
atggtatatg tggctgggag cgcggtatct tgagtttgag gccctgggat tcctgaatga   10200
ggaccattgg gcttccaggg aaaactcagg aggaggagtg gaaggcattg gcttacaata   10260
cctaggatat gtgatcagag acctggctgc aatggatggt ggtggattct acgcggatga   10320
caccgctgga tgggacacgc gcatcacaga ggcagacctt gatgatgaac aggagatctt   10380
gaactacatg agcccacatc acaaaaaact ggcacaagca gtgatggaaa tgacatacaa   10440
gaacaaagtg gtgaaagtgt tgagaccagc cccaggaggg aaagcctaca tggatgtcat   10500
```

```
aagtcgacga gaccagagag gatccgggca ggtagtgact tatgctctga acaccatcac   10560
caacttgaaa gtccaattga tcagaatggc agaagcagag atggtgatac atcaccaaca   10620
tgttcaagat tgtgatgaat cagttctgac caggctggag gcatggctca ctgagcacgg   10680
atgtaacaga ctgaagagga tggcggtgag tggagacgac tgtgtggtcc ggcccatcga   10740
tgacaggttc ggcctggccc tgtcccatct caacgccatg tccaaggtta gaagggacat   10800
atctgaatgg cagccatcaa aagggtggaa tgattgggag aatgtgccct tctgttccca   10860
ccacttccat gaactacagc tgaaggatgg caggaggatt gtggtgcctt gccgagaaca   10920
ggacgagctc attgggagag aagggtgtc tccaggaaac ggctggatga tcaaggaaac   10980
agcttgcctc agcaaagcct atgccaacat gtggtcactg atgtattttc acaaagggga   11040
catgaggcta ctgtcattgg ctgtttcctc agctgttccc acctcatggg ttccacaagg   11100
acgcacaaca tggtcgattc atgggaaagg ggagtggatg accacggaag acatgcttga   11160
ggtgtggaac agagtatgga taaccaacaa cccacacatg caggacaaga caatggtgaa   11220
aaaatggaga gatgtcccct atctaaccaa gagacaagac aagctgtgcg gatcactgat   11280
tggaatgacc aatagggcca cctgggcctc ccacatccat ttagtcatcc atcgtatccg   11340
aacgctgatt ggacaggaga aatacactga ctacctaaca gtcatggaca ggtattctgt   11400
ggatgctgac ctgcaactgg gtgagcttat ctgaaacacc atctaacagg aataaccggg   11460
atacaaacca cgggtggaga accggactcc ccacaacctg aaaccgggat ataaaccacg   11520
gctggagaac cgggctccgc acttaaaatg aaacagaaac cgggataaaa actacggatg   11580
gagaaccgga ctccacacat tgagacagaa gaagttgtca gcccagaacc ccacacgagt   11640
tttgccactg ctaagctgtg aggcagtgca ggctgggaca gccgacctcc aggttgcgaa   11700
aaacctggtt tctgggacct cccaccccag agtaaaaaga acgagccctc cgctaccacc   11760
ctcccacgtg gtggtagaaa gacggggtct agaggttaga ggagaccctc agggaacaa   11820 atagtgggac catattgacg ccagggaaag accggagtgg ttctctgctt ttcctccaga   11880
ggtctgtgag cacagtttgc tcaagaataa gcagacccttt ggatgacaaa cacaaaacca   11940
c                                                                   11941
```

<210> SEQ ID NO 6
<211> LENGTH: 3771
<212> TYPE: PRT
<213> ORGANISM: Yellow fever virus

<400> SEQUENCE: 6

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110
```

```
Leu Gly Met Leu Leu Met Thr Gly Gly Val Thr Leu Val Arg Lys Asn
            115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Ala Arg Lys Val Cys Tyr Asn Ala Val Leu Thr His
            340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
    370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415

Gln Thr Lys Ile Gln Tyr Val Ile Arg Ala Gln Leu His Val Gly Ala
            420                 425                 430

Lys Gln Glu Asn Trp Asn Thr Ser Ile Lys Thr Leu Lys Phe Asp Ala
        435                 440                 445

Leu Ser Gly Ser Gln Glu Val Glu Phe Ile Gly Tyr Gly Lys Ala Thr
    450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
                485                 490                 495

Asp Leu Thr Leu Pro Trp Gln Ser Gly Ser Gly Val Trp Arg Glu
            500                 505                 510

Met His His Leu Val Glu Phe Glu Pro Pro His Ala Ala Thr Ile Arg
        515                 520                 525

Val Leu Ala Leu Gly Asn Gln Glu Gly Ser Leu Lys Thr Ala Leu Thr
```

```
            530                 535                 540
Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
                595                 600                 605

Val Ser Lys Gly Ala Pro Cys Arg Ile Pro Val Ile Val Ala Asp Asp
    610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
                675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
                770                 775                 780

Asn Phe Gly Arg Lys Gly Ser Gln Thr Ser Asn Thr Thr Lys Trp Ala
785                 790                 795                 800

Pro Pro Gly Gln Gly Ser Pro Gly Ser Lys Gly Glu Glu Leu Phe Thr
                805                 810                 815

Gly Val Val Pro Ile Leu Val Glu Leu Asp Gly Asp Val Asn Gly His
                820                 825                 830

Lys Phe Ser Val Ser Gly Glu Gly Glu Gly Asp Ala Thr Tyr Gly Lys
                835                 840                 845

Leu Thr Leu Lys Phe Ile Cys Thr Thr Gly Lys Leu Pro Val Pro Trp
850                 855                 860

Pro Thr Leu Val Thr Thr Leu Thr Tyr Gly Val Gln Cys Phe Ser Arg
865                 870                 875                 880

Tyr Pro Asp His Met Lys Gln His Asp Phe Phe Lys Ser Ala Met Pro
                885                 890                 895

Glu Gly Tyr Val Gln Glu Arg Thr Ile Phe Phe Lys Asp Asp Gly Asn
                900                 905                 910

Tyr Lys Thr Arg Ala Glu Val Lys Phe Glu Gly Asp Thr Leu Val Asn
                915                 920                 925

Arg Ile Glu Leu Lys Gly Ile Asp Phe Lys Glu Asp Gly Asn Ile Leu
930                 935                 940

Gly His Lys Leu Glu Tyr Asn Tyr Asn Ser His Asn Val Tyr Ile Met
945                 950                 955                 960
```

```
Ala Asp Lys Gln Lys Asn Gly Ile Lys Val Asn Phe Lys Ile Arg His
            965                 970                 975
Asn Ile Glu Asp Gly Ser Val Gln Leu Ala Asp His Tyr Gln Gln Asn
                980                 985                 990
Thr Pro Ile Gly Asp Gly Pro Val Leu Leu Pro Asp Asn His Tyr Leu
            995                1000                1005
Ser Thr Gln Ser Ala Leu Ser Lys Asp Pro Asn Glu Lys Arg Asp
           1010                1015                1020
His Met Val Leu Leu Glu Phe Val Thr Ala Ala Gly Ile Thr Leu
           1025                1030                1035
Gly Met Asp Glu Leu Tyr Lys Gly Ser Ser Pro Leu Ser His Arg
           1040                1045                1050
Ser Lys Arg Ser Leu Ser Cys Arg Pro Pro Met Val Lys Glu Gly
           1055                1060                1065
Ser Ser Ile Gly Thr Ser Leu Gly Lys Ala Val His Gln Val Phe
           1070                1075                1080
Gly Ser Val Tyr Thr Thr Met Phe Gly Gly Val Ser Trp Met Ile
           1085                1090                1095
Arg Ile Leu Ile Gly Phe Leu Val Leu Trp Ile Gly Thr Asn Ser
           1100                1105                1110
Arg Asn Thr Ser Met Ala Met Thr Cys Ile Ala Val Gly Gly Ile
           1115                1120                1125
Thr Leu Phe Leu Gly Phe Thr Val Gly Ala Asp Gln Gly Cys Ala
           1130                1135                1140
Ile Asn Phe Gly Lys Arg Glu Leu Lys Cys Gly Asp Gly Ile Phe
           1145                1150                1155
Ile Phe Arg Asp Ser Asp Asp Trp Leu Asn Lys Tyr Ser Tyr Tyr
           1160                1165                1170
Pro Glu Asp Pro Val Lys Leu Ala Ser Ile Val Lys Ala Ser Phe
           1175                1180                1185
Glu Glu Gly Lys Cys Gly Leu Asn Ser Val Asp Ser Leu Glu His
           1190                1195                1200
Glu Met Trp Arg Ser Arg Ala Asp Glu Ile Asn Ala Ile Phe Glu
           1205                1210                1215
Glu Asn Glu Val Asp Ile Ser Val Val Val Gln Asp Pro Lys Asn
           1220                1225                1230
Val Tyr Gln Arg Gly Thr His Pro Phe Ser Arg Ile Arg Asp Gly
           1235                1240                1245
Leu Gln Tyr Gly Trp Lys Thr Trp Gly Lys Asn Leu Val Phe Ser
           1250                1255                1260
Pro Gly Arg Lys Asn Gly Ser Phe Ile Ile Asp Gly Lys Ser Arg
           1265                1270                1275
Lys Glu Cys Pro Phe Ser Asn Arg Val Trp Asn Ser Phe Gln Ile
           1280                1285                1290
Glu Glu Phe Gly Thr Gly Val Phe Thr Thr Arg Val Tyr Met Asp
           1295                1300                1305
Ala Val Phe Glu Tyr Thr Ile Asp Cys Asp Gly Ser Ile Leu Gly
           1310                1315                1320
Ala Ala Val Asn Gly Lys Lys Ser Ala His Gly Ser Pro Thr Phe
           1325                1330                1335
Trp Met Gly Ser His Glu Val Asn Gly Thr Trp Met Ile His Thr
           1340                1345                1350
```

```
Leu Glu  Ala Leu Asp Tyr  Lys Glu Cys  Glu Trp Pro  Leu Thr His
    1355              1360              1365

Thr Ile  Gly Thr Ser Val  Glu Ser Glu  Met Phe Met  Pro Arg
    1370              1375              1380

Ser Ile  Gly Gly Pro Val  Ser Ser His  Asn His Ile  Pro Gly Tyr
    1385              1390              1395

Lys Val  Gln Thr Asn Gly  Pro Trp Met  Gln Val Pro  Leu Glu Val
    1400              1405              1410

Lys Arg  Glu Ala Cys Pro  Gly Thr Ser  Val Ile Ile  Asp Gly Asn
    1415              1420              1425

Cys Asp  Gly Arg Gly Lys  Ser Thr Arg  Ser Thr Thr  Asp Ser Gly
    1430              1435              1440

Lys Val  Ile Pro Glu Trp  Cys Cys Arg  Ser Cys Thr  Met Pro Pro
    1445              1450              1455

Val Ser  Phe His Gly Ser  Asp Gly Cys  Trp Tyr Pro  Met Glu Ile
    1460              1465              1470

Arg Pro  Arg Lys Thr His  Glu Ser His  Leu Val Arg  Ser Trp Val
    1475              1480              1485

Thr Ala  Gly Glu Ile His  Ala Val Pro  Phe Gly Leu  Val Ser Met
    1490              1495              1500

Met Ile  Ala Met Glu Val  Val Leu Arg  Lys Arg Gln  Gly Pro Lys
    1505              1510              1515

Gln Met  Leu Val Gly Gly  Val Val Leu  Leu Gly Ala  Met Leu Val
    1520              1525              1530

Gly Gln  Val Thr Leu Leu  Asp Leu Leu  Lys Leu Thr  Val Ala Val
    1535              1540              1545

Gly Leu  His Phe His Glu  Met Asn Asn  Gly Gly Asp  Ala Met Tyr
    1550              1555              1560

Met Ala  Leu Ile Ala Ala  Phe Ser Ile  Arg Pro Gly  Leu Leu Ile
    1565              1570              1575

Gly Phe  Gly Leu Arg Thr  Leu Trp Ser  Pro Arg Glu  Arg Leu Val
    1580              1585              1590

Leu Thr  Leu Gly Ala Ala  Met Val Glu  Ile Ala Leu  Gly Gly Val
    1595              1600              1605

Met Gly  Gly Leu Trp Lys  Tyr Leu Asn  Ala Val Ser  Leu Cys Ile
    1610              1615              1620

Leu Thr  Ile Asn Ala Val  Ala Ser Arg  Lys Ala Ser  Asn Thr Ile
    1625              1630              1635

Leu Pro  Leu Met Ala Leu  Leu Thr Pro  Val Thr Met  Ala Glu Val
    1640              1645              1650

Arg Leu  Ala Ala Met Phe  Phe Cys Ala  Met Val Ile  Ile Gly Val
    1655              1660              1665

Leu His  Gln Asn Phe Lys  Asp Thr Ser  Met Gln Lys  Thr Ile Pro
    1670              1675              1680

Leu Val  Ala Leu Thr Leu  Thr Ser Tyr  Leu Gly Leu  Thr Gln Pro
    1685              1690              1695

Phe Leu  Gly Leu Cys Ala  Phe Leu Ala  Thr Arg Ile  Phe Gly Arg
    1700              1705              1710

Arg Ser  Ile Pro Val Asn  Glu Ala Leu  Ala Ala Ala  Gly Leu Val
    1715              1720              1725

Gly Val  Leu Ala Gly Leu  Ala Phe Gln  Glu Met Glu  Asn Phe Leu
    1730              1735              1740

Gly Pro  Ile Ala Val Gly  Gly Leu Leu  Met Met Leu  Val Ser Val
```

```
                    1745               1750               1755
Ala Gly Arg Val Asp Gly Leu Glu Leu Lys Lys Leu Gly Glu Val
               1760               1765               1770

Ser Trp Glu Glu Glu Ala Glu Ile Ser Gly Ser Ser Ala Arg Tyr
               1775               1780               1785

Asp Val Ala Leu Ser Glu Gln Gly Glu Phe Lys Leu Leu Ser Glu
               1790               1795               1800

Glu Lys Val Pro Trp Asp Gln Val Val Met Thr Ser Leu Ala Leu
               1805               1810               1815

Val Gly Ala Ala Leu His Pro Phe Ala Leu Leu Val Leu Ala
               1820               1825               1830

Gly Trp Leu Phe His Val Arg Gly Ala Arg Arg Ser Gly Asp Val
               1835               1840               1845

Leu Trp Asp Ile Pro Thr Pro Lys Ile Ile Glu Glu Cys Glu His
               1850               1855               1860

Leu Glu Asp Gly Ile Tyr Gly Ile Phe Gln Ser Thr Phe Leu Gly
               1865               1870               1875

Ala Ser Gln Arg Gly Val Gly Val Ala Gln Gly Val Phe His
               1880               1885               1890

Thr Met Trp His Val Thr Arg Gly Ala Phe Leu Val Arg Asn Gly
               1895               1900               1905

Lys Lys Leu Ile Pro Ser Trp Ala Ser Val Lys Glu Asp Leu Val
               1910               1915               1920

Ala Tyr Gly Gly Ser Trp Lys Leu Glu Gly Arg Trp Asp Gly Glu
               1925               1930               1935

Glu Glu Val Gln Leu Ile Ala Ala Val Pro Gly Lys Asn Val Val
               1940               1945               1950

Asn Val Gln Thr Lys Pro Ser Leu Phe Lys Val Arg Asn Gly Gly
               1955               1960               1965

Glu Ile Gly Ala Val Ala Leu Asp Tyr Pro Ser Gly Thr Ser Gly
               1970               1975               1980

Ser Pro Ile Val Asn Arg Asn Gly Glu Val Ile Gly Leu Tyr Gly
               1985               1990               1995

Asn Gly Ile Leu Val Gly Asp Asn Ser Phe Val Ser Ala Ile Ser
               2000               2005               2010

Gln Thr Glu Val Lys Glu Glu Gly Lys Glu Glu Leu Gln Glu Ile
               2015               2020               2025

Pro Thr Met Leu Lys Lys Gly Met Thr Thr Val Leu Asp Phe His
               2030               2035               2040

Pro Gly Ala Gly Lys Thr Arg Arg Phe Leu Pro Gln Ile Leu Ala
               2045               2050               2055

Glu Cys Ala Arg Arg Arg Leu Arg Thr Leu Val Leu Ala Pro Thr
               2060               2065               2070

Arg Val Val Leu Ser Glu Met Lys Glu Ala Phe His Gly Leu Asp
               2075               2080               2085

Val Lys Phe His Thr Gln Ala Phe Ser Ala His Gly Ser Gly Arg
               2090               2095               2100

Glu Val Ile Asp Ala Met Cys His Ala Thr Leu Thr Tyr Arg Met
               2105               2110               2115

Leu Glu Pro Thr Arg Val Val Asn Trp Glu Val Ile Ile Met Asp
               2120               2125               2130

Glu Ala His Phe Leu Asp Pro Ala Ser Ile Ala Ala Arg Gly Trp
               2135               2140               2145
```

```
Ala Ala His Arg Ala Arg Ala Asn Glu Ser Ala Thr Ile Leu Met
    2150            2155                2160

Thr Ala Thr Pro Pro Gly Thr Ser Asp Glu Phe Pro His Ser Asn
    2165            2170                2175

Gly Glu Ile Glu Asp Val Gln Thr Asp Ile Pro Ser Glu Pro Trp
    2180            2185                2190

Asn Thr Gly His Asp Trp Ile Leu Ala Asp Lys Arg Pro Thr Ala
    2195            2200                2205

Trp Phe Leu Pro Ser Ile Arg Ala Ala Asn Val Met Ala Ala Ser
    2210            2215                2220

Leu Arg Lys Ala Gly Lys Ser Val Val Val Leu Asn Arg Lys Thr
    2225            2230                2235

Phe Glu Arg Glu Tyr Pro Thr Ile Lys Gln Lys Pro Asp Phe
    2240            2245                2250

Ile Leu Ala Thr Asp Ile Ala Glu Met Gly Ala Asn Leu Cys Val
    2255            2260                2265

Glu Arg Val Leu Asp Cys Arg Thr Ala Phe Lys Pro Val Leu Val
    2270            2275                2280

Asp Glu Gly Arg Lys Val Ala Ile Lys Gly Pro Leu Arg Ile Ser
    2285            2290                2295

Ala Ser Ser Ala Ala Gln Arg Arg Gly Arg Ile Gly Arg Asn Pro
    2300            2305                2310

Asn Arg Asp Gly Asp Ser Tyr Tyr Tyr Ser Glu Pro Thr Ser Glu
    2315            2320                2325

Asn Asn Ala His His Val Cys Trp Leu Glu Ala Ser Met Leu Leu
    2330            2335                2340

Asp Asn Met Glu Val Arg Gly Gly Met Val Ala Pro Leu Tyr Gly
    2345            2350                2355

Val Glu Gly Thr Lys Thr Pro Val Ser Pro Gly Glu Met Arg Leu
    2360            2365                2370

Arg Asp Asp Gln Arg Lys Val Phe Arg Glu Leu Val Arg Asn Cys
    2375            2380                2385

Asp Leu Pro Val Trp Leu Ser Trp Gln Val Ala Lys Ala Gly Leu
    2390            2395                2400

Lys Thr Asn Asp Arg Lys Trp Cys Phe Glu Gly Pro Glu Glu His
    2405            2410                2415

Glu Ile Leu Asn Asp Ser Gly Glu Thr Val Lys Cys Arg Ala Pro
    2420            2425                2430

Gly Gly Ala Lys Lys Pro Leu Arg Pro Arg Trp Cys Asp Glu Arg
    2435            2440                2445

Val Ser Ser Asp Gln Ser Ala Leu Ser Glu Phe Ile Lys Phe Ala
    2450            2455                2460

Glu Gly Arg Arg Gly Ala Ala Glu Val Leu Val Val Leu Ser Glu
    2465            2470                2475

Leu Pro Asp Phe Leu Ala Lys Lys Gly Gly Glu Ala Met Asp Thr
    2480            2485                2490

Ile Ser Val Phe Leu His Ser Glu Glu Gly Ser Arg Ala Tyr Arg
    2495            2500                2505

Asn Ala Leu Ser Met Met Pro Glu Ala Met Thr Ile Val Met Leu
    2510            2515                2520

Phe Ile Leu Ala Gly Leu Leu Thr Ser Gly Met Val Ile Phe Phe
    2525            2530                2535
```

Met Ser Pro Lys Gly Ile Ser Arg Met Ser Met Ala Met Gly Thr
    2540                2545                2550

Met Ala Gly Cys Gly Tyr Leu Met Phe Leu Gly Val Lys Pro
    2555                2560                2565

Thr His Ile Ser Tyr Val Met Leu Ile Phe Phe Val Leu Met Val
    2570                2575                2580

Val Val Ile Pro Glu Pro Gly Gln Gln Arg Ser Ile Gln Asp Asn
    2585                2590                2595

Gln Val Ala Tyr Leu Ile Ile Gly Ile Leu Thr Leu Val Ser Ala
    2600                2605                2610

Val Ala Ala Asn Glu Leu Gly Met Leu Glu Lys Thr Lys Glu Asp
    2615                2620                2625

Leu Phe Gly Lys Lys Asn Leu Ile Pro Ser Ser Ala Ser Pro Trp
    2630                2635                2640

Ser Trp Pro Asp Leu Asp Leu Lys Pro Gly Ala Ala Trp Thr Val
    2645                2650                2655

Tyr Val Gly Ile Val Thr Met Leu Ser Pro Met Leu His His Trp
    2660                2665                2670

Ile Lys Val Glu Tyr Gly Asn Leu Ser Leu Ser Gly Ile Ala Gln
    2675                2680                2685

Ser Ala Ser Val Leu Ser Phe Met Asp Lys Gly Ile Pro Phe Met
    2690                2695                2700

Lys Met Asn Ile Ser Val Ile Met Leu Leu Val Ser Gly Trp Asn
    2705                2710                2715

Ser Ile Thr Val Met Pro Leu Leu Cys Gly Ile Gly Cys Ala Met
    2720                2725                2730

Leu His Trp Ser Leu Ile Leu Pro Gly Ile Lys Ala Gln Gln Ser
    2735                2740                2745

Lys Leu Ala Gln Arg Arg Val Phe His Gly Val Ala Lys Asn Pro
    2750                2755                2760

Val Val Asp Gly Asn Pro Thr Val Asp Ile Glu Glu Ala Pro Glu
    2765                2770                2775

Met Pro Ala Leu Tyr Glu Lys Lys Leu Ala Leu Tyr Leu Leu Leu
    2780                2785                2790

Ala Leu Ser Leu Ala Ser Val Ala Met Cys Arg Thr Pro Phe Ser
    2795                2800                2805

Leu Ala Glu Gly Ile Val Leu Ala Ser Ala Ala Leu Gly Pro Leu
    2810                2815                2820

Ile Glu Gly Asn Thr Ser Leu Leu Trp Asn Gly Pro Met Ala Val
    2825                2830                2835

Ser Met Thr Gly Val Met Arg Gly Asn His Tyr Ala Phe Val Gly
    2840                2845                2850

Val Met Tyr Asn Leu Trp Lys Met Lys Thr Gly Arg Arg Gly Ser
    2855                2860                2865

Ala Asn Gly Lys Thr Leu Gly Glu Val Trp Lys Arg Glu Leu Asn
    2870                2875                2880

Leu Leu Asp Lys Arg Gln Phe Glu Leu Tyr Lys Arg Thr Asp Ile
    2885                2890                2895

Val Glu Val Asp Arg Asp Thr Ala Arg Arg His Leu Ala Glu Gly
    2900                2905                2910

Lys Val Asp Thr Gly Val Ala Val Ser Arg Gly Thr Ala Lys Leu
    2915                2920                2925

Arg Trp Phe His Glu Arg Gly Tyr Val Lys Leu Glu Gly Arg Val

```
            2930              2935              2940

Ile Asp Leu Gly Cys Gly Arg Gly Gly Trp Cys Tyr Tyr Ala Ala
    2945              2950              2955

Ala Gln Lys Glu Val Ser Gly Val Lys Gly Phe Thr Leu Gly Arg
    2960              2965              2970

Asp Gly His Glu Lys Pro Met Asn Val Gln Ser Leu Gly Trp Asn
    2975              2980              2985

Ile Ile Thr Phe Lys Asp Lys Thr Asp Ile His Arg Leu Glu Pro
    2990              2995              3000

Val Lys Cys Asp Thr Leu Leu Cys Asp Ile Gly Glu Ser Ser Ser
    3005              3010              3015

Ser Ser Val Thr Glu Gly Glu Arg Thr Val Arg Val Leu Asp Thr
    3020              3025              3030

Val Glu Lys Trp Leu Ala Cys Gly Val Asp Asn Phe Cys Val Lys
    3035              3040              3045

Val Leu Ala Pro Tyr Met Pro Asp Val Leu Glu Lys Leu Glu Leu
    3050              3055              3060

Leu Gln Arg Arg Phe Gly Gly Thr Val Ile Arg Asn Pro Leu Ser
    3065              3070              3075

Arg Asn Ser Thr His Glu Met Tyr Tyr Val Ser Gly Ala Arg Ser
    3080              3085              3090

Asn Val Thr Phe Thr Val Asn Gln Thr Ser Arg Leu Leu Met Arg
    3095              3100              3105

Arg Met Arg Arg Pro Thr Gly Lys Val Thr Leu Glu Ala Asp Val
    3110              3115              3120

Ile Leu Pro Ile Gly Thr Arg Ser Val Glu Thr Asp Lys Gly Pro
    3125              3130              3135

Leu Asp Lys Glu Ala Ile Glu Glu Arg Val Glu Arg Ile Lys Ser
    3140              3145              3150

Glu Tyr Met Thr Ser Trp Phe Tyr Asp Asn Asp Asn Pro Tyr Arg
    3155              3160              3165

Thr Trp His Tyr Cys Gly Ser Tyr Val Thr Lys Thr Ser Gly Ser
    3170              3175              3180

Ala Ala Ser Met Val Asn Gly Val Ile Lys Ile Leu Thr Tyr Pro
    3185              3190              3195

Trp Asp Arg Ile Glu Glu Val Thr Arg Met Ala Met Thr Asp Thr
    3200              3205              3210

Thr Pro Phe Gly Gln Gln Arg Val Phe Lys Glu Lys Val Asp Thr
    3215              3220              3225

Arg Ala Lys Asp Pro Pro Ala Gly Thr Arg Lys Ile Met Lys Val
    3230              3235              3240

Val Asn Arg Trp Leu Phe Arg His Leu Ala Arg Glu Lys Ser Pro
    3245              3250              3255

Arg Leu Cys Thr Lys Glu Glu Phe Ile Ala Lys Val Arg Ser His
    3260              3265              3270

Ala Ala Ile Gly Ala Tyr Leu Glu Glu Gln Glu Gln Trp Lys Thr
    3275              3280              3285

Ala Asn Glu Ala Val Gln Asp Pro Lys Phe Trp Glu Leu Val Asp
    3290              3295              3300

Glu Glu Arg Lys Leu His Gln Gln Gly Arg Cys Arg Thr Cys Val
    3305              3310              3315

Tyr Asn Met Met Gly Lys Arg Glu Lys Lys Leu Ser Glu Phe Gly
    3320              3325              3330
```

-continued

```
Lys Ala Lys Gly Ser Arg Ala Ile Trp Tyr Met Trp Leu Gly Ala
3335                3340                3345
Arg Tyr Leu Glu Phe Glu Ala Leu Gly Phe Leu Asn Glu Asp His
3350                3355                3360
Trp Ala Ser Arg Glu Asn Ser Gly Gly Gly Val Glu Gly Ile Gly
3365                3370                3375
Leu Gln Tyr Leu Gly Tyr Val Ile Arg Asp Leu Ala Ala Met Asp
3380                3385                3390
Gly Gly Gly Phe Tyr Ala Asp Asp Thr Ala Gly Trp Asp Thr Arg
3395                3400                3405
Ile Thr Glu Ala Asp Leu Asp Asp Glu Gln Glu Ile Leu Asn Tyr
3410                3415                3420
Met Ser Pro His His Lys Lys Leu Ala Gln Ala Val Met Glu Met
3425                3430                3435
Thr Tyr Lys Asn Lys Val Val Lys Val Leu Arg Pro Ala Pro Gly
3440                3445                3450
Gly Lys Ala Tyr Met Asp Val Ile Ser Arg Arg Asp Gln Arg Gly
3455                3460                3465
Ser Gly Gln Val Val Thr Tyr Ala Leu Asn Thr Ile Thr Asn Leu
3470                3475                3480
Lys Val Gln Leu Ile Arg Met Ala Glu Ala Glu Met Val Ile His
3485                3490                3495
His Gln His Val Gln Asp Cys Asp Glu Ser Val Leu Thr Arg Leu
3500                3505                3510
Glu Ala Trp Leu Thr Glu His Gly Cys Asn Arg Leu Lys Arg Met
3515                3520                3525
Ala Val Ser Gly Asp Asp Cys Val Val Arg Pro Ile Asp Asp Arg
3530                3535                3540
Phe Gly Leu Ala Leu Ser His Leu Asn Ala Met Ser Lys Val Arg
3545                3550                3555
Lys Asp Ile Ser Glu Trp Gln Pro Ser Lys Gly Trp Asn Asp Trp
3560                3565                3570
Glu Asn Val Pro Phe Cys Ser His His Phe His Glu Leu Gln Leu
3575                3580                3585
Lys Asp Gly Arg Arg Ile Val Val Pro Cys Arg Glu Gln Asp Glu
3590                3595                3600
Leu Ile Gly Arg Gly Arg Val Ser Pro Gly Asn Gly Trp Met Ile
3605                3610                3615
Lys Glu Thr Ala Cys Leu Ser Lys Ala Tyr Ala Asn Met Trp Ser
3620                3625                3630
Leu Met Tyr Phe His Lys Arg Asp Met Arg Leu Leu Ser Leu Ala
3635                3640                3645
Val Ser Ser Ala Val Pro Thr Ser Trp Val Pro Gln Gly Arg Thr
3650                3655                3660
Thr Trp Ser Ile His Gly Lys Gly Glu Trp Met Thr Thr Glu Asp
3665                3670                3675
Met Leu Glu Val Trp Asn Arg Val Trp Ile Thr Asn Asn Pro His
3680                3685                3690
Met Gln Asp Lys Thr Met Val Lys Lys Trp Arg Asp Val Pro Tyr
3695                3700                3705
Leu Thr Lys Arg Gln Asp Lys Leu Cys Gly Ser Leu Ile Gly Met
3710                3715                3720
```

-continued

```
Thr Asn Arg Ala Thr Trp Ala Ser His Ile His Leu Val Ile His
3725                3730                3735

Arg Ile Arg Thr Leu Ile Gly Gln Glu Lys Tyr Thr Asp Tyr Leu
3740                3745                3750

Thr Val Met Asp Arg Tyr Ser Val Asp Ala Asp Leu Gln Leu Gly
3755                3760                3765

Glu Leu Ile
3770

<210> SEQ ID NO 7
<211> LENGTH: 12034
<212> TYPE: DNA
<213> ORGANISM: Yellow fever virus

<400> SEQUENCE: 7
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgaccggtgg     480
agtgaccttg gtgcgaaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc aatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaacccctt ttttgcagtg acggctctga ccattgccta     900
ccttgtggga agcaacatga cgcaacgagt cgtgattgcc ctactggtct ggctgttgg     960 tccggcctac tcagctcact gcattggaat tactgacagg gatttcattg aggggggtgca    1020 tggaggaact tgggttcag ctaccctgga gcaagacaag tgtgtcactg ttatggcccc    1080
tgacaagcct tcattggaca tctcactaga gacagtagcc attgatagac tgctgaggc    1140 gaggaaagtg tgttacaatg cagttctcac tcatgtgaag attaatgaca gtgccccag    1200 cactggagag gccccactag ctgaagagaa cgaaggggac aatgcgtgca agcgcactta    1260
ttctgataga ggctggggca tggctgtggg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccagcat    1440
taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catccttgtcg aatttgaacc    1680 tccgcatgcc gccactatca gagtactggc cctgggaaac caggaaggct ccttgaaaac    1740
agctcttact ggcgcaatga ggttacaaaa ggacacaaat gacaacaacc tttacaaact    1800
```

```
acatggtgga catgtttctt gcagagtgaa attgtcagct ttgacactca agggacatc    1860
ctacaaaata tgcactgaca aaatgttttt tgtcaagaac ccaactgaca ctggccatgg   1920
cactgttgtg atgcaggtga aagtgtcaaa aggagccccc tgcaggattc cagtgatagt   1980
agctgatgat cttacagcgg caatcaataa aggcattttg gttacagtta accccatcgc   2040
ctcaaccaat gatgatgaag tgctgattga ggtgaaccca cctttggag acagctacat     2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aacttcggcc gaaagggatc acaaacctcc aacacaacta atgggctcc    2520
tcccggacaa ggaagtcccg ggagcaaggg cgaggagctg ttcaccgggg tggtgcccat   2580
cctggtcgag ctggacggcg acgtaaacgg ccacaagttc agcgtgtccg gcgagggcga   2640
gggcgatgcc acctacggca agctgaccct gaagttcatc tgcaccaccg gcaagctgcc   2700
cgtgccctgg cccaccctcg tgaccaccct gacctacggc gtgcagtgct tcagccgcta   2760
ccccgaccac atgaagcagc acgacttctt caagtccgcc atgcccgaag gctacgtcca   2820
ggagcgcacc atcttcttca aggacgacgg caactacaag acccgcgccg aggtgaagtt   2880
cgagggcgac accctggtga accgcatcga gctgaagggc atcgacttca aggaggacgg   2940
caacatcctg gggcacaagc tggagtacaa ctacaacagc cacaacgtct atatcatggc   3000
cgacaagcag aagaacggca tcaaggtgaa cttcaagatc cgccacaaca tcgaggacgg   3060
cagcgtgcag ctcgccgacc actaccagca gaacaccccc atcggcgacg gccccgtgct   3120
gctgcccgac aaccactacc tgagcaccca gtccgccctg agcaaagacc ccaacgagaa   3180
gcgcgatcac atggtcctgc tggagttcgt gaccgccgcc gggatcactc tcggcatgga   3240
cgagctgtac aagtccggaa gcagtccact gtctcatcgc agtaaaagga gcctatcctg   3300
tcggccaccc atggtcaaag agggaagctc aataggaaag atgtttgagt ccacatacag   3360
aggtgcaaaa cgaatggcca ttctaggtga acagcttggg attttggtt ccgttggtgg    3420
actgttcaca tcattgggaa aggctgtgca ccaggttttt ggaagtgtgt atacaaccat   3480
gtttggagga gtctcatgga tgattagaat cctaattggg ttcttagtgt gtggattgg    3540
cacgaactcc aggaacactt caatggctat gacgtgcata gctgttggag gaatcactct   3600
gtttctgggc ttcacagttg gcgccgatca aggatgcgcc atcaactttg gcaagagaga   3660
gctcaagtgc ggagatggta tcttcatatt tagagactct gatgactggc tgaacaagta   3720
ctcatactat ccagaagatc ctgtgaagct tgcatcaata gtgaaagcct cttttgaaga   3780
agggaagtgt ggcctaaatt cagttgactc ccttgagcat gagatgtgga agcagggc     3840
agatgagatc aatgccattt ttgaggaaaa cgaggtggac atttctgttg tcgtgcagga   3900
tccaaagaat gtttaccaga gaggaactca tccattttcc agaattcggg atggtctgca   3960
gtatggttgg aagacttggg gtaagaacct tgtgttctcc ccagggagga agaatggaag   4020
cttcatcata gatggaaagt ccaggaaaga atgcccgttt tcaaaccggg tctggaattc   4080
tttccagata gaggagtttg ggacgggagt gttcaccaca cgcgtgtaca tggacgcagt   4140
```

```
ctttgaatac accatagact gcgatggatc tatcttgggt gcagcggtga acggaaaaaa    4200
gagtgcccat ggctctccaa catttttggat gggaagtcat gaagtaaatg ggacatggat    4260
gatccacacc ttggaggcat tagattacaa ggagtgtgag tggccactga cacatacgat    4320
tggaacatca gttgaagaga gtgaaatgtt catgccgaga tcaatcggag cccagttag     4380 ctctcacaat catatccctg gatacaaggt tcagacgaac ggaccttgga tgcaggtacc    4440
actagaagtg aagagagaag cttgcccagg gactagcgtg atcattgatg caactgtga    4500 tggacgggga aaatcaacca gatccaccac ggatagcggg aaagttattc ctgaatggtg    4560
ttgccgctcc tgcacaatgc cgcctgtgag cttccatggt agtgatgggt gttggtatcc    4620
catggaaatt aggccaagga aaacgcatga aagccatctg gtgcgctcct gggttacagc    4680
tggagaaata catgctgtcc cttttggttt ggtgagcatg atgatagcaa tggaagtggt    4740
cctaaggaaa agacagggac caaagcaaat gttggttgga ggagtagtgc tcttgggagc    4800
aatgctggtc gggcaagtaa ctctccttga tttgctgaaa ctcacagtgg ctgtgggatt    4860
gcatttccat gagatgaaca atggaggaga cgccatgtat atggcgttga ttgctgcctt    4920
ttcaatcaga ccagggctgc tcatcggctt tgggctcagg accctatgga gccctcggga    4980
acgccttgtg ctgaccctag gagcagccat ggtggagatt gccttgggtg gcgtgatggg    5040
cggcctgtgg aagtatctaa atgcagtttc tctctgcatc ctgacaataa atgctgttgc    5100
ttctaggaaa gcatcaaata ccatcttgcc cctcatggct ctgttgacac ctgtcactat    5160
ggctgaggtg agacttgccg caatgttctt ttgtgccatg gttatcatag ggtccttca    5220 ccagaatttc aaggacacct ccatgcagaa gactatacct ctggtggccc tcacactcac    5280
atcttacctg ggcttgacac aacctttttt gggcctgtgt gcatttctgg caacccgcat    5340
atttgggcga aggagtatcc cagtgaatga ggcactcgca gcagctggtc tagtgggagt    5400
gctggcagga ctggcttttc aggagatgga gaacttcctt ggtccgattg cagttggagg    5460
actcctgatg atgctggtta gcgtggctgg gagggtggat gggctagagc tcaagaagct    5520
tggtgaagtt tcatgggaag aggaggcgga gatcagcggg agttccgccc gctatgatgt    5580
ggcactcagt gaacaagggg agttcaagct gctttctgaa gagaaagtgc catgggacca    5640
ggttgtgatg acctcgctgg ccttggttgg ggctgccctc catccatttg ctcttctgct    5700
ggtccttgct gggtggctgt ttcatgtcag gggagctagg agaagtgggg atgtcttgtg    5760
ggatattccc actcctaaga tcatcgagga atgtgaacat ctggaggatg ggatttatgg    5820
catattccag tcaaccttct tgggggcctc ccagcgagga gtgggagtgg cacagggagg    5880
ggtgttccac acaatgtggc atgtcacaag aggagctttc cttgtcagga atggcaagaa    5940
gttgattcca tcttgggctt cagtaaagga agaccttgtc gcctatggtg gctcatggaa    6000
gttggaaggc agatgggatg gagaggaaga ggtccagttg atcgcggctg ttccaggaaa    6060
gaacgtggtc aacgtccaga caaaaccgag cttgttcaaa gtgaggaatg ggggagaaat    6120
cggggctgtc gctcttgact atccgagtgg cacttcagga tctcctattg ttaacaggaa    6180
cggagaggtg attgggctgt acggcaatgg catccttgtc ggtgacaact ccttcgtgtc    6240
cgccatatcc cagactgagg tgaaggaaga aggaaaggag gagctccaag agatcccgac    6300
aatgctaaag aaaggaatga caactgtcct tgattttcat cctggagctg ggaagacaag    6360
acgtttcctc ccacagatct tggccgagtg cgcacggaga cgcttgcgca ctcttgtgtt    6420
ggcccccacc agggttgttc tttctgaaat gaaggaggct tttcacgcc tggacgtgaa     6480 attccacaca caggcttttt ccgctcacgg cagcgggaga gaagtcattg atgccatgtg    6540
```

```
ccatgccacc ctaacttaca ggatgttgga accaactagg gttgttaact gggaagtgat    6600
cattatggat gaagcccatt ttttggatcc agctagcata gccgctagag gttgggcagc    6660
gcacagagct agggcaaatg aaagtgcaac aatcttgatg acagccacac cgcctgggac    6720
tagtgatgaa tttccacatt caaatggtga aatagaagat gttcaaacgg acatacccag    6780
tgagccctgg aacacagggc atgactggat cctggctgac aaaaggccca cggcatggtt    6840
ccttccatcc atcagagctg caaatgtcat ggctgcctct ttgcgtaagg ctggaaagag    6900
tgtggtggtc ctgaacagga aaacctttga gagagaatac cccacgataa agcagaagaa    6960
acctgacttt atattggcca ctgacatagc tgaaatggga gccaaccttt gcgtggagcg    7020
agtgctggat tgcaggacgg cttttaagcc tgtgcttgtg gatgaaggga ggaaggtggc    7080
aataaaaggg ccacttcgta tctccgcatc ctctgctgct caaggagggg ggcgcattgg    7140
gagaaatccc aacagagatg gagactcata ctactattct gagcctacaa gtgaaaataa    7200
tgcccaccac gtctgctggt tggaggcctc aatgctcttg acaacatgg aggtgagggg     7260 tggaatggtc gccccactct atggcgttga aggaactaaa acaccagttt ccctggtga     7320 aatgagactg agggatgacc agaggaaagt cttcagagaa ctagtgagga attgtgacct    7380
gcccgtttgg ctttcgtggc aagtggccaa ggctggtttg aagacgaatg atcgtaagtg    7440
gtgttttgaa ggccctgagg aacatgagat cttgaatgac agcggtgaaa cagtgaagtg    7500
cagggctcct ggaggagcaa agaagcctct gcgcccaagg tggtgtgatg aaagggtgtc    7560
atctgaccag agtgcgctgt ctgaatttat taagtttgct gaaggtagga ggggagctgc    7620
tgaagtgcta gttgtgctga gtgaactccc tgatttcctg gctaaaaaag gtggagaggc    7680
aatggatacc atcagtgtgt tcctccactc tgaggaaggc tctagggctt accgcaatgc    7740
actatcaatg atgcctgagg caatgacaat agtcatgctg tttatactgg ctggactact    7800
gacatcggga atggtcatct ttttcatgtc tcccaaaggc atcagtagaa tgtctatggc    7860
gatgggcaca atggccggct gtggatatct catgttcctt ggaggcgtca aacccactca    7920
catctcctat gtcatgctca tattctttgt cctgatggtg gttgtgatcc ccgagccagg    7980
gcaacaaagg tccatccaag acaaccaagt ggcatacctc attattggca tcctgacgct    8040
ggtttcagcg gtggcagcca acgagctagg catgctggag aaaaccaaag aggacctctt    8100
tgggaagaag aacttaattc catctagtgc ttcaccctgg agttggccgg atcttgacct    8160
gaagccagga gctgcctgga cagtgtacgt tggcattgtt acaatgctct ctccaatgtt    8220
gcaccactgg atcaaagtcg aatatggcaa cctgtctctg tctggaatag cccagtcagc    8280
ctcagtcctt tctttcatgg acaaggggat accattcatg aagatgaata tctcggtcat    8340
aatgctgctg gtcagtggct ggaattcaat aacagtgatg cctctgctct gtggcatagg    8400
gtgcgccatg ctccactggt ctctcatttt acctggaatc aaagcgcagc agtcaaagct    8460
tgcacagaga agggtgttcc atggcgttgc caagaaccct gtggttgatg gaatccaac    8520 agttgacatt gaggaagctc ctgaaatgcc tgccctttat gagaagaaac tggctctata    8580
tctccttctt gctctcagcc tagcttctgt tgccatgtgc agaacgccct tttcattggc    8640
tgaaggcatt gtcctagcat cagctgcctt agggccgctc atagagggaa acaccagcct    8700
tctttggaat ggacccatgg ctgtctccat gacaggagtc atgaggggga atcactatgc    8760
ttttgtggga gtcatgtaca atctatggaa gatgaaaact ggacgccggg ggagcgcgaa    8820
tggaaaaact ttgggtgaag tctggaagag ggaactgaat ctgttggaca gcgacagtt     8880
```

```
tgagttgtat aaaaggaccg acattgtgga ggtggatcgt gatacggcac gcaggcattt    8940
ggccgaaggg aaggtggaca ccggggtggc ggtctccagg gggaccgcaa agttaaggtg    9000
gttccatgag cgtggctatg tcaagctgga aggtagggtg attgacctgg ggtgtggccg    9060
cggaggctgg tgttactacg ctgctgcgca aaaggaagtg agtggggtca aaggatttac    9120
tcttggaaga gacggccatg agaaacccat gaatgtgcaa agtctgggat ggaacatcat    9180
caccttcaag gacaaaactg atatccaccg cctagaacca gtgaaatgtg cacccttttt    9240
gtgtgacatt ggagagtcat catcgtcatc ggtcacagag ggggaaagga ccgtgagagt    9300
tcttgatact gtagaaaaat ggctggcttg tggggttgac aacttctgtg tgaaggtgtt    9360
agctccatac atgccagatg ttcttgagaa actggaattg ctccaaagga ggtttggcgg    9420
aacagtgatc aggaaccctc tctccaggaa ttccactcat gaaatgtact acgtgtctgg    9480
agcccgcagc aatgtcacat ttactgtgaa ccaaacatcc cgcctcctga tgaggagaat    9540
gaggcgtcca actggaaaag tgaccctgga ggctgacgtc atcctcccaa ttgggacacg    9600
cagtgttgag acagacaagg gacccctgga caaagaggcc atagaagaaa gggttgagag    9660
gataaaatct gagtacatga cctcttggtt ttatgacaat gacaaccccct acaggacctg    9720
gcactactgt ggctcctatg tcacaaaaac ctcaggaagt gcggcgagca tggtaaatgg    9780
tgttattaaa attctgacat atccatggga caggatagag gaggtcacca gaatggcaat    9840
gactgacaca accccttttg gacagcaaag agtgtttaaa gaaaaagttg acaccagagc    9900
aaaggatcca ccagcgggaa ctaggaagat catgaaagtt gtcaacaggt ggctgttccg    9960
ccacctggcc agagaaaaga gccccagact gtgcacaaag gaagaattta ttgcaaaagt   10020
ccgaagtcat gcagccattg gagcttacct ggaagaacaa gaacagtgga agactgccaa   10080
tgaggctgtc caagacccaa agttctggga actggtggat gaagaaagga agctgccacca   10140
acaaggcagg tgtcggactt gtgtgtacaa catgatgggg aaaagagaga agaagctgtc   10200
agagtttggg aaagcaaagg gaagccgtgc catatggtat atgtggctgg gagcgcggta   10260
tcttgagttt gaggccctgg gattcctgaa tgaggaccat tgggcttcca gggaaaactc   10320
aggaggagga gtgaaggca ttggcttaca atacctagga tatgtgatca gagacctggc   10380
tgcaatggat ggtggtggat tctacgcgga tgacaccgct ggatgggaca cgcgcatcac   10440
agaggcagac cttgatgatg aacaggagat cttgaactac atgagcccac atcacaaaaa   10500
actggcacaa gcagtgatgg aaatgacata caagaacaaa gtggtgaaag tgttgagacc   10560
agccccagga gggaaagcct acatggatgt cataagtcga cgagaccaga gggatccgg   10620
gcaggtagtg acttatgctc tgaacaccat caccaacttg aaagtccaat tgatcagaat   10680
ggcagaagca gagatggtga tacatccacca acatgttcaa gattgtgatg aatcagttct   10740
gaccaggctg gaggcatggc tcactgagca cggatgtaac agactgaaga ggatggcggt   10800
gagtggagac gactgtgtgg tccggcccat cgatgacagg ttcggcctgg ccctgtccca   10860
tctcaacgcc atgtccaagg ttagaaagga catatctgaa tggcagccat caaaagggtg   10920
gaatgattgg gagaatgtgc ccttctgttc ccaccacttc catgaactac agctgaagga   10980
tggcaggagg attgtggtgc cttgccgaga acaggacgag ctcattggga gaggaaggggt   11040
gtctccagga aacggctgga tgatcaagga aacagcttgc ctcagcaaag cctatgccaa   11100
catgtggtca ctgatgtatt ttcacaaaag ggacatgagg ctactgtcat ggctgtttc   11160
ctcagctgtt cccacctcat gggttccaca aggacgcaca acatggtcga ttcatgggaa   11220
aggggagtgg atgaccacgg aagacatgct tgaggtgtgg aacagagtat ggataaccaa   11280
```

```
caacccacac atgcaggaca agacaatggt gaaaaaatgg agagatgtcc cttatctaac    11340
caagagacaa gacaagctgt gcggatcact gattggaatg accaataggg ccacctgggc    11400
ctcccacatc catttagtca tccatcgtat ccgaacgctg attggacagg agaaatacac    11460
tgactaccta acagtcatgg acaggtattc tgtggatgct gacctgcaac tgggtgagct    11520
tatctgaaac accatctaac aggaataacc gggatacaaa ccacgggtgg agaaccggac    11580
tccccacaac ctgaaaccgg gatataaacc acggctggag aaccgggctc cgcacttaaa    11640
atgaaacaga aaccgggata aaaactacgg atggagaacc ggactccaca cattgagaca    11700
gaagaagttg tcagcccaga accccacacg agttttgcca ctgctaagct gtgaggcagt    11760
gcaggctggg acagccgacc tccaggttgc gaaaaacctg gtttctggga cctcccaccc    11820
cagagtaaaa agaacggagc ctccgctacc accctcccac gtggtggtag aaagacgggg    11880
tctagaggtt agaggagacc ctccagggaa caaatagtgg gaccatattg acgccaggga    11940
aagaccggag tggttctctg cttttcctcc agaggtctgt gagcacagtt tgctcaagaa    12000
taagcagacc tttggatgac aaacacaaaa ccac                                12034
```

<210> SEQ ID NO 8
<211> LENGTH: 3802
<212> TYPE: PRT
<213> ORGANISM: Yellow fever virus

<400> SEQUENCE: 8

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Val Arg Lys Asn
            115                 120                 125

Arg Trp Leu Leu Leu Asn Val Thr Ser Glu Asp Leu Gly Lys Thr Phe
        130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240
```

```
Lys Ile Glu Arg Trp Phe Val Arg Asn Pro Phe Ala Val Thr Ala
            245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
            275                 280                 285

Ile Gly Ile Thr Asp Arg Asp Phe Ile Glu Gly Val His Gly Gly Thr
            290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
            325                 330                 335

Arg Pro Ala Glu Ala Arg Lys Val Cys Tyr Asn Ala Val Leu Thr His
            340                 345                 350

Val Lys Ile Asn Asp Lys Cys Pro Ser Thr Gly Glu Ala His Leu Ala
            355                 360                 365

Glu Glu Asn Glu Gly Asp Asn Ala Cys Lys Arg Thr Tyr Ser Asp Arg
            370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
            405                 410                 415

Gln Thr Lys Ile Gln Tyr Val Ile Arg Ala Gln Leu His Val Gly Ala
            420                 425                 430

Lys Gln Glu Asn Trp Asn Thr Ser Ile Lys Thr Leu Lys Phe Asp Ala
            435                 440                 445

Leu Ser Gly Ser Gln Glu Val Glu Phe Ile Gly Tyr Gly Lys Ala Thr
450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
            485                 490                 495

Asp Leu Thr Leu Pro Trp Gln Ser Gly Ser Gly Gly Val Trp Arg Glu
            500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
            530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
            565                 570                 575

Leu Lys Gly Thr Ser Tyr Lys Ile Cys Thr Asp Lys Met Phe Phe Val
            580                 585                 590

Lys Asn Pro Thr Asp Thr Gly His Gly Thr Val Val Met Gln Val Lys
            595                 600                 605

Val Ser Lys Gly Ala Pro Cys Arg Ile Pro Val Ile Val Ala Asp Asp
            610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
            645                 650                 655
```

```
Gly Asp Ser Tyr Ile Ile Val Gly Arg Gly Asp Ser Arg Leu Thr Tyr
            660                 665                 670

Gln Trp His Lys Glu Gly Ser Ser Ile Gly Lys Leu Phe Thr Gln Thr
        675                 680                 685

Met Lys Gly Val Glu Arg Leu Ala Val Met Gly Asp Thr Ala Trp Asp
    690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
            740                 745                 750

Thr Arg Asn Met Thr Met Ser Met Ser Met Ile Leu Val Gly Val Ile
        755                 760                 765

Met Met Phe Leu Ser Leu Gly Val Gly Ala Asp Gln Gly Cys Ala Ile
    770                 775                 780

Asn Phe Gly Arg Lys Gly Ser Gln Thr Ser Asn Thr Thr Lys Trp Ala
785                 790                 795                 800

Pro Pro Gly Gln Gly Ser Pro Gly Ser Lys Gly Glu Glu Leu Phe Thr
                805                 810                 815

Gly Val Val Pro Ile Leu Val Glu Leu Asp Gly Asp Val Asn Gly His
            820                 825                 830

Lys Phe Ser Val Ser Gly Glu Gly Glu Gly Asp Ala Thr Tyr Gly Lys
        835                 840                 845

Leu Thr Leu Lys Phe Ile Cys Thr Thr Gly Lys Leu Pro Val Pro Trp
    850                 855                 860

Pro Thr Leu Val Thr Thr Leu Thr Tyr Gly Val Gln Cys Phe Ser Arg
865                 870                 875                 880

Tyr Pro Asp His Met Lys Gln His Asp Phe Phe Lys Ser Ala Met Pro
                885                 890                 895

Glu Gly Tyr Val Gln Glu Arg Thr Ile Phe Phe Lys Asp Asp Gly Asn
            900                 905                 910

Tyr Lys Thr Arg Ala Glu Val Lys Phe Glu Gly Asp Thr Leu Val Asn
        915                 920                 925

Arg Ile Glu Leu Lys Gly Ile Asp Phe Lys Glu Asp Gly Asn Ile Leu
    930                 935                 940

Gly His Lys Leu Glu Tyr Asn Tyr Asn Ser His Asn Val Tyr Ile Met
945                 950                 955                 960

Ala Asp Lys Gln Lys Asn Gly Ile Lys Val Asn Phe Lys Ile Arg His
                965                 970                 975

Asn Ile Glu Asp Gly Ser Val Gln Leu Ala Asp His Tyr Gln Gln Asn
            980                 985                 990

Thr Pro Ile Gly Asp Gly Pro Val Leu Leu Pro Asp Asn His Tyr Leu
        995                 1000                1005

Ser Thr Gln Ser Ala Leu Ser Lys Asp Pro Asn Glu Lys Arg Asp
    1010                1015                1020

His Met Val Leu Leu Glu Phe Val Thr Ala Ala Gly Ile Thr Leu
    1025                1030                1035

Gly Met Asp Glu Leu Tyr Lys Ser Gly Ser Ser Pro Leu Ser His
    1040                1045                1050

Arg Ser Lys Arg Ser Leu Ser Cys Arg Pro Pro Met Val Lys Glu
    1055                1060                1065

Gly Ser Ser Ile Gly Lys Met Phe Glu Ser Thr Tyr Arg Gly Ala
```

```
              1070                1075                1080
Lys  Arg  Met  Ala  Ile  Leu  Gly  Glu  Thr  Ala  Trp  Asp  Phe  Gly  Ser
              1085                1090                1095

Val  Gly  Gly  Leu  Phe  Thr  Ser  Leu  Gly  Lys  Ala  Val  His  Gln  Val
              1100                1105                1110

Phe  Gly  Ser  Val  Tyr  Thr  Thr  Met  Phe  Gly  Gly  Val  Ser  Trp  Met
              1115                1120                1125

Ile  Arg  Ile  Leu  Ile  Gly  Phe  Leu  Val  Leu  Trp  Ile  Gly  Thr  Asn
              1130                1135                1140

Ser  Arg  Asn  Thr  Ser  Met  Ala  Met  Thr  Cys  Ile  Ala  Val  Gly  Gly
              1145                1150                1155

Ile  Thr  Leu  Phe  Leu  Gly  Phe  Thr  Val  Gly  Ala  Asp  Gln  Gly  Cys
              1160                1165                1170

Ala  Ile  Asn  Phe  Gly  Lys  Arg  Glu  Leu  Lys  Cys  Gly  Asp  Gly  Ile
              1175                1180                1185

Phe  Ile  Phe  Arg  Asp  Ser  Asp  Asp  Trp  Leu  Asn  Lys  Tyr  Ser  Tyr
              1190                1195                1200

Tyr  Pro  Glu  Asp  Pro  Val  Lys  Leu  Ala  Ser  Ile  Val  Lys  Ala  Ser
              1205                1210                1215

Phe  Glu  Glu  Gly  Lys  Cys  Gly  Leu  Asn  Ser  Val  Asp  Ser  Leu  Glu
              1220                1225                1230

His  Glu  Met  Trp  Arg  Ser  Arg  Ala  Asp  Glu  Ile  Asn  Ala  Ile  Phe
              1235                1240                1245

Glu  Glu  Asn  Glu  Val  Asp  Ile  Ser  Val  Val  Val  Gln  Asp  Pro  Lys
              1250                1255                1260

Asn  Val  Tyr  Gln  Arg  Gly  Thr  His  Pro  Phe  Ser  Arg  Ile  Arg  Asp
              1265                1270                1275

Gly  Leu  Gln  Tyr  Gly  Trp  Lys  Thr  Trp  Gly  Lys  Asn  Leu  Val  Phe
              1280                1285                1290

Ser  Pro  Gly  Arg  Lys  Asn  Gly  Ser  Phe  Ile  Ile  Asp  Gly  Lys  Ser
              1295                1300                1305

Arg  Lys  Glu  Cys  Pro  Phe  Ser  Asn  Arg  Val  Trp  Asn  Ser  Phe  Gln
              1310                1315                1320

Ile  Glu  Glu  Phe  Gly  Thr  Gly  Val  Phe  Thr  Thr  Arg  Val  Tyr  Met
              1325                1330                1335

Asp  Ala  Val  Phe  Glu  Tyr  Thr  Ile  Asp  Cys  Asp  Gly  Ser  Ile  Leu
              1340                1345                1350

Gly  Ala  Ala  Val  Asn  Gly  Lys  Lys  Ser  Ala  His  Gly  Ser  Pro  Thr
              1355                1360                1365

Phe  Trp  Met  Gly  Ser  His  Glu  Val  Asn  Gly  Thr  Trp  Met  Ile  His
              1370                1375                1380

Thr  Leu  Glu  Ala  Leu  Asp  Tyr  Lys  Glu  Cys  Glu  Trp  Pro  Leu  Thr
              1385                1390                1395

His  Thr  Ile  Gly  Thr  Ser  Val  Glu  Glu  Ser  Glu  Met  Phe  Met  Pro
              1400                1405                1410

Arg  Ser  Ile  Gly  Gly  Pro  Val  Ser  Ser  His  Asn  His  Ile  Pro  Gly
              1415                1420                1425

Tyr  Lys  Val  Gln  Thr  Asn  Gly  Pro  Trp  Met  Gln  Val  Pro  Leu  Glu
              1430                1435                1440

Val  Lys  Arg  Glu  Ala  Cys  Pro  Gly  Thr  Ser  Val  Ile  Ile  Asp  Gly
              1445                1450                1455

Asn  Cys  Asp  Gly  Arg  Gly  Lys  Ser  Thr  Arg  Ser  Thr  Thr  Asp  Ser
              1460                1465                1470
```

```
Gly Lys Val Ile Pro Glu Trp Cys Cys Arg Ser Cys Thr Met Pro
    1475            1480                1485

Pro Val Ser Phe His Gly Ser Asp Gly Cys Trp Tyr Pro Met Glu
    1490            1495                1500

Ile Arg Pro Arg Lys Thr His Glu Ser His Leu Val Arg Ser Trp
    1505            1510                1515

Val Thr Ala Gly Glu Ile His Ala Val Pro Phe Gly Leu Val Ser
    1520            1525                1530

Met Met Ile Ala Met Glu Val Val Leu Arg Lys Arg Gln Gly Pro
    1535            1540                1545

Lys Gln Met Leu Val Gly Val Val Leu Leu Gly Ala Met Leu
    1550            1555                1560

Val Gly Gln Val Thr Leu Leu Asp Leu Leu Lys Leu Thr Val Ala
    1565            1570                1575

Val Gly Leu His Phe His Glu Met Asn Asn Gly Gly Asp Ala Met
    1580            1585                1590

Tyr Met Ala Leu Ile Ala Ala Phe Ser Ile Arg Pro Gly Leu Leu
    1595            1600                1605

Ile Gly Phe Gly Leu Arg Thr Leu Trp Ser Pro Arg Glu Arg Leu
    1610            1615                1620

Val Leu Thr Leu Gly Ala Ala Met Val Glu Ile Ala Leu Gly Gly
    1625            1630                1635

Val Met Gly Gly Leu Trp Lys Tyr Leu Asn Ala Val Ser Leu Cys
    1640            1645                1650

Ile Leu Thr Ile Asn Ala Val Ala Ser Arg Lys Ala Ser Asn Thr
    1655            1660                1665

Ile Leu Pro Leu Met Ala Leu Leu Thr Pro Val Thr Met Ala Glu
    1670            1675                1680

Val Arg Leu Ala Ala Met Phe Phe Cys Ala Met Val Ile Ile Gly
    1685            1690                1695

Val Leu His Gln Asn Phe Lys Asp Thr Ser Met Gln Lys Thr Ile
    1700            1705                1710

Pro Leu Val Ala Leu Thr Leu Thr Ser Tyr Leu Gly Leu Thr Gln
    1715            1720                1725

Pro Phe Leu Gly Leu Cys Ala Phe Leu Ala Thr Arg Ile Phe Gly
    1730            1735                1740

Arg Arg Ser Ile Pro Val Asn Glu Ala Leu Ala Ala Ala Gly Leu
    1745            1750                1755

Val Gly Val Leu Ala Gly Leu Ala Phe Gln Glu Met Glu Asn Phe
    1760            1765                1770

Leu Gly Pro Ile Ala Val Gly Gly Leu Leu Met Met Leu Val Ser
    1775            1780                1785

Val Ala Gly Arg Val Asp Gly Leu Glu Leu Lys Lys Leu Gly Glu
    1790            1795                1800

Val Ser Trp Glu Glu Glu Ala Glu Ile Ser Gly Ser Ser Ala Arg
    1805            1810                1815

Tyr Asp Val Ala Leu Ser Glu Gln Gly Glu Phe Lys Leu Leu Ser
    1820            1825                1830

Glu Glu Lys Val Pro Trp Asp Gln Val Val Met Thr Ser Leu Ala
    1835            1840                1845

Leu Val Gly Ala Ala Leu His Pro Phe Ala Leu Leu Leu Val Leu
    1850            1855                1860
```

-continued

Ala Gly Trp Leu Phe His Val Arg Gly Ala Arg Ser Gly Asp
1865                    1870                1875

Val Leu Trp Asp Ile Pro Thr Pro Lys Ile Ile Glu Glu Cys Glu
1880                    1885                1890

His Leu Glu Asp Gly Ile Tyr Gly Ile Phe Gln Ser Thr Phe Leu
1895                    1900                1905

Gly Ala Ser Gln Arg Gly Val Gly Val Ala Gln Gly Gly Val Phe
1910                    1915                1920

His Thr Met Trp His Val Thr Arg Gly Ala Phe Leu Val Arg Asn
1925                    1930                1935

Gly Lys Lys Leu Ile Pro Ser Trp Ala Ser Val Lys Glu Asp Leu
1940                    1945                1950

Val Ala Tyr Gly Gly Ser Trp Lys Leu Glu Gly Arg Trp Asp Gly
1955                    1960                1965

Glu Glu Glu Val Gln Leu Ile Ala Ala Val Pro Gly Lys Asn Val
1970                    1975                1980

Val Asn Val Gln Thr Lys Pro Ser Leu Phe Lys Val Arg Asn Gly
1985                    1990                1995

Gly Glu Ile Gly Ala Val Ala Leu Asp Tyr Pro Ser Gly Thr Ser
2000                    2005                2010

Gly Ser Pro Ile Val Asn Arg Asn Gly Glu Val Ile Gly Leu Tyr
2015                    2020                2025

Gly Asn Gly Ile Leu Val Gly Asp Asn Ser Phe Val Ser Ala Ile
2030                    2035                2040

Ser Gln Thr Glu Val Lys Glu Glu Gly Lys Glu Glu Leu Gln Glu
2045                    2050                2055

Ile Pro Thr Met Leu Lys Lys Gly Met Thr Thr Val Leu Asp Phe
2060                    2065                2070

His Pro Gly Ala Gly Lys Thr Arg Arg Phe Leu Pro Gln Ile Leu
2075                    2080                2085

Ala Glu Cys Ala Arg Arg Arg Leu Arg Thr Leu Val Leu Ala Pro
2090                    2095                2100

Thr Arg Val Val Leu Ser Glu Met Lys Glu Ala Phe His Gly Leu
2105                    2110                2115

Asp Val Lys Phe His Thr Gln Ala Phe Ser Ala His Gly Ser Gly
2120                    2125                2130

Arg Glu Val Ile Asp Ala Met Cys His Ala Thr Leu Thr Tyr Arg
2135                    2140                2145

Met Leu Glu Pro Thr Arg Val Val Asn Trp Glu Val Ile Ile Met
2150                    2155                2160

Asp Glu Ala His Phe Leu Asp Pro Ala Ser Ile Ala Ala Arg Gly
2165                    2170                2175

Trp Ala Ala His Arg Ala Arg Ala Asn Glu Ser Ala Thr Ile Leu
2180                    2185                2190

Met Thr Ala Thr Pro Pro Gly Thr Ser Asp Glu Phe Pro His Ser
2195                    2200                2205

Asn Gly Glu Ile Glu Asp Val Gln Thr Asp Ile Pro Ser Glu Pro
2210                    2215                2220

Trp Asn Thr Gly His Asp Trp Ile Leu Ala Asp Lys Arg Pro Thr
2225                    2230                2235

Ala Trp Phe Leu Pro Ser Ile Arg Ala Ala Asn Val Met Ala Ala
2240                    2245                2250

Ser Leu Arg Lys Ala Gly Lys Ser Val Val Val Leu Asn Arg Lys

```
                2255                2260                2265
Thr Phe Glu Arg Glu Tyr Pro Thr Ile Lys Gln Lys Lys Pro Asp
    2270                2275                2280
Phe Ile Leu Ala Thr Asp Ile Ala Glu Met Gly Ala Asn Leu Cys
    2285                2290                2295
Val Glu Arg Val Leu Asp Cys Arg Thr Ala Phe Lys Pro Val Leu
    2300                2305                2310
Val Asp Glu Gly Arg Lys Val Ala Ile Lys Gly Pro Leu Arg Ile
    2315                2320                2325
Ser Ala Ser Ser Ala Ala Gln Arg Arg Gly Arg Ile Gly Arg Asn
    2330                2335                2340
Pro Asn Arg Asp Gly Asp Ser Tyr Tyr Tyr Ser Glu Pro Thr Ser
    2345                2350                2355
Glu Asn Asn Ala His His Val Cys Trp Leu Glu Ala Ser Met Leu
    2360                2365                2370
Leu Asp Asn Met Glu Val Arg Gly Gly Met Val Ala Pro Leu Tyr
    2375                2380                2385
Gly Val Glu Gly Thr Lys Thr Pro Val Ser Pro Gly Glu Met Arg
    2390                2395                2400
Leu Arg Asp Asp Gln Arg Lys Val Phe Arg Glu Leu Val Arg Asn
    2405                2410                2415
Cys Asp Leu Pro Val Trp Leu Ser Trp Gln Val Ala Lys Ala Gly
    2420                2425                2430
Leu Lys Thr Asn Asp Arg Lys Trp Cys Phe Glu Gly Pro Glu Glu
    2435                2440                2445
His Glu Ile Leu Asn Asp Ser Gly Glu Thr Val Lys Cys Arg Ala
    2450                2455                2460
Pro Gly Gly Ala Lys Lys Pro Leu Arg Pro Arg Trp Cys Asp Glu
    2465                2470                2475
Arg Val Ser Ser Asp Gln Ser Ala Leu Ser Glu Phe Ile Lys Phe
    2480                2485                2490
Ala Glu Gly Arg Arg Gly Ala Ala Glu Val Leu Val Val Leu Ser
    2495                2500                2505
Glu Leu Pro Asp Phe Leu Ala Lys Lys Gly Gly Glu Ala Met Asp
    2510                2515                2520
Thr Ile Ser Val Phe Leu His Ser Glu Glu Gly Ser Arg Ala Tyr
    2525                2530                2535
Arg Asn Ala Leu Ser Met Met Pro Glu Ala Met Thr Ile Val Met
    2540                2545                2550
Leu Phe Ile Leu Ala Gly Leu Leu Thr Ser Gly Met Val Ile Phe
    2555                2560                2565
Phe Met Ser Pro Lys Gly Ile Ser Arg Met Ser Met Ala Met Gly
    2570                2575                2580
Thr Met Ala Gly Cys Gly Tyr Leu Met Phe Leu Gly Gly Val Lys
    2585                2590                2595
Pro Thr His Ile Ser Tyr Val Met Leu Ile Phe Phe Val Leu Met
    2600                2605                2610
Val Val Val Ile Pro Glu Pro Gly Gln Gln Arg Ser Ile Gln Asp
    2615                2620                2625
Asn Gln Val Ala Tyr Leu Ile Ile Gly Ile Leu Thr Leu Val Ser
    2630                2635                2640
Ala Val Ala Ala Asn Glu Leu Gly Met Leu Glu Lys Thr Lys Glu
    2645                2650                2655
```

Asp Leu Phe Gly Lys Lys Asn Leu Ile Pro Ser Ser Ala Ser Pro
              2660                2665                2670

Trp Ser Trp Pro Asp Leu Asp Leu Lys Pro Gly Ala Ala Trp Thr
    2675                2680                2685

Val Tyr Val Gly Ile Val Thr Met Leu Ser Pro Met Leu His His
    2690                2695                2700

Trp Ile Lys Val Glu Tyr Gly Asn Leu Ser Leu Ser Gly Ile Ala
    2705                2710                2715

Gln Ser Ala Ser Val Leu Ser Phe Met Asp Lys Gly Ile Pro Phe
    2720                2725                2730

Met Lys Met Asn Ile Ser Val Ile Met Leu Leu Val Ser Gly Trp
    2735                2740                2745

Asn Ser Ile Thr Val Met Pro Leu Leu Cys Gly Ile Gly Cys Ala
    2750                2755                2760

Met Leu His Trp Ser Leu Ile Leu Pro Gly Ile Lys Ala Gln Gln
    2765                2770                2775

Ser Lys Leu Ala Gln Arg Arg Val Phe His Gly Val Ala Lys Asn
    2780                2785                2790

Pro Val Val Asp Gly Asn Pro Thr Val Asp Ile Glu Glu Ala Pro
    2795                2800                2805

Glu Met Pro Ala Leu Tyr Glu Lys Lys Leu Ala Leu Tyr Leu Leu
    2810                2815                2820

Leu Ala Leu Ser Leu Ala Ser Val Ala Met Cys Arg Thr Pro Phe
    2825                2830                2835

Ser Leu Ala Glu Gly Ile Val Leu Ala Ser Ala Ala Leu Gly Pro
    2840                2845                2850

Leu Ile Glu Gly Asn Thr Ser Leu Leu Trp Asn Gly Pro Met Ala
    2855                2860                2865

Val Ser Met Thr Gly Val Met Arg Gly Asn His Tyr Ala Phe Val
    2870                2875                2880

Gly Val Met Tyr Asn Leu Trp Lys Met Lys Thr Gly Arg Arg Gly
    2885                2890                2895

Ser Ala Asn Gly Lys Thr Leu Gly Glu Val Trp Lys Arg Glu Leu
    2900                2905                2910

Asn Leu Leu Asp Lys Arg Gln Phe Glu Leu Tyr Lys Arg Thr Asp
    2915                2920                2925

Ile Val Glu Val Asp Arg Asp Thr Ala Arg Arg His Leu Ala Glu
    2930                2935                2940

Gly Lys Val Asp Thr Gly Val Ala Val Ser Arg Gly Thr Ala Lys
    2945                2950                2955

Leu Arg Trp Phe His Glu Arg Gly Tyr Val Lys Leu Glu Gly Arg
    2960                2965                2970

Val Ile Asp Leu Gly Cys Gly Arg Gly Gly Trp Cys Tyr Tyr Ala
    2975                2980                2985

Ala Ala Gln Lys Glu Val Ser Gly Val Lys Gly Phe Thr Leu Gly
    2990                2995                3000

Arg Asp Gly His Glu Lys Pro Met Asn Val Gln Ser Leu Gly Trp
    3005                3010                3015

Asn Ile Ile Thr Phe Lys Asp Lys Thr Asp Ile His Arg Leu Glu
    3020                3025                3030

Pro Val Lys Cys Asp Thr Leu Leu Cys Asp Ile Gly Glu Ser Ser
    3035                3040                3045

```
Ser Ser Ser Val Thr Glu Gly Glu Arg Thr Val Arg Val Leu Asp
    3050              3055              3060

Thr Val Glu Lys Trp Leu Ala Cys Gly Val Asp Asn Phe Cys Val
3065              3070              3075

Lys Val Leu Ala Pro Tyr Met Pro Asp Val Leu Glu Lys Leu Glu
    3080              3085              3090

Leu Leu Gln Arg Arg Phe Gly Gly Thr Val Ile Arg Asn Pro Leu
3095              3100              3105

Ser Arg Asn Ser Thr His Glu Met Tyr Tyr Val Ser Gly Ala Arg
    3110              3115              3120

Ser Asn Val Thr Phe Thr Val Asn Gln Thr Ser Arg Leu Leu Met
3125              3130              3135

Arg Arg Met Arg Arg Pro Thr Gly Lys Val Thr Leu Glu Ala Asp
    3140              3145              3150

Val Ile Leu Pro Ile Gly Thr Arg Ser Val Glu Thr Asp Lys Gly
3155              3160              3165

Pro Leu Asp Lys Glu Ala Ile Glu Glu Arg Val Glu Arg Ile Lys
    3170              3175              3180

Ser Glu Tyr Met Thr Ser Trp Phe Tyr Asp Asn Asp Asn Pro Tyr
3185              3190              3195

Arg Thr Trp His Tyr Cys Gly Ser Tyr Val Thr Lys Thr Ser Gly
    3200              3205              3210

Ser Ala Ala Ser Met Val Asn Gly Val Ile Lys Ile Leu Thr Tyr
3215              3220              3225

Pro Trp Asp Arg Ile Glu Glu Val Thr Arg Met Ala Met Thr Asp
    3230              3235              3240

Thr Thr Pro Phe Gly Gln Gln Arg Val Phe Lys Glu Lys Val Asp
3245              3250              3255

Thr Arg Ala Lys Asp Pro Pro Ala Gly Thr Arg Lys Ile Met Lys
    3260              3265              3270

Val Val Asn Arg Trp Leu Phe Arg His Leu Ala Arg Glu Lys Ser
3275              3280              3285

Pro Arg Leu Cys Thr Lys Glu Glu Phe Ile Ala Lys Val Arg Ser
    3290              3295              3300

His Ala Ala Ile Gly Ala Tyr Leu Glu Glu Gln Glu Gln Trp Lys
3305              3310              3315

Thr Ala Asn Glu Ala Val Gln Asp Pro Lys Phe Trp Glu Leu Val
    3320              3325              3330

Asp Glu Glu Arg Lys Leu His Gln Gln Gly Arg Cys Arg Thr Cys
3335              3340              3345

Val Tyr Asn Met Met Gly Lys Arg Glu Lys Lys Leu Ser Glu Phe
    3350              3355              3360

Gly Lys Ala Lys Gly Ser Arg Ala Ile Trp Tyr Met Trp Leu Gly
3365              3370              3375

Ala Arg Tyr Leu Glu Phe Glu Ala Leu Gly Phe Leu Asn Glu Asp
    3380              3385              3390

His Trp Ala Ser Arg Glu Asn Ser Gly Gly Val Glu Gly Ile
3395              3400              3405

Gly Leu Gln Tyr Leu Gly Tyr Val Ile Arg Asp Leu Ala Ala Met
    3410              3415              3420

Asp Gly Gly Gly Phe Tyr Ala Asp Asp Thr Ala Gly Trp Asp Thr
3425              3430              3435

Arg Ile Thr Glu Ala Asp Leu Asp Asp Glu Gln Glu Ile Leu Asn
```

```
             3440           3445            3450
Tyr Met Ser Pro His His Lys Lys Leu Ala Gln Ala Val Met Glu
    3455            3460            3465
Met Thr Tyr Lys Asn Lys Val Val Lys Val Leu Arg Pro Ala Pro
    3470            3475            3480
Gly Gly Lys Ala Tyr Met Asp Val Ile Ser Arg Arg Asp Gln Arg
    3485            3490            3495
Gly Ser Gly Gln Val Val Thr Tyr Ala Leu Asn Thr Ile Thr Asn
    3500            3505            3510
Leu Lys Val Gln Leu Ile Arg Met Ala Glu Ala Glu Met Val Ile
    3515            3520            3525
His His Gln His Val Gln Asp Cys Asp Glu Ser Val Leu Thr Arg
    3530            3535            3540
Leu Glu Ala Trp Leu Thr Glu His Gly Cys Asn Arg Leu Lys Arg
    3545            3550            3555
Met Ala Val Ser Gly Asp Asp Cys Val Val Arg Pro Ile Asp Asp
    3560            3565            3570
Arg Phe Gly Leu Ala Leu Ser His Leu Asn Ala Met Ser Lys Val
    3575            3580            3585
Arg Lys Asp Ile Ser Glu Trp Gln Pro Ser Lys Gly Trp Asn Asp
    3590            3595            3600
Trp Glu Asn Val Pro Phe Cys Ser His His Phe His Glu Leu Gln
    3605            3610            3615
Leu Lys Asp Gly Arg Arg Ile Val Val Pro Cys Arg Glu Gln Asp
    3620            3625            3630
Glu Leu Ile Gly Arg Gly Arg Val Ser Pro Gly Asn Gly Trp Met
    3635            3640            3645
Ile Lys Glu Thr Ala Cys Leu Ser Lys Ala Tyr Ala Asn Met Trp
    3650            3655            3660
Ser Leu Met Tyr Phe His Lys Arg Asp Met Arg Leu Leu Ser Leu
    3665            3670            3675
Ala Val Ser Ser Ala Val Pro Thr Ser Trp Val Pro Gln Gly Arg
    3680            3685            3690
Thr Thr Trp Ser Ile His Gly Lys Gly Glu Trp Met Thr Thr Glu
    3695            3700            3705
Asp Met Leu Glu Val Trp Asn Arg Val Trp Ile Thr Asn Asn Pro
    3710            3715            3720
His Met Gln Asp Lys Thr Met Val Lys Lys Trp Arg Asp Val Pro
    3725            3730            3735
Tyr Leu Thr Lys Arg Gln Asp Lys Leu Cys Gly Ser Leu Ile Gly
    3740            3745            3750
Met Thr Asn Arg Ala Thr Trp Ala Ser His Ile His Leu Val Ile
    3755            3760            3765
His Arg Ile Arg Thr Leu Ile Gly Gln Glu Lys Tyr Thr Asp Tyr
    3770            3775            3780
Leu Thr Val Met Asp Arg Tyr Ser Val Asp Ala Asp Leu Gln Leu
    3785            3790            3795
Gly Glu Leu Ile
    3800

<210> SEQ ID NO 9
<211> LENGTH: 11929
<212> TYPE: DNA
<213> ORGANISM: Yellow fever virus
```

<400> SEQUENCE: 9

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgaccggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaacccctt ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg agggggtgca    1020
tggaggaact tgggtttcag ctaccctgga gcaagacaag tgtgtcactg ttatggcccc    1080
tgacaagcct tcattggaca tctcactaga gacagtagcc attgatagac ctgctgaggc    1140
gaggaaagtg tgttacaatg cagttctcac tcatgtgaag attaatgaca agtgccccag    1200
cactggagag gcccacctag ctgaagagaa cgaaggggac aatgcgtgca agcgcactta    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccagcat    1440
taagactctc aagtttgatg ccctgtcagg ctcccaggaa gtcgagttca ttgggtatgg    1500
aaaagctaca ctggaatgcc aggtgcaaac tcgcgttggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
```

```
ggtgtttggc tctgcctttc aggggctatt tggcggcttg aactggataa caaaggtcat    2340
catgggggcg gtacttatat ggggttggcat caacacaaga aacatgacaa tgtccatgag    2400
catgatcttg gtaggagtga tcatgatgtt tttgtctcta ggagttgggg cggatcaagg    2460
atgcgccatc aacttcggcc gaaagtcagg ggaagaacat gcagtcggaa atactacagg    2520
aagtagcaag ggcgaggagc tgttcaccgg ggtggtgccc atcctggtcg agctggacgg    2580
cgacgtaaac ggccacaagt tcagcgtgtc cggcgagggc gagggcgatg ccacctacgg    2640
caagctgacc ctgaagttca tctgcaccac cggcaagctg cccgtgccct ggcccaccct    2700
cgtgaccacc ctgacctacg gcgtgcagtg cttcagccgc tacccgacc acatgaagca    2760 gcacgacttc ttcaagtccg ccatgcccga aggctacgtc caggagcgca ccatcttctt    2820
caaggacgac ggcaactaca agacccgcgc cgaggtgaag ttcgagggcg acaccctggt    2880
gaaccgcatc gagctgaagg gcatcgactt caaggaggac ggcaacatcc tggggcacaa    2940
gctggagtac aactacaaca gccacaacgt ctatatcatg gccgacaagc agaagaacgg    3000
catcaaggtg aacttcaaga tccgccacaa catcgaggac ggcagcgtgc agctcgccga    3060
ccactaccag cagaacaccc ccatcggcga cggccccgtg ctgctgcccg acaaccacta    3120
cctgagcacc cagtccgccc tgagcaaaga ccccaacgag aagcgcgatc acatggtcct    3180
gctggagttc gtgaccgccg ccgggatcac tctcggcatg gacgagctgt acaagagtgg    3240
agggaaacag gaaggctcac ggacaaggcg ctcagtgctg atcccatccc atgctcaggg    3300
aaaagaggga agctcaatag gaacatcatt gggaaaggct gtgcaccagg tttttggaag    3360
tgtgtataca accatgtttg gaggagtctc atggatgatt agaatcctaa ttgggttctt    3420
agtgttgtgg attggcacga actcaaggaa cacttcaatg gctatgacgt gcatagctgt    3480
tggaggaatc actctgtttc tgggcttcac agttggcgcc gatcaaggat gcgccatcaa    3540
ctttggcaag agagagctca gtgcggaga tggtatcttc atatttagag actctgatga    3600
ctggctgaac aagtactcat actatccaga agatcctgtg aagcttgcat caatagtgaa    3660
agcctctttt gaagaaggga gtgtggcct aaattcagtt gactcccttg agcatgagat    3720
gtggagaagc agggcagatg agatcaatgc cattttgag gaaaacgagg tggacatttc    3780
tgttgtcgtg caggatccaa agaatgttta ccagagagga actcatccat tttccagaat    3840 tcggatggt ctgcagtatg gttggaagac ttggggtaag aaccttgtgt tctccccagg    3900
gaggaagaat ggaagcttca tcatagatgg aaagtccagg aaagaatgcc cgttttcaaa    3960
ccgggtctgg aattctttcc agatagagga gtttgggacg ggagtgttca ccacacgcgt    4020
gtacatggac gcagtctttg aatacaccat agactgcgat ggatctatct tgggtgcagc    4080
ggtgaacgga aaaagagtg cccatggctc tccaacattt tggatgggaa gtcatgaagt    4140
aaatgggaca tggatgatcc acaccttgga ggcattagat tacaaggagt gtgagtggcc    4200
actgacacat acgattggaa catcagttga agagagtgaa atgttcatgc cgagatcaat    4260
cggaggccca gttagctctc acaatcatat ccctggatac aaggttcaga cgaacggacc    4320
ttggatgcag gtaccactag aagtgaagag agaagcttgc ccagggacta gcgtgatcat    4380
tgatggcaac tgtgatggac ggggaaaatc aaccagatcc accacggata gcgggaaagt    4440
tattcctgaa tggtgttgcc gctcctgcac aatgccgcct gtgagcttcc atggtagtga    4500
tgggtgttgg tatcccatgg aaattaggcc aaggaaaacg catgaaagcc atctggtgcg    4560 ctcctggggtt acagctggag aaatacatgc tgtccctttt ggtttggtga gcatgatgat    4620
agcaatggaa gtggtcctaa ggaaaagaca gggaccaaag caaatgttgg ttggaggagt    4680
```

-continued

```
agtgctcttg ggagcaatgc tggtcgggca agtaactctc cttgatttgc tgaaactcac    4740
agtggctgtg ggattgcatt tccatgagat gaacaatgga ggagacgcca tgtatatggc    4800
gttgattgct gccttttcaa tcagaccagg gctgctcatc ggctttgggc tcaggaccct    4860
atggagccct cgggaacgcc ttgtgctgac cctaggagca gccatggtgg agattgcctt    4920
gggtggcgtg atgggcggcc tgtggaagta tctaaatgca gtttctctct gcatcctgac    4980
aataaatgct gttgcttcta ggaaagcatc aaataccatc ttgcccctca tggctctgtt    5040
gacacctgtc actatggctg aggtgagact tgccgcaatg ttcttttgtg ccatggttat    5100
catagggtc cttcaccaga atttcaagga cacctccatg cagaagacta tacctctggt     5160
ggccctcaca ctcacatctt acctgggctt gacacaacct tttttgggcc tgtgtgcatt    5220
tctggcaacc cgcatatttg ggcgaaggag tatcccagtg aatgaggcac tcgcagcagc    5280
tggtctagtg ggagtgctgg caggactggc ttttcaggag atggagaact tccttggtcc    5340
gattgcagtt ggaggactcc tgatgatgct ggttagcgtg gctgggaggg tggatgggct    5400
agagctcaag aagcttggtg aagtttcatg ggaagaggag gcggagatca gcgggagttc    5460
cgcccgctat gatgtggcac tcagtgaaca aggggagttc aagctgcttt ctgaagagaa    5520
agtgccatgg gaccaggttg tgatgacctc gctggccttg gttgggctg ccctccatcc     5580
atttgctctt ctgctggtcc ttgctgggtg gctgtttcat gtcaggggag ctaggagaag    5640
tggggatgtc ttgtgggata ttcccactcc taagatcatc gaggaatgtg aacatctgga    5700
ggatgggatt tatggcatat tccagtcaac cttcttgggg gcctcccagc gaggagtggg    5760
agtggcacag ggagggtgt tccacacaat gtggcatgtc acaagaggag ctttccttgt     5820
caggaatggc aagaagttga ttccatcttg ggcttcagta aaggaagacc ttgtcgccta    5880
tggtggctca tggaagttgg aaggcagatg ggatggagag gaagaggtcc agttgatcgc    5940
ggctgttcca ggaaagaacg tggtcaacgt ccagacaaaa ccgagcttgt tcaaagtgag    6000
gaatggggga gaaatcgggg ctgtcgctct tgactatccg agtggcactt caggatctcc    6060
tattgttaac aggaacggag aggtgattgg gctgtacggc aatggcatcc ttgtcggtga    6120
caactccttc gtgtccgcca tatcccagac tgaggtgaag gaagaaggaa aggaggagct    6180
ccaagagatc ccgacaatgc taaagaaagg aatgacaact gtccttgatt ttcatcctgg    6240
agctgggaag acaagacgtt tcctcccaca gatcttggcc gagtgcgcac ggagacgctt    6300
gcgcactctt tgtgttggccc ccaccagggt tgttctttct gaaatgaagg aggcttttca    6360
cggcctggac gtgaaattcc acacacaggc ttttttccgct cacggcagcg ggagagaagt    6420
cattgatgcc atgtgccatg ccaccctaac ttacaggatg ttggaaccaa ctagggttgt    6480
taactgggaa gtgatcatta tggatgaagc ccatttttg gatccagcta gcatagccgc     6540
tagaggttgg gcagcgcaca gagctagggc aaatgaaagt gcaacaatct tgatgacagc    6600
cacaccgcct gggactagtg atgaatttcc acattcaaat ggtgaaatag aagatgttca    6660
aacggacata cccagtgagc cctggaacac agggcatgac tggatcctgg ctgacaaaag    6720
gcccacggca tggttccttc catccatcag agctgcaaat gtcatggctg cctctttgcg    6780
taaggctgga aagagtgtgg tggtcctgaa caggaaaacc tttgagagag atacccac      6840
gataaagcag aagaaacctg actttatatt ggccactgac atagctgaaa tgggagccaa    6900
cctttgcgtg gagcgagtgc tggattgcag gacggctttt aagcctgtgc ttgtggatga    6960
agggaggaag gtggcaataa aagggccact tcgtatctcc gcatcctctg ctgctcaaag    7020
```

```
gaggggcgc attgggagaa atcccaacag agatggagac tcatactact attctgagcc    7080
tacaagtgaa ataatgccc accacgtctg ctggttggag ccctcaatgc tcttggacaa    7140
catggaggtg aggggtggaa tggtcgcccc actctatggc gttgaaggaa ctaaaacacc    7200
agtttcccct ggtgaaatga gactgaggga tgaccagagg aaagtcttca gagaactagt    7260
gaggaattgt gacctgcccg tttggctttc gtggcaagtg gccaaggctg gtttgaagac    7320
gaatgatcgt aagtggtgtt ttgaaggccc tgaggaacat gagatcttga atgacagcgg    7380
tgaaacagtg aagtgcaggg ctcctggagg agcaaagaag cctctgcgcc caaggtggtg    7440
tgatgaaagg gtgtcatctg accagagtgc gctgtctgaa tttattaagt ttgctgaagg    7500
taggagggga gctgctgaag tgctagttgt gctgagtgaa ctccctgatt tcctggctaa    7560
aaaaggtgga gaggcaatgg ataccatcag tgtgttcctc cactctgagg aaggctctag    7620
ggcttaccgc aatgcactat caatgatgcc tgaggcaatg acaatagtca tgctgtttat    7680
actggctgga ctactgacat cgggaatggt catcttttc atgtctccca aaggcatcag    7740
tagaatgtct atgcgatgg gcacaatggc cggctgtgga tatctcatgt tccttggagg    7800
cgtcaaaccc actcacatct cctatgtcat gctcatattc tttgtcctga tggtggttgt    7860
gatccccgag ccagggcaac aaaggtccat ccaagacaac caagtggcat acctcattat    7920
tggcatcctg acgctggttt cagcggtggc agccaacgag ctaggcatgc tggagaaaac    7980
caaagaggac ctctttggga agaagaactt aattccatct agtgcttcac cctggagttg    8040
gccggatctt gacctgaagc caggagctgc ctggacagtg tacgttggca ttgttacaat    8100
gctctctcca atgttgcacc actggatcaa agtcgaatat ggcaacctgt ctctgtctgg    8160
aatagcccag tcagcctcag tcctttcttt catggacaag gggataccat tcatgaagat    8220
gaatatctcg gtcataatgc tgctggtcag tggctggaat tcaataacag tgatgcctct    8280
gctctgtggc atagggtgcg ccatgctcca ctggtctctc attttacctg gaatcaaagc    8340
gcagcagtca aagcttgcac agagaagggt gttccatggc gttgccaaga acctgtggt    8400 tgatgggaat ccaacagttg acattgagga agctcctgaa atgcctgccc tttatgagaa    8460
gaaactggct ctatatctcc ttcttgctct cagcctagct tctgttgcca tgtgcagaac    8520 gccctttca ttggctgaag gcattgtcct agcatcagct gccttagggc cgctcataga    8580
gggaaacacc agccttcttt ggaatggacc catggctgtc tccatgacag gagtcatgag    8640
ggggaatcac tatgctttg tgggagtcat gtacaatcta tggaagatga aaactggacg    8700 ccggggagc gcgaatggaa aactttgggt tgaagtctgg aagagggaac tgaatctgtt    8760
ggacaagcga cagtttgagt tgtataaaag gaccgacatt gtggaggtgg atcgtgatac    8820
ggcacgcagg catttggccg aagggaaggt ggacaccggg gtggcggtct ccaggggac    8880 cgcaaagtta aggtggttcc atgagcgtgg ctatgtcaag ctggaaggta gggtgattga    8940 cctgggtgt ggccgcggag ctggtgttta ctacgctgct gcgcaaaagg aagtgagtgg    9000
ggtcaaagga tttactcttg aagagacgg ccatgagaaa cccatgaatg tgcaaagtct    9060
gggatggaac atcatcacct tcaaggacaa aactgatatc caccgcctag aaccagtgaa    9120
atgtgacacc cttttgtgtg acattggaga gtcatcatcg tcatcggtca cagaggggga    9180
aaggaccgtg agagttcttg atactgtaga aaatggctg gcttgtgggg ttgacaactt    9240
ctgtgtgaag gtgttagctc catacatgcc agatgttctt gagaaactgg aattgctcca    9300
aaggaggttt ggcggaacag tgatcaggaa ccctctctcc aggaattcca ctcatgaaat    9360
gtactacgtg tctggagccc gcagcaatgt cacatttact gtgaaccaaa catcccgcct    9420
```

```
cctgatgagg agaatgaggc gtccaactgg aaaagtgacc ctggaggctg acgtcatcct   9480
cccaattggg acacgcagtg ttgagacaga caagggaccc ctggacaaag aggccataga   9540
agaaagggtt gagaggataa aatctgagta catgacctct tggttttatg acaatgacaa   9600
cccctacagg acctggcact actgtggctc ctatgtcaca aaaacctcag gaagtgcggc   9660
gagcatggta aatggtgtta ttaaaattct gacatatcca tgggacagga tagaggaggt   9720
caccagaatg gcaatgactg acacaacccc ttttggacag caaagagtgt ttaaagaaaa   9780
agttgacacc agagcaaagg atccaccagc gggaactagg aagatcatga aagttgtcaa   9840
caggtggctg ttccgccacc tggccagaga aaagagcccc agactgtgca caaggaaga   9900 atttattgca aaagtccgaa gtcatgcagc cattggagct tacctggaag aacaagaaca   9960
gtggaagact gccaatgagg ctgtccaaga cccaaagttc tgggaactgg tggatgaaga  10020
aaggaagctg caccaacaag gcaggtgtcg gacttgtgtg tacaacatga tggggaaaag  10080
agagaagaag ctgtcagagt ttgggaaagc aaagggaagc cgtgccatat ggtatatgtg  10140
gctgggagcg cggtatcttg agtttgaggc cctgggattc ctgaatgagg accattgggc  10200
ttccagggaa aactcaggag gaggagtgga aggcattggc ttacaatacc taggatatgt  10260
gatcagagac ctggctgcaa tggatggtgg tggattctac gcggatgaca ccgctggatg  10320
ggacacgcgc atcacagagg cagaccttga tgatgaacag gagatcttga actacatgag  10380
cccacatcac aaaaaactgg cacaagcagt gatggaaatg acatacaaga caaagtggt  10440 gaaagtgttg agaccagccc caggagggaa agcctacatg gatgtcataa gtcgacgaga  10500
ccagagagga tccgggcagg tagtgactta tgctctgaac accatcacca acttgaaagt  10560
ccaattgatc agaatggcag aagcagagat ggtgatacat caccaacatg ttcaagattg  10620
tgatgaatca gttctgacca ggctggaggc atggctcact gagcacggat gtaacagact  10680
gaagaggatg gcggtgagtg gagacgactg tgtggtccgg cccatcgatg acaggttcgg  10740
cctggccctg tccatctca acgccatgtc caaggttaga aaggacatat ctgaatggca  10800
gccatcaaaa gggtgaatg attgggagaa tgtgccttc tgttcccacc acttccatga  10860
actacagctg aaggatggca ggaggattgt ggtgccttgc cgagaacagg acgagctcat  10920
tgggagagga agggtgtctc caggaaacgg ctggatgatc aaggaaacag cttgcctcag  10980
caaagcctat gccaacatgt ggtcactgat gtatttccac aaaagggaca tgaggctact  11040
gtcattggct gtttcctcag ctgttcccac ctcatgggtt ccacaaggac gcacaacatg  11100
gtcgattcat gggaaagggg agtggatgac cacggaagac atgcttgagg tgtggaacag  11160
agtatggata accaacaacc cacacatgca ggacaagaca atggtgaaaa aatggagaga  11220
tgtcccttat ctaaccaaga gacaagacaa gctgtgcgga tcactgattg gaatgaccaa  11280
tagggccacc tgggcctccc acatccattt agtcatccat cgtatccgaa cgctgattgg  11340
acaggagaaa tacactgact acctaacagt catggacagg tattctgtgg atgctgacct  11400
gcaactgggt gagcttatct gaaacaccat ctaacaggaa taaccgggat acaaaccacg  11460
ggtggagaac cggactcccc acaacctgaa accgggatat aaaccacggc tggagaaccg  11520
ggctccgcac ttaaaatgaa acagaaaccg ggataaaaac tacggatgga gaccggact  11580 ccacacattg agacagaaga agttgtcagc ccagaaccc acgcgagttt tgccactgct  11640
aagctgtgag gcagtgcagg ctgggacagc cgacctccag gttgcgaaaa acctggtttc  11700
tgggacctcc caccccagag taaaagaac ggagcctccg ctaccaccct cccacgtggt  11760
```

-continued

```
ggtagaaaga cggggtctag aggttagagg agaccctcca gggaacaaat agtgggacca    11820
tattgacgcc agggaaagac cggagtggtt ctctgctttt cctccagagg tctgtgagca    11880
cagtttgctc aagaataagc agacctttgg atgacaaaca caaaaccac               11929
```

<210> SEQ ID NO 10
<211> LENGTH: 3767
<212> TYPE: PRT
<213> ORGANISM: Yellow fever virus

<400> SEQUENCE: 10

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Ala Arg Lys Val Cys Tyr Asn Ala Val Leu Thr His
            340                 345                 350
```

```
Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415

Gln Thr Lys Ile Gln Tyr Val Ile Arg Ala Gln Leu His Val Gly Ala
                420                 425                 430

Lys Gln Glu Asn Trp Asn Thr Ser Ile Lys Thr Leu Lys Phe Asp Ala
            435                 440                 445

Leu Ser Gly Ser Gln Glu Val Glu Phe Ile Gly Tyr Gly Lys Ala Thr
        450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
                485                 490                 495

Asp Leu Thr Leu Pro Trp Gln Ser Gly Ser Gly Gly Val Trp Arg Glu
                500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
        530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
            595                 600                 605

Val Ser Lys Gly Ala Pro Cys Arg Ile Pro Val Ile Val Ala Asp Asp
        610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
            675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
            755                 760                 765
```

```
Met Met Phe Leu Ser Leu Gly Val Gly Ala Asp Gln Gly Cys Ala Ile
770                 775                 780
Asn Phe Gly Arg Lys Ser Gly Glu Glu His Ala Val Gly Asn Thr Thr
785                 790                 795                 800
Gly Ser Ser Lys Gly Glu Glu Leu Phe Thr Gly Val Val Pro Ile Leu
                805                 810                 815
Val Glu Leu Asp Gly Asp Val Asn Gly His Lys Phe Ser Val Ser Gly
                820                 825                 830
Glu Gly Glu Gly Asp Ala Thr Tyr Gly Lys Leu Thr Leu Lys Phe Ile
                835                 840                 845
Cys Thr Thr Gly Lys Leu Pro Val Pro Trp Pro Thr Leu Val Thr Thr
850                 855                 860
Leu Thr Tyr Gly Val Gln Cys Phe Ser Arg Tyr Pro Asp His Met Lys
865                 870                 875                 880
Gln His Asp Phe Phe Lys Ser Ala Met Pro Glu Gly Tyr Val Gln Glu
                885                 890                 895
Arg Thr Ile Phe Phe Lys Asp Asp Gly Asn Tyr Lys Thr Arg Ala Glu
                900                 905                 910
Val Lys Phe Glu Gly Asp Thr Leu Val Asn Arg Ile Glu Leu Lys Gly
                915                 920                 925
Ile Asp Phe Lys Glu Asp Gly Asn Ile Leu Gly His Lys Leu Glu Tyr
930                 935                 940
Asn Tyr Asn Ser His Asn Val Tyr Ile Met Ala Asp Lys Gln Lys Asn
945                 950                 955                 960
Gly Ile Lys Val Asn Phe Lys Ile Arg His Asn Ile Glu Asp Gly Ser
                965                 970                 975
Val Gln Leu Ala Asp His Tyr Gln Gln Asn Thr Pro Ile Gly Asp Gly
                980                 985                 990
Pro Val Leu Leu Pro Asp Asn His Tyr Leu Ser Thr Gln Ser Ala Leu
                995                 1000                1005
Ser Lys Asp Pro Asn Glu Lys Arg Asp His Met Val Leu Leu Glu
    1010                1015                1020
Phe Val Thr Ala Ala Gly Ile Thr Leu Gly Met Asp Glu Leu Tyr
    1025                1030                1035
Lys Ser Gly Gly Lys Gln Glu Gly Ser Arg Thr Arg Arg Ser Val
    1040                1045                1050
Leu Ile Pro Ser His Ala Gln Gly Lys Glu Gly Ser Ser Ile Gly
    1055                1060                1065
Thr Ser Leu Gly Lys Ala Val His Gln Val Phe Gly Ser Val Tyr
    1070                1075                1080
Thr Thr Met Phe Gly Gly Val Ser Trp Met Ile Arg Ile Leu Ile
    1085                1090                1095
Gly Phe Leu Val Leu Trp Ile Gly Thr Asn Ser Arg Asn Thr Ser
    1100                1105                1110
Met Ala Met Thr Cys Ile Ala Val Gly Gly Ile Thr Leu Phe Leu
    1115                1120                1125
Gly Phe Thr Val Gly Ala Asp Gln Gly Cys Ala Ile Asn Phe Gly
    1130                1135                1140
Lys Arg Glu Leu Lys Cys Gly Asp Gly Ile Phe Ile Phe Arg Asp
    1145                1150                1155
Ser Asp Asp Trp Leu Asn Lys Tyr Ser Tyr Tyr Pro Glu Asp Pro
    1160                1165                1170
Val Lys Leu Ala Ser Ile Val Lys Ala Ser Phe Glu Glu Gly Lys
```

-continued

```
                  1175                1180                1185

Cys  Gly  Leu  Asn  Ser  Val  Asp  Ser  Leu  Glu  His  Glu  Met  Trp  Arg
         1190                1195                1200

Ser  Arg  Ala  Asp  Glu  Ile  Asn  Ala  Ile  Phe  Glu  Glu  Asn  Glu  Val
         1205                1210                1215

Asp  Ile  Ser  Val  Val  Val  Gln  Asp  Pro  Lys  Asn  Val  Tyr  Gln  Arg
         1220                1225                1230

Gly  Thr  His  Pro  Phe  Ser  Arg  Ile  Arg  Asp  Gly  Leu  Gln  Tyr  Gly
         1235                1240                1245

Trp  Lys  Thr  Trp  Gly  Lys  Asn  Leu  Val  Phe  Ser  Pro  Gly  Arg  Lys
         1250                1255                1260

Asn  Gly  Ser  Phe  Ile  Ile  Asp  Gly  Lys  Ser  Arg  Lys  Glu  Cys  Pro
         1265                1270                1275

Phe  Ser  Asn  Arg  Val  Trp  Asn  Ser  Phe  Gln  Ile  Glu  Glu  Phe  Gly
         1280                1285                1290

Thr  Gly  Val  Phe  Thr  Thr  Arg  Val  Tyr  Met  Asp  Ala  Val  Phe  Glu
         1295                1300                1305

Tyr  Thr  Ile  Asp  Cys  Asp  Gly  Ser  Ile  Leu  Gly  Ala  Ala  Val  Asn
         1310                1315                1320

Gly  Lys  Lys  Ser  Ala  His  Gly  Ser  Pro  Thr  Phe  Trp  Met  Gly  Ser
         1325                1330                1335

His  Glu  Val  Asn  Gly  Thr  Trp  Met  Ile  His  Thr  Leu  Glu  Ala  Leu
         1340                1345                1350

Asp  Tyr  Lys  Glu  Cys  Glu  Trp  Pro  Leu  Thr  His  Thr  Ile  Gly  Thr
         1355                1360                1365

Ser  Val  Glu  Glu  Ser  Glu  Met  Phe  Met  Pro  Arg  Ser  Ile  Gly  Gly
         1370                1375                1380

Pro  Val  Ser  Ser  His  Asn  His  Ile  Pro  Gly  Tyr  Lys  Val  Gln  Thr
         1385                1390                1395

Asn  Gly  Pro  Trp  Met  Gln  Val  Pro  Leu  Glu  Val  Lys  Arg  Glu  Ala
         1400                1405                1410

Cys  Pro  Gly  Thr  Ser  Val  Ile  Ile  Asp  Gly  Asn  Cys  Asp  Gly  Arg
         1415                1420                1425

Gly  Lys  Ser  Thr  Arg  Ser  Thr  Thr  Asp  Ser  Gly  Lys  Val  Ile  Pro
         1430                1435                1440

Glu  Trp  Cys  Cys  Arg  Ser  Cys  Thr  Met  Pro  Pro  Val  Ser  Phe  His
         1445                1450                1455

Gly  Ser  Asp  Gly  Cys  Trp  Tyr  Pro  Met  Glu  Ile  Arg  Pro  Arg  Lys
         1460                1465                1470

Thr  His  Glu  Ser  His  Leu  Val  Arg  Ser  Trp  Val  Thr  Ala  Gly  Glu
         1475                1480                1485

Ile  His  Ala  Val  Pro  Phe  Gly  Leu  Val  Ser  Met  Met  Ile  Ala  Met
         1490                1495                1500

Glu  Val  Val  Leu  Arg  Lys  Arg  Gln  Gly  Pro  Lys  Gln  Met  Leu  Val
         1505                1510                1515

Gly  Gly  Val  Val  Leu  Leu  Gly  Ala  Met  Leu  Val  Gly  Gln  Val  Thr
         1520                1525                1530

Leu  Leu  Asp  Leu  Leu  Lys  Leu  Thr  Val  Ala  Val  Gly  Leu  His  Phe
         1535                1540                1545

His  Glu  Met  Asn  Asn  Gly  Gly  Asp  Ala  Met  Tyr  Met  Ala  Leu  Ile
         1550                1555                1560

Ala  Ala  Phe  Ser  Ile  Arg  Pro  Gly  Leu  Leu  Ile  Gly  Phe  Gly  Leu
         1565                1570                1575
```

```
Arg Thr Leu Trp Ser Pro Arg Glu Arg Leu Val Leu Thr Leu Gly
    1580            1585                1590

Ala Ala Met Val Glu Ile Ala Leu Gly Gly Val Met Gly Gly Leu
    1595            1600                1605

Trp Lys Tyr Leu Asn Ala Val Ser Leu Cys Ile Leu Thr Ile Asn
    1610            1615                1620

Ala Val Ala Ser Arg Lys Ala Ser Asn Thr Ile Leu Pro Leu Met
    1625            1630                1635

Ala Leu Leu Thr Pro Val Thr Met Ala Glu Val Arg Leu Ala Ala
    1640            1645                1650

Met Phe Phe Cys Ala Met Val Ile Ile Gly Val Leu His Gln Asn
    1655            1660                1665

Phe Lys Asp Thr Ser Met Gln Lys Thr Ile Pro Leu Val Ala Leu
    1670            1675                1680

Thr Leu Thr Ser Tyr Leu Gly Leu Thr Gln Pro Phe Leu Gly Leu
    1685            1690                1695

Cys Ala Phe Leu Ala Thr Arg Ile Phe Gly Arg Arg Ser Ile Pro
    1700            1705                1710

Val Asn Glu Ala Leu Ala Ala Ala Gly Leu Val Gly Val Leu Ala
    1715            1720                1725

Gly Leu Ala Phe Gln Glu Met Glu Asn Phe Leu Gly Pro Ile Ala
    1730            1735                1740

Val Gly Gly Leu Leu Met Met Leu Val Ser Val Ala Gly Arg Val
    1745            1750                1755

Asp Gly Leu Glu Leu Lys Lys Leu Gly Glu Val Ser Trp Glu Glu
    1760            1765                1770

Glu Ala Glu Ile Ser Gly Ser Ser Ala Arg Tyr Asp Val Ala Leu
    1775            1780                1785

Ser Glu Gln Gly Glu Phe Lys Leu Leu Ser Glu Lys Val Pro
    1790            1795                1800

Trp Asp Gln Val Val Met Thr Ser Leu Ala Leu Val Gly Ala Ala
    1805            1810                1815

Leu His Pro Phe Ala Leu Leu Leu Val Leu Ala Gly Trp Leu Phe
    1820            1825                1830

His Val Arg Gly Ala Arg Arg Ser Gly Asp Val Leu Trp Asp Ile
    1835            1840                1845

Pro Thr Pro Lys Ile Ile Glu Glu Cys Glu His Leu Glu Asp Gly
    1850            1855                1860

Ile Tyr Gly Ile Phe Gln Ser Thr Phe Leu Gly Ala Ser Gln Arg
    1865            1870                1875

Gly Val Gly Val Ala Gln Gly Gly Val Phe His Thr Met Trp His
    1880            1885                1890

Val Thr Arg Gly Ala Phe Leu Val Arg Asn Gly Lys Lys Leu Ile
    1895            1900                1905

Pro Ser Trp Ala Ser Val Lys Glu Asp Leu Val Ala Tyr Gly Gly
    1910            1915                1920

Ser Trp Lys Leu Glu Gly Arg Trp Asp Gly Glu Glu Val Gln
    1925            1930                1935

Leu Ile Ala Ala Val Pro Gly Lys Asn Val Val Asn Val Gln Thr
    1940            1945                1950

Lys Pro Ser Leu Phe Lys Val Arg Asn Gly Gly Glu Ile Gly Ala
    1955            1960                1965
```

```
Val Ala Leu Asp Tyr Pro Ser Gly Thr Ser Gly Ser Pro Ile Val
1970                1975                1980

Asn Arg Asn Gly Glu Val Ile Gly Leu Tyr Gly Asn Gly Ile Leu
1985                1990                1995

Val Gly Asp Asn Ser Phe Val Ser Ala Ile Ser Gln Thr Glu Val
2000                2005                2010

Lys Glu Glu Gly Lys Glu Glu Leu Gln Glu Ile Pro Thr Met Leu
2015                2020                2025

Lys Lys Gly Met Thr Thr Val Leu Asp Phe His Pro Gly Ala Gly
2030                2035                2040

Lys Thr Arg Arg Phe Leu Pro Gln Ile Leu Ala Glu Cys Ala Arg
2045                2050                2055

Arg Arg Leu Arg Thr Leu Val Leu Ala Pro Thr Arg Val Val Leu
2060                2065                2070

Ser Glu Met Lys Glu Ala Phe His Gly Leu Asp Val Lys Phe His
2075                2080                2085

Thr Gln Ala Phe Ser Ala His Gly Ser Gly Arg Glu Val Ile Asp
2090                2095                2100

Ala Met Cys His Ala Thr Leu Thr Tyr Arg Met Leu Glu Pro Thr
2105                2110                2115

Arg Val Val Asn Trp Glu Val Ile Ile Met Asp Glu Ala His Phe
2120                2125                2130

Leu Asp Pro Ala Ser Ile Ala Ala Arg Gly Trp Ala Ala His Arg
2135                2140                2145

Ala Arg Ala Asn Glu Ser Ala Thr Ile Leu Met Thr Ala Thr Pro
2150                2155                2160

Pro Gly Thr Ser Asp Glu Phe Pro His Ser Asn Gly Glu Ile Glu
2165                2170                2175

Asp Val Gln Thr Asp Ile Pro Ser Glu Pro Trp Asn Thr Gly His
2180                2185                2190

Asp Trp Ile Leu Ala Asp Lys Arg Pro Thr Ala Trp Phe Leu Pro
2195                2200                2205

Ser Ile Arg Ala Ala Asn Val Met Ala Ala Ser Leu Arg Lys Ala
2210                2215                2220

Gly Lys Ser Val Val Val Leu Asn Arg Lys Thr Phe Glu Arg Glu
2225                2230                2235

Tyr Pro Thr Ile Lys Gln Lys Lys Pro Asp Phe Ile Leu Ala Thr
2240                2245                2250

Asp Ile Ala Glu Met Gly Ala Asn Leu Cys Val Glu Arg Val Leu
2255                2260                2265

Asp Cys Arg Thr Ala Phe Lys Pro Val Leu Val Asp Glu Gly Arg
2270                2275                2280

Lys Val Ala Ile Lys Gly Pro Leu Arg Ile Ser Ala Ser Ser Ala
2285                2290                2295

Ala Gln Arg Arg Gly Arg Ile Gly Arg Asn Pro Asn Arg Asp Gly
2300                2305                2310

Asp Ser Tyr Tyr Tyr Ser Glu Pro Thr Ser Glu Asn Asn Ala His
2315                2320                2325

His Val Cys Trp Leu Glu Ala Ser Met Leu Leu Asp Asn Met Glu
2330                2335                2340

Val Arg Gly Gly Met Val Ala Pro Leu Tyr Gly Val Glu Gly Thr
2345                2350                2355

Lys Thr Pro Val Ser Pro Gly Glu Met Arg Leu Arg Asp Asp Gln
```

-continued

```
                  2360              2365              2370
Arg Lys Val Phe Arg Glu Leu Val Arg Asn Cys Asp Leu Pro Val
    2375              2380              2385
Trp Leu Ser Trp Gln Val Ala Lys Ala Gly Leu Lys Thr Asn Asp
    2390              2395              2400
Arg Lys Trp Cys Phe Glu Gly Pro Glu His Glu Ile Leu Asn
    2405              2410              2415
Asp Ser Gly Glu Thr Val Lys Cys Arg Ala Pro Gly Gly Ala Lys
    2420              2425              2430
Lys Pro Leu Arg Pro Arg Trp Cys Asp Glu Arg Val Ser Ser Asp
    2435              2440              2445
Gln Ser Ala Leu Ser Glu Phe Ile Lys Phe Ala Glu Gly Arg Arg
    2450              2455              2460
Gly Ala Ala Glu Val Leu Val Val Leu Ser Glu Leu Pro Asp Phe
    2465              2470              2475
Leu Ala Lys Lys Gly Gly Glu Ala Met Asp Thr Ile Ser Val Phe
    2480              2485              2490
Leu His Ser Glu Glu Gly Ser Arg Ala Tyr Arg Asn Ala Leu Ser
    2495              2500              2505
Met Met Pro Glu Ala Met Thr Ile Val Met Leu Phe Ile Leu Ala
    2510              2515              2520
Gly Leu Leu Thr Ser Gly Met Val Ile Phe Phe Met Ser Pro Lys
    2525              2530              2535
Gly Ile Ser Arg Met Ser Met Ala Met Gly Thr Met Ala Gly Cys
    2540              2545              2550
Gly Tyr Leu Met Phe Leu Gly Gly Val Lys Pro Thr His Ile Ser
    2555              2560              2565
Tyr Val Met Leu Ile Phe Phe Val Leu Met Val Val Val Ile Pro
    2570              2575              2580
Glu Pro Gly Gln Gln Arg Ser Ile Gln Asp Asn Gln Val Ala Tyr
    2585              2590              2595
Leu Ile Ile Gly Ile Leu Thr Leu Val Ser Ala Val Ala Ala Asn
    2600              2605              2610
Glu Leu Gly Met Leu Glu Lys Thr Lys Glu Asp Leu Phe Gly Lys
    2615              2620              2625
Lys Asn Leu Ile Pro Ser Ser Ala Ser Pro Trp Ser Trp Pro Asp
    2630              2635              2640
Leu Asp Leu Lys Pro Gly Ala Ala Trp Thr Val Tyr Val Gly Ile
    2645              2650              2655
Val Thr Met Leu Ser Pro Met Leu His His Trp Ile Lys Val Glu
    2660              2665              2670
Tyr Gly Asn Leu Ser Leu Ser Gly Ile Ala Gln Ser Ala Ser Val
    2675              2680              2685
Leu Ser Phe Met Asp Lys Gly Ile Pro Phe Met Lys Met Asn Ile
    2690              2695              2700
Ser Val Ile Met Leu Leu Val Ser Gly Trp Asn Ser Ile Thr Val
    2705              2710              2715
Met Pro Leu Leu Cys Gly Ile Gly Cys Ala Met Leu His Trp Ser
    2720              2725              2730
Leu Ile Leu Pro Gly Ile Lys Ala Gln Gln Ser Lys Leu Ala Gln
    2735              2740              2745
Arg Arg Val Phe His Gly Val Ala Lys Asn Pro Val Val Asp Gly
    2750              2755              2760
```

-continued

```
Asn Pro Thr Val Asp Ile Glu Glu Ala Pro Glu Met Pro Ala Leu
        2765            2770            2775

Tyr Glu Lys Lys Leu Ala Leu Tyr Leu Leu Leu Ala Leu Ser Leu
        2780            2785            2790

Ala Ser Val Ala Met Cys Arg Thr Pro Phe Ser Leu Ala Glu Gly
        2795            2800            2805

Ile Val Leu Ala Ser Ala Ala Leu Gly Pro Leu Ile Glu Gly Asn
        2810            2815            2820

Thr Ser Leu Leu Trp Asn Gly Pro Met Ala Val Ser Met Thr Gly
        2825            2830            2835

Val Met Arg Gly Asn His Tyr Ala Phe Val Gly Val Met Tyr Asn
        2840            2845            2850

Leu Trp Lys Met Lys Thr Gly Arg Arg Gly Ser Ala Asn Gly Lys
        2855            2860            2865

Thr Leu Gly Glu Val Trp Lys Arg Glu Leu Asn Leu Leu Asp Lys
        2870            2875            2880

Arg Gln Phe Glu Leu Tyr Lys Arg Thr Asp Ile Val Glu Val Asp
        2885            2890            2895

Arg Asp Thr Ala Arg Arg His Leu Ala Glu Gly Lys Val Asp Thr
        2900            2905            2910

Gly Val Ala Val Ser Arg Gly Thr Ala Lys Leu Arg Trp Phe His
        2915            2920            2925

Glu Arg Gly Tyr Val Lys Leu Glu Gly Arg Val Ile Asp Leu Gly
        2930            2935            2940

Cys Gly Arg Gly Gly Trp Cys Tyr Tyr Ala Ala Ala Gln Lys Glu
        2945            2950            2955

Val Ser Gly Val Lys Gly Phe Thr Leu Gly Arg Asp Gly His Glu
        2960            2965            2970

Lys Pro Met Asn Val Gln Ser Leu Gly Trp Asn Ile Ile Thr Phe
        2975            2980            2985

Lys Asp Lys Thr Asp Ile His Arg Leu Glu Pro Val Lys Cys Asp
        2990            2995            3000

Thr Leu Leu Cys Asp Ile Gly Glu Ser Ser Ser Ser Val Thr
        3005            3010            3015

Glu Gly Glu Arg Thr Val Arg Val Leu Asp Thr Val Glu Lys Trp
        3020            3025            3030

Leu Ala Cys Gly Val Asp Asn Phe Cys Val Lys Val Leu Ala Pro
        3035            3040            3045

Tyr Met Pro Asp Val Leu Glu Lys Leu Glu Leu Leu Gln Arg Arg
        3050            3055            3060

Phe Gly Gly Thr Val Ile Arg Asn Pro Leu Ser Arg Asn Ser Thr
        3065            3070            3075

His Glu Met Tyr Tyr Val Ser Gly Ala Arg Ser Asn Val Thr Phe
        3080            3085            3090

Thr Val Asn Gln Thr Ser Arg Leu Leu Met Arg Arg Met Arg Arg
        3095            3100            3105

Pro Thr Gly Lys Val Thr Leu Glu Ala Asp Val Ile Leu Pro Ile
        3110            3115            3120

Gly Thr Arg Ser Val Glu Thr Asp Lys Gly Pro Leu Asp Lys Glu
        3125            3130            3135

Ala Ile Glu Glu Arg Val Glu Arg Ile Lys Ser Glu Tyr Met Thr
        3140            3145            3150
```

```
Ser Trp Phe Tyr Asp Asn Asp Asn Pro Tyr Arg Thr Trp His Tyr
3155                3160                3165

Cys Gly Ser Tyr Val Thr Lys Thr Ser Gly Ser Ala Ala Ser Met
3170                3175                3180

Val Asn Gly Val Ile Lys Ile Leu Thr Tyr Pro Trp Asp Arg Ile
3185                3190                3195

Glu Glu Val Thr Arg Met Ala Met Thr Asp Thr Thr Pro Phe Gly
3200                3205                3210

Gln Gln Arg Val Phe Lys Glu Lys Val Asp Thr Arg Ala Lys Asp
3215                3220                3225

Pro Pro Ala Gly Thr Arg Lys Ile Met Lys Val Val Asn Arg Trp
3230                3235                3240

Leu Phe Arg His Leu Ala Arg Glu Lys Ser Pro Arg Leu Cys Thr
3245                3250                3255

Lys Glu Glu Phe Ile Ala Lys Val Arg Ser His Ala Ala Ile Gly
3260                3265                3270

Ala Tyr Leu Glu Glu Gln Glu Gln Trp Lys Thr Ala Asn Glu Ala
3275                3280                3285

Val Gln Asp Pro Lys Phe Trp Glu Leu Val Asp Glu Glu Arg Lys
3290                3295                3300

Leu His Gln Gln Gly Arg Cys Arg Thr Cys Val Tyr Asn Met Met
3305                3310                3315

Gly Lys Arg Glu Lys Lys Leu Ser Glu Phe Gly Lys Ala Lys Gly
3320                3325                3330

Ser Arg Ala Ile Trp Tyr Met Trp Leu Gly Ala Arg Tyr Leu Glu
3335                3340                3345

Phe Glu Ala Leu Gly Phe Leu Asn Glu Asp His Trp Ala Ser Arg
3350                3355                3360

Glu Asn Ser Gly Gly Gly Val Glu Gly Ile Gly Leu Gln Tyr Leu
3365                3370                3375

Gly Tyr Val Ile Arg Asp Leu Ala Ala Met Asp Gly Gly Gly Phe
3380                3385                3390

Tyr Ala Asp Asp Thr Ala Gly Trp Asp Thr Arg Ile Thr Glu Ala
3395                3400                3405

Asp Leu Asp Asp Glu Gln Glu Ile Leu Asn Tyr Met Ser Pro His
3410                3415                3420

His Lys Lys Leu Ala Gln Ala Val Met Glu Met Thr Tyr Lys Asn
3425                3430                3435

Lys Val Val Lys Val Leu Arg Pro Ala Pro Gly Gly Lys Ala Tyr
3440                3445                3450

Met Asp Val Ile Ser Arg Arg Asp Gln Arg Gly Ser Gly Gln Val
3455                3460                3465

Val Thr Tyr Ala Leu Asn Thr Ile Thr Asn Leu Lys Val Gln Leu
3470                3475                3480

Ile Arg Met Ala Glu Ala Glu Met Val Ile His His Gln His Val
3485                3490                3495

Gln Asp Cys Asp Glu Ser Val Leu Thr Arg Leu Glu Ala Trp Leu
3500                3505                3510

Thr Glu His Gly Cys Asn Arg Leu Lys Arg Met Ala Val Ser Gly
3515                3520                3525

Asp Asp Cys Val Val Arg Pro Ile Asp Asp Arg Phe Gly Leu Ala
3530                3535                3540

Leu Ser His Leu Asn Ala Met Ser Lys Val Arg Lys Asp Ile Ser
```

|  |  |  | 3545 |  |  |  | 3550 |  |  |  | 3555 |  |
|---|---|---|---|---|---|---|---|---|---|---|---|---|

Glu Trp Gln Pro Ser Lys Gly Trp Asn Asp Trp Glu Asn Val Pro
3560                3565                3570

Phe Cys Ser His His Phe His Glu Leu Gln Leu Lys Asp Gly Arg
3575                3580                3585

Arg Ile Val Val Pro Cys Arg Glu Gln Asp Glu Leu Ile Gly Arg
3590                3595                3600

Gly Arg Val Ser Pro Gly Asn Gly Trp Met Ile Lys Glu Thr Ala
3605                3610                3615

Cys Leu Ser Lys Ala Tyr Ala Asn Met Trp Ser Leu Met Tyr Phe
3620                3625                3630

His Lys Arg Asp Met Arg Leu Leu Ser Leu Ala Val Ser Ser Ala
3635                3640                3645

Val Pro Thr Ser Trp Val Pro Gln Gly Arg Thr Thr Trp Ser Ile
3650                3655                3660

His Gly Lys Gly Glu Trp Met Thr Thr Glu Asp Met Leu Glu Val
3665                3670                3675

Trp Asn Arg Val Trp Ile Thr Asn Asn Pro His Met Gln Asp Lys
3680                3685                3690

Thr Met Val Lys Lys Trp Arg Asp Val Pro Tyr Leu Thr Lys Arg
3695                3700                3705

Gln Asp Lys Leu Cys Gly Ser Leu Ile Gly Met Thr Asn Arg Ala
3710                3715                3720

Thr Trp Ala Ser His Ile His Leu Val Ile His Arg Ile Arg Thr
3725                3730                3735

Leu Ile Gly Gln Glu Lys Tyr Thr Asp Tyr Leu Thr Val Met Asp
3740                3745                3750

Arg Tyr Ser Val Asp Ala Asp Leu Gln Leu Gly Glu Leu Ile
3755                3760                3765

<210> SEQ ID NO 11
<211> LENGTH: 12046
<212> TYPE: DNA
<213> ORGANISM: Yellow fever virus

<400> SEQUENCE: 11

| agtaaatcct | gtgtgctaat | tgaggtgcat | tggtctgcaa | atcgagttgc | taggcaataa | 60 |
|---|---|---|---|---|---|---|
| acacatttgg | attaatttta | atcgttcgtt | gagcgattag | cagagaactg | accagaacat | 120 |
| gtctggtcgt | aaagctcagg | gaaaaaccct | gggcgtcaat | atggtacgac | gaggagttcg | 180 |
| ctccttgtca | aacaaaataa | aacaaaaaac | aaaacaaatt | ggaaacagac | ctggaccttc | 240 |
| aagaggtgtt | caaggattta | tcttttttctt | tttgttcaac | attttgactg | aaaaaagat | 300 |
| cacagcccac | ctaaagaggt | tgtggaaaat | gctggaccca | agacaaggct | tggctgttct | 360 |
| aaggaaagtc | aagagagtgg | tggccagttt | gatgagagga | ttgtcctcaa | ggaaacgccg | 420 |
| ttcccatgat | gttctgactg | tgcaattcct | aattttggga | atgctgttga | tgaccggtgg | 480 |
| agtgaccttg | gtgcggaaaa | acagatggtt | gctcctaaat | gtgacatctg | aggacctcgg | 540 |
| gaaacattc | tctgtgggca | caggcaactg | acaacaaac | attttggaag | ccaagtactg | 600 |
| gtgcccagac | tcaatggaat | acaactgtcc | caatctcagt | ccaagagagg | agccagatga | 660 |
| cattgattgc | tggtgctatg | gggtggaaaa | cgttagagtc | gcatatggta | agtgtgactc | 720 |
| agcaggcagg | tctaggagt | caagaagggc | cattgacttg | cctacgcatg | aaaaccatgg | 780 |
| tttgaagacc | cggcaagaaa | aatggatgac | tggaagaatg | ggtgaaaggc | aactccaaaa | 840 |

```
gattgagaga tggttcgtga ggaaccccttttttgcagtg acggctctga ccattgccta    900
ccttgtggga agcaacatga cgcaacgagt cgtgattgcc ctactggtct tggctgttgg    960
tccggcctac tcagctcact gcattggaat tactgacagg gatttcattg agggggtgca   1020
tggaggaact tgggtttcag ctaccctgga gcaagacaag tgtgtcactg ttatggcccc   1080
tgacaagcct tcattggaca tctcactaga gacagtagcc attgataga ctgctgaggc   1140
gaggaaagtg tgttacaatg cagttctcac tcatgtgaag attaatgaca gtgccccag   1200
cactggagag gcccacctag ctgaagagaa cgaaggggac aatgcgtgca agcgcactta   1260
ttctgataga ggctggggca atggctgtgg cctatttggg aaagggagca ttgtggcatg   1320
cgccaaattc acttgtgcca atccatgag tttgtttgag gttgatcaga ccaaaattca   1380
gtatgtcatc agagcacaat tgcatgtagg ggccaagcag gaaaattgga ataccagcat   1440
taagactctc aagtttgatg ccctgtcagg ctcccaggaa gtcgagttca ttgggtatgg   1500
aaaagctaca ctggaatgcc aggtgcaaac tgccgtggac tttggtaaca gttacatcgc   1560
tgagatggaa acagagagct ggatagtgga cagacagtgg gcccaggact tgaccctgcc   1620
atggcagagt ggaagtggcg gggtgtggag agagatgcat catcttgtcg aatttgaacc   1680
tccgcatgcc gccactatca gagtactggc cctgggaaac caggaaggct ccttgaaaac   1740
agctcttact ggcgcaatga gggttacaaa ggacacaaat gacaacaacc tttacaaact   1800
acatggtgga catgtttctt gcagagtgaa attgtcagct ttgacactca aggggacatc   1860
ctacaaata tgcactgaca aaatgttttt tgtcaagaac ccaactgaca ctggccatgg   1920
cactgttgtg atgcaggtga aagtgtcaaa aggagccccc tgcaggattc cagtgatagt   1980
agctgatgat cttacagcgg caatcaataa aggcattttg gttacagtta accccatcgc   2040
ctcaaccaat gatgatgaag tgctgattga ggtgaaccca ccttttggag acagctacat   2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aacttcggcc gaaagggatc acaaacctcc aacacaacta aatgggctcc   2520
tcccggacaa ggaagtcccg ggagcaaggg cgaggagctc ttcaccgggg tggtgcccat   2580
cctggtcgag ctggacggcg acgtaaacgg ccacaagttc agcgtgtccg gcgagggcga   2640
gggcgatgcc acctacggca agctgaccct gaagttcatc tgcaccaccg gcaagctgcc   2700
cgtgccctgg cccaccctcg tgaccaccct gacctacggc gtgcagtgct tcagccgcta   2760
ccccgaccac atgaagcagc acgacttctt caagtccgcc atgcccgaag ctacgtcca   2820
ggagcgcacc atcttcttca aggacgacgg caactacaag acccgcgccg aggtgaagtt   2880
cgagggcgac accctggtga accgcatcga gctgaagggc atcgacttca aggaggacgg   2940
caacatcctg gggcacaagc tggagtacaa ctacaacagc cacaacgtct atatcatggc   3000
cgacaagcag aagaacggca tcaaggtgaa cttcaagatc cgccacaaca tcgaggacgg   3060
cagcgtgcag ctcgccgacc actaccagca gaacacccc atcggcgacg gccccgtgct   3120
gctgcccgac aaccactacc tgagcaccca gtccgccctg agcaaagacc ccaacgagaa   3180
```

-continued

```
gcgcgatcac atggtcctgc tggagttcgt gaccgccgcc gggatcactc tcggcatgga   3240
cgagctgtac aagtccggaa gcagtccaca gctgttgaat tttgaccttc ttaagcttgc   3300
tggagacgtc gagtccaacc ctgggccaaa ggagggaagc tcaataggaa agatgtttga   3360
gtccacatac agaggtgcaa aacgaatggc cattctaggt gaaacagctt gggattttgg   3420
ttccgttggt ggactgttca catcattggg aaaggctgtg caccaggttt ttggaagtgt   3480
gtatacaacc atgtttggag gagtctcatg gatgattaga atcctaattg ggttcttagt   3540
gttgtggatt ggcacgaact ccaggaacac ttcaatggct atgacgtgca tagctgttgg   3600
aggaatcact ctgtttctgg gcttcacagt tggcgccgat caaggatgcg ccatcaactt   3660
tggcaagaga gagctcaagt gcggagatgg tatcttcata tttagagact ctgatgactg   3720
gctgaacaag tactcatact atccagaaga tcctgtgaag cttgcatcaa tagtgaaagc   3780
ctcttttgaa aagggaagt gtggcctaaa ttcagttgac tcccttgagc atgagatgtg   3840
gagaagcagg gcagatgaga tcaatgccat ttttgaggaa aacgaggtgg acatttctgt   3900
tgtcgtgcag gatccaaaga atgtttacca gagaggaact catccatttt ccagaattcg   3960
ggatggtctg cagtatggtt ggaagacttg gggtaagaac cttgtgttct ccccagggag   4020
gaagaatgga agcttcatca tagatggaaa gtccaggaaa gaatgccgt tttcaaaccg   4080 ggtctggaat tctttccaga tagaggagtt tgggacggga gtgttcacca cacgcgtgta   4140 catgacgca gtctttgaat acaccataga ctgcgatgga tctatcttgg gtgcagcggt   4200
gaacggaaaa aagagtgccc atggctctcc aacatttgg atgggaagtc atgaagtaaa   4260
tgggacatgg atgatccaca ccttggaggc attagattac aaggagtgtg agtggccact   4320
gacacatacg attggaacat cagttgaaga gagtgaaatg ttcatgccga tcaatcgg   4380 aggcccagtt agctctcaca atcatatccc tggatacaag gttcagacga acggaccttg   4440
gatgcaggta ccactagaag tgaagagaga agcttgccca gggactagcg tgatcattga   4500
tggcaactgt gatggacggg gaaaatcaac cagatccacc acggatagcg ggaaagttat   4560
tcctgaatgg tgttgccgct cctgcacaat gccgcctgtg agcttccatg gtagtgatgg   4620
gtgttggtat cccatggaaa ttaggccaag gaaaacgcat gaaagccatc tggtgcgctc   4680
ctgggttaca gctggagaaa tacatgctgt ccctttttgt ttggtgagca tgatgatagc   4740 aatgaagtg gtcctaagga aaagacaggg accaaagcaa atgttggttg gaggagtagt   4800
gctcttggga gcaatgctgg tcgggcaagt aactctcctt gatttgctga aactcacagt   4860
ggctgtggga ttgcatttcc atgagatgaa caatggagga gacgccatgt atatggcgtt   4920
gattgctgcc ttttcaatca gaccagggct gctcatcggc tttgggctca ggaccctatg   4980
gagccctcgg gaacgccttg tgctgacccct aggagcagcc atggtggaga ttgccttggg   5040
tggcgtgatg ggcggcctgt ggaagtatct aaatgcagtt tctctctgca tcctgacaat   5100
aaatgctgtt gcttctagga aagcatcaaa taccatcttg ccctcatgg ctctgttgac   5160 acctgtcact atggctgagg tgagacttgc cgcaatgttc ttttgtgcca tggttatcat   5220 agggggtcctt caccagaatt tcaaggacac ctccatgcag aagactatac ctctggtggc   5280
cctcacactc acatcttacc tgggcttgac acaaccttt ttgggcctgt gtgcatttct   5340
ggcaacccgc atatttggc gaaggagtat cccagtgaat gaggcactcg cagcagctgg   5400
tctagtggga gtgctggcag gactggcttt tcaggagatg gagaacttcc ttggtccgat   5460
tgcagttgga ggactcctga tgatgctggt tagcgtggct gggagggtgg atgggctaga   5520
gctcaagaag cttggtgaag tttcatggga agaggaggcg gagatcagcg ggagttccgc   5580
```

```
ccgctatgat gtggcactca gtgaacaagg ggagttcaag ctgctttctg aagagaaagt   5640
gccatgggac caggttgtga tgacctcgct ggccttggtt ggggctgccc tccatccatt   5700
tgctcttctg ctggtccttg ctgggtggct gtttcatgtc aggggagcta ggagaagtgg   5760
ggatgtcttg tgggatattc ccactcctaa gatcatcgag gaatgtgaac atctggagga   5820
tgggatttat ggcatattcc agtcaacctt cttgggggcc tcccagcgag gagtgggagt   5880
ggcacaggga ggggtgttcc acacaatgtg gcatgtcaca agaggagctt tccttgtcag   5940
gaatggcaag aagttgattc catcttgggc ttcagtaaag gaagaccttg tcgcctatgg   6000
tggctcatgg aagttggaag gcagatggga tggagaggaa gaggtccagt tgatcgcggc   6060
tgttccagga aagaacgtgg tcaacgtcca gacaaaaccg agcttgttca aagtgaggaa   6120
tgggggagaa atcggggctg tcgctcttga ctatccgagt ggcacttcag gatctcctat   6180
tgttaacagg aacggagagg tgattgggct gtacggcaat ggcatccttg tcggtgacaa   6240
ctccttcgtg tccgccatat cccagactga ggtgaaggaa gaaggaaagg aggagctcca   6300
agagatcccg acaatgctaa agaaaggaat gacaactgtc cttgattttc atcctggagc   6360
tgggaagaca agacgtttcc tcccacagat cttggccgag tgcgcacgga gacgcttgcg   6420
cactcttgtg ttggcccccca ccagggttgt tctttctgaa atgaaggagg cttttcacgg   6480
cctggacgtg aaattccaca cacaggcttt ttccgctcac ggcagcggga gagaagtcat   6540
tgatgccatg tgccatgcca ccctaactta caggatgttg gaaccaacta gggttgttaa   6600
ctgggaagtg atcattatgg atgaagccca ttttttggat ccagctagca tagccgctag   6660
aggttgggca gcgcacagag ctagggcaaa tgaaagtgca acaatcttga tgacagccac   6720
accgcctggg actagtgatg aatttccaca ttcaaatggt gaaatagaag atgttcaaac   6780
ggacataccc agtgagccct ggaacacagg gcatgactgg atcctggctg acaaaaggcc   6840
cacggcatgg ttccttccat ccatcagagc tgcaaatgtc atggctgcct ctttgcgtaa   6900
ggctggaaag agtgtggtgg tcctgaacag gaaaacccttt gagagagaat accccacgat   6960
aaagcagaag aaacctgact ttatattggc cactgacata gctgaaatgg gagccaacct   7020
ttgcgtggag cgagtgctgg attgcaggac ggcttttaag cctgtgcttg tggatgaagg   7080
gaggaaggtg gcaataaaag ggccacttcg tatctccgca tcctctgctg ctcaaaggag   7140
ggggcgcatt gggagaaatc ccaacagaga tggagactca tactactatt ctgagcctac   7200
aagtgaaaat aatgcccacc acgtctgctg gttggaggcc tcaatgctct tggacaacat   7260
ggaggtgagg ggtggaatgg tcgccccact ctatggcgtt gaaggaacta aaacaccagt   7320
ttcccctggt gaaatgagac tgagggatga ccagaggaaa gtcttcagag aactagtgag   7380
gaattgtgac ctgcccgttt ggcttttcgtg gcaagtggcc aaggctggtt tgaagacgaa   7440
tgatcgtaag tggtgttttg aaggccctga ggaacatgag atcttgaatg acagcggtga   7500
aacagtgaag tgcagggctc ctggaggagc aaagaagcct ctgcgcccaa ggtggtgtga   7560
tgaaagggtg tcatctgacc agagtgcgct gtctgaattt attaagtttg ctgaaggtag   7620
gaggggagct gctgaagtgc tagttgtgct gagtgaactc cctgatttcc tggctaaaaa   7680
aggtggagag gcaatggata ccatcagtgt gttcctccac tctgaggaag ctctagggc   7740 ttaccgcaat gcactatcaa tgatgcctga ggcaatgaca atagtcatgc tgtttatact   7800
ggctggacta ctgacatcgg gaatggtcat ctttttcatg tctcccaaag gcatcagtag   7860
aatgtctatg gcgatgggca caatggccgg ctgtggatat ctcatgttcc ttggaggcgt   7920
```

```
caaacccact cacatctcct atgtcatgct catattcttt gtcctgatgg tggttgtgat    7980
ccccgagcca gggcaacaaa ggtccatcca agacaaccaa gtggcatacc tcattattgg    8040
catcctgacg ctggtttcag cggtggcagc aacgagcta ggcatgctgg agaaaaccaa     8100
agaggacctc tttgggaaga agaacttaat tccatctagt gcttcaccct ggagttggcc    8160
ggatcttgac ctgaagccag gagctgcctg gacagtgtac gttggcattg ttacaatgct    8220
ctctccaatg ttgcaccact ggatcaaagt cgaatatggc aacctgtctc tgtctggaat    8280
agcccagtca gcctcagtcc tttctttcat ggacaagggg ataccattca tgaagatgaa    8340
tatctcggtc ataatgctgc tggtcagtgg ctggaattca ataacagtga tgcctctgct    8400
ctgtggcata gggtgcgcca tgctccactg gtctctcatt ttacctggaa tcaaagcgca    8460
gcagtcaaag cttgcacaga gaagggtgtt ccatggcgtt gccaagaacc ctgtggttga    8520
tgggaatcca acagttgaca ttgaggaagc tcctgaaatg cctgcccttt atgagaagaa    8580
actggctcta tatctccttc ttgctctcag cctagcttct gttgccatgt gcagaacgcc    8640
cttttcattg gctgaaggca ttgtcctagc atcagctgcc ttagggccgc tcatagaggg    8700
aaacaccagc cttctttgga atggaccccat ggctgtctcc atgacaggag tcatgagggg   8760
gaatcactat gcttttgtgg gagtcatgta caatctatgg aagatgaaaa ctggacgccg    8820
ggggagcgcg aatggaaaaa ctttgggtga agtctggaag agggaactga atctgttgga    8880
caagcgacag tttgagttgt ataaaaggac cgacattgtg gaggtggatc gtgatacggc    8940
acgcaggcat ttggccgaag ggaaggtgga caccggggtg gcggtctcca ggggaccgc    9000
aaagttaagg tggttccatg agcgtggcta tgtcaagctg gaaggtaggg tgattgacct   9060
ggggtgtggc cgcggaggct ggtgttacta cgctgctgcg caaaaggaag tgagtgggt    9120
caaaggattt actcttggaa gagacggcca tgagaaaccc atgaatgtgc aaagtctggg   9180
atggaacatc atcaccttca aggacaaaac tgatatccac cgcctagaac cagtgaaatg   9240
tgacacccctt ttgtgtgaca ttggagagtc atcatcgtca tcggtcacag ggggggaaag   9300
gaccgtgaga gttcttgata ctgtagaaaa atggctggct tgtgggggttg acaacttctg   9360
tgtgaaggtg ttagctccat acatgccaga tgttcttgag aaactggaat tgctccaaag   9420
gaggtttggc ggaacagtga tcaggaaccc tctctccagg aattccactc atgaaatgta   9480
ctacgtgtct ggagcccgca gcaatgtcac atttactgtg aaccaaacat cccgcctcct   9540
gatgaggaga atgaggcgtc caactggaaa agtgaccctg gaggctgacg tcatcctccc   9600
aattgggaca cgcagtgttg agacagacaa gggaccctg gacaaagagg ccatagaaga   9660
aagggttgag aggataaaat ctgagtacat gacctcttgg ttttatgaca atgacaaccc   9720
ctacaggacc tggcactact gtggctccta tgtcacaaaa acctcaggaa gtgcggcgag   9780
catggtaaat ggtgttatta aaattctgac atatccatgg gacaggatag aggaggtcac   9840
cagaatggca atgactgaca caaccccttt tggacagcaa agagtgttta agaaaaagt    9900
tgacaccaga gcaaaggatc caccagcggg aactaggaag atcatgaaag ttgtcaacag   9960
gtggctgttc cgccacctgg ccagagaaaa gagccccaga ctgtgcacaa aggaagaatt  10020
tattgcaaaa gtccgaagtc atgcagccat tggagcttac ctggaagaac aagaacagtg  10080
gaagactgcc aatgaggctg tccaagaccc aaagttctgg gaactggtgg atgaagaaag  10140
gaagctgcac caacaaggca ggtgtcggac ttgtgtgtac aacatgatgg ggaaaagaga  10200
gaagaagctg tcagagtttg ggaaagcaaa gggaagccgt gccatatggt atatgtggct  10260
gggagcgcgg tatcttgagt ttgaggccct gggattcctg aatgaggacc attgggcttc  10320
```

```
cagggaaaac tcaggaggag gagtggaagg cattggctta caatacctag gatatgtgat   10380
cagagacctg gctgcaatgg atggtggtgg attctacgcg gatgacaccg ctggatggga   10440
cacgcgcatc acagaggcag accttgatga tgaacaggag atcttgaact acatgagccc   10500
acatcacaaa aaactggcac aagcagtgat ggaaatgaca tacaagaaca agtggtgaa    10560
agtgttgaga ccagcccag gagggaaagc ctacatggat gtcataagtc gacgagacca   10620
gagaggatcc gggcaggtag tgacttatgc tctgaacacc atcaccaact tgaaagtcca   10680
attgatcaga atggcagaag cagagatggt gatacatcac caacatgttc aagattgtga   10740
tgaatcagtt ctgaccaggc tggaggcatg gctcactgag cacggatgta acagactgaa   10800
gaggatggcg gtgagtggag acgactgtgt ggtccggccc atcgatgaca ggttcggcct   10860
ggccctgtcc catctcaacg ccatgtccaa ggttagaaag gacatatctg aatggcagcc   10920
atcaaaaggg tggaatgatt gggagaatgt gcccttctgt tcccaccact ccatgaact   10980
acagctgaag gatggcagga ggattgtggt gccttgccga gaacaggacg agctcattgg   11040
gagaggaagg gtgtctccag gaaacggctg gatgatcaag gaaacagctt gcctcagcaa   11100
agcctatgcc aacatgtggt cactgatgta ttttcacaaa agggacatga ggctactgtc   11160
attggctgtt cctcagctg ttcccacctc atgggttcca caaggacgca caacatggtc   11220
gattcatggg aaaggggagt ggatgaccac ggaagacatg cttgaggtgt ggaacagagt   11280
atggataacc aacaacccac acatgcagga caagacaatg gtgaaaaaat ggagagatgt   11340
cccttatcta accaagagac aagacaagct gtgcggatca ctgattggaa tgaccaatag   11400
ggccacctgg gcctcccaca tccatttagt catccatcgt atccgaacgc tgattggaca   11460
ggagaaatac actgactacc taacagtcat ggacaggtat tctgtggatg ctgacctgca   11520
actgggtgag cttatctgaa acaccatcta acaggaataa ccgggataca aaccacgggt   11580
ggagaaccgg actccccaca acctgaaacc gggatataaa ccacggctgg agaaccgggc   11640
tccgcactta aaatgaaaca gaaaccggga taaaaactac ggatggagaa ccggactcca   11700
cacattgaga cagaagaagt tgtcagccca gaaccccaca cgagttttgc cactgctaag   11760
ctgtgaggca gtgcaggctg gacagccga cctccaggtt gcgaaaaacc tggtttctgg   11820
gacctcccac cccagagtaa aaagaacgga gcctccgcta ccaccctccc acgtggtggt   11880
agaaagacgg ggtctagagg ttagaggaga ccctccaggg aacaaatagt gggaccatat   11940
tgacgccagg gaaagaccgg agtggttctc tgcttttcct ccagaggtct gtgagcacag   12000
tttgctcaag aataagcaga cctttggatg acaaacacaa aaccac             12046
```

<210> SEQ ID NO 12
<211> LENGTH: 12046
<212> TYPE: PRT
<213> ORGANISM: Yellow fever virus

<400> SEQUENCE: 12

Ala Gly Thr Ala Ala Ala Thr Cys Cys Thr Gly Thr Gly Thr Gly Cys
1               5                   10                  15

Thr Ala Ala Thr Thr Gly Ala Gly Gly Thr Gly Cys Ala Thr Thr Gly
            20                  25                  30

Gly Thr Cys Thr Gly Cys Ala Ala Ala Thr Cys Gly Ala Gly Thr Thr
        35                  40                  45

Gly Cys Thr Ala Gly Gly Cys Ala Ala Thr Ala Ala Cys Ala Cys
    50                  55                  60

-continued

```
Ala Thr Thr Thr Gly Gly Ala Thr Thr Ala Ala Thr Thr Thr Thr Ala
65                  70                  75                  80

Ala Thr Cys Gly Thr Thr Cys Gly Thr Thr Gly Ala Gly Cys Gly Ala
                85                  90                  95

Thr Thr Ala Gly Cys Ala Gly Ala Gly Ala Ala Cys Thr Gly Ala Cys
            100                 105                 110

Cys Ala Gly Ala Ala Cys Ala Thr Gly Thr Cys Thr Gly Gly Thr Cys
        115                 120                 125

Gly Thr Ala Ala Ala Gly Cys Thr Cys Ala Gly Gly Gly Ala Ala Ala
    130                 135                 140

Ala Ala Cys Cys Cys Thr Gly Gly Gly Cys Gly Thr Cys Ala Ala Thr
145                 150                 155                 160

Ala Thr Gly Gly Thr Ala Cys Gly Ala Cys Gly Ala Gly Gly Ala Gly
                165                 170                 175

Thr Thr Cys Gly Cys Thr Cys Cys Thr Thr Gly Thr Cys Ala Ala Ala
            180                 185                 190

Cys Ala Ala Ala Ala Thr Ala Ala Ala Ala Cys Ala Ala Ala Ala Ala
        195                 200                 205

Ala Cys Ala Ala Ala Ala Cys Ala Ala Ala Thr Thr Gly Gly Ala Ala
    210                 215                 220

Ala Cys Ala Gly Ala Cys Cys Thr Gly Gly Ala Cys Cys Thr Thr Cys
225                 230                 235                 240

Ala Ala Gly Ala Gly Gly Thr Gly Thr Thr Cys Ala Ala Gly Gly Ala
                245                 250                 255

Thr Thr Thr Ala Thr Cys Thr Thr Thr Thr Thr Cys Thr Thr Thr Thr
            260                 265                 270

Thr Gly Thr Thr Cys Ala Ala Cys Ala Thr Thr Thr Thr Gly Ala Cys
        275                 280                 285

Thr Gly Gly Ala Ala Ala Ala Ala Ala Gly Ala Thr Cys Ala Cys Ala
    290                 295                 300

Gly Cys Cys Cys Ala Cys Cys Thr Ala Ala Ala Gly Ala Gly Gly Thr
305                 310                 315                 320

Thr Gly Thr Gly Gly Ala Ala Ala Ala Thr Gly Cys Thr Gly Gly Ala
                325                 330                 335

Cys Cys Cys Ala Ala Gly Ala Cys Ala Ala Gly Gly Cys Thr Thr Gly
            340                 345                 350

Gly Cys Thr Gly Thr Thr Cys Thr Ala Ala Gly Gly Ala Ala Ala Gly
        355                 360                 365

Thr Cys Ala Ala Gly Ala Gly Ala Gly Thr Gly Gly Thr Gly Gly Cys
    370                 375                 380

Cys Ala Gly Thr Thr Thr Gly Ala Thr Gly Ala Gly Ala Gly Gly Ala
385                 390                 395                 400

Thr Thr Gly Thr Cys Cys Thr Cys Ala Ala Gly Gly Ala Ala Ala Cys
                405                 410                 415

Gly Cys Cys Gly Thr Thr Cys Cys Cys Ala Thr Gly Ala Thr Gly Thr
            420                 425                 430

Thr Cys Thr Gly Ala Cys Thr Gly Thr Gly Cys Ala Ala Thr Thr Cys
        435                 440                 445

Cys Thr Ala Ala Thr Thr Thr Thr Gly Gly Gly Ala Ala Thr Gly Cys
    450                 455                 460

Thr Gly Thr Thr Gly Ala Thr Gly Ala Cys Cys Gly Gly Thr Gly Gly
465                 470                 475                 480

Ala Gly Thr Gly Ala Cys Cys Thr Thr Gly Gly Thr Gly Cys Gly Gly
```

-continued

```
                485                 490                 495

Ala Ala Ala Ala Ala Cys Ala Gly Ala Thr Gly Gly Thr Thr Gly Cys
            500                 505                 510

Thr Cys Cys Thr Ala Ala Ala Thr Gly Thr Gly Ala Cys Ala Thr Cys
        515                 520                 525

Thr Gly Ala Gly Gly Ala Cys Cys Thr Cys Gly Gly Gly Ala Ala Ala
    530                 535                 540

Ala Cys Ala Thr Thr Cys Thr Cys Thr Gly Thr Gly Gly Gly Cys Ala
545                 550                 555                 560

Cys Ala Gly Gly Cys Ala Ala Cys Thr Gly Cys Ala Cys Ala Ala Cys
                565                 570                 575

Ala Ala Ala Cys Ala Thr Thr Thr Thr Gly Gly Ala Ala Gly Cys Cys
            580                 585                 590

Ala Ala Gly Thr Ala Cys Thr Gly Gly Thr Gly Cys Cys Cys Ala Gly
        595                 600                 605

Ala Cys Thr Cys Ala Ala Thr Gly Gly Ala Ala Thr Ala Cys Ala Ala
    610                 615                 620

Cys Thr Gly Thr Cys Cys Cys Ala Ala Thr Cys Thr Cys Ala Gly Thr
625                 630                 635                 640

Cys Cys Ala Ala Gly Ala Gly Ala Gly Gly Ala Gly Cys Cys Ala Gly
                645                 650                 655

Ala Thr Gly Ala Cys Ala Thr Thr Gly Ala Thr Thr Gly Cys Thr Gly
            660                 665                 670

Gly Thr Gly Cys Thr Ala Thr Gly Gly Gly Gly Thr Gly Gly Ala Ala
        675                 680                 685

Ala Ala Cys Gly Thr Thr Ala Gly Ala Gly Thr Cys Gly Cys Ala Thr
    690                 695                 700

Ala Thr Gly Gly Thr Ala Ala Gly Thr Gly Thr Gly Ala Cys Thr Cys
705                 710                 715                 720

Ala Gly Cys Ala Gly Gly Cys Ala Gly Gly Thr Cys Thr Ala Gly Gly
                725                 730                 735

Ala Gly Gly Thr Cys Ala Ala Gly Ala Ala Gly Gly Gly Cys Cys Ala
            740                 745                 750

Thr Thr Gly Ala Cys Thr Thr Gly Cys Cys Thr Ala Cys Gly Cys Ala
        755                 760                 765

Thr Gly Ala Ala Ala Ala Cys Cys Ala Thr Gly Gly Thr Thr Thr Gly
    770                 775                 780

Ala Ala Gly Ala Cys Cys Cys Gly Gly Cys Ala Ala Gly Ala Ala Ala
785                 790                 795                 800

Ala Ala Thr Gly Gly Ala Thr Gly Ala Cys Thr Gly Gly Ala Ala Gly
                805                 810                 815

Ala Ala Thr Gly Gly Gly Thr Gly Ala Ala Ala Gly Gly Cys Ala Ala
            820                 825                 830

Cys Thr Cys Cys Ala Ala Ala Ala Gly Ala Thr Thr Gly Ala Gly Ala
        835                 840                 845

Gly Ala Thr Gly Gly Thr Thr Cys Gly Thr Gly Ala Gly Gly Ala Ala
    850                 855                 860

Cys Cys Cys Cys Thr Thr Thr Thr Thr Thr Gly Cys Ala Gly Thr Gly
865                 870                 875                 880

Ala Cys Gly Gly Cys Thr Cys Thr Gly Ala Cys Cys Ala Thr Thr Gly
                885                 890                 895

Cys Cys Thr Ala Cys Cys Thr Thr Gly Thr Gly Gly Gly Ala Ala Gly
            900                 905                 910
```

-continued

Cys Ala Ala Cys Ala Thr Gly Ala Cys Gly Cys Ala Ala Cys Gly Ala
915 920 925

Gly Thr Cys Gly Thr Gly Ala Thr Thr Gly Cys Cys Cys Thr Ala Cys
930 935 940

Thr Gly Gly Thr Cys Thr Thr Gly Gly Cys Thr Gly Thr Thr Gly Gly
945 950 955 960

Thr Cys Cys Gly Gly Cys Cys Thr Ala Cys Thr Cys Ala Gly Cys Thr
965 970 975

Cys Ala Cys Thr Gly Cys Ala Thr Thr Gly Gly Ala Ala Thr Thr Ala
980 985 990

Cys Thr Gly Ala Cys Ala Gly Gly Gly Ala Thr Thr Thr Cys Ala Thr
995 1000 1005

Thr Gly Ala Gly Gly Gly Gly Gly Thr Gly Cys Ala Thr Gly Gly
1010 1015 1020

Ala Gly Gly Ala Ala Cys Thr Thr Gly Gly Gly Thr Thr Thr Cys
1025 1030 1035

Ala Gly Cys Thr Ala Cys Cys Cys Thr Gly Gly Ala Gly Cys Ala
1040 1045 1050

Ala Gly Ala Cys Ala Ala Gly Thr Gly Thr Gly Thr Cys Ala Cys
1055 1060 1065

Thr Gly Thr Thr Ala Thr Gly Gly Cys Cys Cys Cys Thr Gly Ala
1070 1075 1080

Cys Ala Ala Gly Cys Cys Thr Thr Cys Ala Thr Thr Gly Gly Ala
1085 1090 1095

Cys Ala Thr Cys Thr Cys Ala Cys Thr Ala Gly Ala Gly Ala Cys
1100 1105 1110

Ala Gly Thr Ala Gly Cys Cys Ala Thr Thr Gly Ala Thr Ala Gly
1115 1120 1125

Ala Cys Cys Thr Gly Cys Thr Gly Ala Gly Gly Cys Gly Ala Gly
1130 1135 1140

Gly Ala Ala Ala Gly Thr Gly Thr Gly Thr Thr Ala Cys Ala Ala
1145 1150 1155

Thr Gly Cys Ala Gly Thr Thr Cys Thr Cys Ala Cys Thr Cys Ala
1160 1165 1170

Thr Gly Thr Gly Ala Ala Gly Ala Thr Thr Ala Ala Thr Gly Ala
1175 1180 1185

Cys Ala Ala Gly Thr Gly Cys Cys Cys Cys Ala Gly Cys Ala Cys
1190 1195 1200

Thr Gly Gly Ala Gly Ala Gly Gly Cys Cys Cys Ala Cys Cys Thr
1205 1210 1215

Ala Gly Cys Thr Gly Ala Ala Gly Ala Gly Ala Ala Cys Gly Ala
1220 1225 1230

Ala Gly Gly Gly Gly Ala Cys Ala Ala Thr Gly Cys Gly Thr Gly
1235 1240 1245

Cys Ala Ala Gly Cys Gly Cys Ala Cys Thr Thr Ala Thr Thr Cys
1250 1255 1260

Thr Gly Ala Thr Ala Gly Ala Gly Gly Cys Thr Gly Gly Gly Gly
1265 1270 1275

Cys Ala Ala Thr Gly Gly Cys Thr Gly Thr Gly Gly Cys Cys Thr
1280 1285 1290

Ala Thr Thr Thr Gly Gly Gly Ala Ala Ala Gly Gly Gly Ala Gly
1295 1300 1305

-continued

```
Cys Ala Thr Thr Gly Thr Gly Cys Ala Thr Gly Cys Gly Cys
    1310            1315            1320

Cys Ala Ala Ala Thr Thr Cys Ala Cys Thr Thr Gly Thr Gly Cys
    1325            1330            1335

Cys Ala Ala Ala Thr Cys Cys Ala Thr Gly Ala Gly Thr Thr Thr
    1340            1345            1350

Gly Thr Thr Thr Gly Ala Gly Gly Thr Thr Gly Ala Thr Cys Ala
    1355            1360            1365

Gly Ala Cys Cys Ala Ala Ala Ala Thr Thr Cys Ala Gly Thr Ala
    1370            1375            1380

Thr Gly Thr Cys Ala Thr Cys Ala Gly Ala Gly Cys Ala Cys Ala
    1385            1390            1395

Ala Thr Thr Gly Cys Ala Thr Gly Thr Ala Gly Gly Gly Gly Cys
    1400            1405            1410

Cys Ala Ala Gly Cys Ala Gly Gly Ala Ala Ala Thr Thr Gly
    1415            1420            1425

Gly Ala Ala Thr Ala Cys Cys Ala Gly Cys Ala Thr Thr Ala Ala
    1430            1435            1440

Gly Ala Cys Thr Cys Thr Cys Ala Ala Gly Thr Thr Thr Gly Ala
    1445            1450            1455

Thr Gly Cys Cys Cys Thr Gly Thr Cys Ala Gly Cys Thr Cys
    1460            1465            1470

Cys Cys Ala Gly Gly Ala Ala Gly Thr Cys Gly Ala Gly Thr Thr
    1475            1480            1485

Cys Ala Thr Thr Gly Gly Gly Thr Ala Thr Gly Ala Ala Ala
    1490            1495            1500

Ala Gly Cys Thr Ala Cys Ala Cys Thr Gly Gly Ala Ala Thr Gly
    1505            1510            1515

Cys Cys Ala Gly Gly Thr Gly Cys Ala Ala Ala Cys Thr Gly Cys
    1520            1525            1530

Gly Gly Thr Gly Gly Ala Cys Thr Thr Thr Gly Gly Thr Ala Ala
    1535            1540            1545

Cys Ala Gly Thr Thr Ala Cys Ala Thr Cys Gly Cys Thr Gly Ala
    1550            1555            1560

Gly Ala Thr Gly Gly Ala Ala Ala Cys Ala Gly Ala Gly Ala Gly
    1565            1570            1575

Cys Thr Gly Gly Ala Thr Ala Gly Thr Gly Gly Ala Cys Ala Gly
    1580            1585            1590

Ala Cys Ala Gly Thr Gly Gly Gly Cys Cys Cys Ala Gly Gly Ala
    1595            1600            1605

Cys Thr Thr Gly Ala Cys Cys Thr Gly Cys Cys Ala Thr Gly
    1610            1615            1620

Gly Cys Ala Gly Ala Gly Thr Gly Gly Ala Ala Gly Thr Gly Gly
    1625            1630            1635

Cys Gly Gly Gly Thr Gly Thr Gly Gly Ala Gly Ala Gly Ala
    1640            1645            1650

Gly Ala Thr Gly Cys Ala Thr Cys Ala Thr Cys Thr Thr Gly Thr
    1655            1660            1665

Cys Gly Ala Ala Thr Thr Thr Gly Ala Ala Cys Cys Thr Cys Cys
    1670            1675            1680

Gly Cys Ala Thr Gly Cys Cys Gly Cys Cys Ala Cys Thr Ala Thr
    1685            1690            1695

Cys Ala Gly Ala Gly Thr Ala Cys Thr Gly Gly Cys Cys Cys Thr
```

-continued

```
                1700                1705                1710

Gly Gly Gly Ala Ala Ala Cys Cys Ala Gly Ala Ala Gly Gly
            1715                1720                1725

Cys Thr Cys Cys Thr Thr Gly Ala Ala Ala Cys Ala Gly Cys
            1730                1735                1740

Thr Cys Thr Thr Ala Cys Thr Gly Gly Cys Gly Cys Ala Ala Thr
            1745                1750                1755

Gly Ala Gly Gly Gly Thr Thr Ala Cys Ala Ala Gly Gly Ala
            1760                1765                1770

Cys Ala Cys Ala Ala Ala Thr Gly Ala Cys Ala Ala Cys Ala Ala
            1775                1780                1785

Cys Cys Thr Thr Thr Ala Cys Ala Ala Ala Cys Thr Ala Cys Ala
            1790                1795                1800

Thr Gly Gly Thr Gly Gly Ala Cys Ala Thr Gly Thr Thr Cys
            1805                1810                1815

Thr Thr Gly Cys Ala Gly Ala Gly Thr Gly Ala Ala Ala Thr Thr
            1820                1825                1830

Gly Thr Cys Ala Gly Cys Thr Thr Thr Gly Ala Cys Ala Cys Thr
            1835                1840                1845

Cys Ala Ala Gly Gly Gly Gly Ala Cys Ala Thr Cys Cys Thr Ala
            1850                1855                1860

Cys Ala Ala Ala Ala Thr Ala Thr Gly Cys Ala Cys Thr Gly Ala
            1865                1870                1875

Cys Ala Ala Ala Ala Thr Gly Thr Thr Thr Thr Thr Thr Gly Thr
            1880                1885                1890

Cys Ala Ala Gly Ala Ala Cys Cys Cys Ala Ala Cys Thr Gly Ala
            1895                1900                1905

Cys Ala Cys Thr Gly Gly Cys Cys Ala Thr Gly Gly Cys Ala Cys
            1910                1915                1920

Thr Gly Thr Thr Gly Thr Gly Ala Thr Gly Cys Ala Gly Gly Thr
            1925                1930                1935

Gly Ala Ala Ala Gly Thr Gly Thr Cys Ala Ala Ala Ala Gly Gly
            1940                1945                1950

Ala Gly Cys Cys Cys Cys Cys Thr Gly Cys Ala Gly Gly Ala Thr
            1955                1960                1965

Thr Cys Cys Ala Gly Thr Gly Ala Thr Ala Gly Thr Ala Gly Cys
            1970                1975                1980

Thr Gly Ala Thr Gly Ala Thr Cys Thr Thr Ala Cys Ala Gly Cys
            1985                1990                1995

Gly Gly Cys Ala Ala Thr Cys Ala Ala Thr Ala Ala Ala Gly Gly
            2000                2005                2010

Cys Ala Thr Thr Thr Thr Gly Gly Thr Thr Ala Cys Ala Gly Thr
            2015                2020                2025

Thr Ala Ala Cys Cys Cys Cys Ala Thr Cys Gly Cys Cys Thr Cys
            2030                2035                2040

Ala Ala Cys Cys Ala Ala Thr Gly Ala Thr Gly Ala Thr Gly Ala
            2045                2050                2055

Ala Gly Thr Gly Cys Thr Gly Ala Thr Thr Gly Ala Gly Gly Thr
            2060                2065                2070

Gly Ala Ala Cys Cys Cys Ala Cys Cys Thr Thr Thr Thr Gly Gly
            2075                2080                2085

Ala Gly Ala Cys Ala Gly Cys Thr Ala Cys Ala Thr Thr Ala Thr
            2090                2095                2100
```

-continued

Cys Gly Thr Thr Gly Gly Gly Ala Gly Ala Gly Ala Gly Ala
    2105                2110                2115
Thr Thr Cys Ala Cys Gly Thr Cys Thr Cys Ala Cys Thr Thr Ala
    2120                2125                2130
Cys Cys Ala Gly Thr Gly Gly Cys Ala Cys Ala Ala Ala Gly Ala
    2135                2140                2145
Gly Gly Gly Ala Ala Gly Cys Thr Cys Ala Ala Thr Ala Gly Gly
    2150                2155                2160
Ala Ala Ala Gly Thr Thr Gly Thr Thr Cys Ala Cys Thr Cys Ala
    2165                2170                2175
Gly Ala Cys Cys Ala Thr Gly Ala Ala Ala Gly Gly Cys Gly Thr
    2180                2185                2190
Gly Gly Ala Ala Cys Gly Cys Cys Thr Gly Gly Cys Cys Gly Thr
    2195                2200                2205
Cys Ala Thr Gly Gly Gly Ala Gly Ala Cys Ala Cys Cys Gly Cys
    2210                2215                2220
Cys Thr Gly Gly Gly Ala Thr Thr Thr Cys Ala Gly Cys Thr Cys
    2225                2230                2235
Cys Gly Cys Thr Gly Gly Ala Gly Gly Gly Thr Thr Cys Thr Thr
    2240                2245                2250
Cys Ala Cys Thr Thr Cys Gly Gly Thr Thr Gly Gly Gly Ala Ala
    2255                2260                2265
Ala Gly Gly Ala Ala Thr Thr Cys Ala Thr Ala Cys Gly Gly Thr
    2270                2275                2280
Gly Thr Thr Thr Gly Gly Cys Thr Cys Thr Gly Cys Cys Thr Thr
    2285                2290                2295
Thr Cys Ala Gly Gly Gly Gly Cys Thr Ala Thr Thr Gly Gly
    2300                2305                2310
Cys Gly Gly Cys Thr Thr Gly Ala Ala Cys Thr Gly Gly Ala Thr
    2315                2320                2325
Ala Ala Cys Ala Ala Ala Gly Gly Thr Cys Ala Thr Cys Ala Thr
    2330                2335                2340
Gly Gly Gly Gly Gly Cys Gly Gly Thr Ala Cys Thr Thr Ala Thr
    2345                2350                2355
Ala Thr Gly Gly Gly Thr Thr Gly Gly Cys Ala Thr Cys Ala Ala
    2360                2365                2370
Cys Ala Cys Ala Ala Gly Ala Ala Ala Cys Ala Thr Gly Ala Cys
    2375                2380                2385
Ala Ala Thr Gly Thr Cys Cys Ala Thr Gly Ala Gly Cys Ala Thr
    2390                2395                2400
Gly Ala Thr Cys Thr Thr Gly Gly Thr Ala Gly Gly Ala Gly Thr
    2405                2410                2415
Gly Ala Thr Cys Ala Thr Gly Ala Thr Gly Thr Thr Thr Thr Thr
    2420                2425                2430
Gly Thr Cys Thr Cys Thr Ala Gly Gly Ala Gly Thr Thr Gly Gly
    2435                2440                2445
Gly Gly Cys Gly Gly Ala Thr Cys Ala Ala Gly Ala Thr Gly Gly
    2450                2455                2460
Cys Gly Cys Cys Ala Thr Cys Ala Ala Cys Thr Thr Cys Gly Gly
    2465                2470                2475
Cys Cys Gly Ala Ala Ala Gly Gly Gly Ala Thr Cys Ala Cys Ala
    2480                2485                2490

-continued

```
Ala Ala Cys Cys Thr Cys Cys Ala Ala Cys Ala Cys Ala Ala Cys
    2495            2500                2505

Thr Ala Ala Ala Thr Gly Gly Gly Cys Thr Cys Cys Thr Cys Cys
    2510            2515                2520

Cys Gly Gly Ala Cys Ala Ala Gly Gly Ala Ala Gly Thr Cys Cys
    2525            2530                2535

Cys Gly Gly Gly Ala Gly Cys Ala Ala Gly Gly Gly Cys Gly Ala
    2540            2545                2550

Gly Gly Ala Gly Cys Thr Gly Thr Thr Cys Ala Cys Cys Gly Gly
    2555            2560                2565

Gly Gly Thr Gly Gly Thr Gly Cys Cys Cys Ala Thr Cys Cys Thr
    2570            2575                2580

Gly Gly Thr Cys Gly Ala Gly Cys Thr Gly Gly Ala Cys Gly Gly
    2585            2590                2595

Cys Gly Ala Cys Gly Thr Ala Ala Ala Cys Gly Gly Cys Cys Ala
    2600            2605                2610

Cys Ala Ala Gly Thr Thr Cys Ala Gly Cys Gly Thr Gly Thr Cys
    2615            2620                2625

Cys Gly Gly Cys Gly Ala Gly Gly Gly Cys Gly Ala Gly Gly Gly
    2630            2635                2640

Cys Gly Ala Thr Gly Cys Cys Ala Cys Cys Thr Ala Cys Gly Gly
    2645            2650                2655

Cys Ala Ala Gly Cys Thr Gly Ala Cys Cys Cys Thr Gly Ala Ala
    2660            2665                2670

Gly Thr Thr Cys Ala Thr Cys Thr Gly Cys Ala Cys Cys Ala Cys
    2675            2680                2685

Cys Gly Gly Cys Ala Ala Gly Cys Thr Gly Cys Cys Cys Gly Thr
    2690            2695                2700

Gly Cys Cys Cys Thr Gly Gly Cys Cys Cys Ala Cys Cys Cys Thr
    2705            2710                2715

Cys Gly Thr Gly Ala Cys Cys Ala Cys Cys Cys Thr Gly Ala Cys
    2720            2725                2730

Cys Thr Ala Cys Gly Gly Cys Gly Thr Gly Cys Ala Gly Thr Gly
    2735            2740                2745

Cys Thr Thr Cys Ala Gly Cys Cys Gly Cys Thr Ala Cys Cys Cys
    2750            2755                2760

Cys Gly Ala Cys Cys Ala Cys Ala Thr Gly Ala Ala Gly Cys Ala
    2765            2770                2775

Gly Cys Ala Cys Gly Ala Cys Thr Thr Cys Thr Thr Cys Ala Ala
    2780            2785                2790

Gly Thr Cys Cys Gly Cys Cys Ala Thr Gly Cys Cys Cys Gly Ala
    2795            2800                2805

Ala Gly Gly Cys Thr Ala Cys Gly Thr Cys Cys Ala Gly Gly Ala
    2810            2815                2820

Gly Cys Gly Cys Ala Cys Cys Ala Thr Cys Thr Thr Cys Thr Thr
    2825            2830                2835

Cys Ala Ala Gly Gly Ala Cys Gly Ala Cys Gly Gly Cys Ala Ala
    2840            2845                2850

Cys Thr Ala Cys Ala Ala Gly Ala Cys Cys Cys Gly Cys Gly Cys
    2855            2860                2865

Cys Gly Ala Gly Gly Thr Gly Ala Ala Gly Thr Thr Cys Gly Ala
    2870            2875                2880

Gly Gly Gly Cys Gly Ala Cys Ala Cys Cys Cys Thr Gly Gly Thr
```

```
    2885                2890                2895

Gly Ala  Ala Cys Cys Gly Cys  Ala Thr Cys Gly Ala  Gly Cys Thr
    2900                2905                2910

Gly Ala  Ala Gly Gly Gly Cys  Ala Thr Cys Gly Ala  Cys Thr Thr
    2915                2920                2925

Cys Ala  Ala Gly Gly Ala Gly  Gly Ala Cys Gly Gly  Cys Ala Ala
    2930                2935                2940

Cys Ala  Thr Cys Cys Thr Gly  Gly Gly Gly Cys Ala  Cys Ala Ala
    2945                2950                2955

Gly Cys  Thr Gly Gly Ala Gly  Thr Ala Cys Ala Ala  Cys Thr Ala
    2960                2965                2970

Cys Ala  Ala Cys Ala Gly Cys  Cys Ala Cys Ala Ala  Cys Gly Thr
    2975                2980                2985

Cys Thr  Ala Thr Ala Thr Cys  Ala Thr Gly Gly Cys  Cys Gly Ala
    2990                2995                3000

Cys Ala  Ala Gly Cys Ala Gly  Ala Ala Gly Ala Ala  Cys Gly Gly
    3005                3010                3015

Cys Ala  Thr Cys Ala Ala Gly  Gly Thr Gly Ala Ala  Cys Thr Thr
    3020                3025                3030

Cys Ala  Ala Gly Ala Thr Cys  Cys Gly Cys Cys Ala  Cys Ala Ala
    3035                3040                3045

Cys Ala  Thr Cys Gly Ala Gly  Gly Ala Cys Gly Gly  Cys Ala Gly
    3050                3055                3060

Cys Gly  Thr Gly Cys Ala Gly  Cys Thr Cys Gly Cys  Cys Gly Ala
    3065                3070                3075

Cys Cys  Ala Cys Thr Ala Cys  Cys Ala Gly Cys Ala  Gly Ala Ala
    3080                3085                3090

Cys Ala  Cys Cys Cys Cys Cys  Ala Thr Cys Gly Gly  Cys Gly Ala
    3095                3100                3105

Cys Gly  Gly Cys Cys Cys Cys  Gly Thr Gly Cys Thr  Gly Cys Thr
    3110                3115                3120

Gly Cys  Cys Cys Gly Ala Cys  Ala Ala Cys Cys Ala  Cys Thr Ala
    3125                3130                3135

Cys Cys  Thr Gly Ala Gly Cys  Ala Cys Cys Cys Ala  Gly Thr Cys
    3140                3145                3150

Cys Gly  Cys Cys Cys Thr Gly  Ala Gly Cys Ala Ala  Ala Gly Ala
    3155                3160                3165

Cys Cys  Cys Cys Ala Ala Cys  Gly Ala Gly Ala Ala  Gly Cys Gly
    3170                3175                3180

Cys Gly  Ala Thr Cys Ala Cys  Ala Thr Gly Gly Thr  Cys Cys Thr
    3185                3190                3195

Gly Cys  Thr Gly Gly Ala Gly  Thr Thr Cys Gly Thr  Gly Ala Cys
    3200                3205                3210

Cys Gly  Cys Cys Gly Cys Cys  Gly Gly Gly Ala Thr  Cys Ala Cys
    3215                3220                3225

Thr Cys  Thr Cys Gly Gly Cys  Ala Thr Gly Gly Ala  Cys Gly Ala
    3230                3235                3240

Gly Cys  Thr Gly Thr Ala Cys  Ala Ala Gly Thr Cys  Cys Gly Gly
    3245                3250                3255

Ala Ala  Gly Cys Ala Gly Thr  Cys Cys Ala Cys Ala  Gly Cys Thr
    3260                3265                3270

Gly Thr  Thr Gly Ala Ala Thr  Thr Thr Thr Gly Ala  Cys Cys Thr
    3275                3280                3285
```

```
Thr Cys  Thr Thr Ala Ala Gly  Cys Thr Thr Gly Cys  Thr Gly Gly
    3290                 3295                 3300

Ala Gly  Ala Cys Gly Thr Cys  Gly Ala Gly Thr Cys  Cys Ala Ala
    3305                 3310                 3315

Cys Cys  Cys Thr Gly Gly Gly  Cys Cys Ala Ala Ala  Gly Gly Ala
    3320                 3325                 3330

Gly Gly  Gly Ala Ala Gly Cys  Thr Cys Ala Ala Thr  Ala Gly Gly
    3335                 3340                 3345

Ala Ala  Ala Gly Ala Thr Gly  Thr Thr Thr Gly Ala  Gly Thr Cys
    3350                 3355                 3360

Cys Ala  Cys Ala Thr Ala Cys  Ala Gly Ala Gly Gly  Thr Gly Cys
    3365                 3370                 3375

Ala Ala  Ala Ala Cys Gly Ala  Ala Thr Gly Gly Cys  Cys Ala Thr
    3380                 3385                 3390

Thr Cys  Thr Ala Gly Gly Thr  Gly Ala Ala Ala Cys  Ala Gly Cys
    3395                 3400                 3405

Thr Thr  Gly Gly Gly Ala Thr  Thr Thr Thr Gly Gly  Thr Thr Cys
    3410                 3415                 3420

Cys Gly  Thr Thr Gly Gly Thr  Gly Gly Ala Cys Thr  Gly Thr Thr
    3425                 3430                 3435

Cys Ala  Cys Ala Thr Cys Ala  Thr Thr Gly Gly Gly  Ala Ala Ala
    3440                 3445                 3450

Gly Gly  Cys Thr Gly Thr Gly  Cys Ala Cys Cys Ala  Gly Gly Thr
    3455                 3460                 3465

Thr Thr  Thr Thr Gly Gly Ala  Ala Gly Thr Gly Thr  Gly Thr Ala
    3470                 3475                 3480

Thr Ala  Cys Ala Ala Cys Cys  Ala Thr Gly Thr Thr  Thr Gly Gly
    3485                 3490                 3495

Ala Gly  Gly Ala Gly Thr Cys  Thr Cys Ala Thr Gly  Gly Ala Thr
    3500                 3505                 3510

Gly Ala  Thr Thr Ala Gly Ala  Ala Thr Cys Cys Thr  Ala Ala Thr
    3515                 3520                 3525

Thr Gly  Gly Gly Thr Thr Cys  Thr Thr Ala Gly Thr  Gly Thr Thr
    3530                 3535                 3540

Gly Thr  Gly Gly Ala Thr Thr  Gly Gly Cys Ala Cys  Gly Ala Ala
    3545                 3550                 3555

Cys Thr  Cys Cys Ala Gly Gly  Ala Ala Cys Ala Cys  Thr Thr Cys
    3560                 3565                 3570

Ala Ala  Thr Gly Gly Cys Thr  Ala Thr Gly Ala Cys  Gly Thr Gly
    3575                 3580                 3585

Cys Ala  Thr Ala Gly Cys Thr  Gly Thr Thr Gly Gly  Ala Gly Gly
    3590                 3595                 3600

Ala Ala  Thr Cys Ala Cys Thr  Cys Thr Gly Thr Thr  Thr Cys Thr
    3605                 3610                 3615

Gly Gly  Gly Cys Thr Thr Cys  Ala Cys Ala Gly Thr  Thr Gly Gly
    3620                 3625                 3630

Cys Gly  Cys Cys Gly Ala Thr  Cys Ala Ala Gly Gly  Ala Thr Gly
    3635                 3640                 3645

Cys Gly  Cys Cys Ala Thr Cys  Ala Ala Cys Thr Thr  Thr Gly Gly
    3650                 3655                 3660

Cys Ala  Ala Gly Ala Gly Ala  Gly Ala Gly Cys Thr  Cys Ala Ala
    3665                 3670                 3675
```

```
Gly Thr Gly Cys Gly Gly Ala Gly Ala Thr Gly Thr Ala Thr
    3680            3685            3690

Cys Thr Thr Cys Ala Thr Ala Thr Thr Thr Ala Gly Ala Gly Ala
    3695            3700            3705

Cys Thr Cys Thr Gly Ala Thr Gly Ala Cys Thr Gly Gly Cys Thr
    3710            3715            3720

Gly Ala Ala Cys Ala Ala Gly Thr Ala Cys Thr Cys Ala Thr Ala
    3725            3730            3735

Cys Thr Ala Thr Cys Cys Ala Gly Ala Ala Gly Ala Thr Cys Cys
    3740            3745            3750

Thr Gly Thr Gly Ala Ala Gly Cys Thr Thr Gly Cys Ala Thr Cys
    3755            3760            3765

Ala Ala Thr Ala Gly Thr Gly Ala Ala Ala Gly Cys Cys Thr Cys
    3770            3775            3780

Thr Thr Thr Thr Gly Ala Ala Gly Ala Ala Gly Gly Gly Ala Ala
    3785            3790            3795

Gly Thr Gly Thr Gly Gly Cys Cys Thr Ala Ala Ala Thr Thr Cys
    3800            3805            3810

Ala Gly Thr Thr Gly Ala Cys Thr Cys Cys Cys Thr Thr Gly Ala
    3815            3820            3825

Gly Cys Ala Thr Gly Ala Gly Ala Thr Gly Thr Gly Gly Ala Gly
    3830            3835            3840

Ala Ala Gly Cys Ala Gly Gly Gly Cys Ala Gly Ala Thr Gly Ala
    3845            3850            3855

Gly Ala Thr Cys Ala Ala Thr Gly Cys Cys Ala Thr Thr Thr Thr
    3860            3865            3870

Thr Gly Ala Gly Gly Ala Ala Ala Ala Cys Gly Ala Gly Gly Thr
    3875            3880            3885

Gly Gly Ala Cys Ala Thr Thr Thr Cys Thr Gly Thr Thr Gly Thr
    3890            3895            3900

Cys Gly Thr Gly Cys Ala Gly Gly Ala Thr Cys Cys Ala Ala Ala
    3905            3910            3915

Gly Ala Ala Thr Gly Thr Thr Thr Ala Cys Cys Ala Gly Ala Gly
    3920            3925            3930

Ala Gly Gly Ala Ala Cys Thr Cys Ala Thr Cys Cys Ala Thr Thr
    3935            3940            3945

Thr Thr Cys Cys Ala Gly Ala Ala Thr Cys Gly Gly Gly Ala
    3950            3955            3960

Thr Gly Gly Thr Cys Thr Gly Cys Ala Gly Thr Ala Thr Gly Gly
    3965            3970            3975

Thr Thr Gly Gly Ala Ala Gly Ala Cys Thr Thr Gly Gly Gly Gly
    3980            3985            3990

Thr Ala Ala Gly Ala Ala Cys Cys Thr Thr Gly Thr Gly Thr Thr
    3995            4000            4005

Cys Thr Cys Cys Cys Cys Ala Gly Gly Gly Ala Gly Gly Ala Ala
    4010            4015            4020

Gly Ala Ala Thr Gly Gly Ala Ala Gly Cys Thr Thr Cys Ala Thr
    4025            4030            4035

Cys Ala Thr Ala Gly Ala Thr Gly Gly Ala Ala Ala Gly Thr Cys
    4040            4045            4050

Cys Ala Gly Gly Ala Ala Ala Gly Ala Ala Thr Gly Cys Cys Cys
    4055            4060            4065

Gly Thr Thr Thr Thr Cys Ala Ala Ala Cys Cys Gly Gly Gly Thr
```

```
                    4070            4075            4080
Cys Thr Gly Gly Ala Ala Thr Thr Cys Thr Thr Thr Cys Cys Ala
    4085            4090            4095
Gly Ala Thr Ala Gly Ala Gly Gly Ala Gly Thr Thr Thr Gly Gly
    4100            4105            4110
Gly Ala Cys Gly Gly Gly Ala Gly Thr Gly Thr Thr Cys Ala Cys
    4115            4120            4125
Cys Ala Cys Ala Cys Gly Cys Gly Thr Gly Thr Ala Cys Ala Thr
    4130            4135            4140
Gly Gly Ala Cys Gly Cys Ala Gly Thr Cys Thr Thr Gly Ala
    4145            4150            4155
Ala Thr Ala Cys Ala Cys Cys Ala Thr Ala Gly Ala Cys Thr Gly
    4160            4165            4170
Cys Gly Ala Thr Gly Gly Ala Thr Cys Thr Ala Thr Cys Thr Thr
    4175            4180            4185
Gly Gly Gly Thr Gly Cys Ala Gly Cys Gly Gly Thr Gly Ala Ala
    4190            4195            4200
Cys Gly Gly Ala Ala Ala Ala Ala Gly Ala Gly Thr Gly Cys
    4205            4210            4215
Cys Cys Ala Thr Gly Gly Cys Thr Cys Thr Cys Cys Ala Ala Cys
    4220            4225            4230
Ala Thr Thr Thr Thr Gly Gly Ala Thr Gly Gly Ala Ala Gly
    4235            4240            4245
Thr Cys Ala Thr Gly Ala Ala Gly Thr Ala Ala Ala Thr Gly Gly
    4250            4255            4260
Gly Ala Cys Ala Thr Gly Gly Ala Thr Gly Ala Thr Cys Cys Ala
    4265            4270            4275
Cys Ala Cys Cys Thr Thr Gly Gly Ala Gly Gly Cys Ala Thr Thr
    4280            4285            4290
Ala Gly Ala Thr Thr Ala Cys Ala Ala Gly Gly Ala Gly Thr Gly
    4295            4300            4305
Thr Gly Ala Gly Thr Gly Gly Cys Cys Ala Cys Thr Gly Ala Cys
    4310            4315            4320
Ala Cys Ala Thr Ala Cys Gly Ala Thr Thr Gly Gly Ala Ala Cys
    4325            4330            4335
Ala Thr Cys Ala Gly Thr Thr Gly Ala Ala Gly Ala Gly Ala Gly
    4340            4345            4350
Thr Gly Ala Ala Ala Thr Gly Thr Thr Cys Ala Thr Gly Cys Cys
    4355            4360            4365
Gly Ala Gly Ala Thr Cys Ala Ala Thr Cys Gly Gly Ala Gly Gly
    4370            4375            4380
Cys Cys Cys Ala Gly Thr Thr Ala Gly Cys Thr Cys Thr Cys Ala
    4385            4390            4395
Cys Ala Ala Thr Cys Ala Thr Ala Thr Cys Cys Cys Thr Gly Gly
    4400            4405            4410
Ala Thr Ala Cys Ala Ala Gly Gly Thr Thr Cys Ala Gly Ala Cys
    4415            4420            4425
Gly Ala Ala Cys Gly Gly Ala Cys Cys Thr Thr Gly Gly Ala Thr
    4430            4435            4440
Gly Cys Ala Gly Gly Thr Ala Cys Cys Ala Cys Thr Ala Gly Ala
    4445            4450            4455
Ala Gly Thr Gly Ala Ala Gly Ala Gly Ala Gly Ala Ala Gly Cys
    4460            4465            4470
```

-continued

```
Thr  Thr  Gly  Cys  Cys  Cys  Ala  Gly  Gly  Ala  Cys  Thr  Ala  Gly
     4475                4480                4485

Cys  Gly  Thr  Gly  Ala  Thr  Cys  Ala  Thr  Gly  Ala  Thr  Gly  Gly
     4490                4495                4500

Cys  Ala  Ala  Cys  Thr  Gly  Thr  Gly  Ala  Thr  Gly  Gly  Ala  Cys  Gly
     4505                4510                4515

Gly  Gly  Gly  Ala  Ala  Ala  Ala  Thr  Cys  Ala  Ala  Cys  Cys  Ala  Gly
     4520                4525                4530

Ala  Thr  Cys  Cys  Ala  Cys  Cys  Ala  Cys  Gly  Gly  Ala  Thr  Ala  Gly
     4535                4540                4545

Cys  Gly  Gly  Gly  Ala  Ala  Ala  Gly  Thr  Thr  Ala  Thr  Thr  Cys  Cys
     4550                4555                4560

Thr  Gly  Ala  Ala  Thr  Gly  Gly  Thr  Gly  Thr  Thr  Gly  Cys  Cys  Gly
     4565                4570                4575

Cys  Thr  Cys  Cys  Thr  Gly  Cys  Ala  Cys  Ala  Ala  Thr  Gly  Cys  Cys
     4580                4585                4590

Gly  Cys  Cys  Thr  Gly  Thr  Gly  Ala  Gly  Cys  Thr  Thr  Cys  Cys  Ala
     4595                4600                4605

Thr  Gly  Gly  Thr  Ala  Gly  Thr  Gly  Ala  Thr  Gly  Gly  Gly  Thr  Gly
     4610                4615                4620

Thr  Thr  Gly  Gly  Thr  Ala  Thr  Cys  Cys  Cys  Ala  Thr  Gly  Gly  Ala
     4625                4630                4635

Ala  Ala  Thr  Thr  Ala  Gly  Gly  Cys  Cys  Ala  Ala  Gly  Gly  Ala  Ala
     4640                4645                4650

Ala  Ala  Cys  Gly  Cys  Ala  Thr  Gly  Ala  Ala  Ala  Gly  Cys  Cys  Ala
     4655                4660                4665

Thr  Cys  Thr  Gly  Gly  Thr  Gly  Cys  Gly  Cys  Thr  Cys  Cys  Thr  Gly
     4670                4675                4680

Gly  Gly  Thr  Thr  Ala  Cys  Ala  Gly  Cys  Thr  Gly  Gly  Ala  Gly  Ala
     4685                4690                4695

Ala  Ala  Thr  Ala  Cys  Ala  Thr  Gly  Cys  Thr  Gly  Thr  Cys  Cys  Cys
     4700                4705                4710

Thr  Thr  Thr  Thr  Gly  Gly  Thr  Thr  Thr  Gly  Gly  Thr  Gly  Ala  Gly
     4715                4720                4725

Cys  Ala  Thr  Gly  Ala  Thr  Gly  Ala  Thr  Ala  Gly  Cys  Ala  Ala  Thr
     4730                4735                4740

Gly  Gly  Ala  Ala  Gly  Thr  Gly  Gly  Thr  Cys  Cys  Thr  Ala  Ala  Gly
     4745                4750                4755

Gly  Ala  Ala  Ala  Ala  Gly  Ala  Cys  Ala  Gly  Gly  Gly  Ala  Cys  Cys
     4760                4765                4770

Ala  Ala  Ala  Gly  Cys  Ala  Ala  Ala  Thr  Gly  Thr  Thr  Gly  Gly  Thr
     4775                4780                4785

Thr  Gly  Gly  Ala  Gly  Gly  Ala  Gly  Thr  Ala  Gly  Thr  Gly  Cys  Thr
     4790                4795                4800

Cys  Thr  Thr  Gly  Gly  Gly  Ala  Gly  Cys  Ala  Ala  Thr  Gly  Cys  Thr
     4805                4810                4815

Gly  Gly  Thr  Cys  Gly  Gly  Gly  Cys  Ala  Ala  Gly  Thr  Ala  Ala  Cys
     4820                4825                4830

Thr  Cys  Thr  Cys  Cys  Thr  Thr  Gly  Ala  Thr  Thr  Thr  Gly  Cys  Thr
     4835                4840                4845

Gly  Ala  Ala  Ala  Cys  Thr  Cys  Ala  Cys  Ala  Gly  Thr  Gly  Gly  Cys
     4850                4855                4860
```

```
Thr Gly Thr Gly Gly Gly Ala Thr Thr Gly Cys Ala Thr Thr Thr
    4865                4870                4875
Cys Cys Ala Thr Gly Ala Gly Ala Thr Gly Ala Ala Cys Ala Ala
    4880                4885                4890
Thr Gly Gly Ala Gly Gly Ala Gly Ala Cys Gly Cys Cys Ala Thr
    4895                4900                4905
Gly Thr Ala Thr Ala Thr Gly Gly Cys Gly Thr Thr Gly Ala Thr
    4910                4915                4920
Thr Gly Cys Thr Gly Cys Cys Thr Thr Thr Thr Cys Ala Ala Thr
    4925                4930                4935
Cys Ala Gly Ala Cys Cys Ala Gly Gly Gly Cys Thr Gly Cys Thr
    4940                4945                4950
Cys Ala Thr Cys Gly Gly Cys Thr Thr Thr Gly Gly Gly Cys Thr
    4955                4960                4965
Cys Ala Gly Gly Ala Cys Cys Cys Thr Ala Thr Gly Gly Ala Gly
    4970                4975                4980
Cys Cys Cys Thr Cys Gly Gly Gly Ala Ala Cys Gly Cys Cys Thr
    4985                4990                4995
Thr Gly Thr Gly Cys Thr Gly Ala Cys Cys Cys Thr Ala Gly Gly
    5000                5005                5010
Ala Gly Cys Ala Gly Cys Cys Ala Thr Gly Gly Thr Gly Gly Ala
    5015                5020                5025
Gly Ala Thr Thr Gly Cys Cys Thr Thr Gly Gly Gly Thr Gly Gly
    5030                5035                5040
Cys Gly Thr Gly Ala Thr Gly Gly Gly Cys Gly Gly Cys Cys Thr
    5045                5050                5055
Gly Thr Gly Gly Ala Ala Gly Thr Ala Thr Cys Thr Ala Ala Ala
    5060                5065                5070
Thr Gly Cys Ala Gly Thr Thr Cys Thr Cys Thr Cys Thr Gly
    5075                5080                5085
Cys Ala Thr Cys Cys Thr Gly Ala Cys Ala Ala Thr Ala Ala Ala
    5090                5095                5100
Thr Gly Cys Thr Gly Thr Thr Gly Cys Thr Thr Cys Thr Ala Gly
    5105                5110                5115
Gly Ala Ala Ala Gly Cys Ala Thr Cys Ala Ala Ala Thr Ala Cys
    5120                5125                5130
Cys Ala Thr Cys Thr Thr Gly Cys Cys Cys Cys Thr Cys Ala Thr
    5135                5140                5145
Gly Gly Cys Thr Cys Thr Gly Thr Thr Gly Ala Cys Ala Cys Cys
    5150                5155                5160
Thr Gly Thr Cys Ala Cys Thr Ala Thr Gly Gly Cys Thr Gly Ala
    5165                5170                5175
Gly Gly Thr Gly Ala Gly Ala Cys Thr Thr Gly Cys Cys Gly Cys
    5180                5185                5190
Ala Ala Thr Gly Thr Thr Cys Thr Thr Thr Thr Gly Thr Gly Cys
    5195                5200                5205
Cys Ala Thr Gly Gly Thr Thr Ala Thr Cys Ala Thr Ala Gly Gly
    5210                5215                5220
Gly Gly Thr Cys Cys Thr Thr Cys Ala Cys Cys Ala Gly Ala Ala
    5225                5230                5235
Thr Thr Thr Cys Ala Ala Gly Gly Ala Cys Ala Cys Cys Thr Cys
    5240                5245                5250
Cys Ala Thr Gly Cys Ala Gly Ala Ala Gly Ala Cys Thr Ala Thr
```

-continued

|  |  | 5255 |  |  |  | 5260 |  |  |  | 5265 |  |
| --- | --- | --- | --- | --- | --- | --- | --- | --- | --- | --- | --- |
| Ala | Cys | Cys | Thr | Cys | Thr | Gly | Gly | Thr | Gly | Gly | Cys | Cys | Cys | Thr |
|  |  | 5270 |  |  |  | 5275 |  |  |  | 5280 |  |
| Cys | Ala | Cys | Ala | Cys | Thr | Cys | Ala | Cys | Ala | Thr | Cys | Thr | Thr | Ala |
|  |  | 5285 |  |  |  | 5290 |  |  |  | 5295 |  |
| Cys | Cys | Thr | Gly | Gly | Gly | Cys | Thr | Thr | Gly | Ala | Cys | Ala | Cys | Ala |
|  |  | 5300 |  |  |  | 5305 |  |  |  | 5310 |  |
| Ala | Cys | Cys | Thr | Thr | Thr | Thr | Thr | Thr | Gly | Gly | Gly | Cys | Cys | Thr |
|  |  | 5315 |  |  |  | 5320 |  |  |  | 5325 |  |
| Gly | Thr | Gly | Thr | Gly | Cys | Ala | Thr | Thr | Thr | Cys | Thr | Gly | Gly | Cys |
|  |  | 5330 |  |  |  | 5335 |  |  |  | 5340 |  |
| Ala | Ala | Cys | Cys | Cys | Gly | Cys | Ala | Thr | Ala | Thr | Thr | Thr | Gly | Gly |
|  |  | 5345 |  |  |  | 5350 |  |  |  | 5355 |  |
| Gly | Cys | Gly | Ala | Ala | Gly | Gly | Ala | Gly | Thr | Ala | Thr | Cys | Cys | Cys |
|  |  | 5360 |  |  |  | 5365 |  |  |  | 5370 |  |
| Ala | Gly | Thr | Gly | Ala | Ala | Thr | Gly | Ala | Gly | Gly | Cys | Ala | Cys | Thr |
|  |  | 5375 |  |  |  | 5380 |  |  |  | 5385 |  |
| Cys | Gly | Cys | Ala | Gly | Cys | Ala | Gly | Cys | Thr | Gly | Thr | Cys | Thr | Thr |
|  |  | 5390 |  |  |  | 5395 |  |  |  | 5400 |  |
| Ala | Gly | Thr | Gly | Gly | Gly | Ala | Gly | Thr | Gly | Cys | Thr | Gly | Gly | Cys |
|  |  | 5405 |  |  |  | 5410 |  |  |  | 5415 |  |
| Ala | Gly | Gly | Ala | Cys | Thr | Gly | Gly | Cys | Thr | Thr | Thr | Cys | Ala |
|  |  | 5420 |  |  |  | 5425 |  |  |  | 5430 |  |
| Gly | Gly | Ala | Gly | Ala | Thr | Gly | Ala | Gly | Ala | Ala | Cys | Thr | Thr |
|  |  | 5435 |  |  |  | 5440 |  |  |  | 5445 |  |
| Cys | Cys | Thr | Thr | Gly | Gly | Thr | Cys | Cys | Gly | Ala | Thr | Thr | Gly | Cys |
|  |  | 5450 |  |  |  | 5455 |  |  |  | 5460 |  |
| Ala | Gly | Thr | Thr | Gly | Gly | Ala | Gly | Gly | Ala | Cys | Thr | Cys | Cys | Thr |
|  |  | 5465 |  |  |  | 5470 |  |  |  | 5475 |  |
| Gly | Ala | Thr | Gly | Ala | Thr | Gly | Cys | Thr | Gly | Gly | Thr | Thr | Ala | Gly |
|  |  | 5480 |  |  |  | 5485 |  |  |  | 5490 |  |
| Cys | Gly | Thr | Gly | Gly | Cys | Thr | Gly | Gly | Ala | Gly | Gly | Gly | Thr |
|  |  | 5495 |  |  |  | 5500 |  |  |  | 5505 |  |
| Gly | Gly | Ala | Thr | Gly | Gly | Gly | Cys | Thr | Ala | Gly | Ala | Gly | Cys | Thr |
|  |  | 5510 |  |  |  | 5515 |  |  |  | 5520 |  |
| Cys | Ala | Ala | Gly | Ala | Ala | Gly | Cys | Thr | Thr | Gly | Thr | Gly | Ala |
|  |  | 5525 |  |  |  | 5530 |  |  |  | 5535 |  |
| Ala | Gly | Thr | Thr | Thr | Cys | Ala | Thr | Gly | Gly | Gly | Ala | Ala | Gly | Ala |
|  |  | 5540 |  |  |  | 5545 |  |  |  | 5550 |  |
| Gly | Gly | Ala | Gly | Gly | Cys | Gly | Ala | Gly | Ala | Thr | Cys | Ala | Gly |
|  |  | 5555 |  |  |  | 5560 |  |  |  | 5565 |  |
| Cys | Gly | Gly | Gly | Ala | Gly | Thr | Thr | Cys | Cys | Gly | Cys | Cys | Cys | Gly |
|  |  | 5570 |  |  |  | 5575 |  |  |  | 5580 |  |
| Cys | Thr | Ala | Thr | Gly | Ala | Thr | Gly | Thr | Gly | Gly | Cys | Ala | Cys | Thr |
|  |  | 5585 |  |  |  | 5590 |  |  |  | 5595 |  |
| Cys | Ala | Gly | Thr | Gly | Ala | Ala | Cys | Ala | Ala | Gly | Gly | Gly | Ala |
|  |  | 5600 |  |  |  | 5605 |  |  |  | 5610 |  |
| Gly | Thr | Thr | Cys | Ala | Ala | Gly | Cys | Thr | Gly | Cys | Thr | Thr | Thr | Cys |
|  |  | 5615 |  |  |  | 5620 |  |  |  | 5625 |  |
| Thr | Gly | Ala | Ala | Gly | Ala | Gly | Ala | Ala | Ala | Gly | Thr | Gly | Cys | Cys |
|  |  | 5630 |  |  |  | 5635 |  |  |  | 5640 |  |
| Ala | Thr | Gly | Gly | Gly | Ala | Cys | Cys | Ala | Gly | Gly | Thr | Thr | Gly | Thr |
|  |  | 5645 |  |  |  | 5650 |  |  |  | 5655 |  |

```
Gly Ala Thr Gly Ala Cys Cys Thr Cys Gly Cys Thr Gly Gly Cys
        5660            5665            5670

Cys Thr Thr Gly Gly Thr Thr Gly Gly Gly Gly Cys Thr Gly Cys
        5675            5680            5685

Cys Cys Thr Cys Cys Ala Thr Cys Cys Ala Thr Thr Thr Gly Cys
        5690            5695            5700

Thr Cys Thr Thr Cys Thr Gly Cys Thr Gly Thr Cys Cys Thr
        5705            5710            5715

Thr Gly Cys Thr Gly Gly Gly Thr Gly Cys Thr Gly Thr Thr
        5720            5725            5730

Thr Cys Ala Thr Gly Thr Cys Ala Gly Gly Gly Ala Gly Cys
        5735            5740            5745

Thr Ala Gly Gly Ala Gly Ala Ala Gly Thr Gly Gly Gly Ala
        5750            5755            5760

Thr Gly Thr Cys Thr Thr Gly Thr Gly Gly Gly Ala Thr Ala Thr
        5765            5770            5775

Thr Cys Cys Cys Ala Cys Thr Cys Cys Thr Ala Ala Gly Ala Thr
        5780            5785            5790

Cys Ala Thr Cys Gly Ala Gly Gly Ala Ala Thr Gly Thr Gly Ala
        5795            5800            5805

Ala Cys Ala Thr Cys Thr Gly Ala Gly Gly Ala Thr Gly Gly
        5810            5815            5820

Gly Ala Thr Thr Thr Ala Thr Gly Gly Cys Ala Thr Ala Thr Thr
        5825            5830            5835

Cys Cys Ala Gly Thr Cys Ala Ala Cys Cys Thr Thr Cys Thr Thr
        5840            5845            5850

Gly Gly Gly Gly Gly Cys Cys Thr Cys Cys Cys Ala Gly Cys Gly
        5855            5860            5865

Ala Gly Gly Ala Gly Thr Gly Gly Ala Gly Thr Gly Gly Cys
        5870            5875            5880

Ala Cys Ala Gly Gly Gly Ala Gly Gly Gly Gly Thr Gly Thr Thr
        5885            5890            5895

Cys Cys Ala Cys Ala Cys Ala Ala Thr Gly Thr Gly Gly Cys Ala
        5900            5905            5910

Thr Gly Thr Cys Ala Cys Ala Ala Gly Ala Gly Gly Ala Gly Cys
        5915            5920            5925

Thr Thr Thr Cys Cys Thr Thr Gly Thr Cys Ala Gly Gly Ala Ala
        5930            5935            5940

Thr Gly Gly Cys Ala Ala Gly Ala Ala Gly Thr Thr Gly Ala Thr
        5945            5950            5955

Thr Cys Cys Ala Thr Cys Thr Thr Gly Gly Gly Cys Thr Thr Cys
        5960            5965            5970

Ala Gly Thr Ala Ala Ala Gly Gly Ala Ala Gly Ala Cys Cys Thr
        5975            5980            5985

Thr Gly Thr Cys Gly Cys Cys Thr Ala Thr Gly Gly Thr Gly Gly
        5990            5995            6000

Cys Thr Cys Ala Thr Gly Gly Ala Ala Gly Thr Thr Gly Gly Ala
        6005            6010            6015

Ala Gly Gly Cys Ala Gly Ala Thr Gly Gly Gly Ala Thr Gly Gly
        6020            6025            6030

Ala Gly Ala Gly Gly Ala Ala Gly Ala Gly Gly Thr Cys Cys Ala
        6035            6040            6045
```

```
Gly Thr Thr Gly Ala Thr Cys Gly Cys Gly Cys Thr Gly Thr
        6050                6055                6060

Thr Cys Cys Ala Gly Gly Ala Ala Ala Gly Ala Ala Cys Gly Thr
        6065                6070                6075

Gly Gly Thr Cys Ala Ala Cys Gly Thr Cys Cys Ala Gly Ala Cys
        6080                6085                6090

Ala Ala Ala Ala Cys Cys Gly Ala Gly Cys Thr Thr Gly Thr Thr
        6095                6100                6105

Cys Ala Ala Ala Gly Thr Gly Ala Gly Gly Ala Ala Thr Gly Gly
        6110                6115                6120

Gly Gly Gly Ala Gly Ala Ala Ala Thr Cys Gly Gly Gly Gly Cys
        6125                6130                6135

Thr Gly Thr Cys Gly Cys Thr Cys Thr Thr Gly Ala Cys Thr Ala
        6140                6145                6150

Thr Cys Cys Gly Ala Gly Thr Gly Gly Cys Ala Cys Thr Thr Cys
        6155                6160                6165

Ala Gly Gly Ala Thr Cys Thr Cys Cys Thr Ala Thr Thr Gly Thr
        6170                6175                6180

Thr Ala Ala Cys Ala Gly Gly Ala Ala Cys Gly Gly Ala Gly Ala
        6185                6190                6195

Gly Gly Thr Gly Ala Thr Thr Gly Gly Gly Cys Thr Gly Thr Ala
        6200                6205                6210

Cys Gly Gly Cys Ala Ala Thr Gly Gly Cys Ala Thr Cys Cys Thr
        6215                6220                6225

Thr Gly Thr Cys Gly Gly Thr Gly Ala Cys Ala Ala Cys Thr Cys
        6230                6235                6240

Cys Thr Thr Cys Gly Thr Gly Thr Cys Cys Gly Cys Cys Ala Thr
        6245                6250                6255

Ala Thr Cys Cys Cys Ala Gly Ala Cys Thr Gly Ala Gly Gly Thr
        6260                6265                6270

Gly Ala Ala Gly Gly Ala Ala Gly Ala Ala Gly Gly Ala Ala Ala
        6275                6280                6285

Gly Gly Ala Gly Gly Ala Gly Cys Thr Cys Cys Ala Ala Gly Ala
        6290                6295                6300

Gly Ala Thr Cys Cys Cys Gly Ala Cys Ala Ala Thr Gly Cys Thr
        6305                6310                6315

Ala Ala Ala Gly Ala Ala Ala Gly Gly Ala Ala Thr Gly Ala Cys
        6320                6325                6330

Ala Ala Cys Thr Gly Thr Cys Cys Thr Thr Gly Ala Thr Thr Thr
        6335                6340                6345

Thr Cys Ala Thr Cys Cys Thr Gly Gly Ala Gly Cys Thr Gly Gly
        6350                6355                6360

Gly Ala Ala Gly Ala Cys Ala Ala Gly Ala Cys Gly Thr Thr Thr
        6365                6370                6375

Cys Cys Thr Cys Cys Cys Ala Cys Ala Gly Ala Thr Cys Thr Thr
        6380                6385                6390

Gly Gly Cys Cys Gly Ala Gly Thr Gly Cys Gly Cys Ala Cys Gly
        6395                6400                6405

Gly Ala Gly Ala Cys Gly Cys Thr Thr Gly Cys Gly Cys Ala Cys
        6410                6415                6420

Thr Cys Thr Thr Gly Thr Gly Thr Thr Gly Gly Cys Cys Cys Cys
        6425                6430                6435

Cys Ala Cys Cys Ala Gly Gly Gly Thr Thr Gly Thr Thr Cys Thr
```

-continued

```
                 6440              6445              6450
Thr Thr Cys Thr Gly Ala Ala Thr Gly Ala Ala Gly Gly Ala
                 6455              6460              6465
Gly Gly Cys Thr Thr Thr Thr Cys Ala Cys Gly Cys Cys Thr
                 6470              6475              6480
Gly Gly Ala Cys Gly Thr Gly Ala Ala Ala Thr Thr Cys Cys Ala
                 6485              6490              6495
Cys Ala Cys Ala Cys Ala Gly Gly Cys Thr Thr Thr Thr Cys
                 6500              6505              6510
Cys Gly Cys Thr Cys Ala Cys Gly Gly Cys Ala Gly Cys Gly Gly
                 6515              6520              6525
Gly Ala Gly Ala Gly Ala Ala Gly Thr Cys Ala Thr Thr Gly Ala
                 6530              6535              6540
Thr Gly Cys Cys Ala Thr Gly Thr Gly Cys Cys Ala Thr Gly Cys
                 6545              6550              6555
Cys Ala Cys Cys Cys Thr Ala Ala Cys Thr Thr Ala Cys Ala Gly
                 6560              6565              6570
Gly Ala Thr Gly Thr Thr Gly Gly Ala Ala Cys Cys Ala Ala Cys
                 6575              6580              6585
Thr Ala Gly Gly Gly Thr Thr Gly Thr Ala Ala Cys Thr Gly
                 6590              6595              6600
Gly Gly Ala Ala Gly Thr Gly Ala Thr Cys Ala Thr Thr Ala Thr
                 6605              6610              6615
Gly Gly Ala Thr Gly Ala Ala Gly Cys Cys Cys Ala Thr Thr Thr
                 6620              6625              6630
Thr Thr Thr Gly Gly Ala Thr Cys Cys Ala Gly Cys Thr Ala Gly
                 6635              6640              6645
Cys Ala Thr Ala Gly Cys Cys Gly Cys Thr Ala Gly Ala Gly Gly
                 6650              6655              6660
Thr Thr Gly Gly Gly Cys Ala Gly Cys Gly Cys Ala Cys Ala Gly
                 6665              6670              6675
Ala Gly Cys Thr Ala Gly Gly Gly Cys Ala Ala Ala Thr Gly Ala
                 6680              6685              6690
Ala Ala Gly Thr Gly Cys Ala Ala Cys Ala Ala Thr Cys Thr Thr
                 6695              6700              6705
Gly Ala Thr Gly Ala Cys Ala Gly Cys Cys Ala Cys Ala Cys Cys
                 6710              6715              6720
Gly Cys Cys Thr Gly Gly Gly Ala Cys Thr Ala Gly Thr Gly Ala
                 6725              6730              6735
Thr Gly Ala Ala Thr Thr Thr Cys Cys Ala Cys Ala Thr Thr Cys
                 6740              6745              6750
Ala Ala Ala Thr Gly Gly Thr Gly Ala Ala Ala Thr Ala Gly Ala
                 6755              6760              6765
Ala Gly Ala Thr Gly Thr Thr Cys Ala Ala Ala Cys Gly Gly Ala
                 6770              6775              6780
Cys Ala Thr Ala Cys Cys Cys Ala Gly Thr Gly Ala Gly Cys Cys
                 6785              6790              6795
Cys Thr Gly Gly Ala Ala Cys Ala Cys Ala Gly Gly Gly Cys Ala
                 6800              6805              6810
Thr Gly Ala Cys Thr Gly Gly Ala Thr Cys Cys Thr Gly Gly Cys
                 6815              6820              6825
Thr Gly Ala Cys Ala Ala Ala Ala Gly Gly Cys Cys Cys Ala Cys
                 6830              6835              6840
```

```
Gly Gly Cys Ala Thr Gly Gly Thr Thr Cys Cys Thr Thr Cys Cys
            6845             6850                 6855

Ala Thr Cys Cys Ala Thr Cys Ala Gly Ala Gly Cys Thr Gly Cys
            6860             6865                 6870

Ala Ala Ala Thr Gly Thr Cys Ala Thr Gly Gly Cys Thr Gly Cys
            6875             6880                 6885

Cys Thr Cys Thr Thr Thr Gly Cys Gly Thr Ala Ala Gly Gly Cys
            6890             6895                 6900

Thr Gly Gly Ala Ala Ala Gly Ala Gly Thr Gly Thr Gly Gly Thr
            6905             6910                 6915

Gly Gly Thr Cys Cys Thr Gly Ala Ala Cys Ala Gly Gly Ala Ala
            6920             6925                 6930

Ala Ala Cys Cys Thr Thr Thr Gly Ala Gly Ala Gly Ala Gly Ala
            6935             6940                 6945

Ala Thr Ala Cys Cys Cys Cys Ala Cys Gly Ala Thr Ala Ala Ala
            6950             6955                 6960

Gly Cys Ala Gly Ala Ala Gly Ala Ala Ala Cys Cys Thr Gly Ala
            6965             6970                 6975

Cys Thr Thr Thr Ala Thr Ala Thr Thr Gly Gly Cys Cys Ala Cys
            6980             6985                 6990

Thr Gly Ala Cys Ala Thr Ala Gly Cys Thr Gly Ala Ala Ala Thr
            6995             7000                 7005

Gly Gly Gly Ala Gly Cys Cys Ala Ala Cys Cys Thr Thr Thr Gly
            7010             7015                 7020

Cys Gly Thr Gly Gly Ala Gly Cys Gly Ala Gly Thr Gly Cys Thr
            7025             7030                 7035

Gly Gly Ala Thr Thr Gly Cys Ala Gly Gly Ala Cys Gly Gly Cys
            7040             7045                 7050

Thr Thr Thr Thr Ala Ala Gly Cys Cys Thr Gly Thr Gly Cys Thr
            7055             7060                 7065

Thr Gly Thr Gly Gly Ala Thr Gly Ala Ala Gly Gly Gly Ala Gly
            7070             7075                 7080

Gly Ala Ala Gly Gly Thr Gly Gly Cys Ala Ala Thr Ala Ala Ala
            7085             7090                 7095

Ala Gly Gly Gly Cys Cys Ala Cys Thr Thr Cys Gly Thr Ala Thr
            7100             7105                 7110

Cys Thr Cys Cys Gly Cys Ala Thr Cys Cys Thr Cys Thr Gly Cys
            7115             7120                 7125

Thr Gly Cys Thr Cys Ala Ala Ala Gly Gly Ala Gly Gly Gly Gly
            7130             7135                 7140

Gly Cys Gly Cys Ala Thr Thr Gly Gly Gly Ala Gly Ala Ala Ala
            7145             7150                 7155

Thr Cys Cys Cys Ala Ala Cys Ala Gly Ala Gly Ala Thr Gly Gly
            7160             7165                 7170

Ala Gly Ala Cys Thr Cys Ala Thr Ala Cys Thr Ala Cys Thr Ala
            7175             7180                 7185

Thr Thr Cys Thr Gly Ala Gly Cys Cys Thr Ala Cys Ala Ala Gly
            7190             7195                 7200

Thr Gly Ala Ala Ala Ala Thr Ala Ala Thr Gly Cys Cys Cys Ala
            7205             7210                 7215

Cys Cys Ala Cys Gly Thr Cys Thr Gly Cys Thr Gly Gly Thr Thr
            7220             7225                 7230
```

|   |   |   |   |   |   |   |   |   |   |   |   |
|---|---|---|---|---|---|---|---|---|---|---|---|
| Gly | Gly | Ala | Gly | Gly | Cys | Thr | Cys | Ala | Ala | Thr | Gly | Cys | Thr |
|  | 7235 |  |  |  | 7240 |  |  |  | 7245 |  |  |

Gly Gly Ala Gly Gly Cys Cys Thr Cys Ala Ala Thr Gly Cys Thr
    7235                7240                7245

Cys Thr Thr Gly Gly Ala Cys Ala Ala Cys Ala Thr Gly Gly Ala
    7250                7255                7260

Gly Gly Thr Gly Ala Gly Gly Gly Gly Thr Gly Gly Ala Ala Thr
    7265                7270                7275

Gly Gly Thr Cys Gly Cys Cys Cys Cys Ala Cys Thr Cys Thr Ala
    7280                7285                7290

Thr Gly Gly Cys Gly Thr Thr Gly Ala Ala Gly Gly Ala Ala Cys
    7295                7300                7305

Thr Ala Ala Ala Ala Cys Ala Cys Cys Ala Gly Thr Thr Thr Cys
    7310                7315                7320

Cys Cys Cys Thr Gly Gly Thr Gly Ala Ala Ala Thr Gly Ala Gly
    7325                7330                7335

Ala Cys Thr Gly Ala Gly Gly Gly Ala Thr Gly Ala Cys Cys Ala
    7340                7345                7350

Gly Ala Gly Gly Ala Ala Ala Gly Thr Cys Thr Thr Cys Ala Gly
    7355                7360                7365

Ala Gly Ala Ala Cys Thr Ala Gly Thr Gly Ala Gly Gly Ala Ala
    7370                7375                7380

Thr Thr Gly Thr Gly Ala Cys Cys Thr Gly Cys Cys Cys Gly Thr
    7385                7390                7395

Thr Thr Gly Gly Cys Thr Thr Thr Cys Gly Thr Gly Gly Cys Ala
    7400                7405                7410

Ala Gly Thr Gly Gly Cys Cys Ala Ala Gly Gly Cys Thr Gly Gly
    7415                7420                7425

Thr Thr Thr Gly Ala Ala Gly Ala Cys Gly Ala Ala Thr Gly Ala
    7430                7435                7440

Thr Cys Gly Thr Ala Ala Gly Thr Gly Gly Thr Gly Thr Thr Thr
    7445                7450                7455

Thr Gly Ala Ala Gly Gly Cys Cys Cys Thr Gly Ala Gly Gly Ala
    7460                7465                7470

Ala Cys Ala Thr Gly Ala Gly Ala Thr Cys Thr Thr Gly Ala Ala
    7475                7480                7485

Thr Gly Ala Cys Ala Gly Cys Gly Gly Thr Gly Ala Ala Ala Cys
    7490                7495                7500

Ala Gly Thr Gly Ala Ala Gly Thr Gly Cys Ala Gly Gly Gly Cys
    7505                7510                7515

Thr Cys Cys Thr Gly Gly Ala Gly Gly Ala Gly Cys Ala Ala Ala
    7520                7525                7530

Gly Ala Ala Gly Cys Cys Thr Cys Thr Gly Cys Gly Cys Cys Cys
    7535                7540                7545

Ala Ala Gly Gly Thr Gly Gly Thr Gly Thr Gly Ala Thr Gly Ala
    7550                7555                7560

Ala Ala Gly Gly Gly Thr Gly Thr Cys Ala Thr Cys Thr Gly Ala
    7565                7570                7575

Cys Cys Ala Gly Ala Gly Thr Gly Cys Gly Cys Thr Gly Thr Cys
    7580                7585                7590

Thr Gly Ala Ala Thr Thr Thr Ala Thr Ala Ala Gly Thr Thr
    7595                7600                7605

Thr Gly Cys Thr Gly Ala Ala Gly Gly Thr Ala Gly Gly Ala Gly
    7610                7615                7620

Gly Gly Gly Ala Gly Cys Thr Gly Cys Thr Gly Ala Ala Gly Thr

```
                    7625                7630                7635

Gly Cys Thr Ala Gly Thr Thr Gly Thr Gly Cys Thr Gly Ala Gly
                    7640                7645                7650

Thr Gly Ala Ala Cys Thr Cys Cys Cys Thr Gly Ala Thr Thr Thr
                    7655                7660                7665

Cys Cys Thr Gly Gly Cys Thr Ala Ala Ala Ala Ala Gly Gly
                    7670                7675                7680

Thr Gly Gly Ala Gly Ala Gly Gly Cys Ala Ala Thr Gly Gly Ala
                    7685                7690                7695

Thr Ala Cys Cys Ala Thr Cys Ala Gly Thr Gly Thr Gly Thr Thr
                    7700                7705                7710

Cys Cys Thr Cys Cys Ala Cys Thr Cys Thr Gly Ala Gly Gly Ala
                    7715                7720                7725

Ala Gly Gly Cys Thr Cys Thr Ala Gly Gly Gly Cys Thr Thr Ala
                    7730                7735                7740

Cys Cys Gly Cys Ala Ala Thr Gly Cys Ala Cys Thr Ala Thr Cys
                    7745                7750                7755

Ala Ala Thr Gly Ala Thr Gly Cys Cys Thr Gly Ala Gly Gly Cys
                    7760                7765                7770

Ala Ala Thr Gly Ala Cys Ala Ala Thr Ala Gly Thr Cys Ala Thr
                    7775                7780                7785

Gly Cys Thr Gly Thr Thr Thr Ala Thr Ala Cys Thr Gly Gly Cys
                    7790                7795                7800

Thr Gly Gly Ala Cys Thr Ala Cys Thr Gly Ala Cys Ala Thr Cys
                    7805                7810                7815

Gly Gly Gly Ala Ala Thr Gly Thr Cys Ala Thr Cys Thr Thr
                    7820                7825                7830

Thr Thr Thr Cys Ala Thr Gly Thr Cys Thr Cys Cys Cys Ala Ala
                    7835                7840                7845

Ala Gly Gly Cys Ala Thr Cys Ala Gly Thr Ala Gly Ala Ala Thr
                    7850                7855                7860

Gly Thr Cys Thr Ala Thr Gly Gly Cys Gly Ala Thr Gly Gly Gly
                    7865                7870                7875

Cys Ala Cys Ala Ala Thr Gly Gly Cys Cys Gly Gly Cys Thr Gly
                    7880                7885                7890

Thr Gly Gly Ala Thr Ala Thr Cys Thr Cys Ala Thr Gly Thr Thr
                    7895                7900                7905

Cys Cys Thr Thr Gly Gly Ala Gly Gly Cys Gly Thr Cys Ala Ala
                    7910                7915                7920

Ala Cys Cys Cys Ala Cys Thr Cys Ala Cys Ala Thr Cys Thr Cys
                    7925                7930                7935

Cys Thr Ala Thr Gly Thr Cys Ala Thr Gly Cys Cys Ala Thr
                    7940                7945                7950

Ala Thr Thr Cys Thr Thr Thr Gly Thr Cys Cys Thr Gly Ala Thr
                    7955                7960                7965

Gly Gly Thr Gly Gly Thr Thr Gly Thr Gly Ala Thr Cys Cys Cys
                    7970                7975                7980

Cys Gly Ala Gly Cys Cys Ala Gly Gly Gly Cys Ala Ala Cys Ala
                    7985                7990                7995

Ala Ala Gly Gly Thr Cys Cys Ala Thr Cys Cys Ala Ala Gly Ala
                    8000                8005                8010

Cys Ala Ala Cys Cys Ala Ala Gly Thr Gly Gly Cys Ala Thr Ala
                    8015                8020                8025
```

-continued

```
Cys Cys  Thr Cys Ala Thr Thr  Ala Thr Thr Gly Gly  Cys Ala Thr
    8030                 8035                 8040

Cys Cys  Thr Gly Ala Cys Gly  Cys Thr Gly Gly Thr  Thr Thr Cys
    8045                 8050                 8055

Ala Gly  Cys Gly Gly Thr Gly  Gly Cys Ala Gly Cys  Cys Ala Ala
    8060                 8065                 8070

Cys Gly  Ala Gly Cys Thr Ala  Gly Gly Cys Ala Thr  Gly Cys Thr
    8075                 8080                 8085

Gly Gly  Ala Gly Ala Ala Ala  Ala Cys Cys Ala Ala  Ala Gly Ala
    8090                 8095                 8100

Gly Gly  Ala Cys Cys Thr Cys  Thr Thr Thr Gly Gly  Gly Ala Ala
    8105                 8110                 8115

Gly Ala  Ala Gly Ala Ala Cys  Thr Thr Ala Ala Thr  Thr Cys Cys
    8120                 8125                 8130

Ala Thr  Cys Thr Ala Gly Thr  Gly Cys Thr Thr Cys  Ala Cys Cys
    8135                 8140                 8145

Cys Thr  Gly Gly Ala Gly Thr  Thr Gly Gly Cys Cys  Gly Gly Ala
    8150                 8155                 8160

Thr Cys  Thr Thr Gly Ala Cys  Cys Thr Gly Ala Ala  Gly Cys Cys
    8165                 8170                 8175

Ala Gly  Gly Ala Gly Cys Thr  Gly Cys Cys Thr Gly  Gly Ala Cys
    8180                 8185                 8190

Ala Gly  Thr Gly Thr Ala Cys  Gly Thr Thr Gly Gly  Cys Ala Thr
    8195                 8200                 8205

Thr Gly  Thr Thr Ala Cys Ala  Ala Thr Gly Cys Thr  Cys Thr Cys
    8210                 8215                 8220

Thr Cys  Cys Ala Ala Thr Gly  Thr Thr Gly Cys Ala  Cys Cys Ala
    8225                 8230                 8235

Cys Thr  Gly Gly Ala Thr Cys  Ala Ala Ala Gly Thr  Cys Gly Ala
    8240                 8245                 8250

Ala Thr  Ala Thr Gly Gly Cys  Ala Ala Cys Cys Thr  Gly Thr Cys
    8255                 8260                 8265

Thr Cys  Thr Gly Thr Cys Thr  Gly Gly Ala Ala Thr  Ala Gly Cys
    8270                 8275                 8280

Cys Cys  Ala Gly Thr Cys Ala  Gly Cys Cys Thr Cys  Ala Gly Thr
    8285                 8290                 8295

Cys Cys  Thr Thr Thr Cys Thr  Thr Thr Cys Ala Thr  Gly Gly Ala
    8300                 8305                 8310

Cys Ala  Ala Gly Gly Gly Gly  Ala Thr Ala Cys Cys  Ala Thr Thr
    8315                 8320                 8325

Cys Ala  Thr Gly Ala Ala Gly  Ala Thr Gly Ala Ala  Thr Ala Thr
    8330                 8335                 8340

Cys Thr  Cys Gly Gly Thr Cys  Ala Thr Ala Ala Thr  Gly Cys Thr
    8345                 8350                 8355

Gly Cys  Thr Gly Gly Thr Cys  Ala Gly Thr Gly Gly  Cys Thr Gly
    8360                 8365                 8370

Gly Ala  Ala Thr Thr Cys Ala  Ala Thr Ala Ala Cys  Ala Gly Thr
    8375                 8380                 8385

Gly Ala  Thr Gly Cys Cys Thr  Cys Thr Gly Cys Thr  Cys Thr Gly
    8390                 8395                 8400

Thr Gly  Gly Cys Ala Thr Ala  Gly Gly Gly Thr Gly  Cys Gly Cys
    8405                 8410                 8415
```
Cys Ala Thr Gly Cys Thr Cys Cys Ala Cys Thr Gly Gly Thr Cys
8420 8425 8430

Thr Cys Thr Cys Ala Thr Thr Thr Thr Ala Cys Cys Thr Gly Gly
8435 8440 8445

Ala Ala Thr Cys Ala Ala Ala Gly Cys Gly Cys Ala Gly Cys Ala
8450 8455 8460

Gly Thr Cys Ala Ala Ala Gly Cys Thr Thr Gly Cys Ala Cys Ala
8465 8470 8475

Gly Ala Gly Ala Ala Gly Gly Gly Thr Gly Thr Thr Cys Cys Ala
8480 8485 8490

Thr Gly Gly Cys Gly Thr Thr Gly Cys Cys Ala Ala Gly Ala Ala
8495 8500 8505

Cys Cys Cys Thr Gly Thr Gly Gly Thr Thr Gly Ala Thr Gly Gly
8510 8515 8520

Gly Ala Ala Thr Cys Cys Ala Ala Cys Ala Gly Thr Thr Gly Ala
8525 8530 8535

Cys Ala Thr Thr Gly Ala Gly Gly Ala Ala Gly Cys Thr Cys Cys
8540 8545 8550

Thr Gly Ala Ala Ala Thr Gly Cys Cys Thr Gly Cys Cys Cys Thr
8555 8560 8565

Thr Thr Ala Thr Gly Ala Gly Ala Ala Gly Ala Ala Ala Cys Thr
8570 8575 8580

Gly Gly Cys Thr Cys Thr Ala Thr Ala Thr Cys Thr Cys Cys Thr
8585 8590 8595

Thr Cys Thr Thr Gly Cys Thr Cys Thr Cys Ala Gly Cys Cys Thr
8600 8605 8610

Ala Gly Cys Thr Thr Cys Thr Gly Thr Thr Gly Cys Cys Ala Thr
8615 8620 8625

Gly Thr Gly Cys Ala Gly Ala Ala Cys Gly Cys Cys Cys Thr Thr
8630 8635 8640

Thr Thr Cys Ala Thr Thr Gly Gly Cys Thr Gly Ala Ala Gly Gly
8645 8650 8655

Cys Ala Thr Thr Gly Thr Cys Cys Thr Ala Gly Cys Ala Thr Cys
8660 8665 8670

Ala Gly Cys Thr Gly Cys Cys Thr Thr Ala Gly Gly Gly Cys Cys
8675 8680 8685

Gly Cys Thr Cys Ala Thr Ala Gly Ala Gly Gly Gly Ala Ala Ala
8690 8695 8700

Cys Ala Cys Cys Ala Gly Cys Cys Thr Thr Cys Thr Thr Thr Gly
8705 8710 8715

Gly Ala Ala Thr Gly Gly Ala Cys Cys Cys Ala Thr Gly Gly Cys
8720 8725 8730

Thr Gly Thr Cys Thr Cys Cys Ala Thr Gly Ala Cys Ala Gly Gly
8735 8740 8745

Ala Gly Thr Cys Ala Thr Gly Ala Gly Gly Gly Gly Gly Ala Ala
8750 8755 8760

Thr Cys Ala Cys Thr Ala Thr Gly Cys Thr Thr Thr Thr Gly Thr
8765 8770 8775

Gly Gly Gly Ala Gly Thr Cys Ala Thr Gly Thr Ala Cys Ala Ala
8780 8785 8790

Thr Cys Thr Ala Thr Gly Gly Ala Ala Gly Ala Thr Gly Ala Ala
8795 8800 8805

Ala Ala Cys Thr Gly Gly Ala Cys Gly Cys Cys Gly Gly Gly Gly

|  |  |  |  |  |  |  |  |  |  |
|---|---|---|---|---|---|---|---|---|---|
| | | 8810 | | | 8815 | | | 8820 | |
| Gly | Ala | Gly | Cys | Gly | Cys | Gly | Ala | Ala | Thr Gly Ala Ala Ala |
| | | 8825 | | | 8830 | | | 8835 | |
| Ala | Ala | Cys | Thr | Thr | Thr | Gly | Gly | Gly | Thr Gly Ala Ala Gly Thr |
| | | 8840 | | | 8845 | | | 8850 | |
| Cys | Thr | Gly | Gly | Ala | Ala | Gly | Ala | Gly | Gly Gly Ala Ala Cys Thr |
| | | 8855 | | | 8860 | | | 8865 | |
| Gly | Ala | Ala | Thr | Cys | Thr | Gly | Thr | Thr | Gly Gly Ala Cys Ala Ala |
| | | 8870 | | | 8875 | | | 8880 | |
| Gly | Cys | Gly | Ala | Cys | Ala | Gly | Thr | Thr | Thr Gly Ala Gly Thr Thr |
| | | 8885 | | | 8890 | | | 8895 | |
| Gly | Thr | Ala | Thr | Ala | Ala | Ala | Gly | Gly | Ala Cys Cys Gly Ala |
| | | 8900 | | | 8905 | | | 8910 | |
| Cys | Ala | Thr | Thr | Gly | Thr | Gly | Gly | Ala | Gly Gly Thr Gly Gly Ala |
| | | 8915 | | | 8920 | | | 8925 | |
| Thr | Cys | Gly | Thr | Gly | Ala | Thr | Ala | Cys | Gly Gly Cys Ala Cys Gly |
| | | 8930 | | | 8935 | | | 8940 | |
| Cys | Ala | Gly | Gly | Cys | Ala | Thr | Thr | Gly | Gly Cys Cys Gly Ala |
| | | 8945 | | | 8950 | | | 8955 | |
| Ala | Gly | Gly | Gly | Ala | Ala | Gly | Gly | Thr | Gly Gly Ala Cys Ala Cys |
| | | 8960 | | | 8965 | | | 8970 | |
| Cys | Gly | Gly | Gly | Gly | Thr | Gly | Gly | Cys | Gly Gly Thr Cys Thr Cys |
| | | 8975 | | | 8980 | | | 8985 | |
| Cys | Ala | Gly | Gly | Gly | Gly | Ala | Cys | Cys | Gly Cys Ala Ala Ala |
| | | 8990 | | | 8995 | | | 9000 | |
| Gly | Thr | Thr | Ala | Ala | Gly | Gly | Thr | Gly | Gly Thr Thr Cys Cys Ala |
| | | 9005 | | | 9010 | | | 9015 | |
| Thr | Gly | Ala | Gly | Cys | Gly | Thr | Gly | Gly | Cys Thr Ala Thr Gly Thr |
| | | 9020 | | | 9025 | | | 9030 | |
| Cys | Ala | Ala | Gly | Cys | Thr | Gly | Gly | Ala | Ala Gly Gly Thr Ala Gly |
| | | 9035 | | | 9040 | | | 9045 | |
| Gly | Gly | Thr | Gly | Ala | Thr | Thr | Gly | Ala | Cys Cys Thr Gly Gly Gly |
| | | 9050 | | | 9055 | | | 9060 | |
| Gly | Thr | Gly | Thr | Gly | Gly | Cys | Cys | Gly | Cys Gly Gly Ala Gly Gly |
| | | 9065 | | | 9070 | | | 9075 | |
| Cys | Thr | Gly | Gly | Thr | Gly | Thr | Thr | Ala | Cys Thr Ala Cys Gly Cys |
| | | 9080 | | | 9085 | | | 9090 | |
| Thr | Gly | Cys | Thr | Gly | Cys | Gly | Cys | Ala | Ala Ala Gly Gly Ala |
| | | 9095 | | | 9100 | | | 9105 | |
| Ala | Gly | Thr | Gly | Ala | Gly | Thr | Gly | Gly | Gly Gly Thr Cys Ala Ala |
| | | 9110 | | | 9115 | | | 9120 | |
| Ala | Gly | Gly | Ala | Thr | Thr | Thr | Ala | Cys | Thr Cys Thr Thr Gly Gly |
| | | 9125 | | | 9130 | | | 9135 | |
| Ala | Ala | Gly | Ala | Gly | Ala | Cys | Gly | Gly | Cys Cys Ala Thr Gly Ala |
| | | 9140 | | | 9145 | | | 9150 | |
| Gly | Ala | Ala | Ala | Cys | Cys | Cys | Ala | Thr | Gly Ala Ala Thr Gly Thr |
| | | 9155 | | | 9160 | | | 9165 | |
| Gly | Cys | Ala | Ala | Ala | Gly | Thr | Cys | Thr | Gly Gly Ala Thr Gly |
| | | 9170 | | | 9175 | | | 9180 | |
| Gly | Ala | Ala | Cys | Ala | Thr | Cys | Ala | Thr | Cys Ala Cys Cys Thr Thr |
| | | 9185 | | | 9190 | | | 9195 | |
| Cys | Ala | Ala | Gly | Gly | Ala | Cys | Ala | Ala | Ala Ala Cys Thr Gly Ala |
| | | 9200 | | | 9205 | | | 9210 | |

```
Thr Ala Thr Cys Cys Ala Cys Cys Gly Cys Cys Thr Ala Gly Ala
    9215             9220                 9225

Ala Cys Cys Ala Gly Thr Gly Ala Ala Thr Gly Thr Gly Ala
    9230             9235                 9240

Cys Ala Cys Cys Cys Thr Thr Thr Thr Gly Thr Gly Thr Gly Ala
    9245             9250                 9255

Cys Ala Thr Thr Gly Gly Ala Gly Ala Gly Thr Cys Ala Thr Cys
    9260             9265                 9270

Ala Thr Cys Gly Thr Cys Ala Thr Cys Gly Gly Thr Cys Ala Cys
    9275             9280                 9285

Ala Gly Ala Gly Gly Gly Gly Ala Ala Ala Gly Gly Ala Cys
    9290             9295                 9300

Cys Gly Thr Gly Ala Gly Ala Gly Thr Thr Cys Thr Thr Gly Ala
    9305             9310                 9315

Thr Ala Cys Thr Gly Thr Ala Gly Ala Ala Ala Ala Thr Gly
    9320             9325                 9330

Gly Cys Thr Gly Gly Cys Thr Thr Gly Thr Gly Gly Gly Thr
    9335             9340                 9345

Thr Gly Ala Cys Ala Ala Cys Thr Thr Cys Thr Gly Thr Gly Thr
    9350             9355                 9360

Gly Ala Ala Gly Gly Thr Gly Thr Thr Ala Gly Cys Thr Cys Cys
    9365             9370                 9375

Ala Thr Ala Cys Ala Thr Gly Cys Cys Ala Gly Ala Thr Gly Thr
    9380             9385                 9390

Thr Cys Thr Thr Gly Ala Gly Ala Ala Ala Cys Thr Gly Gly Ala
    9395             9400                 9405

Ala Thr Thr Gly Cys Thr Cys Cys Ala Ala Ala Gly Gly Ala Gly
    9410             9415                 9420

Gly Thr Thr Thr Gly Gly Cys Gly Gly Ala Ala Cys Ala Gly Thr
    9425             9430                 9435

Gly Ala Thr Cys Ala Gly Gly Ala Ala Cys Cys Cys Thr Cys Thr
    9440             9445                 9450

Cys Thr Cys Cys Ala Gly Gly Ala Ala Thr Thr Cys Cys Ala Cys
    9455             9460                 9465

Thr Cys Ala Thr Gly Ala Ala Ala Thr Gly Thr Ala Cys Thr Ala
    9470             9475                 9480

Cys Gly Thr Gly Thr Cys Thr Gly Gly Ala Gly Cys Cys Cys Gly
    9485             9490                 9495

Cys Ala Gly Cys Ala Ala Thr Gly Thr Cys Ala Cys Ala Thr Thr
    9500             9505                 9510

Thr Ala Cys Thr Gly Thr Gly Ala Ala Cys Cys Ala Ala Ala Cys
    9515             9520                 9525

Ala Thr Cys Cys Cys Gly Cys Cys Thr Cys Thr Gly Ala Thr
    9530             9535                 9540

Gly Ala Gly Gly Ala Gly Ala Ala Thr Gly Ala Gly Gly Cys Gly
    9545             9550                 9555

Thr Cys Cys Ala Ala Cys Thr Gly Gly Ala Ala Ala Ala Gly Thr
    9560             9565                 9570

Gly Ala Cys Cys Cys Thr Gly Gly Ala Gly Gly Cys Thr Gly Ala
    9575             9580                 9585

Cys Gly Thr Cys Ala Thr Cys Cys Thr Cys Cys Cys Ala Ala Thr
    9590             9595                 9600
```

| | | | | | | | | | | | |
|---|---|---|---|---|---|---|---|---|---|---|---|
|Thr|Gly|Gly|Gly|Ala|Cys|Ala|Cys|Gly|Cys|Ala|Gly|Thr|Gly|Thr|
| |9605| | | |9610| | | |9615| | | | | |
|Thr|Gly|Ala|Gly|Ala|Cys|Ala|Gly|Ala|Cys|Ala|Ala|Gly|Gly|Gly|
| |9620| | | |9625| | | |9630| | | | | |
|Ala|Cys|Cys|Cys|Cys|Thr|Gly|Gly|Ala|Cys|Ala|Ala|Ala|Gly|Ala|
| |9635| | | |9640| | | |9645| | | | | |
|Gly|Gly|Cys|Cys|Ala|Thr|Ala|Gly|Ala|Ala|Gly|Ala|Ala|Ala|Gly|
| |9650| | | |9655| | | |9660| | | | | |
|Gly|Gly|Thr|Thr|Gly|Ala|Gly|Ala|Gly|Gly|Ala|Thr|Ala|Ala|Ala|
| |9665| | | |9670| | | |9675| | | | | |
|Ala|Thr|Cys|Thr|Gly|Ala|Gly|Thr|Ala|Cys|Ala|Thr|Gly|Ala|Cys|
| |9680| | | |9685| | | |9690| | | | | |
|Cys|Thr|Cys|Thr|Thr|Gly|Gly|Thr|Thr|Thr|Thr|Ala|Thr|Gly|Ala|
| |9695| | | |9700| | | |9705| | | | | |
|Cys|Ala|Ala|Thr|Gly|Ala|Cys|Ala|Ala|Cys|Cys|Cys|Cys|Thr|Ala|
| |9710| | | |9715| | | |9720| | | | | |
|Cys|Ala|Gly|Gly|Ala|Cys|Cys|Thr|Gly|Gly|Cys|Ala|Cys|Thr|Ala|
| |9725| | | |9730| | | |9735| | | | | |
|Cys|Thr|Gly|Thr|Gly|Gly|Cys|Thr|Cys|Cys|Thr|Ala|Thr|Gly|Thr|
| |9740| | | |9745| | | |9750| | | | | |
|Cys|Ala|Cys|Ala|Ala|Ala|Ala|Cys|Cys|Thr|Cys|Ala|Gly|Gly|
| |9755| | | |9760| | | |9765| | | | |
|Ala|Ala|Gly|Thr|Gly|Cys|Gly|Gly|Cys|Gly|Ala|Gly|Cys|Ala|Thr|
| |9770| | | |9775| | | |9780| | | | | |
|Gly|Gly|Thr|Ala|Ala|Ala|Thr|Gly|Gly|Thr|Gly|Thr|Thr|Ala|Thr|
| |9785| | | |9790| | | |9795| | | | | |
|Thr|Ala|Ala|Ala|Ala|Thr|Thr|Cys|Thr|Gly|Ala|Cys|Ala|Thr|Ala|
| |9800| | | |9805| | | |9810| | | | | |
|Thr|Cys|Cys|Ala|Thr|Gly|Gly|Gly|Ala|Cys|Ala|Gly|Gly|Ala|Thr|
| |9815| | | |9820| | | |9825| | | | | |
|Ala|Gly|Ala|Gly|Gly|Ala|Gly|Gly|Thr|Cys|Ala|Cys|Cys|Ala|Gly|
| |9830| | | |9835| | | |9840| | | | | |
|Ala|Ala|Thr|Gly|Gly|Cys|Ala|Ala|Thr|Gly|Ala|Cys|Thr|Gly|Ala|
| |9845| | | |9850| | | |9855| | | | | |
|Cys|Ala|Cys|Ala|Ala|Cys|Cys|Cys|Thr|Thr|Thr|Thr|Gly|Gly|
| |9860| | | |9865| | | |9870| | | | |
|Ala|Cys|Ala|Gly|Cys|Ala|Ala|Ala|Gly|Ala|Gly|Thr|Gly|Thr|Thr|
| |9875| | | |9880| | | |9885| | | | | |
|Thr|Ala|Ala|Ala|Gly|Ala|Ala|Ala|Ala|Ala|Gly|Thr|Thr|Gly|Ala|
| |9890| | | |9895| | | |9900| | | | | |
|Cys|Ala|Cys|Cys|Ala|Gly|Ala|Gly|Cys|Ala|Ala|Ala|Gly|Gly|Ala|
| |9905| | | |9910| | | |9915| | | | | |
|Thr|Cys|Cys|Ala|Cys|Cys|Ala|Gly|Cys|Gly|Gly|Gly|Ala|Ala|Cys|
| |9920| | | |9925| | | |9930| | | | | |
|Thr|Ala|Gly|Gly|Ala|Ala|Gly|Ala|Thr|Cys|Ala|Thr|Gly|Ala|Ala|
| |9935| | | |9940| | | |9945| | | | | |
|Ala|Gly|Thr|Thr|Gly|Thr|Cys|Ala|Ala|Cys|Ala|Gly|Gly|Thr|Gly|
| |9950| | | |9955| | | |9960| | | | | |
|Gly|Cys|Thr|Gly|Thr|Thr|Cys|Cys|Gly|Cys|Ala|Cys|Cys|Thr|
| |9965| | | |9970| | | |9975| | | | |
|Gly|Gly|Cys|Cys|Ala|Gly|Ala|Gly|Ala|Ala|Ala|Gly|Ala|Gly|
| |9980| | | |9985| | | |9990| | | | |
|Cys|Cys|Cys|Cys|Ala|Gly|Ala| |Cys|Thr|Gly|Thr|Gly| |Cys|Ala|Cys|

-continued

```
             9995              10000             10005
     Ala  Ala  Ala  Gly  Gly  Ala  Ala  Gly  Ala  Ala  Thr  Thr  Thr  Ala  Thr
              10010              10015             10020
     Thr  Gly  Cys  Ala  Ala  Ala  Gly  Thr  Cys  Cys  Gly  Ala  Ala  Gly
              10025              10030             10035
     Thr  Cys  Ala  Thr  Gly  Cys  Ala  Gly  Cys  Cys  Ala  Thr  Thr  Gly  Gly
              10040              10045             10050
     Ala  Gly  Cys  Thr  Thr  Ala  Cys  Cys  Thr  Gly  Gly  Ala  Ala  Gly  Ala
              10055              10060             10065
     Ala  Cys  Ala  Ala  Gly  Ala  Ala  Cys  Ala  Gly  Thr  Gly  Gly  Ala  Ala
              10070              10075             10080
     Gly  Ala  Cys  Thr  Gly  Cys  Cys  Ala  Ala  Thr  Gly  Ala  Gly  Gly  Cys
              10085              10090             10095
     Thr  Gly  Thr  Cys  Cys  Ala  Ala  Gly  Ala  Cys  Cys  Cys  Ala  Ala  Ala
              10100              10105             10110
     Gly  Thr  Thr  Cys  Thr  Gly  Gly  Gly  Ala  Ala  Cys  Thr  Gly  Gly  Thr
              10115              10120             10125
     Gly  Gly  Ala  Thr  Gly  Ala  Ala  Gly  Ala  Ala  Ala  Gly  Gly  Ala  Ala
              10130              10135             10140
     Gly  Cys  Thr  Gly  Cys  Ala  Cys  Cys  Ala  Ala  Cys  Ala  Ala  Gly  Gly
              10145              10150             10155
     Cys  Ala  Gly  Gly  Thr  Gly  Thr  Cys  Gly  Gly  Ala  Cys  Thr  Thr  Gly
              10160              10165             10170
     Thr  Gly  Thr  Gly  Thr  Ala  Cys  Ala  Ala  Cys  Ala  Thr  Gly  Ala  Thr
              10175              10180             10185
     Gly  Gly  Gly  Gly  Ala  Ala  Ala  Ala  Gly  Ala  Gly  Ala  Gly  Ala  Ala
              10190              10195             10200
     Gly  Ala  Ala  Gly  Cys  Thr  Gly  Thr  Cys  Ala  Gly  Ala  Gly  Thr  Thr
              10205              10210             10215
     Thr  Gly  Gly  Gly  Ala  Ala  Ala  Gly  Cys  Ala  Ala  Ala  Gly  Gly  Gly
              10220              10225             10230
     Ala  Ala  Gly  Cys  Cys  Gly  Thr  Gly  Cys  Cys  Ala  Thr  Ala  Thr  Gly
              10235              10240             10245
     Gly  Thr  Ala  Thr  Ala  Thr  Gly  Thr  Gly  Gly  Cys  Thr  Gly  Gly  Gly
              10250              10255             10260
     Ala  Gly  Cys  Gly  Cys  Gly  Gly  Thr  Ala  Thr  Cys  Thr  Thr  Gly  Ala
              10265              10270             10275
     Gly  Thr  Thr  Thr  Gly  Ala  Gly  Gly  Cys  Cys  Cys  Thr  Gly  Gly  Gly
              10280              10285             10290
     Ala  Thr  Cys  Cys  Thr  Gly  Ala  Ala  Thr  Gly  Ala  Gly  Gly  Ala
              10295              10300             10305
     Cys  Cys  Ala  Thr  Thr  Gly  Gly  Gly  Cys  Thr  Thr  Cys  Cys  Ala  Gly
              10310              10315             10320
     Gly  Gly  Ala  Ala  Ala  Ala  Cys  Thr  Cys  Ala  Gly  Gly  Ala  Gly  Gly
              10325              10330             10335
     Ala  Gly  Gly  Ala  Gly  Thr  Gly  Gly  Ala  Ala  Gly  Gly  Cys  Ala  Thr
              10340              10345             10350
     Thr  Gly  Gly  Cys  Thr  Thr  Ala  Cys  Ala  Ala  Thr  Ala  Cys  Cys  Thr
              10355              10360             10365
     Ala  Gly  Gly  Ala  Thr  Ala  Thr  Gly  Thr  Gly  Ala  Thr  Cys  Ala  Gly
              10370              10375             10380
     Ala  Gly  Ala  Cys  Cys  Thr  Gly  Gly  Cys  Thr  Gly  Cys  Ala  Ala  Thr
              10385              10390             10395
```

```
Gly Gly Ala Thr Gly Gly Thr Gly Gly Thr Gly Gly Ala Thr Thr
    10400               10405               10410

Cys Thr Ala Cys Gly Cys Gly Gly Ala Thr Gly Ala Cys Ala Cys
    10415               10420               10425

Cys Gly Cys Thr Gly Gly Ala Thr Gly Gly Gly Ala Cys Ala Cys
    10430               10435               10440

Gly Cys Gly Cys Ala Thr Cys Ala Cys Ala Gly Ala Gly Gly Cys
    10445               10450               10455

Ala Gly Ala Cys Cys Thr Thr Gly Ala Thr Gly Ala Thr Gly Ala
    10460               10465               10470

Ala Cys Ala Gly Gly Ala Gly Ala Thr Cys Thr Thr Gly Ala Ala
    10475               10480               10485

Cys Thr Ala Cys Ala Thr Gly Ala Gly Cys Cys Cys Ala Cys Ala
    10490               10495               10500

Thr Cys Ala Cys Ala Ala Ala Ala Ala Ala Cys Thr Gly Gly Cys
    10505               10510               10515

Ala Cys Ala Ala Gly Cys Ala Gly Thr Gly Ala Thr Gly Gly Ala
    10520               10525               10530

Ala Ala Thr Gly Ala Cys Ala Thr Ala Cys Ala Ala Gly Ala Ala
    10535               10540               10545

Cys Ala Ala Ala Gly Thr Gly Gly Thr Gly Ala Ala Ala Gly Thr
    10550               10555               10560

Gly Thr Thr Gly Ala Gly Ala Cys Cys Ala Gly Cys Cys Cys Cys
    10565               10570               10575

Ala Gly Gly Ala Gly Gly Gly Ala Ala Ala Gly Cys Cys Thr Ala
    10580               10585               10590

Cys Ala Thr Gly Gly Ala Thr Gly Thr Cys Ala Thr Ala Ala Gly
    10595               10600               10605

Thr Cys Gly Ala Cys Gly Ala Gly Ala Cys Cys Ala Gly Ala Gly
    10610               10615               10620

Ala Gly Gly Ala Thr Cys Cys Gly Gly Gly Cys Ala Gly Gly Thr
    10625               10630               10635

Ala Gly Thr Gly Ala Cys Thr Thr Ala Thr Gly Cys Thr Cys Thr
    10640               10645               10650

Gly Ala Ala Cys Ala Cys Cys Ala Thr Cys Ala Cys Cys Ala Ala
    10655               10660               10665

Cys Thr Thr Gly Ala Ala Ala Gly Thr Cys Cys Ala Ala Thr Thr
    10670               10675               10680

Gly Ala Thr Cys Ala Gly Ala Ala Thr Gly Gly Cys Ala Gly Ala
    10685               10690               10695

Ala Gly Cys Ala Gly Ala Gly Ala Thr Gly Gly Thr Gly Ala Thr
    10700               10705               10710

Ala Cys Ala Thr Cys Ala Cys Cys Ala Ala Cys Ala Thr Gly Thr
    10715               10720               10725

Thr Cys Ala Ala Gly Ala Thr Thr Gly Thr Gly Ala Thr Gly Ala
    10730               10735               10740

Ala Thr Cys Ala Gly Thr Thr Cys Thr Gly Ala Cys Cys Ala Gly
    10745               10750               10755

Gly Cys Thr Gly Gly Ala Gly Gly Cys Ala Thr Gly Gly Cys Thr
    10760               10765               10770

Cys Ala Cys Thr Gly Ala Gly Cys Ala Cys Gly Gly Ala Thr Gly
    10775               10780               10785
```

-continued

```
Thr Ala   Ala Cys Ala Gly Ala   Cys Thr Gly Ala Ala   Gly Ala Gly
    10790                 10795                 10800

Gly Ala   Thr Gly Gly Cys Gly   Gly Thr Gly Ala Gly   Thr Gly Gly
    10805                 10810                 10815

Ala Gly   Ala Cys Gly Ala Cys   Thr Gly Thr Gly Thr   Gly Gly Thr
    10820                 10825                 10830

Cys Cys   Gly Gly Cys Cys Cys   Ala Thr Cys Gly Ala   Thr Gly Ala
    10835                 10840                 10845

Cys Ala   Gly Gly Thr Thr Cys   Gly Gly Cys Cys Thr   Gly Gly Cys
    10850                 10855                 10860

Cys Cys   Thr Gly Thr Cys Cys   Cys Ala Thr Cys Thr   Cys Ala Ala
    10865                 10870                 10875

Cys Gly   Cys Cys Ala Thr Gly   Thr Cys Cys Ala Ala   Gly Gly Thr
    10880                 10885                 10890

Thr Ala   Gly Ala Ala Ala Gly   Gly Ala Cys Ala Thr   Ala Thr Cys
    10895                 10900                 10905

Thr Gly   Ala Ala Thr Gly Gly   Cys Ala Gly Cys Cys   Ala Thr Cys
    10910                 10915                 10920

Ala Ala   Ala Ala Gly Gly Gly   Thr Gly Gly Ala Ala   Thr Gly Ala
    10925                 10930                 10935

Thr Thr   Gly Gly Gly Ala Gly   Ala Ala Thr Gly Thr   Gly Cys Cys
    10940                 10945                 10950

Cys Thr   Thr Cys Thr Gly Thr   Thr Cys Cys Cys Ala   Cys Cys Ala
    10955                 10960                 10965

Cys Thr   Thr Cys Cys Ala Thr   Gly Ala Ala Cys Thr   Ala Cys Ala
    10970                 10975                 10980

Gly Cys   Thr Gly Ala Ala Gly   Gly Ala Thr Gly Gly   Cys Ala Gly
    10985                 10990                 10995

Gly Ala   Gly Gly Ala Thr Thr   Gly Thr Gly Gly Thr   Gly Cys Cys
    11000                 11005                 11010

Thr Thr   Gly Cys Cys Gly Ala   Gly Ala Ala Cys Ala   Gly Gly Ala
    11015                 11020                 11025

Cys Gly   Ala Gly Cys Thr Cys   Ala Thr Thr Gly Gly   Gly Ala Gly
    11030                 11035                 11040

Ala Gly   Gly Ala Ala Gly Gly   Gly Thr Gly Thr Cys   Thr Cys Cys
    11045                 11050                 11055

Ala Gly   Gly Ala Ala Ala Cys   Gly Gly Cys Thr Gly   Gly Ala Thr
    11060                 11065                 11070

Gly Ala   Thr Cys Ala Ala Gly   Gly Ala Ala Ala Cys   Ala Gly Cys
    11075                 11080                 11085

Thr Thr   Gly Cys Cys Thr Cys   Ala Gly Cys Ala Ala   Ala Gly Cys
    11090                 11095                 11100

Cys Thr   Ala Thr Gly Cys Cys   Ala Ala Cys Ala Thr   Gly Thr Gly
    11105                 11110                 11115

Gly Thr   Cys Ala Cys Thr Gly   Ala Thr Gly Thr Ala   Thr Thr Thr
    11120                 11125                 11130

Thr Cys   Ala Cys Ala Ala Ala   Ala Gly Gly Gly Ala   Cys Ala Thr
    11135                 11140                 11145

Gly Ala   Gly Gly Cys Thr Ala   Cys Thr Gly Thr Cys   Ala Thr Thr
    11150                 11155                 11160

Gly Gly   Cys Thr Gly Thr Thr   Thr Cys Cys Thr Cys   Ala Gly Cys
    11165                 11170                 11175

Thr Gly   Thr Thr Cys Cys Cys   Ala Cys Cys Thr Cys   Ala Thr Gly
```

-continued

|  | 11180 |  |  | 11185 |  |  | 11190 |  |  |
|---|---|---|---|---|---|---|---|---|---|
| Gly | Gly | Thr | Thr | Cys | Cys | Ala | Cys | Ala | Ala | Gly | Gly | Ala | Cys | Gly |
|  | 11195 |  |  | 11200 |  |  | 11205 |  |  |
| Cys | Ala | Cys | Ala | Ala | Cys | Ala | Thr | Gly | Gly | Thr | Cys | Gly | Ala | Thr |
|  | 11210 |  |  | 11215 |  |  | 11220 |  |  |
| Thr | Cys | Ala | Thr | Gly | Gly | Gly | Ala | Ala | Ala | Gly | Gly | Gly | Gly | Ala |
|  | 11225 |  |  | 11230 |  |  | 11235 |  |  |
| Gly | Thr | Gly | Gly | Ala | Thr | Gly | Ala | Cys | Cys | Ala | Cys | Gly | Gly | Ala |
|  | 11240 |  |  | 11245 |  |  | 11250 |  |  |
| Ala | Gly | Ala | Cys | Ala | Thr | Gly | Cys | Thr | Thr | Gly | Ala | Gly | Gly | Thr |
|  | 11255 |  |  | 11260 |  |  | 11265 |  |  |
| Gly | Thr | Gly | Gly | Ala | Ala | Cys | Ala | Gly | Ala | Gly | Thr | Ala | Thr | Gly |
|  | 11270 |  |  | 11275 |  |  | 11280 |  |  |
| Gly | Ala | Thr | Ala | Ala | Cys | Cys | Ala | Ala | Cys | Ala | Ala | Cys | Cys | Cys |
|  | 11285 |  |  | 11290 |  |  | 11295 |  |  |
| Ala | Cys | Ala | Cys | Ala | Thr | Gly | Cys | Ala | Gly | Gly | Ala | Cys | Ala | Ala |
|  | 11300 |  |  | 11305 |  |  | 11310 |  |  |
| Gly | Ala | Cys | Ala | Ala | Thr | Gly | Gly | Thr | Gly | Ala | Ala | Ala | Ala | Ala |
|  | 11315 |  |  | 11320 |  |  | 11325 |  |  |
| Ala | Thr | Gly | Gly | Ala | Gly | Ala | Gly | Ala | Thr | Gly | Thr | Cys | Cys | Cys |
|  | 11330 |  |  | 11335 |  |  | 11340 |  |  |
| Thr | Thr | Ala | Thr | Cys | Thr | Ala | Ala | Cys | Cys | Ala | Ala | Gly | Ala | Gly |
|  | 11345 |  |  | 11350 |  |  | 11355 |  |  |
| Ala | Cys | Ala | Ala | Gly | Ala | Cys | Ala | Ala | Gly | Cys | Thr | Gly | Thr | Gly |
|  | 11360 |  |  | 11365 |  |  | 11370 |  |  |
| Cys | Gly | Gly | Ala | Thr | Cys | Ala | Cys | Thr | Gly | Ala | Thr | Thr | Gly | Gly |
|  | 11375 |  |  | 11380 |  |  | 11385 |  |  |
| Ala | Ala | Thr | Gly | Ala | Cys | Cys | Ala | Ala | Thr | Ala | Gly | Gly | Gly | Cys |
|  | 11390 |  |  | 11395 |  |  | 11400 |  |  |
| Cys | Ala | Cys | Cys | Thr | Gly | Gly | Gly | Cys | Cys | Thr | Cys | Cys | Cys | Ala |
|  | 11405 |  |  | 11410 |  |  | 11415 |  |  |
| Cys | Ala | Thr | Cys | Cys | Ala | Thr | Thr | Thr | Ala | Gly | Thr | Cys | Ala | Thr |
|  | 11420 |  |  | 11425 |  |  | 11430 |  |  |
| Cys | Cys | Ala | Thr | Cys | Gly | Thr | Ala | Thr | Cys | Cys | Gly | Ala | Ala | Cys |
|  | 11435 |  |  | 11440 |  |  | 11445 |  |  |
| Gly | Cys | Thr | Gly | Ala | Thr | Thr | Gly | Gly | Ala | Cys | Ala | Gly | Gly | Ala |
|  | 11450 |  |  | 11455 |  |  | 11460 |  |  |
| Gly | Ala | Ala | Ala | Thr | Ala | Cys | Ala | Cys | Thr | Gly | Ala | Cys | Thr | Ala |
|  | 11465 |  |  | 11470 |  |  | 11475 |  |  |
| Cys | Cys | Thr | Ala | Ala | Cys | Ala | Gly | Thr | Cys | Ala | Thr | Gly | Gly | Ala |
|  | 11480 |  |  | 11485 |  |  | 11490 |  |  |
| Cys | Ala | Gly | Gly | Thr | Ala | Thr | Thr | Cys | Thr | Gly | Thr | Gly | Gly | Ala |
|  | 11495 |  |  | 11500 |  |  | 11505 |  |  |
| Thr | Gly | Cys | Thr | Gly | Ala | Cys | Cys | Thr | Gly | Cys | Ala | Ala | Cys | Thr |
|  | 11510 |  |  | 11515 |  |  | 11520 |  |  |
| Gly | Gly | Gly | Thr | Gly | Ala | Gly | Cys | Thr | Thr | Ala | Thr | Cys | Thr | Gly |
|  | 11525 |  |  | 11530 |  |  | 11535 |  |  |
| Ala | Ala | Ala | Cys | Ala | Cys | Cys | Ala | Thr | Cys | Thr | Ala | Ala | Cys | Ala |
|  | 11540 |  |  | 11545 |  |  | 11550 |  |  |
| Gly | Gly | Ala | Ala | Thr | Ala | Ala | Cys | Cys | Gly | Gly | Gly | Ala | Thr | Ala |
|  | 11555 |  |  | 11560 |  |  | 11565 |  |  |
| Cys | Ala | Ala | Ala | Cys | Cys | Ala | Cys | Gly | Gly | Gly | Thr | Gly | Gly |

| | | | | | | | | | | |
|---|---|---|---|---|---|---|---|---|---|---|
|Gly|Ala|Ala|Cys|Cys|Gly|Gly|Ala|Cys|Thr|Cys|Cys|Cys|Ala|
| |11585| | | |11590| | | |11595| | | | |
|Cys|Ala|Ala|Cys|Cys|Thr|Gly|Ala|Ala|Ala|Cys|Cys|Gly|Gly|Gly|
| |11600| | | |11605| | | |11610| | | | |
|Ala|Thr|Ala|Thr|Ala|Ala|Ala|Cys|Cys|Ala|Cys|Gly|Gly|Cys|Thr|
| |11615| | | |11620| | | |11625| | | | |
|Gly|Gly|Ala|Gly|Ala|Ala|Cys|Cys|Gly|Gly|Gly|Cys|Thr|Cys|Cys|
| |11630| | | |11635| | | |11640| | | | |
|Gly|Cys|Ala|Cys|Thr|Thr|Ala|Ala|Ala|Ala|Thr|Gly|Ala|Ala|Ala|
| |11645| | | |11650| | | |11655| | | | |
|Cys|Ala|Gly|Ala|Ala|Ala|Cys|Cys|Gly|Gly|Gly|Ala|Thr|Ala|Ala|
| |11660| | | |11665| | | |11670| | | | |
|Ala|Ala|Ala|Cys|Thr|Ala|Cys|Gly|Gly|Ala|Thr|Gly|Gly|Ala|Gly|
| |11675| | | |11680| | | |11685| | | | |
|Ala|Ala|Cys|Cys|Gly|Gly|Ala|Cys|Thr|Cys|Cys|Ala|Cys|Ala|Cys|
| |11690| | | |11695| | | |11700| | | | |
|Ala|Thr|Thr|Gly|Ala|Gly|Ala|Cys|Ala|Gly|Ala|Ala|Gly|Ala|Ala|
| |11705| | | |11710| | | |11715| | | | |
|Gly|Thr|Thr|Gly|Thr|Cys|Ala|Gly|Cys|Cys|Cys|Ala|Gly|Ala|Ala|
| |11720| | | |11725| | | |11730| | | | |
|Cys|Cys|Cys|Cys|Ala|Cys|Ala|Cys|Gly|Ala|Gly|Thr|Thr|Thr|Thr|
| |11735| | | |11740| | | |11745| | | | |
|Gly|Cys|Cys|Ala|Cys|Thr|Gly|Cys|Thr|Ala|Ala|Gly|Cys|Thr|Gly|
| |11750| | | |11755| | | |11760| | | | |
|Thr|Gly|Ala|Gly|Gly|Cys|Ala|Gly|Thr|Gly|Cys|Ala|Gly|Gly|Cys|
| |11765| | | |11770| | | |11775| | | | |
|Thr|Gly|Gly|Gly|Ala|Cys|Ala|Gly|Cys|Cys|Gly|Ala|Cys|Cys|Thr|
| |11780| | | |11785| | | |11790| | | | |
|Cys|Cys|Ala|Gly|Gly|Thr|Thr|Gly|Cys|Gly|Ala|Ala|Ala|Ala|Ala|
| |11795| | | |11800| | | |11805| | | | |
|Cys|Cys|Thr|Gly|Gly|Thr|Thr|Thr|Cys|Thr|Gly|Gly|Gly|Ala|Cys|
| |11810| | | |11815| | | |11820| | | | |
|Cys|Thr|Cys|Cys|Cys|Ala|Cys|Cys|Cys|Cys|Ala|Gly|Ala|Gly|Thr|
| |11825| | | |11830| | | |11835| | | | |
|Ala|Ala|Ala|Ala|Ala|Gly|Ala|Ala|Cys|Gly|Gly|Ala|Gly|Cys|Cys|
| |11840| | | |11845| | | |11850| | | | |
|Thr|Cys|Cys|Gly|Cys|Thr|Ala|Cys|Cys|Ala|Cys|Cys|Cys|Thr|Cys|
| |11855| | | |11860| | | |11865| | | | |
|Cys|Cys|Ala|Cys|Gly|Thr|Gly|Gly|Thr|Gly|Gly|Thr|Ala|Gly|Ala|
| |11870| | | |11875| | | |11880| | | | |
|Ala|Ala|Gly|Ala|Cys|Gly|Gly|Gly|Gly|Thr|Cys|Thr|Ala|Gly|Ala|
| |11885| | | |11890| | | |11895| | | | |
|Gly|Gly|Thr|Thr|Ala|Gly|Ala|Gly|Gly|Ala|Gly|Ala|Cys|Cys|Cys|
| |11900| | | |11905| | | |11910| | | | |
|Thr|Cys|Cys|Ala|Gly|Gly|Gly|Ala|Ala|Cys|Ala|Ala|Ala|Thr|Ala|
| |11915| | | |11920| | | |11925| | | | |
|Gly|Thr|Gly|Gly|Gly|Ala|Cys|Cys|Ala|Thr|Ala|Thr|Thr|Gly|Ala|
| |11930| | | |11935| | | |11940| | | | |
|Cys|Gly|Cys|Cys|Ala|Gly|Gly|Gly|Ala|Ala|Ala|Gly|Ala|Cys|Cys|
| |11945| | | |11950| | | |11955| | | | |
|Gly|Gly|Ala|Gly|Thr|Gly|Gly|Thr|Thr|Cys|Thr|Cys|Thr|Gly|Cys|
| |11960| | | |11965| | | |11970| | | | |

| Thr | Thr | Thr | Cys | Cys | Thr | Cys | Cys | Ala | Gly | Ala | Gly | Gly | Thr |
| | 11975 | | | 11980 | | | | 11985 | | | | | |

| Cys | Thr | Gly | Thr | Gly | Ala | Gly | Cys | Ala | Cys | Ala | Gly | Thr | Thr | Thr |
| | 11990 | | | | 11995 | | | | 12000 | | | | | |

| Gly | Cys | Thr | Cys | Ala | Ala | Gly | Ala | Ala | Thr | Ala | Ala | Gly | Cys | Ala |
| | 12005 | | | | 12010 | | | | 12015 | | | | | |

| Gly | Ala | Cys | Cys | Thr | Thr | Thr | Gly | Gly | Ala | Thr | Gly | Ala | Cys | Ala |
| | 12020 | | | | 12025 | | | | 12030 | | | | | |

| Ala | Ala | Cys | Ala | Cys | Ala | Ala | Ala | Ala | Cys | Cys | Ala | Cys | | |
| | 12035 | | | | 12040 | | | | 12045 | | | | | |

<210> SEQ ID NO 13
<211> LENGTH: 939
<212> TYPE: DNA
<213> ORGANISM: Yellow fever virus

<400> SEQUENCE: 13

```
gatcaaggat gcgccatcaa ctttggcgtg agcaagggcg aggagctgtt caccggggtg    60
gtgcccatcc tggtcgagct ggacggcgac gtaaacggcc acaagttcag cgtgtccggc   120
gagggcgagg gcgatgccac ctacggcaag ctgaccctga agttcatctg caccaccggc   180
aagctgcccg tgccctggcc caccctcgtg accaccctga cctacggcgt gcagtgcttc   240
agccgctacc ccgaccacat gaagcagcac gacttcttca agtccgccat gcccgaaggc   300
tacgtccagg agcgcaccat cttcttcaag gacgacggca actacaagac ccgcgccgag   360
gtgaagttcg agggcgacac cctggtgaac cgcatcgagc tgaagggcat cgacttcaag   420
gaggacggca acatcctggg gcacaagctg gagtacaact acaacagcca caacgtctat   480
atcatggccg acaagcagaa gaacggcatc aaggtgaact tcaagatccg ccacaacatc   540
gaggacggca gcgtgcagct cgccgaccac taccagcaga cacccccat cggcgacggc   600
cccgtgctgc tgcccgacaa ccactacctg agcacccagt ccgccctgag caaagacccc   660
aacgagaagc gcgatcacat ggtcctgctg gagttcgtga ccgccgccgg gatcactctc   720
ggcatggacg agctgtacaa gacatcattg ggaaaggctg tgcaccaggt ttttggaagt   780
gtgtatacaa ccatgtttgg aggagtctca tggatgatta gaatcctaat tgggttctta   840
gtgttgtgga ttggcacgaa ctcgaggaac acttcaatgg ctatgacgtg catagctgtt   900
ggaggaatca ctctgtttct ggccttcaca gttggcgcc                          939
```

<210> SEQ ID NO 14
<211> LENGTH: 313
<212> TYPE: PRT
<213> ORGANISM: Yellow fever virus

<400> SEQUENCE: 14

Asp Gln Gly Cys Ala Ile Asn Phe Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala

```
                  85                  90                  95
Met Pro Glu Gly Tyr Val Gln Glu Arg Thr Ile Phe Phe Lys Asp Asp
            100                 105                 110
Gly Asn Tyr Lys Thr Arg Ala Glu Val Lys Phe Glu Gly Asp Thr Leu
        115                 120                 125
Val Asn Arg Ile Glu Leu Lys Gly Ile Asp Phe Lys Glu Asp Gly Asn
    130                 135                 140
Ile Leu Gly His Lys Leu Glu Tyr Asn Tyr Asn Ser His Asn Val Tyr
145                 150                 155                 160
Ile Met Ala Asp Lys Gln Lys Asn Gly Ile Lys Val Asn Phe Lys Ile
                165                 170                 175
Arg His Asn Ile Glu Asp Gly Ser Val Gln Leu Ala Asp His Tyr Gln
            180                 185                 190
Gln Asn Thr Pro Ile Gly Asp Gly Pro Val Leu Leu Pro Asp Asn His
        195                 200                 205
Tyr Leu Ser Thr Gln Ser Ala Leu Ser Lys Asp Pro Asn Glu Lys Arg
    210                 215                 220
Asp His Met Val Leu Leu Glu Phe Val Thr Ala Ala Gly Ile Thr Leu
225                 230                 235                 240
Gly Met Asp Glu Leu Tyr Lys Thr Ser Leu Gly Lys Ala Val His Gln
                245                 250                 255
Val Phe Gly Ser Val Tyr Thr Thr Met Phe Gly Gly Val Ser Trp Met
            260                 265                 270
Ile Arg Ile Leu Ile Gly Phe Leu Val Leu Trp Ile Gly Thr Asn Ser
        275                 280                 285
Arg Asn Thr Ser Met Ala Met Thr Cys Ile Ala Val Gly Gly Ile Thr
    290                 295                 300
Leu Phe Leu Gly Phe Thr Val Gly Ala
305                 310
```

<210> SEQ ID NO 15
<211> LENGTH: 1029
<212> TYPE: DNA
<213> ORGANISM: Yellow fever virus

<400> SEQUENCE: 15

```
gatcaaggat gcgccatcaa ctttggcgtg agcaagggcg aggagctgtt caccggggtg    60
gtgcccatcc tggtcgagct ggacggcgac gtaaacggcc acaagttcag cgtgtccggc   120
gagggcgagg gcgatgccac ctacggcaag ctgaccctga agttcatctg caccaccggc   180
aagctgcccg tgccctggcc caccctcgtg accaccctga cctacggcgt gcagtgcttc   240
agccgctacc ccgaccacat gaagcagcac gacttcttca gtccgccat gcccgaaggc   300
tacgtccagg agcgcaccat cttcttcaag gacgacggca actacaagac ccgcgccgag   360
gtgaagttcg agggcgacac cctggtgaac cgcatcgagc tgaagggcat cgacttcaag   420
gaggacggca acatcctggg gcacaagctg gagtacaact acaacagcca caacgtctat   480
atcatggccg acaagcagaa gaacggcatc aaggtgaact tcaagatccg ccacaacatc   540
gaggacggca cgtgcagct cgccgaccac taccagcaga acaccccat cggcgacggc   600
cccgtgctgc tgcccgacaa ccactacctg agcacccagt ccgccctgag caaagacccc   660
aacgagaagc gcgatcacat ggtcctgctg gagttcgtga ccgccgccgg gatcactctc   720
ggcatggacg agctgtacaa gaagatgttt gagtccacat acagaggtgc aaaacgaatg   780
gccattctag gtgaaacagc ttgggatttt ggttccgttg gtggactgtt cacatcattg   840
```

```
ggaaaggctg tgcaccaggt ttttggaagt gtgtatacaa ccatgtttgg aggagtctca      900
tggatgatta gaatcctaat tgggttctta gtgttgtgga ttggcacgaa ctccaggaac      960
acttcaatgg ctatgacgtg catagctgtt ggaggaatca ctctgtttct gggcttcaca     1020
gttggcgcc                                                             1029
```

<210> SEQ ID NO 16
<211> LENGTH: 343
<212> TYPE: PRT
<213> ORGANISM: Yellow fever virus

<400> SEQUENCE: 16

```
Asp Gln Gly Cys Ala Ile Asn Phe Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser G

Leu Gly Phe Thr Val Gly Ala
                340

<210> SEQ ID NO 17
<211> LENGTH: 1080
<212> TYPE: DNA
<213> ORGANISM: Yellow fever virus

<400> SEQUENCE: 17
gatcaaggat gcgccatcaa cttcggccga aagggatcac aaacctccaa cacaactaaa     60
tgggctcctc ccggacaagg aagtccaggt agcaagggcg aggagctgtt caccggggtg    120
gtgcccatcc tggtcgagct ggacggcgac gtaaacggcc acaagttcag cgtgtccggc    180
gagggcgagg gcgatgccac ctacggcaag ctgaccctga agttcatctg caccaccggc    240
aagctgcccg tgccctggcc caccctcgtg accaccctga cctacggcgt gcagtgcttc    300
agccgctacc ccgaccacat gaagcagcac gacttcttca gtccgccat gcccgaaggc     360
tacgtccagg agcgcaccat cttcttcaag gacgacggca actacaagac ccgcgccgag    420
gtgaagttcg agggcgacac cctggtgaac cgcatcgagc tgaagggcat cgacttcaag    480
gaggacggca acatcctggg gcacaagctg gagtacaact acaacagcca caacgtctat    540
atcatggccg acaagcagaa gaacggcatc aaggtgaact tcaagatccg ccacaacatc    600
gaggacggca gcgtgcagct cgccgaccac taccagcaga cacccccat cggcgacggc      660
cccgtgctgc tgcccgacaa ccactacctg agcacccagt ccgccctgag caaagacccc    720
aacgagaagc gcgatcacat ggtcctgctg gagttcgtga ccgccgccgg gatcactctc    780
ggcatggacg agctgtacaa gggtagcagt ccactgtctc atcgcagtaa aaggagccta    840
tcctgtcggc cacccatggt caaagaggga agctcaatag gaacatcatt gggaaaggct    900
gtgcaccagg tttttggaag tgtgtataca accatgtttg gaggagtctc atggatgatt    960
agaatcctaa ttgggttctt agtgttgtgg attggcacga actcaaggaa cacttcaatg   1020
gctatgacgt gcatagctgt tggaggaatc actctgtttc tgggcttcac agttggcgcc   1080

<210> SEQ ID NO 18
<211> LENGTH: 1080
<212> TYPE: PRT
<213> ORGANISM: Yellow fever virus

<400> SEQUENCE: 18

Gly Ala Thr Cys Ala Ala Gly Gly Ala Thr Gly Cys Gly Cys Cys Ala
1               5                   10                  15

Thr Cys Ala Ala Cys Thr Thr Cys Gly Gly Cys Cys Gly Ala Ala Ala
                20                  25                  30

Gly Gly Gly Ala Thr Cys Ala Cys Ala Ala Ala Cys Cys Thr Cys Cys
            35                  40                  45

Ala Ala Cys Ala Cys Ala Ala Cys Thr Ala Ala Ala Thr Gly Gly Gly
        50                  55                  60

Cys Thr Cys Cys Thr Cys Cys Cys Gly Gly Ala Cys Ala Ala Gly Gly
65                  70                  75                  80

Ala Ala Gly Thr Cys Cys Ala Gly Gly Thr Ala Gly Cys Ala Ala Gly
                85                  90                  95

Gly Gly Cys Gly Ala Gly Gly Ala Gly Cys Thr Gly Thr Thr Cys Ala
            100                 105                 110

Cys Cys Gly Gly Gly Gly Thr Gly Gly Thr Gly Cys Cys Cys Ala Thr
        115                 120                 125

Cys Cys Thr Gly Gly Thr Cys Gly Ala Gly Cys Gly Ala Cys
    130                 135                 140

Gly Gly Cys Gly Ala Cys Gly Thr Ala Ala Ala Cys Gly Gly Cys Cys
145                 150                 155                 160

Ala Cys Ala Ala Gly Thr Thr Cys Ala Gly Cys Gly Thr Gly Thr Cys
                165                 170                 175

Cys Gly Gly Cys Gly Ala Gly Gly Cys Gly Ala Gly Gly Gly Cys
            180                 185                 190

Gly Ala Thr Gly Cys Cys Ala Cys Cys Thr Ala Cys Gly Gly Cys Ala
    195                 200                 205

Ala Gly Cys Thr Gly Ala Cys Cys Cys Thr Gly Ala Ala Gly Thr Thr
    210                 215                 220

Cys Ala Thr Cys Thr Gly Cys Ala Cys Cys Ala Cys Cys Gly Gly Cys
225                 230                 235                 240

Ala Ala Gly Cys Thr Gly Cys Cys Cys Gly Thr Gly Cys Cys Cys Thr
                245                 250                 255

Gly Gly Cys Cys Cys Ala Cys Cys Cys Thr Cys Gly Thr Gly Ala Cys
            260                 265                 270

Cys Ala Cys Cys Cys Thr Gly Ala Cys Cys Thr Ala Cys Gly Gly Cys
    275                 280                 285

Gly Thr Gly Cys Ala Gly Thr Gly Cys Thr Thr Cys Ala Gly Cys Cys
290 295 300

Gly Cys Thr Ala Cys Cys Cys Cys Gly Ala Cys Cys Ala Cys Ala Thr
305 310 315 320

Gly Ala Ala Gly Cys Ala Gly Cys Ala Cys Gly Ala Cys Thr Thr Cys
325 330 335

Thr Thr Cys Ala Ala Gly Thr Cys Cys Gly Cys Cys Ala Thr Gly Cys
340 345 350

Cys Cys Gly Ala Ala Gly Gly Cys Thr Ala Cys Gly Thr Cys Cys Ala
355 360 365

Gly Gly Ala Gly Cys Gly Cys Ala Cys Cys Ala Thr Cys Thr Thr Cys
370 375 380

Thr Thr Cys Ala Ala Gly Gly Ala Cys Gly Ala Cys Gly Gly Cys Ala
385 390 395 400

Ala Cys Thr Ala Cys Ala Ala Gly Ala Cys Cys Cys Gly Cys Gly Cys
405 410 415

Cys Gly Ala Gly Gly Thr Gly Ala Ala Gly Thr Thr Cys Gly Ala Gly
420 425 430

Gly Gly Cys Gly Ala Cys Ala Cys Cys Cys Thr Gly Gly Thr Gly Ala
435 440 445

Ala Cys Cys Gly Cys Ala Thr Cys Gly Ala Gly Cys Thr Gly Ala Ala
450 455 460

Gly Gly Gly Cys Ala Thr Cys Gly Ala Cys Thr Thr Cys Ala Ala Gly
465 470 475 480

Gly Ala Gly Gly Ala Cys Gly Gly Cys Ala Ala Cys Ala Thr Cys Cys
485 490 495

Thr Gly Gly Gly Gly Cys Ala Cys Ala Ala Gly Cys Thr Gly Gly Ala
500 505 510

Gly Thr Ala Cys Ala Ala Cys Thr Ala Cys Ala Ala Cys Ala Gly Cys
515 520 525

Cys Ala Cys Ala Ala Cys Gly Thr Cys Thr Ala Thr Ala Thr Cys Ala
530 535 540

-continued

```
Thr Gly Gly Cys Cys Gly Ala Cys Ala Ala Gly Cys Ala Gly Ala Ala
545                 550                 555                 560

Gly Ala Ala Cys Gly Cys Ala Thr Cys Ala Ala Gly Gly Thr Gly
            565                 570                 575

Ala Ala Cys Thr Thr Cys Ala Ala Gly Ala Thr Cys Cys Gly Cys Cys
                580                 585                 590

Ala Cys Ala Ala Cys Ala Thr Cys Gly Ala Gly Ala Cys Gly Gly
            595                 600                 605

Cys Ala Gly Cys Gly Thr Gly Cys Ala Gly Cys Thr Cys Gly Cys Cys
            610                 615                 620

Gly Ala Cys Cys Ala Cys Thr Ala Cys Cys Ala Gly Cys Ala Gly Ala
625                 630                 635                 640

Ala Cys Ala Cys Cys Cys Cys Ala Thr Cys Gly Gly Cys Gly Ala
            645                 650                 655

Cys Gly Gly Cys Cys Cys Cys Gly Thr Gly Cys Thr Gly Cys Thr Gly
            660                 665                 670

Cys Cys Cys Gly Ala Cys Ala Ala Cys Cys Ala Cys Thr Ala Cys Cys
            675                 680                 685

Thr Gly Ala Gly Cys Ala Cys Cys Ala Gly Thr Cys Cys Gly Cys
690                 695                 700

Cys Cys Thr Gly Ala Gly Cys Ala Ala Ala Gly Ala Cys Cys Cys
705                 710                 715                 720

Ala Ala Cys Gly Ala Gly Ala Ala Gly Cys Gly Cys Gly Ala Thr Cys
            725                 730                 735

Ala Cys Ala Thr Gly Gly Thr Cys Cys Thr Gly Cys Thr Gly Gly Ala
                740                 745                 750

Gly Thr Thr Cys Gly Thr Gly Ala Cys Cys Gly Cys Cys Gly Cys Cys
                755                 760                 765

Gly Gly Gly Ala Thr Cys Ala Cys Thr Cys Thr Cys Gly Gly Cys Ala
            770                 775                 780

Thr Gly Gly Ala Cys Gly Ala Gly Cys Thr Gly Thr Ala Cys Ala Ala
785                 790                 795                 800

Gly Gly Gly Thr Ala Gly Cys Ala Gly Thr Cys Cys Ala Cys Thr Gly
            805                 810                 815

Thr Cys Thr Cys Ala Thr Cys Gly Cys Ala Gly Thr Ala Ala Ala
            820                 825                 830

Gly Gly Ala Gly Cys Cys Thr Ala Cys Cys Thr Gly Thr Cys Gly
            835                 840                 845

Gly Cys Cys Ala Cys Cys Cys Ala Thr Gly Gly Thr Cys Ala Ala Ala
            850                 855                 860

Gly Ala Gly Gly Ala Ala Gly Cys Thr Cys Ala Ala Thr Ala Gly
865                 870                 875                 880

Gly Ala Ala Cys Ala Thr Cys Ala Thr Gly Gly Gly Ala Ala Ala
            885                 890                 895

Gly Gly Cys Thr Gly Thr Gly Cys Ala Cys Ala Gly Gly Thr Thr
            900                 905                 910

Thr Thr Thr Gly Gly Ala Ala Gly Thr Gly Thr Gly Thr Ala Thr Ala
                915                 920                 925

Cys Ala Ala Cys Cys Ala Thr Gly Thr Thr Gly Ala Gly Gly
            930                 935                 940

Ala Gly Thr Cys Thr Cys Ala Thr Gly Gly Ala Thr Gly Ala Thr
945                 950                 955                 960

Ala Gly Ala Ala Thr Cys Cys Thr Ala Ala Thr Thr Gly Gly Gly Thr
```

|  | 965 |  |  | 970 |  |  | 975 |  |
|---|---|---|---|---|---|---|---|---|
| Thr | Cys | Thr | Thr | Ala | Gly | Thr | Gly | Thr |
| Thr | Gly | Thr | Gly | Gly | Ala | Thr |  |  |
| 980 |  |  | 985 |  |  | 990 |  |  |

| Thr | Gly | Gly | Cys | Ala | Cys | Gly | Ala | Ala | Cys | Thr | Cys | Ala | Ala | Gly | Gly |
|---|---|---|---|---|---|---|---|---|---|---|---|---|---|---|---|
| 995 |  |  |  | 1000 |  |  |  | 1005 |  |  |  |  |  |  |  |

| Ala | Ala | Cys | Ala | Cys | Thr | Thr | Cys | Ala | Ala | Thr | Gly | Gly | Cys | Thr |
|---|---|---|---|---|---|---|---|---|---|---|---|---|---|---|
| 1010 |  |  |  | 1015 |  |  |  | 1020 |  |  |  |  |  |  |

| Ala | Thr | Gly | Ala | Cys | Gly | Thr | Gly | Cys | Ala | Thr | Ala | Gly | Cys | Thr |
|---|---|---|---|---|---|---|---|---|---|---|---|---|---|---|
| 1025 |  |  |  | 1030 |  |  |  | 1035 |  |  |  |  |  |  |

| Gly | Thr | Thr | Gly | Gly | Ala | Gly | Gly | Ala | Ala | Thr | Cys | Ala | Cys | Thr |
|---|---|---|---|---|---|---|---|---|---|---|---|---|---|---|
| 1040 |  |  |  | 1045 |  |  |  | 1050 |  |  |  |  |  |  |

| Cys | Thr | Gly | Thr | Thr | Thr | Cys | Thr | Gly | Gly | Gly | Cys | Thr | Thr | Cys |
|---|---|---|---|---|---|---|---|---|---|---|---|---|---|---|
| 1055 |  |  |  | 1060 |  |  |  | 1065 |  |  |  |  |  |  |

| Ala | Cys | Ala | Gly | Thr | Thr | Gly | Gly | Cys | Gly | Cys | Cys |
|---|---|---|---|---|---|---|---|---|---|---|---|
| 1070 |  |  |  | 1075 |  |  |  | 1080 |  |  |  |

<210> SEQ ID NO 19
<211> LENGTH: 1173
<212> TYPE: DNA
<213> ORGANISM: Yellow fever virus

<400> SEQUENCE: 19

```
gatcaaggat gcgccatcaa cttcggccga aagggatcac aaacctccaa cacaactaaa      60
tgggctcctc ccggacaagg aagtcccggg agcaagggcg aggagctgtt caccggggtg     120
gtgcccatcc tggtcgagct ggacggcgac gtaaacggcc acaagttcag cgtgtccggc     180
gagggcgagg gcgatgccac ctacggcaag ctgaccctga agttcatctg caccaccggc     240
aagctgcccg tgccctggcc caccctcgtg accaccctga cctacggcgt gcagtgcttc     300
agccgctacc ccgaccacat gaagcagcac gacttcttca gtccgccat gcccgaaggc      360
tacgtccagg agcgcaccat cttcttcaag gacgacggca actacaagac ccgcgccgag     420
gtgaagttcg agggcgacac cctggtgaac cgcatcgagc tgaagggcat cgacttcaag     480
gaggacggca acatcctggg gcacaagctg gagtacaact acaacagcca caacgtctat     540
atcatggccg acaagcagaa gaacggcatc aaggtgaact tcaagatccg ccacaacatc     600
gaggacggca gcgtgcagct cgccgaccac taccagcaga acacccccat cggcgacggc     660
cccgtgctgc tgcccgacaa ccactacctg agcacccagt ccgccctgag caaagacccc     720
aacgagaagc gcgatcacat ggtcctgctg gagttcgtga ccgccgccgg gatcactctc     780
ggcatggacg agctgtacaa gtccggaagc agtccactgt ctcatcgcag taaaaggagc     840
ctatcctgtc ggccacccat ggtcaaagag ggaagctcaa taggaaagat gtttgagtcc     900
acatacagag gtgcaaaacg aatgccatt ctaggtgaaa cagcttggga ttttggttcc      960
gttggtggac tgttcacatc attgggaaag gctgtgcacc aggttttgg aagtgtgtat     1020
acaaccatgt ttggaggagt ctcatggatg attagaatcc taattgggtt cttagtgttg    1080
tggattggca cgaactccag gaacacttca atggctatga cgtgcatagc tgttggagga    1140
atcactctgt ttctgggctt cacagttggc gcc                                 1173
```

<210> SEQ ID NO 20
<211> LENGTH: 391
<212> TYPE: PRT
<213> ORGANISM: Yellow fever virus

<400> SEQUENCE: 20

Asp Gln Gly Cys Ala Ile Asn Phe Gly Arg Lys Gly Ser Gln Thr Ser
1               5                   10                  15

Asn Thr Thr Lys Trp Ala Pro Pro Gly Gln Gly Ser Pro Gly Ser Lys
            20                  25                  30

Gly Glu Glu Leu Phe Thr Gly Val Val Pro Ile Leu Val Glu Leu Asp
            35                  40                  45

Gly Asp Val Asn Gly His Lys Phe Ser Val Ser Gly Glu Gly Glu Gly
50                      55                  60

Asp Ala Thr Tyr Gly Lys Leu Thr Leu Lys Phe Ile Cys Thr Thr Gly
65                  70                  75                  80

Lys Leu Pro Val Pro Trp Pro Thr Leu Val Thr Thr Leu Thr Tyr Gly
                85                  90                  95

Val Gln Cys Phe Ser Arg Tyr Pro Asp His Met Lys Gln His Asp Phe
            100                 105                 110

Phe Lys Ser Ala Met Pro Glu Gly Tyr Val Gln Glu Arg Thr Ile Phe
            115                 120                 125

Phe Lys Asp Asp Gly Asn Tyr Lys Thr Arg Ala Glu Val Lys Phe Glu
            130                 135                 140

Gly Asp Thr Leu Val Asn Arg Ile Glu Leu Lys Gly Ile Asp Phe Lys
145                 150                 155                 160

Glu Asp Gly Asn Ile Leu Gly His Lys Leu Glu Tyr Asn Tyr Asn Ser
                165                 170                 175

His Asn Val Tyr Ile Met Ala Asp Lys Gln Lys Asn Gly Ile Lys Val
                180                 185                 190

Asn Phe Lys Ile Arg His Asn Ile Glu Asp Gly Ser Val Gln Leu Ala
            195                 200                 205

Asp His Tyr Gln Gln Asn Thr Pro Ile Gly Asp Gly Pro Val Leu Leu
            210                 215                 220

Pro Asp Asn His Tyr Leu Ser Thr Gln Ser Ala Leu Ser Lys Asp Pro
225                 230                 235                 240

Asn Glu Lys Arg Asp His Met Val Leu Leu Glu Phe Val Thr Ala Ala
                245                 250                 255

Gly Ile Thr Leu Gly Met Asp Glu Leu Tyr Lys Ser Gly Ser Ser Pro
            260                 265                 270

Leu Ser His Arg Ser Lys Arg Ser Leu Ser Cys Arg Pro Pro Met Val
            275                 280                 285

Lys Glu Gly Ser Ser Ile Gly Lys Met Phe Glu Ser Thr Tyr Arg Gly
            290                 295                 300

Ala Lys Arg Met Ala Ile Leu Gly Glu Thr Ala Trp Asp Phe Gly Ser
305                 310                 315                 320

Val Gly Gly Leu Phe Thr Ser Leu Gly Lys Ala Val His Gln Val Phe
                325                 330                 335

Gly Ser Val Tyr Thr Thr Met Phe Gly Gly Val Ser Trp Met Ile Arg
                340                 345                 350

Ile Leu Ile Gly Phe Leu Val Leu Trp Ile Gly Thr Asn Ser Arg Asn
            355                 360                 365

Thr Ser Met Ala Met Thr Cys Ile Ala Val Gly Gly Ile Thr Leu Phe
370                 375                 380

Leu Gly Phe Thr Val Gly Ala
385                 390

<210> SEQ ID NO 21
<211> LENGTH: 1068
<212> TYPE: DNA

<213> ORGANISM: Yellow fever virus

<400> SEQUENCE: 21

```
gatcaaggat gcgccatcaa cttcggccga aagtcagggg aagaacatgc agtcggaaat      60
actacaggaa gtagcaaggg cgaggagctg ttcaccgggg tggtgcccat cctggtcgag     120
ctggacggcg acgtaaacgg ccacaagttc agcgtgtccg gcgagggcga gggcgatgcc     180
acctacggca agctgaccct gaagttcatc tgcaccaccg gcaagctgcc cgtgccctgg     240
cccaccctcg tgaccaccct gacctacggc gtgcagtgct tcagccgcta ccccgaccac     300
atgaagcagc acgacttctt caagtccgcc atgcccgaag gctacgtcca ggagcgcacc     360
atcttcttca aggacgacgg caactacaag acccgcgccg aggtgaagtt cgagggcgac     420
accctggtga accgcatcga gctgaagggc atcgacttca aggaggacgg caacatcctg     480
gggcacaagc tggagtacaa ctacaacagc cacaacgtct atatcatggc cgacaagcag     540
aagaacggca tcaaggtgaa cttcaagatc cgccacaaca tcgaggacgg cagcgtgcag     600
ctcgccgacc actaccagca gaacaccccc atcggcgacg gccccgtgct gctgcccgac     660
aaccactacc tgagcaccca gtccgccctg agcaaagacc ccaacgagaa gcgcgatcac     720
atggtcctgc tggagttcgt gaccgccgcc gggatcactc tcggcatgga cgagctgtac     780
aagagtggag ggaaacagga aggctcacgg acaaggcgct cagtgctgat cccatcccat     840
gctcaggaa aagagggaag ctcaatagga acatcattgg aaaggctgt gcaccaggtt     900
tttggaagtg tgtatacaac catgtttgga ggagtctcat ggatgattag aatcctaatt     960
gggttcttag tgttgtggat tggcacgaac tcaaggaaca cttcaatggc tatgacgtgc    1020
atagctgttg gaggaatcac tctgtttctg ggcttcacag ttggcgcc                1068
```

<210> SEQ ID NO 22
<211> LENGTH: 356
<212> TYPE: PRT
<213> ORGANISM: Yellow fever virus

<400> SEQUENCE: 22

```
Asp Gln Gly Cys Ala Ile Asn Phe Gly Arg Lys Ser Gly Glu His
1               5                   10                  15

Ala Val Gly Asn Thr Thr Gly Ser Ser Lys Gly Glu Glu Leu Phe Thr
            20                  25                  30

Gly Val Val Pro Ile Leu Val Glu Leu Asp Gly Asp Val Asn Gly His
        35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
65                  70                  75                  80

Pro Thr Leu Val Thr Thr Leu Thr Tyr Gly Val Gln Cys Phe Ser Arg
                85                  90                  95

Tyr Pro Asp His Met Lys Gln His Asp Phe Phe Lys Ser Ala Met Pro
            100                 105                 110

Glu Gly Tyr Val Gln Glu Arg Thr Ile Phe Phe Lys Asp Asp Gly Asn
        115                 120                 125

Tyr Lys Thr Arg Ala Glu Val Lys Phe Glu Gly Asp Thr Leu Val Asn
    130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Met
```

```
                165                 170                 175
Ala Asp Lys Gln Lys Asn Gly Ile Lys Val Asn Phe Lys Ile Arg His
            180                 185                 190

Asn Ile Glu Asp Gly Ser Val Gln Leu Ala Asp His Tyr Gln Gln Asn
        195                 200                 205

Thr Pro Ile Gly Asp Gly Pro Val Leu Leu Pro Asp Asn His Tyr Leu
    210                 215                 220

Ser Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
                245                 250                 255

Asp Glu Leu Tyr Lys Ser Gly Gly Lys Gln Glu Gly Ser Arg Thr Arg
            260                 265                 270

Arg Ser Val Leu Ile Pro Ser His Ala Gln Gly Lys Glu Gly Ser Ser
        275                 280                 285

Ile Gly Thr Ser Leu Gly Lys Ala Val His Gln Val Phe Gly Ser Val
    290                 295                 300

Tyr Thr Thr Met Phe Gly Gly Val Ser Trp Met Ile Arg Ile Leu Ile
305                 310                 315                 320

Gly Phe Leu Val Leu Trp Ile Gly Thr Asn Ser Arg Asn Thr Ser Met
                325                 330                 335

Ala Met Thr Cys Ile Ala Val Gly Gly Ile Thr Leu Phe Leu Gly Phe
            340                 345                 350

Thr Val Gly Ala
        355

<210> SEQ ID NO 23
<211> LENGTH: 1185
<212> TYPE: DNA
<213> ORGANISM: Yellow fever virus

<400> SEQUENCE: 23
gatcaaggat gcgccatcaa cttcggccga aagggatcac aaacctccaa cacaactaaa    60
tgggctcctc ccggacaagg aagtcccggg agcaagggcg aggagctgtt caccggggtg   120
gtgcccatcc tggtcgagct ggacggcgac gtaaacggcc acaagttcag cgtgtccggc   180
gagggcgagg gcgatgccac ctacggcaag ctgaccctga agttcatctg caccaccggc   240
aagctgcccg tgccctggcc caccctcgtg accaccctga cctacggcgt gcagtgcttc   300
agccgctacc ccgaccacat gaagcagcac gacttcttca agtccgccat gcccgaaggc   360
tacgtccagg agcgcaccat cttcttcaag gacgacggca actacaagac ccgcgccgag   420
gtgaagttcg agggcgacac cctggtgaac cgcatcgagc tgaagggcat cgacttcaag   480
gaggacggca acatcctggg gcacaagctg gagtacaact acaacagcca caacgtctat   540
atcatggccg acaagcagaa gaacggcatc aaggtgaact tcaagatccg ccacaacatc   600
gaggacggca gcgtgcagct cgccgaccac taccagcaga cacccccat cggcgacggc    660 cccgtgctgc tgcccgacaa ccactacctg agcacccagt ccgccctgag caagacccc    720 aacgagaagc gcgatcacat ggtcctgctg gagttcgtga ccgccgccgg gatcactctc   780
ggcatggacg agctgtacaa gtccggaagc agtccacagc tgttgaattt tgaccttctt   840
aagcttgctg agacgtcga gtccaaccct gggccaaagg agggaagctc aataggaaag   900
atgtttgagt ccacatacag aggtgcaaaa cgaatggcca ttctaggtga aacagcttgg   960
gattttggtt ccgttggtgg actgttcaca tcattgggaa aggctgtgca ccaggttttt  1020
```

-continued

```
ggaagtgtgt atacaaccat gtttggagga gtctcatgga tgattagaat cctaattggg    1080
ttcttagtgt tgtggattgg cacgaactcc aggaacactt caatggctat gacgtgcata    1140
gctgttggag gaatcactct gtttctgggc ttcacagttg gcgcc                    1185
```

<210> SEQ ID NO 24
<211> LENGTH: 395
<212> TYPE: PRT
<213> ORGANISM: Yellow fever virus

<400> SEQUENCE: 24

```
Asp Gln Gly Cys Ala Ile Asn Phe Gly Arg Lys Gly Ser Gln Thr Ser
1               5                   10                  15

Asn Thr Thr Lys Trp Ala Pro Pro Gln Gly Ser Pro Gly Ser Lys
            20                  25                  30

Gly Glu Glu Leu Phe Thr Gly Val Val Pro Ile Leu Val Glu Leu Asp
        35                  40                  45

Gly Asp Val Asn Gly His Lys Phe Ser Val Ser Gly Glu Gly Glu Gly
    50                  55                  60

Asp Ala Thr Tyr Gly Lys Leu Thr Leu Lys Phe Ile Cys Thr Thr Gly
65                  70                  75                  80

Lys Leu Pro Val Pro Trp Pro Thr Leu Val Thr Thr Leu Thr Tyr Gly
                85                  90                  95

Val Gln Cys Phe Ser Arg Tyr Pro Asp His Met Lys Gln His Asp Phe
            100                 105                 110

Phe Lys Ser Ala Met Pro Glu Gly Tyr Val Gln Glu Arg Thr Ile Phe
        115                 120                 125

Phe Lys Asp Asp Gly Asn Tyr Lys Thr Arg Ala Glu Val Lys Phe Glu
    130                 135                 140

Gly Asp Thr Leu Val Asn Arg Ile Glu Leu Lys Gly Ile Asp Phe Lys
145                 150                 155                 160

Glu Asp Gly Asn Ile Leu Gly His Lys Leu Glu Tyr Asn Tyr Asn Ser
                165                 170                 175

His Asn Val Tyr Ile Met Ala Asp Lys Gln Lys Asn Gly Ile Lys Val
            180                 185                 190

Asn Phe Lys Ile Arg His Asn Ile Glu Asp Gly Ser Val Gln Leu Ala
        195                 200                 205

Asp His Tyr Gln Gln Asn Thr Pro Ile Gly Asp Gly Pro Val Leu Leu
    210                 215                 220

Pro Asp Asn His Tyr Leu Ser Thr Gln Ser Ala Leu Ser Lys Asp Pro
225                 230                 235                 240

Asn Glu Lys Arg Asp His Met Val Leu Leu Glu Phe Val Thr Ala Ala
                245                 250                 255

Gly Ile Thr Leu Gly Met Asp Glu Leu Tyr Lys Ser Gly Ser Ser Pro
            260                 265                 270

Gln Leu Leu Asn Phe Asp Leu Leu Lys Leu Ala Gly Asp Val Glu Ser
        275                 280                 285

Asn Pro Gly Pro Lys Glu Gly Ser Ser Ile Gly Lys Met Phe Glu Ser
    290                 295                 300

Thr Tyr Arg Gly Ala Lys Arg Met Ala Ile Leu Gly Glu Thr Ala Trp
305                 310                 315                 320

Asp Phe Gly Ser Val Gly Gly Leu Phe Thr Ser Leu Gly Lys Ala Val
                325                 330                 335

His Gln Val Phe Gly Ser Val Tyr Thr Thr Met Phe Gly Gly Val Ser
```

-continued

```
                340             345             350
Trp Met Ile Arg Ile Leu Ile Gly Phe Leu Val Leu Trp Ile Gly Thr
            355                 360                 365

Asn Ser Arg Asn Thr Ser Met Ala Met Thr Cys Ile Ala Val Gly Gly
        370                 375                 380

Ile Thr Leu Phe Leu Gly Phe Thr Val Gly Ala
385                 390                 395

<210> SEQ ID NO 25
<211> LENGTH: 711
<212> TYPE: DNA
<213> ORGANISM: Aequorea victoria

<400> SEQUENCE: 25
agcaagggcg aggagctgtt caccggggtg gtgcccatcc tggtcgagct ggacggcgac     60
gtaaacggcc acaagttcag cgtgtccggc gagggcgagg gcgatgccac ctacggcaag    120
ctgaccctga agttcatctg caccaccggc aagctgcccg tgccctggcc caccctcgtg    180
accaccctga cctacggcgt gcagtgcttc agccgctacc ccgaccacat gaagcagcac    240
gacttcttca gtccgccat gcccgaaggc tacgtccagg agcgcaccat cttcttcaag    300
gacgacggca actacaagac ccgcgccgag gtgaagttcg agggcgacac cctggtgaac    360
cgcatcgagc tgaagggcat cgacttcaag gaggacggca acatcctggg cacaagctg    420 gagtacaact acaacagcca caacgtctat atcatggccg acaagcagaa gaacggcatc    480
aaggtgaact tcaagatccg ccacaacatc gaggacggca gcgtgcagct cgccgaccac    540
taccagcaga acacccccat cggcgacggc cccgtgctgc tgcccgacaa ccactacctg    600
agcacccagt ccgccctgag caaagacccc aacgagaagc gcgatcacat ggtcctgctg    660
gagttcgtga ccgccgccgg gatcactctc ggcatggacg agctgtacaa g             711

<210> SEQ ID NO 26
<211> LENGTH: 237
<212> TYPE: PRT
<213> ORGANISM: Aequorea victoria

<400> SEQUENCE: 26

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
        35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Gln His
65                  70                  75                  80

Asp Phe Phe Lys Ser Ala Met Pro Glu Gly Tyr Val Gln Glu Arg Thr
                85                  90                  95

Ile Phe Phe Lys Asp Asp Gly Asn Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Tyr
    130                 135                 140

Asn Ser His Asn Val Tyr Ile Met Ala Asp Lys Gln Lys Asn Gly Ile
```

```
                145                 150                 155                 160
Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
        195                 200                 205

Asp Pro Asn Glu Lys Arg Asp His Met Val Leu Leu Glu Phe Val Thr
    210                 215                 220

Ala Ala Gly Ile Thr Leu Gly Met Asp Glu Leu Tyr Lys
225                 230                 235

<210> SEQ ID NO 27
<211> LENGTH: 27
<212> TYPE: DNA
<213> ORGANISM: Yellow fever virus

<400> SEQUENCE: 27
gatcaaggat gcgccatcaa cttcggc                                          27

<210> SEQ ID NO 28
<211> LENGTH: 9
<212> TYPE: PRT
<213> ORGANISM: Yellow fever virus

<400> SEQUENCE: 28

Asp Gln Gly Cys Ala Ile Asn Phe Gly
1               5

<210> SEQ ID NO 29
<211> LENGTH: 63
<212> TYPE: DNA
<213> ORGANISM: Rabies virus

<400> SEQUENCE: 29
cgaaagggat cacaaacctc aacacaact aaatgggctc ctcccggaca aggaagtccc      60
ggg                                                                    63

<210> SEQ ID NO 30
<211> LENGTH: 21
<212> TYPE: PRT
<213> ORGANISM: Rabies virus

<400> SEQUENCE: 30

Arg Lys Gly Ser Gln Thr Ser Asn Thr Thr Lys Trp Ala Pro Pro Gly
1               5                   10                  15

Gln Gly Ser Pro Gly
            20

<210> SEQ ID NO 31
<211> LENGTH: 39
<212> TYPE: DNA
<213> ORGANISM: Rabies virus

<400> SEQUENCE: 31
caaacctcca acacaactaa atgggctcct cccggacaa                             39

<210> SEQ ID NO 32
<211> LENGTH: 13
<212> TYPE: PRT
<213> ORGANISM: Rabies virus
```

<400> SEQUENCE: 32

Gln Thr Ser Asn Thr Thr Lys Trp Ala Pro Pro Gly Gln
1               5                   10

<210> SEQ ID NO 33
<211> LENGTH: 12
<212> TYPE: DNA
<213> ORGANISM: Artificial Sequence
<220> FEATURE:
<223> OTHER INFORMATION: 5' spacer of the motif containing the
      N-glycosylation site of the G protein of rabies virus

<400> SEQUENCE: 33
cgaaagggat ca                                                          12

<210> SEQ ID NO 34
<211> LENGTH: 4
<212> TYPE: PRT
<213> ORGANISM: Artificial Sequence
<220> FEATURE:
<223> OTHER INFORMATION: N-terminal spacer of the motif containing the
      N-glycosylation site of the G protein from rabies virus

<400> SEQUENCE: 34

Arg Lys Gly Ser
1

<210> SEQ ID NO 35
<211> LENGTH: 12
<212> TYPE: DNA
<213> ORGANISM: Artificial Sequence
<220> FEATURE:
<223> OTHER INFORMATION: 3' spacer of the motif containing the
      N-glycosylation site of the G protein from rabies virus

<400> SEQUENCE: 35
ggaagtcccg gg                                                          12

<210> SEQ ID NO 36
<211> LENGTH: 4
<212> TYPE: PRT
<213> ORGANISM: Artificial Sequence
<220> FEATURE:
<223> OTHER INFORMATION: C-terminal spacer of the motif containing the
      N-glycosylation site of the G protein of the rabies virus

<400> SEQUENCE: 36

Gly Ser Pro Gly
1

<210> SEQ ID NO 37
<211> LENGTH: 45
<212> TYPE: DNA
<213> ORGANISM: Dengue virus type 2

<400> SEQUENCE: 37
cgaaagtcag gggaagaaca tgcagtcgga aatactacag gaagt                      45

<210> SEQ ID NO 38
<211> LENGTH: 15
<212> TYPE: PRT
<213> ORGANISM: Dengue virus type 2

<400> SEQUENCE: 38

Arg Lys Ser Gly Glu Glu His Ala Val Gly Asn Thr Thr Gly Ser

<210> SEQ ID NO 39
<211> LENGTH: 33
<212> TYPE: DNA
<213> ORGANISM: Dengue virus type 2

<400> SEQUENCE: 39
tcaggggaag aacatgcagt cggaaatact aca                                33

<210> SEQ ID NO 40
<211> LENGTH: 11
<212> TYPE: PRT
<213> ORGANISM: Dengue virus type 2

<400> SEQUENCE: 40

Ser Gly Glu Glu His Ala Val Gly Asn Thr Thr
1               5                   10

<210> SEQ ID NO 41
<211> LENGTH: 6
<212> TYPE: DNA
<213> ORGANISM: Artificial Sequence
<220> FEATURE:
<223> OTHER INFORMATION: 5' spacer motif containing the N-glycosylation
      site of the E protein of dengue virus type 2

<400> SEQUENCE: 41 cgaaag                                                              6

<210> SEQ ID NO 42
<211> LENGTH: 2
<212> TYPE: PRT
<213> ORGANISM: Artificial Sequence
<220> FEATURE:
<223> OTHER INFORMATION: N-terminal motif containing the N-glycosylation
      site of the E protein of dengue virus type 2

<400> SEQUENCE: 42

Arg Lys
1

<210> SEQ ID NO 43
<211> LENGTH: 6
<212> TYPE: DNA
<213> ORGANISM: Artificial Sequence
<220> FEATURE:
<223> OTHER INFORMATION: 3' spacer motif containing the N-glycosylation
      site of the E protein of dengue virus type 2

<400> SEQUENCE: 43 ggaagt                                                              6

<210> SEQ ID NO 44
<211> LENGTH: 2
<212> TYPE: PRT
<213> ORGANISM: Artificial Sequence
<220> FEATURE:
<223> OTHER INFORMATION: C-terminal spacer motif containing the
      N-glycosylation site of the E protein of dengue virus type 2

<400> SEQUENCE: 44

Gly Ser
1

<210> SEQ ID NO 45

```
<211> LENGTH: 84
<212> TYPE: DNA
<213> ORGANISM: Homo sapiens

<400> SEQUENCE: 45
tccggaagca gtccactgtc tcatcgcagt aaaaggagcc tatcctgtcg gccacccatg      60
gtcaaagagg gaagctcaat agga                                            84

<210> SEQ ID NO 46
<211> LENGTH: 28
<212> TYPE: PRT
<213> ORGANISM: Homo sapiens

<400> SEQUENCE: 46

Ser Gly Ser Ser Pro Leu Ser His Arg Ser Lys Arg Ser Leu Ser Cys
1               5                   10                  15

Arg Pro Pro Met Val Lys Glu Gly Ser Ser Ile Gly
            20                  25

<210> SEQ ID NO 47
<211> LENGTH: 57
<212> TYPE: DNA
<213> ORGANISM: Homo sapiens

<400> SEQUENCE: 47
agcagtccac tgtctcatcg cagtaaaagg agcctatcct gtcggccacc catggtc         57

<210> SEQ ID NO 48
<211> LENGTH: 19
<212> TYPE: PRT
<213> ORGANISM: Homo sapiens

<400> SEQUENCE: 48

Ser Ser Pro Leu Ser His Arg Ser Lys Arg Ser Leu Ser Cys Arg Pro
1               5                   10                  15

Pro Met Val

<210> SEQ ID NO 49
<211> LENGTH: 6
<212> TYPE: DNA
<213> ORGANISM: Artificial Sequence
<220> FEATURE:
<223> OTHER INFORMATION: 5' spacer motif containing the furin cleavage
      site of the von Willebrand human factor

<400> SEQUENCE: 49 tccgga                                                                 6

<210> SEQ ID NO 50
<211> LENGTH: 2
<212> TYPE: PRT
<213> ORGANISM: Artificial Sequence
<220> FEATURE:
<223> OTHER INFORMATION: N-terminal spacer motif containing the furin
      cleavage site of the von Willebrand human factor

<400> SEQUENCE: 50

Ser Gly
1

<210> SEQ ID NO 51
<211> LENGTH: 21
<212> TYPE: DNA
<213> ORGANISM: Artificial Sequence
```

```
<220> FEATURE:
<223> OTHER INFORMATION: 3' spacer motif containing the furin cleavage
      site of the von Willebrand human factor

<400> SEQUENCE: 51
aaagagggaa gctcaatagg a                                              21

<210> SEQ ID NO 52
<211> LENGTH: 7
<212> TYPE: PRT
<213> ORGANISM: Artificial Sequence
<220> FEATURE:
<223> OTHER INFORMATION: C-terminal spacer motif containing the furin
      cleavage site of the von Willebrand human factor

<400> SEQUENCE: 52

Lys Glu Gly Ser Ser Ile Gly
1               5

<210> SEQ ID NO 53
<211> LENGTH: 87
<212> TYPE: DNA
<213> ORGANISM: Tick-borne encephalitis virus

<400> SEQUENCE: 53
agtggaggga acaggaagg ctcacggaca aggcgctcag tgctgatccc atcccatgct    60
cagggaaaag agggaagctc aatagga                                        87

<210> SEQ ID NO 54
<211> LENGTH: 29
<212> TYPE: PRT
<213> ORGANISM: Tick-borne encephalitis virus

<400> SEQUENCE: 54

Ser Gly Gly Lys Gln Glu Gly Ser Arg Thr Arg Arg Ser Val Leu Ile
1               5                   10                  15

Pro Ser His Ala Gln Gly Lys Glu Gly Ser Ser Ile Gly
            20                  25

<210> SEQ ID NO 55
<211> LENGTH: 60
<212> TYPE: DNA
<213> ORGANISM: Tick-borne encephalitis virus

<400> SEQUENCE: 55
gggaaacagg aaggctcacg gacaaggcgc tcagtgctga tcccatccca tgctcaggga    60

<210> SEQ ID NO 56
<211> LENGTH: 20
<212> TYPE: PRT
<213> ORGANISM: Tick-borne encephalitis virus

<400> SEQUENCE: 56

Gly Lys Gln Glu Gly Ser Arg Thr Arg Arg Ser Val Leu Ile Pro Ser
1               5                   10                  15

His Ala Gln Gly
            20

<210> SEQ ID NO 57
<211> LENGTH: 6
<212> TYPE: DNA
<213> ORGANISM: Artificial Sequence
<220> FEATURE:
<223> OTHER INFORMATION: 5' spacer motif containing the furin cleavage
``` site of the pRM protein of the tick-born encephalitis virus

<400> SEQUENCE: 57 agtgga                                                                    6

<210> SEQ ID NO 58
<211> LENGTH: 2
<212> TYPE: PRT
<213> ORGANISM: Artificial Sequence
<220> FEATURE:
<223> OTHER INFORMATION: N-terminal spacer motif containing the furin
      cleavage site of the pRM protein of the tick-born encephalitis
      virus

<400> SEQUENCE: 58

Ser Gly
1

<210> SEQ ID NO 59
<211> LENGTH: 21
<212> TYPE: DNA
<213> ORGANISM: Artificial Sequence
<220> FEATURE:
<223> OTHER INFORMATION: 3' spacer motif containing the furin cleavage
      site of the pRM protein of the tick-born encephalitis virus

<400> SEQUENCE: 59
aaagagggaa gctcaatagg a                                                  21

<210> SEQ ID NO 60
<211> LENGTH: 7
<212> TYPE: PRT
<213> ORGANISM: Artificial Sequence
<220> FEATURE:
<223> OTHER INFORMATION: C-terminal spacer motif containing the furin
      cleavage site of the pRM protein of the tick-born encephalitis
      virus

<400> SEQUENCE: 60

Lys Glu Gly Ser Ser Ile Gly
1               5

<210> SEQ ID NO 61
<211> LENGTH: 96
<212> TYPE: DNA
<213> ORGANISM: Foot-and-mouth disease virus

<400> SEQUENCE: 61
tccggaagca gtccacagct gttgaatttt gaccttctta agcttgctgg agacgtcgag        60
tccaaccctg ggccaaagga gggaagctca atagga                                  96

<210> SEQ ID NO 62
<211> LENGTH: 32
<212> TYPE: PRT
<213> ORGANISM: Foot-and-mouth disease virus

<400> SEQUENCE: 62

Ser Gly Ser Ser Pro Gln Leu Leu Asn Phe Asp Leu Leu Lys Leu Ala
1               5                   10                  15

Gly Asp Val Glu Ser Asn Pro Gly Pro Lys Glu Gly Ser Ser Ile Gly
            20                  25                  30

<210> SEQ ID NO 63
<211> LENGTH: 60
<212> TYPE: DNA

```
<213> ORGANISM: Foot-and-mouth disease virus

<400> SEQUENCE: 63
cagctgttga attttgacct tcttaagctt gctggagacg tcgagtccaa ccctgggcca      60

<210> SEQ ID NO 64
<211> LENGTH: 20
<212> TYPE: PRT
<213> ORGANISM: Foot-and-mouth disease virus

<400> SEQUENCE: 64

Gln Leu Leu Asn Phe Asp Leu Leu Lys Leu Ala Gly Asp Val Glu Ser
1               5                  10                  15

Asn Pro Gly Pro
            20

<210> SEQ ID NO 65
<211> LENGTH: 15
<212> TYPE: DNA
<213> ORGANISM: Foot-and-mouth disease virus

<400> SEQUENCE: 65
tccggaagca gtcca                                                       15

<210> SEQ ID NO 66
<211> LENGTH: 5
<212> TYPE: PRT
<213> ORGANISM: Artificial Sequence
<220> FEATURE:
<223> OTHER INFORMATION: 5' spacer motif containing the 2A peptide of
      the aphthous fever virus

<400> SEQUENCE: 66

Ser Gly Ser Ser Pro
1               5

<210> SEQ ID NO 67
<211> LENGTH: 21
<212> TYPE: DNA
<213> ORGANISM: Artificial Sequence
<220> FEATURE:
<223> OTHER INFORMATION: N-terminal spacer motif containing the 2A
      peptide of the aphthous fever virus

<400> SEQUENCE: 67
aaggagggaa gctcaatagg a                                                21

<210> SEQ ID NO 68
<211> LENGTH: 7
<212> TYPE: PRT
<213> ORGANISM: Artificial Sequence
<220> FEATURE:
<223> OTHER INFORMATION: 3' spacer motif containing the 2A peptide of
      the aphthous fever virus

<400> SEQUENCE: 68

Lys Glu Gly Ser Ser Ile Gly
1               5

<210> SEQ ID NO 69
<211> LENGTH: 198
<212> TYPE: DNA
<213> ORGANISM: Dengue virus type 4

<400> SEQUENCE: 69
```

```
acatcattgg gaaaggctgt gcaccaggtt tttggaagtg tgtatacaac catgtttgga      60
ggagtctcat ggatgattag aatcctaatt gggttcttag tgttgtggat tggcacgaac     120
tcaaggaaca cttcaatggc tatgacgtgc atagctgttg aggaatcac tctgtttctg      180 ggcttcacag ttggcgcc                                                   198
```

<210> SEQ ID NO 70
<211> LENGTH: 66
<212> TYPE: PRT
<213> ORGANISM: Dengue virus type 4

<400> SEQUENCE: 70

```
Thr Ser Leu Gly Lys Ala Val His Gln Val Phe Gly Ser Val Tyr Thr
1               5                   10                  15

Thr Met Phe Gly Val Ser Trp Met Ile Arg Ile Leu Ile Gly Phe
            20                  25                  30

Leu Val Leu Trp Ile Gly Thr Asn Ser Arg Asn Thr Ser Met Ala Met
        35                  40                  45

Thr Cys Ile Ala Val Gly Gly Ile Thr Leu Phe Leu Gly Phe Thr Val
    50                  55                  60

Gly Ala
65
```

<210> SEQ ID NO 71
<211> LENGTH: 288
<212> TYPE: DNA
<213> ORGANISM: Dengue virus type 4

<400> SEQUENCE: 71

```
aagatgtttg agtccacata cagaggtgca aaacgaatgg ccattctagg tgaaacagct      60
tgggattttg gttccgttgg tggactgttc acatcattgg gaaaggctgt gcaccaggtt    120
tttggaagtg tgtatacaac catgtttgga ggagtctcat ggatgattag aatcctaatt    180
gggttcttag tgttgtggat tggcacgaac tccaggaaca cttcaatggc tatgacgtgc    240
atagctgttg gaggaatcac tctgtttctg ggcttcacag ttggcgcc                 288
```

<210> SEQ ID NO 72
<211> LENGTH: 96
<212> TYPE: PRT
<213> ORGANISM: Dengue virus type 4

<400> SEQUENCE: 72

```
Lys Met Phe Glu Ser Thr Tyr Arg Gly Ala Lys Arg Met Ala Ile Leu
1               5                   10                  15

Gly Glu Thr Ala Trp Asp Phe Gly Ser Val Gly Gly Leu Phe Thr Ser
            20                  25                  30

Leu Gly Lys Ala Val His Gln Val Phe Gly Ser Val Tyr Thr Thr Met
        35                  40                  45

Phe Gly Gly Val Ser Trp Met Ile Arg Ile Leu Ile Gly Phe Leu Val
    50                  55                  60

Leu Trp Ile Gly Thr Asn Ser Arg Asn Thr Ser Met Ala Met Thr Cys
65                  70                  75                  80

Ile Ala Val Gly Gly Ile Thr Leu Phe Leu Gly Phe Thr Val Gly Ala
                85                  90                  95
```

<210> SEQ ID NO 73
<211> LENGTH: 18
<212> TYPE: PRT

```
<213> ORGANISM: Aphthous fever virus

<400> SEQUENCE: 73

Leu Leu Asn Phe Asp Leu Leu Lys Leu Ala Gly Asp Val Glu Ser Asn
1               5                   10                  15

Pro Gly

<210> SEQ ID NO 74
<211> LENGTH: 13
<212> TYPE: PRT
<213> ORGANISM: Rabies virus

<400> SEQUENCE: 74

Gln Thr Ser Asn Glu Thr Lys Trp Cys Pro Pro Gly Gln
1               5                   10

<210> SEQ ID NO 75
<211> LENGTH: 13
<212> TYPE: PRT
<213> ORGANISM: Dengue virus 2

<400> SEQUENCE: 75

Ser Gly Glu Glu His Ala Val Gly Asn Asp Thr Gly Ser
1               5                   10

<210> SEQ ID NO 76
<211> LENGTH: 35
<212> TYPE: DNA
<213> ORGANISM: Yellow fever virus

<400> SEQUENCE: 76
cacaaacctc caacacagct aaatgggctc ctccc                              35

<210> SEQ ID NO 77
<211> LENGTH: 35
<212> TYPE: DNA
<213> ORGANISM: Yellow fever virus

<400> SEQUENCE: 77
gggaggagcc catttagctg tgttggaggt ttgtg                              35
```

HETEROLOGOUS EXPRESSION CASSETTE, DNA CONSTRUCT AND VACCINE COMPOSITION TO IMMUNIZE AGAINST FLAVIVIRUS AND/OR OTHER PATHOGENS

CROSS-REFERENCE TO RELATED APPLICATIONS

This application is a National Phase entry of, and claims priority to PCT Application No. PCT/BR2017/050221, filed Aug. 4, 2017, entitled "Heterologous Expression Cassette, DNA Construct and Vaccine Composition to Immunize Against Flavivirus and/or Other Pathogens," which claims benefit of Brazilian Patent Application No. BR102016018430-4, filed Aug. 10, 2016, entitled "Heterologous Expression Cassette, DNA Construct and Vaccine Composition to Immunize Against Flavivirus and/or Other Pathogens," the entire contents of each being hereby incorporated herein by reference in their entirety for all purposes.

STATEMENT REGARDING FEDERALLY SPONSORED RESEARCH OR DEVELOPMENT

Not applicable

BACKGROUND

This disclosure concerns DNA constructs, recombinant viruses and vaccine compositions containing the recombinant viruses. This disclosure also concerns the improvement of an expression vector of the live attenuated yellow fever 17D virus.

The Flavivirus genus of the Flaviviridae family includes around 70 viruses. The flaviviruses are small (40-60 nm), spherical, enveloped viruses which present a single-stranded RNA genome, with positive polarity, containing around 11 kb. The transmission of the flaviviruses is generally carried out by arthropods, such as mosquitos and ticks, causing serious illnesses in man, which vary from clinical symptoms similar to mild flu to severe and even lethal manifestations, such as symptoms of encephalitis and meningitis caused by the Japanese Encephalitis Virus (JEV), the West Nile Virus (WNV) and Tick-Borne Encephalitis Virus (TBE), and hemorrhagic fever such as that caused by the Dengue Virus (DENV), or even Zika Fever caused by the Zika Virus (ZIKV).

The Yellow Fever Virus (YF), one of the members of the Flaviviruses, is transmitted in urban and forest cycles in Africa and South America. It may be transmitted by different mosquito vectors, principally of the genus Aedes and Haemagoggus spp. The majority of the cases are asymptomatic. However, viral infection, which begins with an incubation period of 3 to 6 days, may result in the manifestation of febrile symptoms, headache, nausea, vomiting, myalgia and prostration. In some cases, around 15%, following a period of remission from the illness of 3 to 5 days, there may be development of liver and kidney failure which can develop into hemorrhagic fever and multiple organ failure. It is estimated that there are 200,000 cases of yellow fever globally each year, with 30,000 deaths, the majority (90%) in Africa.

Controlling yellow fever in most of the world has been made possible due to the development of a live attenuated viral vaccine. Indeed, yellow fever was the first disease in which viral etiology was characterized and the third to be controlled by the use of a vaccine, after smallpox and rabies. The YF vaccine was developed by Max Theiler, the Nobel laureate of 1951, and associates, based on serial passages of the Asibi strain, isolated in an African patient of this name [1, 2], in different types of tissue. In the 176 passage, the 17D strain was identified, which gave rise to the 17DD substrains, in passage 195, and 17D-204, in passage 204. The 17DD substrain was subsequently cultivated into passage 243 and submitted to 43 extra passages in chicken embryos, with the vaccine being obtained in passage 287. The 17D-204 substrain, in turn, gave rise to different vaccine seed viruses used in various countries. The 17D-204 and 17DD viruses are currently used in the global production of the yellow fever vaccine. These two lineages have accumulated genotype and phenotype differences due to their independent serial passages [3]. However, both are equally immunogenic and safe for man [4].

It is estimated that the YF vaccine has been given to over 600 million people in the 70 years of its use, with a minimal incidence of adverse effects [5]. The vaccine possesses a well established production methodology and rigorous quality control [5]. The YF 17D vaccine is considered one of the most effective available at the moment because a single dose of the vaccine is capable of providing effective and safe protection in over 90% of those vaccinated for an average period of 10 years. However, some individuals present neutralizing antibodies even 40 years after vaccination [6, 7]. Different studies have demonstrated that the titers of neutralizing antibodies induced are correlated with complete protection against infection by the wild virus. For a long time, the effectiveness of this vaccine was attributed solely to its capacity to induce antibodies. Recently, however, interest has grown in elucidating the cell and molecular bases involved in the development of the immune response against this vaccine [8, 9]. Immunization with the YF 17D virus is characterized by the stimulation of a broad range of innate immune responses, which results in the activation of a long-lasting polyvalent adaptive immune response. In addition to resulting in the production of neutralizing antibodies, vaccination with the YF 17D virus is also capable of inducing the activation of T lymphocytes which produce a cellular immune response involving $T_H1$ and $T_H2$ cytokines [10, 11].

In general, vaccination with the YF 17D virus results in an acute viral infection, with low-level viremia (<200 PFU/mL) which can be detected in over half the vaccinated individuals [12]. The activation and maturation of different types of dendritic cells (DC) and other cellular types of innate immune response very likely contributes to the effective adaptive immune response following administration of the YF 17D vaccine [8]. Dendritic cells (DC) perform a key role in the initiation of the innate immune response to the vaccination [9, 13, 14]. The YF 17D virus is capable of infecting several subsets of DC, through Toll-like receptors (TLR), including TLRs 7, 8 and 9, inducing the release of pro-inflammatory cytokines, such as interleukin (IL)-12p40, IL-6 and interferon (IFN)-α [14]. In addition to this, DC myeloids also express the cytosolic receptors RIG-I (retinoic-acid-inducible protein 1) and MDA5 (melanoma-differentiation-associated gene 5), which activate the signal transduction pathways triggering the production of type I IFNs [13]. In addition to this, the mTOR signaling pathway (mammalian target of rapamycin) was also related to the regulation of the TLR 7 and 9 dependent production of IFN-α/β in DC plasmacytoids [13]. Systems biology studies have revealed the role of NK cells and monocytes which is also important in the innate immunity induced by YF vaccination [15]. In this regard, it has been demonstrated that a set of genes in these cells is better expressed in the peripheral blood of vaccinated individuals, suggesting the involvement of these cells in viral removal. An important characteristic in the activation of cell types of the innate immune response, such as NK and T γδ cells, is the early production of IFN-γ, as observed in vaccine studies in man, rhesus monkeys and mice [16-18].

One of the principal properties of human immunization with YF 17D in the adaptive immune response is the detection of elevated levels of CD8+T effectors in the peripheral blood, which present polyfunctional properties with the capacity to control viral infection [11, 19, 20]. The frequency of CD8+ effector T cells, specific to the YF virus, dramatically increases, reaching its peak around 15 days after vaccination. After this period, the progressive differentiation of these effector cells into memory cells occurs. A more detailed phenotype analysis provided additional evidence for the activation and differentiation of CD8+ T cells induced by FA17D Vaccination, demonstrating the alteration of the functional profile of these lymphocytes in terms of composition, since these cells pass from effectors into memory cells. So, during the course of this transition, this type of cell becomes less polyfunctional correlating with the profile of a memory cell [20]. Various specific epitopes of CD8+ T cells have been identified in mice, rhesus monkeys and man. The E and NS3 viral proteins constituted the principal targets of the cytotoxic response against the YF 17D virus [21-23].

CD4+T and Treg (FoxP3+ regulatory T cell) cells respond to the YF virus, presenting an activation profile which precedes the response by CD8+ T cells. This data indicates that a response by rapid CD4+ T cells could be related to the pronounced presentation capacity of antigens of the YF virus by DC cells. The secretion of Th1 type cytokines by CD4+ cells was associated with the induction of high titers of neutralizing antibodies [11]. So the effective response of CD4+ T cells specific to the YF virus has maximum expression two weeks after vaccination and correlates with the induction of high titers of neutralizing antibodies in relation to the YF virus [24].

This set of vaccine properties makes the YF 17D virus attractive in terms of its development as an expression platform for antigens of human pathogens [25]. Indeed, in addition to the YF 17D virus, other commercial attenuated viral vaccines, such as those for poliomyelitis, measles, mumps and German measles are used in the establishment of expression vectors, as these vaccines are also immunogenic, highly efficient and promote lasting immunity. An important factor is that they are all very suitable for production on a large scale with well-established methodologies and production quality control procedures, in addition to having a low cost. The establishment of attenuated viral vectors, based on these vaccine viruses, takes into account that live attenuated vaccine viruses are competent proliferation vectors, so they have a capacity for replication in the host and mass expansion of the viral antigen in many cells and tissues, generally leading to lasting and effective protection, based on polyvalent immunity.

In the case of the YF 17D virus, as in other flaviviruses and other viruses with an RNA genome, genetic alterations such as that of establishing strategies for cloning and heterologous antigen expression, are possible due to the availability of infectious clone technology [26-28]. Using this methodology, different technical approaches have been established for the expression of heterological sequences in the genome of the YF 17D virus, which vary in accordance with the antigen to be expressed. One of the most successful approaches has been the creation of chimeric viruses through the exchange of structural prM/E genes, its being possible to obtain chimeric viruses of the 17D genome containing the prM/E genes of the Japanese Encephalitis Virus (JE) [29], of the four blood types of the dengue virus [30, 31] and of the West Nile Virus [32]. Although the prM/E genes vary among the flaviviruses, with around 40% identity in the amino acids sequence, the chimeric viruses are viable. These live attenuated chimeric viruses have been tested in man to different extents, with greater importance given to the tests of immunogenicity and safety of the tetravalent FA/Den chimeric vaccine [33, 34]. The most important aspect of these studies was the reduction in cases of hemorrhagic dengue.

Another group of approaches involves the insertion of heterologous sequences in the genome of the YF virus and other flaviviruses (FIG. 1). This concerns a more complex focus, since the genome of the flaviviruses is small and there is no possibility for deletions to accommodate exogenous sequences as is done with the adenoviral vectors, for example [35]. The first model described consists of the insertion of codifier sequences, between non-structural proteins, of heterologous epitopes flanked by specific cleavage sites of the viral proteolytic complex NS2B/NS3 [36]. This strategy has been tested in all the regions of the precursor polyprotein processed by the viral protease, but in only one of these three regions was it possible to obtain viable YF viruses, which are: in the amino terminus of the polyprotein precursor, and in the intergenic regions between C-prM and NS2B-NS3. This methodology was subsequently explored in the expression of other epitopes [37, 38]. However, these intergenic regions appear to have low tolerance for the insertion of larger genic sequences.

Another important advance was the development of the expression of exogenous sequence of 10 to 25 amino acids in the principal immune response viral inducer protein, the E protein of the envelope [39-41]. It can be established in this model that most of the viruses obtained possess replication rates compatible with large scale production for the generation of seed batches, that the heterologous epitopes are expressed on the surface of the viral particle and that they are capable of inducing an appropriate immunological response both directed at the recombinant peptide and to induce a response, by neutralizing antibodies, to the YF virus. This type of construction generates attenuated YF viruses as can be demonstrated in neurovirulence tests on mice and non-human primates.

The viral platforms developed until then did not allow for the introduction of heterologous sequences greater than 50 pb, without compromising the structure and replication of the virus. As a result of this, our research group developed a new approach which allows for the expression of protein cassettes in the E/NS1 intergenic region. It is important to consider that the strategy of inserting heterologous genes between the E and NS1 genes of the YF genome was adopted because this region represents a transition in the functional organization of the genome, which results in less deleterious effects for viral visibility, since the genes located on the 5'-terminal side codify the structural proteins of the virion, while on the 3'-terminal the genes are located for non-structural proteins, essential for viral replication.

This methodology of protein cassette expression in the E/NS1 intergenic region allows for the insertion of entire proteins and was the object of the filing of patent BR PI 0504945, filed in Brazil on 31 Oct. 2005, published on Jul. 8, 2007 and also available as document WO2007/051267, incorporated here for reference. This technique is similar, theoretically, to insertion between genes that codify proteins cleaved by viral protease. However, the cleavage between E and NS1 is realized by the cellular enzyme (signal peptidase) present in the endoplasmatic reticulum, such that the cleavage sites and other structural elements necessary for viral viability are different, constituting novelty in this methodology. The strategy basically consists of the fusion of the heterologous gene on its 5' end coding with an identical sequence to the 27 nucleotides of the N-terminal of the NS1 protein (SEQ ID NO: 27 and SEQ ID NO: 28) and at its 3' end, with the genic region corresponding to the stem and anchor domains of the C-terminal of the E protein [42] (FIG. 2). FIG. 2 shows the establishment of new viral variants for expression of heterologous proteins in the genome of the YF 17D vaccine virus. FIG. 2A represents the organization of the genome of the YF virus and the flaviviruses. The positive-sense viral RNA of around 11 kb possesses in its 5' and 3' ends untranslated regions (5'UTR and 3'UTR). There is a single open reading phase which codifies a precursor polyprotein of around 3400 amino acids. FIG. 2B shows the organization of the precursor polyprotein transcribed from the viral genomic RNA of the flaviviruses. The first third consists of structural proteins, components of the viral particle, which are the proteins of the capsid and proteins of the viral envelope, prM and E. The other proteins are components of the virus replication complex, known as non-structural proteins (NS1, NS2A, NS2B, NS3, NS4A, NS4B and NS5) and which do not form part of the viral particles. This part of the figure shows the proteolytic cleavage sites and the maturation of the different viral proteins, which correspond to the cleavage by the cellular signal peptidase (black arrow), by the viral protease, NS2N/NS3 complex (clear arrows) and by the furin cellular protease (clear triangle). The circular star figure indicates the site of insertion of the heterologous sequences used in this study. FIG. 2C schematizes the original insertion of heterologous proteins between the E and NS1 protein in the viral precursor polyprotein. In the original design of the YF viral vector, known as expression platform I (SEQ ID NO:1, SEQ ID NO:2, SEQ ID NO:3 and SEQ ID NO:4), there are two motifs fused to the heterologous protein, in this case EGFP (SEQ ID NO:25 and SEQ ID NO:26), in the heterologous expression cassette. The first motif consists of the first nine amino acids of the NS1 protein of the YF virus (motif DQGCAINFG—SEQ ID NO:27 and SEQ ID NO:28) and the second, on the C-terminal of the recombinant protein, is equivalent to the stem-anchor domain of the E protein (complete or truncated version), which in the case of the figure corresponds to that of dengue virus 4 (DEN 4) (SEQ ID NO: 69, SEQ ID NO: 70, SEQ ID NO:71 and SEQ ID NO:72), but which, originally, in the prior disclosure, corresponded to this same domain, but of the sequence similar to the YF virus (FIG. 2C).

Thus, with these genomic regions of duplicated flaviviruses flanking the insert, it was expected that the exogenous protein, fused to the duplicated viral genomic sequences, would be correctly processed by the signal peptidase of the membrane of the rough endoplasmatic reticulum (ER)—without causing significant disturbances in the cellular addressing and proteolytic processing of the E and NS1 proteins—resulting in the correct topology of the viral proteins in relation to their addressing the ER. In accordance with this strategy, it is expected that the fusion of the stem-anchor domain to the C-terminal of the exogenous protein will promote its anchoring to the membrane of the ER. The first heterologous gene expressed in this region was that of the gene of the EGFP autofluorescent protein, a variant of the "Green Fluorescent Protein" or GFP of *Aequorea victoria* [43] (SEQ ID NO:25, SEQ ID NO:26). The YF viruses (SEQ ID NO:1, SEQ ID NO:2, SEQ ID NO;3 e SEQ ID NO:4) presented good properties of proliferation in Vero cells and proved to be genetically stable up to the tenth serial passage. The expression of EGFP in these cells was associated with the ER, where it seems to be retained. The immunization of mice with the recombinant virus was capable of inducing the formation of neutralizing antibodies directed at the YF virus and antibodies directed at the EGFP protein. The current version of this platform uses the stem-anchor elements of the E protein of the dengue 4 virus (DEN4) (SEQ ID NO:69, SEQ ID NO:70, SEQ ID NO:71 and SEQ ID NO:72) fused to the recombinant protein, in such a way as to lead to an increase in viral stability. This system may be useful in the development of human vaccines based on the expression of antigens of human pathogens in the YF 17D genome, in addition to being able to be used for in vivo studies related to cell and tissue tropism and other processes associated with infection by flaviviruses.

Up to the present this methodology has allowed for the obtention of YF 17D viruses, which express, in addition to GFP, a fragment of 120 amino acids of the protein Asp-2 of *Trypanosoma cruzi*, a fragment of 250 amino acids of the gag protein and a "string" of SIV ("Simian Immunodeficiency Virus) CD4+ epitopes; and the 19 kDa fragments of the MSP-1 protein of *Plasmodium falciparum* and *P. vivax*. These viruses present levels of viral proliferation in Vero cells compatible with vaccine production in GMP ("Good Manufacturing Practices") and are, in their majority, genetically stable at least until the tenth serial passage in cell culture. Immunization with these different viruses induces, as evaluated in some animal models, an expected immunological response for a given antigen—such as the induction of GFP antibodies in mice, immune response mediated by CD8+ T cells in the Asp-2 constructs in mice and in that of SIV Gag in rhesus monkeys [44, 45].

One of the principal characteristics of this expression cassette in the E/NS1 intergenic region is related to the retention of the recombinant protein in the interior of the ER, due to the presence of the two transmembrane motifs of the E protein of DEN4 in the carboxy-terminus portion of the recombinant protein (SEQ ID NO:69, SEQ ID NO:70, SEQ ID NO:71 and SEQ ID NO:72). These antiparallel transmembrane segments, fused to the recombinant protein, are naturally important in the retention of the prM and E proteins of flaviviruses, components of the viral envelope. The accumulation of these viral proteins in the lumen of the ER is important for their association and the formation of the virions [46-48], which then undergo rapid transportation by the secretory pathway [49, 50]. The C-terminus region of these proteins, formed of alpha-helices and antiparallel transmembrane segments (TM1 and TM2), has proven to be well preserved among the flaviviruses. It was possible to determine that TM1 of the envelope protein carries retention motifs to the ER [51, 52]. These studies were based on the relationship between an increase in the number of amino acid residues in TM and the cell location of a given protein [52-54]. There is a tendency for membrane proteins associated with ER and Golgi to possess a smaller TM size than proteins with transmembrane segments forming part of the cell surface, as is the case of these domains in the prM and E domains of the flaviviruses [54]. This process of retention is important in this organelle because it is where the assembly and budding of the viral particle occur, followed by the trafficking, through the Golgi system and secretory pathway, to the exterior of the cell [55]. However, the assembly process of the viral particle in the ER in flaviviruses involves the hypertrophy of the membranes of the ER, due to the accumulation of the structural proteins and virions, which contributes to the stress of the ER and the induction of apoptosis or other kinds of cell death [56-58]. Consequently, the strategy of the expression of proteins which leads a given recombinant virus to increase cell death by viral infection is a strategy that would lead to a reduction in viral dissemination and a reduction in antigenic stimulus. The retention of the recombinant protein expressed by the YF 17D virus due to its association with these transmembrane elements may be a limiting factor in viral immunogenicity, since it can cause cell death through stress induced by the ER. So, the expression of recombinant proteins in different cell compartments would be an advantageous aspect for the formulation of vaccines which presented antigens in different manners, with the aim of stimulating a broader immunological response.

BRIEF SUMMARY

This disclosure provides for the introduction of modifications in the expression cassette of heterologous proteins in the E/NS1 intergenic region of the yellow fever 17D vaccine virus. The two new functional domains inserted in the expression cassette were (1) a coding sequence due to the N-glycosylation motif, located between the N-terminal NS1 motif and the heterologous protein and (2) a sequence which promoted the proteolytic cleavage, or not, of the recombinant protein in such a way as to release it from its C-terminal containing the transmembrane domains and, consequently, from its association with the endoplasmatic reticulum membrane (ER).

The present disclosure provides DNA constructs, recombinant viruses and vaccine compositions containing the recombinant viruses obtained through improved vector expression of the live attenuated yellow fever 17D virus. The present disclosure provides for the introduction of modifications in the expression cassette of heterologous proteins in the E/NS1 intergenic region of the yellow fever 17D vaccine virus. The two new functional domains inserted in the expression cassette were: (1) a coding sequence for the N-glycosylation motif, selected from the group of sequences defined by SEQ ID NO:29 to SEQ ID NO:44, the N-glycosylation motif being located between the NS1 N-terminal motif (SEQ ID NO:27 and SEQ ID NO:28) and the heterologous protein (SEQ ID NO:25, SEQ ID NO:26); and, (2) a sequence selected from the group of sequences defined by SEQ ID NO:45 to SEQ ID NO:68 to promote the proteolytic cleavage, or not, of the recombinant protein in order to release it from its C-terminal containing the transmembrane domains (SEQ ID NO:69, SEQ ID NO:70, SEQ ID NO:71 and SEQ ID NO:72) and, consequently, from its association with the membrane of the endoplasmatic reticulum (ER).

Through the present disclosure, it has been demonstrated that the retention of the recombinant protein in the endoplasmatic reticulum (ER) produces greater disturbance of the viral processes associated with this cell compartment.

All the references hereby cited are incorporated by way of reference in full and for all purposes.

BRIEF DESCRIPTION OF THE FIGURES

FIG. 1 shows a schema of the principal sites described for insertion of heterologous sequences in the genome of flaviviruses.

FIGS. 2A-2D show schemas for the establishment of new viral variants for expression of heterologous proteins in the genome of the YF 17D vaccine virus.

FIGS. 4A-4B show the results of the detection by fluorescence optical microscopy of the autofluorescence of the EGFP protein in Vero cells.

FIG. 4C shows flow cytometry panel analysis of the detection of the autofluorescence of the EGFP (x axis; GFP) and of the E protein of the YF virus (y axis; E α-protein) by the monoclonal antibody 2D12.

FIG. 4D shows the expression of the recombinant EGFP in infected Vero cell lysates, detected by the Western blot technique.

DETAILED DESCRIPTION

Figure 3:
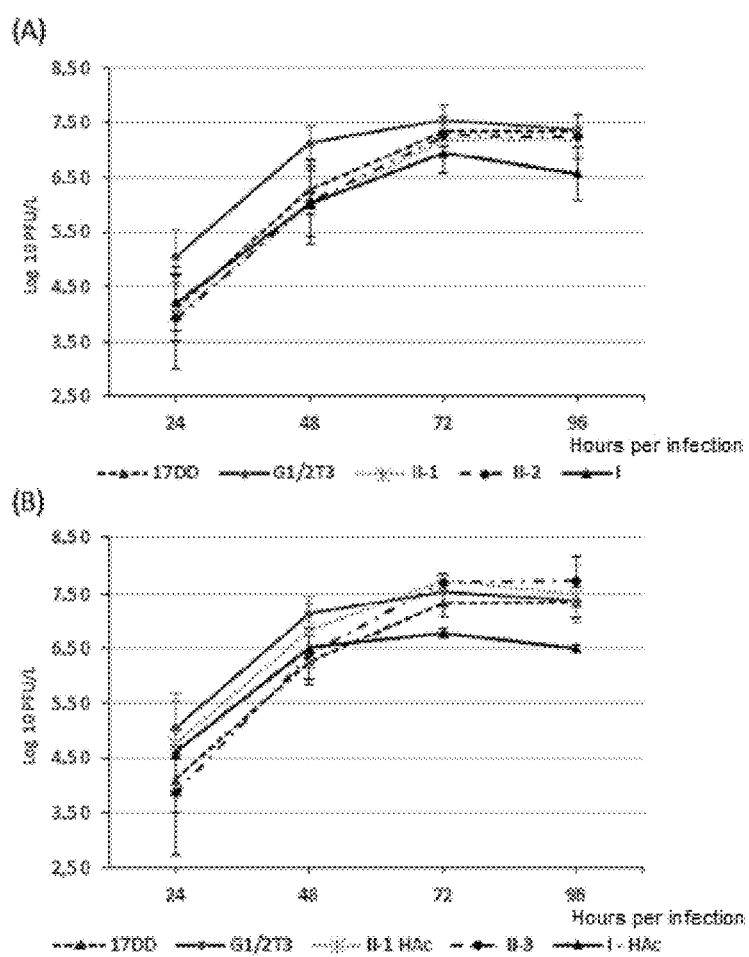
FIGS. 3A and 3B show the result of the determination of the viral proliferation throughout the infection in Vero cells.

Thus, in the present disclosure, it can be demonstrated that the retention of the recombinant protein in the ER produces greater disturbance of the viral processes associated with this cell compartment.

Two modifications were made in this disclosure. In the first, motifs were fused between the heterologous protein (SEQ ID NO:25, SEQ ID NO:26) and the stem-anchor domain of the E protein of DEN4 (SEQ ID NO:69, SEQ ID NO:70, SEQ ID NO:71 and SEQ ID NO:72) for the removal of the transmembrane anchors. Two kinds of motifs were used:

Option (1)—target sequences of the cell furin proprotein convertase, represented by SEQ ID NO:45 to SEQ ID NO:60; and, Option (2) the autocleavage motif of the 2A peptide of the picornavirus represented by SEQ ID NO:61 to SEQ ID NO:68.

In the first option (Option 1), two different cleavage motifs of the furin proprotein convertase were used. Furin is a member of the family of secretory proprotein convertases, which possesses a proteolytic domain of the subtilisin type. This is a type I transmembrane protein and occurs in vertebrates and invertebrates. Furin cleaves proprotein sequences to liberate mature proteins, preferably by the cleavage motif R-X-(R/K)R↓, where R means the amino acid arginine, K represents lysin, X can be any amino acid and the symbol indicates the proteolytic cleavage site [60]. The furin is mainly located in the Golgi and Trans-Golgi network (TGN). However, its circulation also occurs from the endocytic system to the cell membrane, with its return to the Trans-Golgi network or release to the extracellular medium in truncated form.

The proteolytic activity of furin is essential to the activation of proproteins, such as hormones, zymogenes and proteins of the cell surface [61]. Examples of proteins which are processed by furin are albumin, the component of the complement C3, the von Willebrand (vWF) coagulation factor. Elsewhere this enzyme performs a function of great importance in viral infectivity, such as in HIV [62] and in the flu virus [63].

In flaviviruses, the furin protein performs an important role in the maturation of the viral particle. This process begins during the assembly of the viral particle, when the budding of the nucleocapsid occurs (C protein associated with viral genomic RNA) for the lumen of the ER, becoming enveloped by a lipidic membrane surrounded by the envelope proteins (E) and the membrane (prM). The prM protein is associated in such a way as to protect the region of the E protein which contains the peptide motif for fusion to the membrane, in order to prevent the fusion of E to the internal membranes of the cell during the intracellular transportation of the immature viral particles. In the TGN, at pH 6.0, this association of prM and E undergoes a rearrangement which exposes the cleavage motive to furin, allowing for its proteolysis. However, the viral particle originated, despite possessing a form similar to the infective particle, also has a pr fragment associated with the E protein. As the process is dependent on the pH, the dissociation of the pr fragment only occurs after the release of the virion of the cell, thus forming the infective viral particle [64, 65].

The second motif (Option 2) which was used to remove the two transmembrane alpha-helices (TM1 and TM2) of the expression cassette in substitution of the cleavage motif by furin, was the 2A peptide of the aphthous fever virus, a picornavirus. The principal functional characteristic of this 2A peptide is to promote the decoupling of the ribosome from the nascent chain of a polypeptide during the process of protein synthesis. In this event, the translation may conclude at the end of the 2A peptide or continue onwards. The interruption in the protein elongation occurs following a proline and glycine sequence. The 2A motif of the apthhous fever virus consists of a sequence of around 18 amino acids SEQ ID NO:73 (LLNFDLLKLAGDVES<u>NPG</u>↓P), where the carboxy-terminal asparagine, proline and glycine motif (underlined), on being followed by a sequence with proline (bold) causes a pause in the translation and its decoupling. This autoprocessing motif is present in several picornaviruses, and in some insect viruses and type C rotaviruses. Several types of 2A motifs are used in the expression of recombinant proteins [66]. It is important to highlight that the sequence represented by SEQ ID NO: 63 and SEQ ID NO:64 (QLLNFDLLKLAGDVESNPGP) corresponds to the sequence of amino acids of the 2A peptide of the aphthous virus. As can be observed, there is a glutamine (Q) at the start of the sequence SEQ ID NO:64, which forms part of the viral sequence, but is not decisive in the motif's being functional. This motif was included to reduce the hydrophobicity of the start of the sequence.

The second modification of the present disclosure was the introduction of a glycan acceptor motif (SEQ ID NO: 29 to SEQ ID NO: 44) in the anterior region to the amino terminus of the recombinant protein fragment in the heterologous expression cassette. This allows any heterologous protein to be expressed by the YF virus to carry an N-glycosylation motif not necessarily present in its amino acid sequence, but present in the heterologous expression cassette. This post-translational modification is the most common occurring in the ER. Thus, most nascent proteins destined for this cell compartment, for the plasmatic membrane, for secretion or other endocytic compartments, are N-glycosylated. In addition to increasing protein solubility, in an environment with a high concentration of proteins, the addition of glycans assists in the correct process of protein folding, which occurs in the ER, since the processing of protein-bound oligosaccharides provides signals for the recruitment of lectin chaperones resident in the ER and which modulate the protein folding [67, 68]. Initially, to the NXS/T acceptor motif—which corresponds to the asparagine amino acids—any amino acid with the exception of proline—serine or threonine; present in the protein—a block of preformed oligosaccharides is added covalently to the asparagine residue of this arrangement. This precast oligosaccharide precursor is originally bound to a lipid (dolichol phosphate) and is translocated to the protein to be modified by the enzyme oligosaccharyltransferase (OST). The oligosaccharide precursor in eukaryotes consists of three glucoses, nine mannoses, and two N-acetylglucosamines (Glc3Man9GlcNAc2) [67, 69]. Most nascent polypeptides emergent in the ER lumen are glycosylated, receiving from 1 to 14 glycan residues [70]. The glycosylation of proteins post-translationally directed by the specialized catalytic subunit of oligosaccharyltransferase, STT3B, may also occur at a lower rate, with the assistance of accessory proteins [71]. An important aspect in the quality control of recently synthesized and glycosylated proteins is provided by the differential processing of the precursor oligosaccharides associated with these. This creates an identification that is recognized by the quality control system, for the correct protein folding, and by the machinery of the ERAD (degradation associated with ER, in English: "ER-associated degradation"), which directs the nascent glycoprotein to the different compartments of the ER and the secretory pathway. Thus, in this system the structure of the oligosaccharide in the polyprotein indicates the state of its folding allowing it to differentiate between correctly folded, unfolded and incorrectly folded forms [69].

Figures 1, 2:
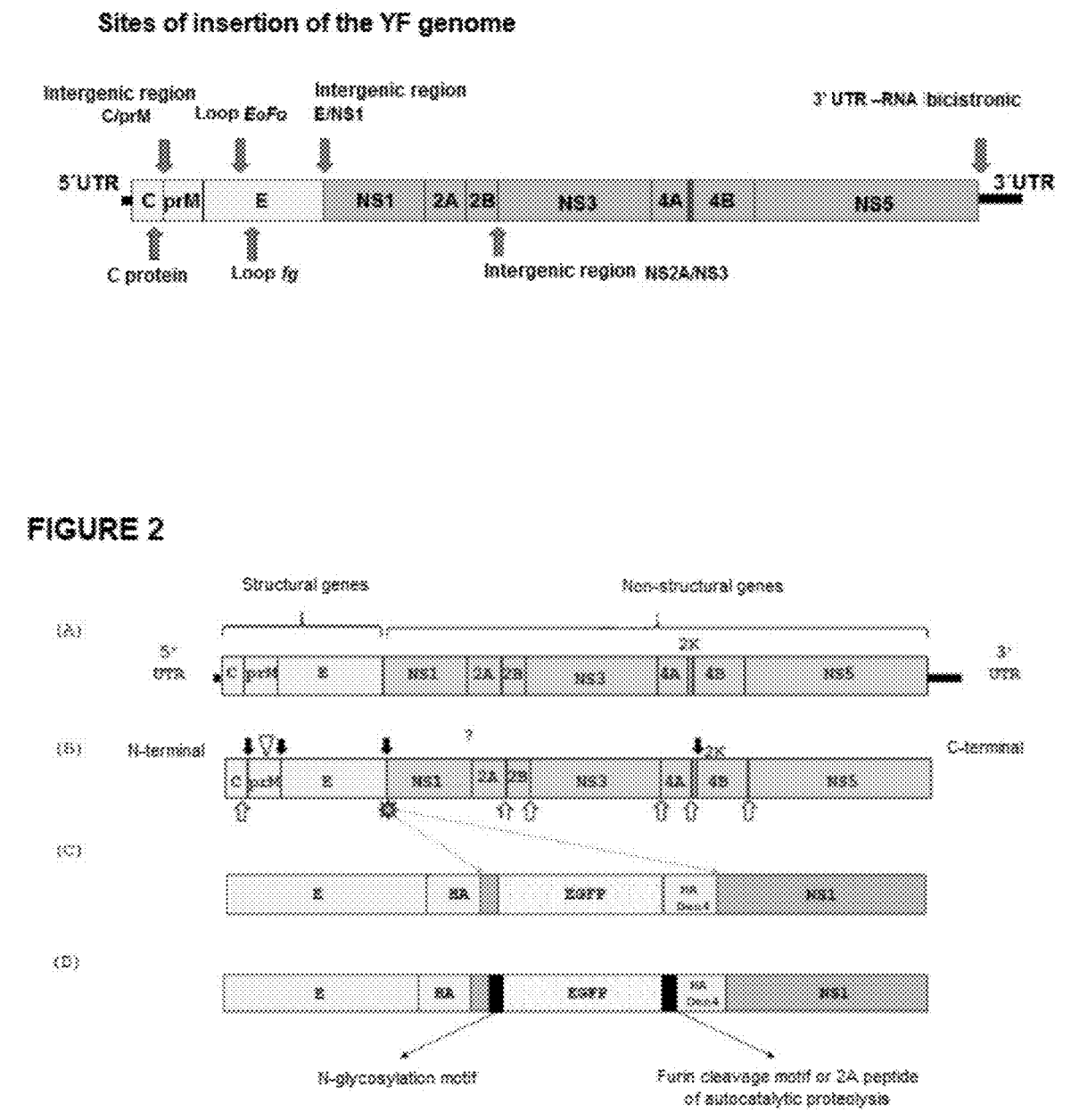

Thus, a new methodology and expression of heterologous proteins by the YF 17D virus in the E/NS 1 was developed. Basically, two new functional domains were introduced into the expression cassette; the first was a coding sequence for the N-glycosylation motif, located between the N-terminal NS1 motif and the heterologous protein (FIG. 2D). The second motif was the introduction of a sequence that promotes the proteolytic cleavage of the recombinant protein to release it from its C-terminus containing the transmembrane domains and, consequently, from their association with the ER membrane (FIG. 2).

Further illustration is provided with reference to the following examples, but it should be understood that the present invention should not be limited thereto.

The Examples below provide representative methods. A person skilled in the art will know how to substitute the appropriate reagents, raw materials and purification methods known.

EXAMPLES

Example 1. Design and Obtention of New Viral Expression Platforms in the Intergenic E/NS1 Region Two important modifications were made to the original expression platform of the yellow fever 17D vaccine virus, known as I [43, 72], in which heterologous genes could be inserted and expressed in the intergenic E/NS1 region (FIG. 2). The methodology of platform I is described in patent application PI BR 0504945, the contents of which are hereby incorporated for reference purposes. The sequences SEQ ID NO: I, SEQ ID NO: 2, SEQ ID NO: 3 and SEQ ID NO: 4 represent the viruses of platform I—with a complete or truncated stem-anchor. In the approach of patent application BR PI 0504945, the first 9 amino acids of the NS1 protein were duplicated at the N-terminus of the heterologous protein (SEQ ID NO: 27 and SEQ ID NO: 28), thus ensuring appropriate cleavage by the cellular signal peptidase present in the lumen of the endoplasmic reticulum. In addition to this, around 100 of the final amino acids of the E protein corresponding to the stem and anchor domains (HA) were duplicated at the C-terminal end of the insert to ensure the correct membrane topology of the precursor polyprotein and thus maintain the translocation signal peptide of the NS1 protein.

Subsequently, to promote the greater genetic stability of the construct, the HA elements of the C-terminus of the expression cassette, originating from the E protein of the YF virus, were replaced by the equivalent sequences of the dengue 4 virus (SEQ ID NO:69, SEQ ID NO: 70) and truncated versions were derived from this domain (SEQ ID NO: 71 and SEQ ID NO: 72) in which the H1 and CS elements were removed from the stem portion [43, 73].

The introduction of an N-glycosylation site in a flanking region of the recombinant protein ensures that, independently of the presence of added glycan motifs in a given heterologous sequence of interest, this will have greater stability of expression, and this modification will also facilitate the exodus thereof from the ER. In the case of the chosen protein, green fluorescent protein, this does not possess N-glycan acceptor motifs and, moreover, it has two cysteine residues, but which do not naturally form disulfide bridges. In the present disclosure, it has been shown that the GFP expressed by this new version of the yellow fever viral vector acquires greater stability in this expression strategy.

Two alternative versions of this new viral vector were designed, which versions used an N-glycosylation motif of the G protein of the rabies virus and another of the E protein of the dengue 2 virus, shown here in Table 1.

shown in Table 1. However, this underwent a change whereby the C residue, position 274, was altered to A (SEQ ID NO: 31 and SEQ ID NO: 32). This was done to avoid undesirable effects such as the formation of a disulfide bridge with another cysteine of the cassette, which could lead to an altered conformational structure. Finally, amino acid spacer sequences were associated with this glycan addition motif, at its N-terminus, RKGS amino acids (SEQ ID NO: 33 and SEQ ID NO: 34), and, at the C-terminus, GSPG (SEQ ID NO: 35 and SEQ ID NO: 36) in order to confer flexibility on this section of the expression cassette for GFP.

The other motif used consisted of one of the sugar acceptor sequences of the E protein of the dengue virus 2, as shown in Table 1. The sequence corresponds to the acceptor asparagine of position 154 of the E protein, comprised within the chosen region SEQ ID NO:75 SGEE-HAVGNDTGS. However, the acceptor motif of N-glycans NDT was changed to the NTT equivalent (SEQ ID NO: 39 and SEQ ID NO: 40). The glycosylation motif, in both the sugar acceptor sequences, was placed in the expression cassette between the amino terminal portion of a similar motif to the first nine amino acids of the NS1 protein (SEQ ID NO: 27 and SEQ ID NO: 28) of the YF virus and the start of the heterologous protein. The RK spacer amino acids (SEQ ID NO: 41 and SEQ ID NO: 42) and GS (SEQ ID NO: 43 and SEQ ID NO: 44) are located flanking this motif.

TABLE 1

| Platform II (variant) | Origin | Modification: N-glycosylation | GeneBank | Sequence Modification: |
|---|---|---|---|---|
| II-1 and II-1 HAc | G Glycoprotein of the rabies virus | 267-QTSNETKWCPPGQ-275 | NP056796.1 | RKGSQTSNTTKWAPPGQGSPG (SEQ ID NO: 29 until SEQ ID NO: 36) |
| II-2 | E Protein- Den 2 virus | SGEEHAVGNDTGS | Q9WDA6 | RKSGEEHAVGNTTGS (SEQ ID NO: 37 until SEQ ID NO: 44) |
| II-3 | G Glycoprotein of the rabies virus | 267-QTSNETKWCPPGQ-275 | NP056796.1 | RKGSQTSNTTKWAPPGQGSPG (SEQ ID NO: 29 until SEQ ID NO: 36) |

| Platform II (variant) | Origin | Modification: Release of transmembrane anchoring | GeneBank | Sequence Modification |
|---|---|---|---|---|
| II-1 | Furin cleavage motif of the von Willebrand (vWF) human coagulation factor | 754-SSPLSHRSKR↓SLSCR PPMVK-773 | NP 000543 | SGSSPLSHRSKR↓SLSCRPPM VKEGSSIG (SEQ ID NO: 45 until SEQ ID NO: 52) |
| II-2 | Furin cleavage motif of the prM protein - TBE virus | 84-GKQEGSRTRR↓SVLIP SHAQG-103 | NP775501.1 | SGGKQEGSRTRR↓SVLIPSHA QGKEGSSIG (SEQ ID NO: 53 until SEQ ID NO: 60) |
| II-3 | 2A cleavage site of the aphthous fever virus | QLLNFDLLKLAGDVES NPGP | | SGSSPQLLNFDLLKLAGDV ESNPGPKEGSSIG (SEQ ID NO: 61 until SEQ ID NO: 68) |

HAc-means complete stem-anchor
II-1 is represented by the sequences SEQ ID NO: 5 and SEQ ID NO: 6
II-1 HAc is represented by SEQ ID NO: 7 and SEQ ID NO: 8.
II-2 is represented by the sequences SEQ ID NO: 9 and SEQ ID NO: 10
II-3 is represented by the sequences SEQ ID NO: 11 and SEQ ID NO: 12

The five N-glycosylation acceptor sites of the G protein of the rabies virus had been described previously [74] [75]. The third site of this protein was chosen, with the sequence SEQ ID NO:74 QTSNETKWCPPGQ (position 263-275, as In the present disclosure, the expression cassette was further modified in order to increase the stability of the recombinant protein and release it from the anchoring in the membrane of the endoplasmic reticulum (ER). The first motif which was fused to the cassette consisted of adding an N-glycosylation motif in the region close to the amino terminus of the recombinant protein. In this methodology, it was considered that the N-glycosylation motif would be located in the amino portion of the exposed recombinant protein in the lumen of the ER so that there would be no structural disruption of the N-terminal domains of the NSL motif (of the amino terminus of the recombinant protein) and the GFP. Flanking the N-glycosylation motif of the G glycoprotein of the rabies virus, in the amino terminal, the RKGS motif (SEQ ID NO: 33 and SEQ ID NO: 34) and, in the carboxy-terminal, the GSPG motif (SEQ ID NO: 35 and SEQ ID NO: 36) were placed. In the N-glycosylation motif of the E protein of the dengue 2 virus, in the amino-terminal, the RK motif (SEQ ID NO: 41 and SEQ ID NO: 42) and, in the carboxy-terminal, the GS motif (SEQ ID NO: 43 and 44) were used. Spacer sequences were used to provide greater flexibility between the different functional domains of this carboxy-terminal region. FIG. 2D shows a representative schema of the strategy of inserting heterologous sequences in the YF virus genome in the intergenic E/NS1 region relating to this invention.

The second functional motif was added before the stem-anchor region of the E protein of dengue 4 virus, located in the carboxy terminus of the expression cassette, which promotes anchoring of the heterologous protein to the ER membrane. This motif promotes the separation of the heterologous protein from these domains for anchoring the recombinant protein to the membrane (Table 1). Thus, one of the motifs used, the furin cleavage motif of the von Willebrand coagulation factor (vWF), represented by the amino acid sequence SSPLSHRSKRSLSCRPPMVK (SEQ ID NO: 47 and 48) was placed in the expression cassette between the GFP and the stem-anchor portion. This functional domain was flanked by the SG amino acids (SEQ ID NO: 49 and SEQ ID NO: 50) and KEGSSIG (SEQ ID NO: 51 and SEQ ID NO: 52) to promote greater flexibility of the region and, consequently, greater exposure to proteolytic cleavage by furin. The final motif was then SGSSPLSHR-SKRSLSCRPPMVKEGSSIG (SEQ ID NO: 45 and SEQ ID NO: 46). In another version of this approach, the furin cleavage motif, GKQEGSRTRRSVLIPSHAQG (SEQ ID NO: 55 and SEQ ID NO: 56) present in the prM protein of the virus transmitted by ticks, the TBE virus ("Tick-borne encephalitis virus") was used and received the SG flanking amino acids (SEQ ID NO: 57 and SEQ ID NO: 58) and KEGSSIG (SEQ ID NO: 59 and SEQ ID NO. 60). The final motif resulted in SIV Gag the sequence SGGKQEGSR-TRRSVLIPSHAQGKEGSSIG (SEQ ID NO: 53 and SEQ ID NO: 54).

By way of an alternative, the present invention provides the option of testing, in the carboxy-terminal region of the expression cassette preceding the HA domain of the recombinant protein, another option that does not involve proteolytic cleavage. As such, the 2A motif of the aphthous fever virus (shown in Table 1), the QLLNFDLLKLAGD-VESNPGP motif, was chosen (SEQ ID NO: 63 and SEQ ID NO: 64), which promotes the decoupling of the nascent viral polyprotein from the ribosomal translation complex. Although this strategy is different from proteolytic cleavage by furin, the same result is produced, i.e., the recombinant protein without its carboxy-terminal (stem and anchor domain) and, consequently, without association with the ER membrane. To this motif were fused the flanking amino acids SGSSP (SEQ ID NO: 65 and 66) and KEGSSIG (SEQ ID NO: 67 and 68). The final motif resulted in the sequence SGSSPQLLNFDLLKLAGDVESNPGPKEGSSIG (SEQ ID NO: 61 and SEQ ID NO: 62).

The new constructs derived from this methodology present different combinations of the carboxy-terminal region of the expression cassette, which are the complete region of the stem-anchor of the E protein of the dengue 4 virus or its truncated version, without the H1 alpha-helix or the SC motif, and are presented, regarding this aspect, in Table 1A.

TABLE 1A

| Platform II | Variant fragment of the stem and anchor of the E protein of the dengue 4 virus |
|---|---|
| II-1 and 11-2 | TSLGKAVHQVFGSVYTTMFGGVSWM1RILIGFLVL WIGTNSRNTSMAMTCIAVGGITLFLGFTVGA (SEQ ID NO: 69 and SEQ ID NO: 70) |
| II-1 Hac and II-3 | KMFESTYRGAKRMAILGETAWDFGSVGGLFTSLGK AVHQVFGSVYTTMFGGVSWMIRILIGFLVLWIGTN SRNTSMAMTCIAVGGITLFLGFTVGA (SEQ ID NO: 71 and SEQ ID NO: 72) |

HAc - means complete stem-anchor

Table 1A shows the amino acid sequence of the carboxy-terminal domain of the expression cassette of the different constructs of expression platform II. Viral variants containing the complete (96 amino acids) and partial (66 amino acids) domain of the stem-anchor domain of the E protein of the dengue virus 4 were created.

The table below shows a description of the sizes of the expression cassettes and the predicted size of the recombinant proteins expressed in comparison with those foreseen for the viruses of platform I. The molecular weights of the recombinant proteins were calculated using the ProtParam program (available on the ExPASy web page of the Swiss Institute of Bioinformatics) and refer to the molecular weights of the recombinant proteins without any desired post-translational modification, such as glycosylation or the removal of the transmembrane anchors from the carboxy terminus. It would be expected that the glycosylation of the recombinant protein would lead to an increase of 2 to 3 kDa in the molecular weight. On the other hand, the removal of the stem-anchor domains would lead to a reduction of about 7 kDa in the truncated version and 10 kDa, in its complete version.

TABLE 2

Size of the expression cassettes codified by the different viruses

| Construct | Virus | Size (nt) | Size (aa) | Predicted Molecular Weight (kDa) |
|---|---|---|---|---|
| Platform I | I-1 | 939 SEQ ID NO: 13 | 313 SEQ ID NO: 14 | 34.7 |
|  | I-1 HAc | 1029 SEQ ID NO: 15 | 343 SEQ ID NO: 16 | 37.9 |
| Platform II | II-1 | 1083 SEQ ID NO: 17 | 361 SEQ ID NO: 18 | 39.6 |
|  | II-1 HAc | 1173 SEQ ID NO: 19 | 391 SEQ ID NO: 20 | 42.9 |
|  | II-2 | 1068 SEQ ID NO: 21 | 356 SEQ ID NO: 22 | 39.1 |

TABLE 2-continued

Size of the expression cassettes codified by the different viruses

| Construct | Virus | Size (nt) | Size (aa) | Predicted Molecular Weight (kDa) |
|---|---|---|---|---|
| | II-3 | 1185 SEQ ID NO: 23 | 395 SEQ ID NO: 24 | 43.2 |

HAc - Haste means complete stem-anchor

The construction of the recombinant viruses was realized through molecular cloning of synthetic genes in the plasmid pT3. The synthetic genes (GenScript) were designed with codon optimization for the frequency of use of the YF virus. The binding of the synthetic genes of the constructions was realized in the plasmid pT3 EagI/NarI in directional form, which is to say, both the plasmid and the synthetic genes presented sites of cleavage by the restriction enzymes EagI (C/GGCCG) and NarI (GG/CGCC). This procedure allowed the insertion of the cassette in the correct orientation into the plasmid pT3 Eag IWar I, as the site for Eag I is present in the N-terminal of the cassette while Nar I is found in the C-terminus of the expression cassette. In a step prior to the binding, 1 ug of each plasmid or insert was digested with 5U of the respective restriction enzymes at 37° C. for 2 h, in a final volume of 100 µE. The binding of the insert to the vector was realized with the enzyme T4 DNA ligase (Invitrogen) using 100 ng of the plasmid pT3 to 50 ng of the insert, in the equimolar proportion of 5:1 respectively. Recombinant clones were selected and sequenced to confirm the integrity of the construct.

The plasmids cloned from the pT3, or the pT3 without insert (viral control without insertion), and the plasmid pG1/2, which contains the complementary DNA of the genome of the YF virus, were digested by the enzymes Nsi I and Sal I (Promega) with 20U of each enzyme to 2 ug of plasmid DNA. The completely digested plasmids were purified using the system "QIAquick PCR Purification Kit" (Qiagen).

Each binding reaction was realized with 200 ng of the PGI/2 and 300 ng of the pT3 or derivative, with 1U of the enzyme T4 DNA ligase (Invitrogen) under the conditions established by the manufacturer. The samples were then treated with 30 U of the enzyme Xho I (Promega), by incubation at 37° C. for 3 h, followed by inactivation of the enzyme by heating at 65° C. for 15 minutes. The DNA molds generated were concentrated by precipitation with 10% 3M ammonium acetate and ethanol and, the DNA resuspended in 10 mM Tris pH 7.5.

The cDNA mold preparations were transcribed using the mMessage mMACHINE Kit (SP6) (Ambion) in accordance with the manufacturer's instructions. 2 ug of total RNA transcribed in vitro was used for transfection of Vero cells by electroporation. The RNA sample was added to the Vero cells in PBS suspension (free of endonucleases) and the cell suspension was then subjected to a controlled electric pulse (200 V, 850 mF, resistance ∞ in 4 mm cuvette) in Gene PulserXcell equipment (Bio Rad). The cell suspension was seeded in 25 cm$^2$ bottles with a density of 40,000 cells/cm2 with 12 ml of complete medium 199 with Earle's salts. The bottles containing the transfected cells were incubated at 37° C. in an oven containing 5% $CO_2$, and monitored until the appearance of the cytopathic effect (CPE). The supernatant of this culture (known as IP, first cell passage) was collected in aliquots and stored at −80° C. All the recombinant viruses generated were submitted to RNA extraction, followed by RT-PCR and nucleotide sequencing to verify the integrity of the insert.

All the new constructs were viable and presented CPE after 4 to 5 days post-transfection.

For the characterization studies of the new recombinant viruses, second cell passage viral stocks (2P) were obtained after infection of an aliquot (IP) in a T-175 flask containing 62,500 cells/cm$^2$ and a Medium 199 w/Earle's 5% $NaHCO_3$ and 5% fetal bovine serum. The viral inoculum was incubated in a $CO_2$ oven at 37° C. until the appearance of CPE, when the supernatant (2P) was collected and stored in aliquots which were conserved at −80° C.

Example 2. Biological Characterization of the Viruses of Expression Platform II

The growth rate of the new viral variant platforms was evaluated in relation to the original viruses of expression platform I and the control viruses. The control viruses used were the 17DD YF vaccine virus strain and the G1/2T3 virus, with a similar genome to the recombinant viruses, but without heterologous insertion. Vero cells cultured at a density of 62,500 cells/cm$^2$ in 25 cm$^2$ bottles containing 12.5 ml of Medium 199, w/Earle's 5% $NaHCO_3$ and 5% fetal bovine serum were infected in a multiplicity of infection (MOI Multiplicity of Infection) of 0.02. Aliquots of the supernatant of the infected culture were collected at 24h intervals until 96h, of which 100 µl were titrated in cell monolayers. The analyses were performed at least in triplicate. From these data growth kinetic profiles were obtained, whose statistical analysis was performed using the One Way ANOVA test, Dunnett's post-test, using the GraphPadPrism 5.03 program (GraphPad, Inc.). The differences were only considered significant when P<0.05.

FIG. 3 shows the different growth profiles of the viral variants of expression platform II in comparison with those of the viruses of platform I and the control viruses, vaccine virus 17DD and the G1/2T3 virus. During the first 48h of incubation, the recombinant viruses of platforms I and II did not present significant differences in relation to the 17DD vaccine virus. However, there was less growth in all these viruses, including the vaccine control 17DD, when compared with the viral titers obtained from the parental control virus G1/2T3, which presented higher rates of proliferation. After 48h, the viruses of platform I (I and I HAc) exhibited significantly lower rates of proliferation than the viruses of platform II which, in turn, had no significant differences in relation to the vaccine virus 17DD. A greater difference was detected in the growth of the viruses of platform I virus at 96h post infection. These data indicate the greater replicative capacity of platform 11 in relation to the original viruses of platform I, indicating that the genetic modifications introduced contribute to increased viral viability.

Regarding the determination of the viral proliferation during the course of the infection in Vero cells, FIG. 3 also shows average and standard deviation values determined in the supernatant of infected cells for 24h to 96h (Log 10 PFU/ml) in at least three independent experiments, where (i) FIG. 3A shows the proliferation profile of the viruses II-1 and II-2 in relation to virus 1 (original platform). These viruses express GFP fused to the truncated stem-anchor portion of the E protein of dengue virus 4; and (ii) FIG. 3B shows proliferation profiles of the viruses HAc II-1 and II-3 in relation to the virus 1 HAc (original platform). These viruses express GFP fused to the complete stem-anchor portion of the E protein of dengue virus 4. In both trials, the control vaccine virus strain 17DD and the virus vector without insert (G1/2T3) were included.

Figure 4:
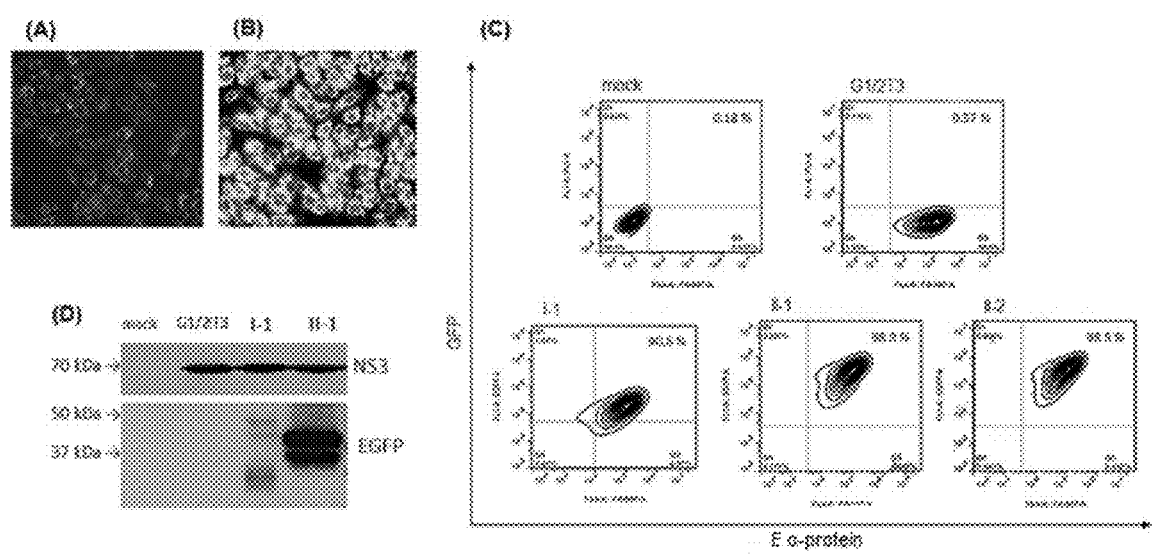
FIG. 4 shows the difference in the expression of the EGFP heterologous protein by platforms I and II of the YF vaccine virus.

Example 3. Expression of the Heterologous Protein by the YA Viruses of Platform II Recombinant viruses of platform II were also characterized in relation to the expression of the heterologous protein through three different analyses: fluorescence microscopy, flow cytometry and Western blotting. For these analyses, Vero cells were infected for 72h in MOI (multiplicity of infection) of 0.02 (FIG. 4). FIG. 4 shows the results of detection by fluorescence optical microscopy of the autofluorescence of the EGFP protein in Vero cells, 72 hours after infection (M.O.I. of 0.1), by the I-1 (FIG. 4A) and II-1 viruses (FIG. 4B). Observation made on an IX 51 microscope (Olympus) with FITC filter and 40× objective. FIG. 4C shows the panels of analysis by flow cytometry, at 72 hours post infection, of the detection of the autofluorescence of the EGFP (x-axis; GFP) and the E protein of the YF virus (y-axis, E α-protein) by monoclonal antibody 2D12. The controls consist of cells uninfected (mock) and infected with the parental virus G1/2T3.

Cells infected with the new recombinant viruses of platform II presented, on analysis by fluorescence optical microscopy, much more intense autofluorescence than observed in cells infected with the I-1 YF virus under the same conditions of infection and image capture. These data indicate a greater capacity for expression of the heterologous protein, in the case of EGFP, by the YF II viruses. This was confirmed by the analysis of different samples of infected Vero cells using flow cytometry. The cell infection was realized in MOI of 0.02 for 72h, and the samples were subjected to staining with the antibody VFA in order to compare GFP fluorescence with the staining for viral antigens in infected cells. At least 10,000 events per sample were obtained.

The conditions used are described in Bonaldo, M C, et al., *Construction and characterization of recombinant flaviviruses bearing insertions between E and NS1 genes*. Virol J, 2007. 4: p. 115. Briefly, Vero cells were cultured and infected in 6-well plates with 62,500 cells/cm². At 72 hours of incubation, the culture medium was removed and cells were subjected to treatment with trypsin and centrifuged at 400 g for 7 min, followed by two washes with sterile PBS and then fixed in 2% paraformaldehyde. The cells were permeabilized with PBS supplemented with 1% BSA containing 0.15% saponin for 15 min at 4° C., centrifuged at 400 g for 7 min, and then stained with mouse monoclonal antibody directed at the YF virus (Biogenesis), diluted 1:200 in PBS with 1% BSA and 0.15% saponin for 1h in an ice bath. The cell suspensions were washed with 1 ml of PBS supplemented with 1% BSA also containing 0.15% saponin and centrifuged at 400 g for 7 min and resuspended in the presence of the secondary antibody Alexa Fluor 647 goat anti mouse IgG (Molecular Probes) at a dilution of 1:400 as described above. Finally, the cells were resuspended in 0.3 ml of 2% paraformaldehyde and analyzed in C6 Flow Cytometer System equipment using the program C-Flow Plus (Accuri cytometers). The data were analyzed using the program Flow J (TreeStar Inc.).

The data presented in FIG. 4C derive from three independent series of experiments and show the fluorescence emitted by cells which express the GFP protein (L1-A detector, Y-axis) and the fluorescence emitted by cells which express viral antigens (FL4-A, X axis). Uninfected cells (Mock; 98.4%) did not present detection in these channels, since the cells infected with the G1/2T3 control virus presented 98% positivity for the FL4 channel which detects viral antigens. The recombinant viruses, as expected, presented double staining for FL1-A and FL4-A, and indicate 90.6% for I-1, 98.3% for II-1 and 98.5% for II-2. As for the expression of GFP by the recombinant viruses, it is of note that the values differ on a scale of $10^4$ to $10^5$ for cells infected with the I-1 virus and $10^5$ to $10^6$ for the other recombinants (II-1 and II-2). However, these differences are not related to the viral proliferation properties of platforms I and II, since there was no significant difference for the staining of antigens of the YF virus, in contrast to the intensity of fluorescence emitted by the GFP protein in infected cells, which proved to be significantly different for the I-1 virus in relation to the II-1 and II-2 viruses (One Way ANOVA—Bonferroni's Multiple Comparison Test, P<0.0001), confirming the data obtained by fluorescence microscopy.

This difference in the pattern of expression of the heterologous protein in platforms I and II was also confirmed by the analysis of extracts of Vero cells infected by Western blotting, obtained as previously described in Bonaldo, M. C., et al., *Construction and characterization of recombinant flaviviruses bearing insertions between E and NS1 genes*. Virol J, 2007. 4: p. 115. [76] (FIG. 2D). In this analysis, protein extracts in a Laemmli buffer containing 5% β-mercaptoethanol were heated at 95° C. for 5 mins and subjected to denaturing electrophoresis in 12% polyacrylamide with SDS. After the electrophoresis, the proteins were transferred from the gel to PVDF membranes using the iBlot Dry Bloting system (Invitrogen) in accordance with the manufacturer's recommendations. The membrane was incubated in TBS-T (TBS pH 7.4 with 0.1% Tween 20) with 5% skimmed milk for 45 mins at room temperature (around 20-23° C.), washed 4 times in TBS-T prior to incubation with the specific primary antibody (Table 3), diluted in TBS-T solution containing 1% skimmed milk and incubated for 2h at room temperature, followed by washes in TBS-T. The incubation with the secondary antibody conjugated to the peroxidase (Table 3) was realized for 1 h at room temperature with constant agitation under the same conditions described above. After washing the membrane, the protein profile was determined using SuperSignal West Pico Chemiluminescent Substrate (Thermo Scientific) in accordance with the manufacturer's instructions, in a darkroom, and detected by autoradiography.

TABLE 3

| Antibodies used for the detection of proteins by Western-blotting | | |
|---|---|---|
| | DILUTION | ORIGIN |
| PRIMARY ANTIBODY | | |
| GFP (JL-8) - mouse IgG | 1:8000 | Living Colors A.v. Monoclonal Antibody - Clontech |
| β-tubulin - mouse IgG | 1:1000 | Invitrogen |
| Yellow Fever NS3 - rabbit IgG | 1:500 | LABMOF |
| SECONDARY ANTIBODY (CONJUGATED TO PEROXIDASE) | | |
| Mouse IgG | 1:2000 | KPL |
| Rabbit IgG | 1:4000 | Amersham Biosciences |

Thus, the profiles obtained in the Western blotting show that the mass of the recombinant protein detected in infected cells is much greater in those that were infected by the recombinant virus of platform II (II-1) than evidenced for those of platform I (I-1) and, again, that these differences are not due to lower rates of translation in platform I, since the non-structural protein NS3 is detected at the same intensity in both conditions. These profiles associated with the intensity of fluorescence emitted by the recombinant protein in infected cells in the flow cytometry analysis, allow us to estimate a difference of around twenty times greater than the fluorescence and mass detected for GFP in cells infected with the virus of the original platform I.

These differences were also proven through the determination by RT-PCR in real time of the number of copies of viral RNA present in these samples of infected Vero cells. For the PCR assay in real time the target region selected was the fragment of the NS5 region (nt 10188-10264) of the YF genome with a size of 77 pb, amplified with the oligonucleotides sense YF 17D 10188 (5-GCG GAT CAC TGA TTG GAA TGA C-3) and reverse YF 17D 10264 (5-CGT TGG GAT ACG ATG GAT GAC TA-3), and TaqMan probe (5-6FAM-AAT AGG GCC ACC TGG GCC TCC C-TAMRA-3). For absolute quantification of the viral RNA present in the samples, a standard curve was included in the assay composed of synthetic RNA containing the region to be amplified in the concentrations equivalent to $10^3$ to $10^9$ copies of the YF genome. The synthetic RNA was obtained in our laboratory by cloning the cDNA of 673 bp of the NS5 region of the 17D virus (10055-10728) in the plasmid vector pGEM-T Easy Vector (Promega), followed by purification, in vitro transcription and treatment with DNase. The calculation of the number of RNA molecules was realized through verifying the mass by optical density. For amplification, 3 µM of both oligonucleotides (sense and reverse) were applied, 2.5 µM of probe, MultiScribe/RNase Inhibitor mix 40×, TaqMan One-Step RT-PCR Master Mix 2×, 10 to 100 ng of RNA and free water of nucleases to complete the total volume of 20 µl per reaction. The cycling conditions were: 1 cycle of 48° C. for 30 minutes and 95° C. for 10 minutes followed by 40 cycles of 95° C. for 15 seconds and 60° C. for 1 minute, in StepOnePlus Real-Time PCR System equipment (Applied Biosystems).

The values obtained in the quantitative RT-PCR were 8.4 Log 10 copies/reaction for the parental virus G1/2T3; 8.6 Log 10 copies/reaction for the virus I-1, 8.4 Log 10 copies/reaction for the virus II-1 and 8.3 log 10 copies/reaction for the virus II-2, and indicate that there was no significant difference between the number of RNA copies present in the infected cell extract for all the viruses analyzed, demonstrating that the viral infection was homogeneous in the cell density established for the viruses studied, as had been observed by flow cytometry and fluorescence microscopy with the staining of AF antigens. It was also confirmed that the differences in the fluorescence of the GFP observed are not due to variations in viral proliferation.

Example 4. Secretion of the Heterologous Protein by the YF Viruses of Platform II In order to better characterize heterologous expression in the viral variants of Platform II, an analysis was undertaken of extracts and the extracellular medium of Vero cell monolayers infected by the recombinant viruses II-1, II-1 HAc and II-3.

Figure 5:
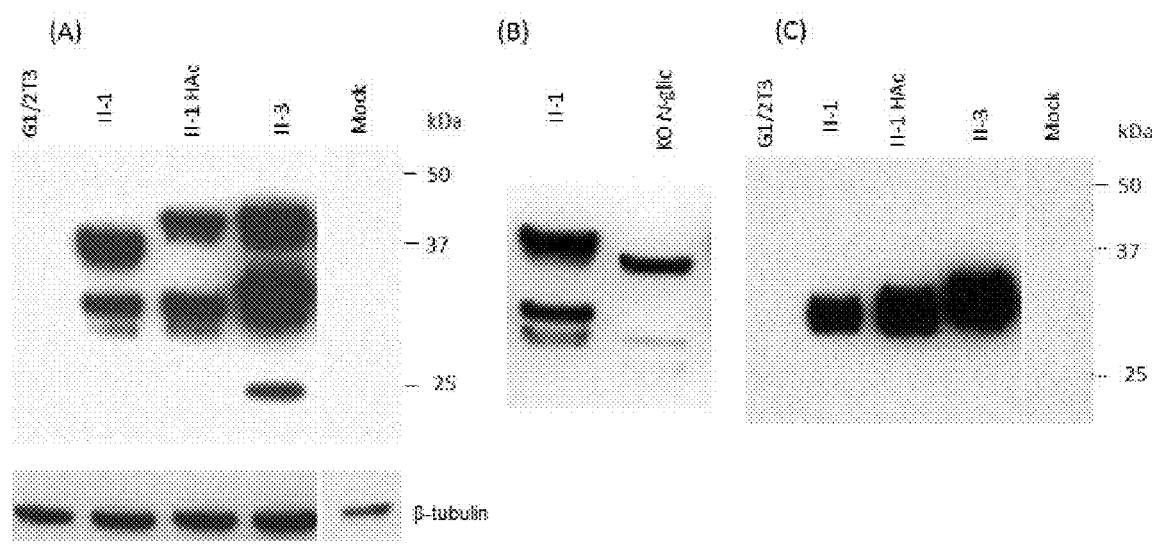
FIGS. 5A-5C show the results of the analysis by Western Blotting of the expression profile of the GFP recombinant protein expressed by the different YF viruses of platform II.

FIG. 5 shows the Western blotting analysis of the expression profile of the recombinant protein GFP expressed by the YF virus of platform II. FIG. 5A shows GFP detected in protein extracts of Vero cells infected by the parental control virus G1/2T3 and by the recombinant viruses II-1, II-1 HAc and II-3, in addition to the control extract of uninfected cells (Mock). At the top of FIG. 5, the detection of GFP by a specific antibody is shown and, at the bottom, the detection of these same extracts by an antibody specific to δ-tubulin, indicating the normalization of the profiles. In FIG. 5B, the profiles of cells infected by the virus II-1 are shown along with the same construct in which the N-glycans acceptor NTT motif was knocked out. FIG. 5C shows the acellular supernatant of Vero cell cultures infected by the recombinant viruses II-1, II-1 HAc and II-3, presenting broad bands around 30 kDa. The molecular weight markers are indicated on the right.

The recombinant protein exhibits a similar band profile in Vero cell extracts (FIG. 5A), where one can distinguish a higher broadband of around 40 kDa and a lower one of around 30 kDa. To further clarify this profile, a mutant virus II-1 was obtained for the N-glycosylation motif, which was knocked out (knockout) by site-directed mutation (kit "QuikChange II XL Site-Directed Mutagenesis of Agilent Technologies) with pairs of positive strand SEQ ID NO:76 (CAC AAA CCT CCA ACA CAG CTA AAT GGG CTC CTC CC) and negative strand SEQ ID NO:77 (GGG AGG AGC CCA TTT AGC TGT GTT GGA GGT TTG TG) oligonucleotides. Thus, the subject went from NTT to NTA. Extracts of cells infected with the II-1 virus without the N-glycosylation motif (N-glycyl KO) presented two bands in the regions of 30 and 40 kDa, but more defined and with regions of greater electrophoretic migration, indicating that the bands around 30 kDa and 40 kDa correspond to a higher double band of the recombinant protein in its glycosylated form, with greater molecular weight, and non-glycosylated, with lower weight, and a lower double band also composed of one glycosylated form and another non-glycosylated one but without the transmembrane stem-anchor portion. The variations observed between the different profiles of cell extracts infected with different viruses of the platform are due to the differences in size of the expression cassettes of the viral variants of platform II (Table 2).

Another important property of expression platform II is that it has the capacity to allow the secretion of the recombinant protein by the infected cell. This characteristic has been confirmed through the detection of this protein by Western blotting of protein extracts from an extracellular medium of cell cultures infected with the viruses II-1, II-1 HAc and II-3 (FIG. 5C). The supernatants of cell cultures infected with these viruses were concentrated by filtration with an exclusion limit of 30 kD (Amicon Ultra 0.5— Millipore). In all the variants of platform II, the isoform of the glycosylated heterologous protein was detected, and without the carboxy-terminal of the transmembrane stem-anchor domain. This indicates that the methodology of inserting the furin cleavage motif or the Picornaviridae 2A motif into the new expression platform II of the YF virus promotes the secretion of the recombinant protein into the extracellular medium.

In this patent application, significant modifications were introduced into the expression cassette of heterologous proteins in the intergenic E/NS1 region of the yellow fever vaccine virus 17D, whose original strategy was the object of patent application P10504945 (WO2007/051267).

The modifications introduced into the present invention, the N-glycosylation motifs and the dissociation of the recombinant protein from its carboxy end containing transmembrane alpha-helices, by furin cleavage or by the presence of the picornaviruses 2A motif, caused a significant impact on the expression of the recombinant GFP, principally in the quality of its folding and its trafficking to the secretory pathway.

In addition to this, the present invention provides the option of testing in the carboxy-terminal region of the expression cassette, antecedent to the HA domain of the recombinant protein, without involving proteolytic cleavage, through the use of the 2A motif of the aphthous fever virus (QLLNFDLLKLAGDVESNPGP—SEQ ID NO: 63 and SEQ ID NO: 64), which promotes the decoupling of the nascent viral polyprotein from the ribosomal translation complex. Although this strategy is different from proteolytic cleavage by furin, the same result is produced, which is to say, the recombinant protein without its carboxy-terminal (stem and anchor domains) and, consequently, without association with the ER membrane.

The composition of the present invention is intended to immunize against the viral vector or virulent forms homologous thereto and/or other pathogens, from which the gene of the heterologous protein expressed by the recombinant virus originated. The composition uses pharmaceutically acceptable carriers.

As used herein, a pharmaceutically acceptable carrier is understood to be a compound that does not adversely affect the health of the organism to be vaccinated. Various pharmaceutically acceptable solutions for use in the preparation of the vaccine composition of the present invention are well known and can be readily adapted by those skilled in this art (see, for example, Remington's Pharmaceutical Sciences (18th edition), ed. A. Gennaro, 1990, Mack Publishing Co., Easton, Pa.).

Table 4 is presented below with a description of the sequences cited and used in the present invention.

TABLE 4

| Numbering of the sequence and description | Organism |
|---|---|
| Full sequences of the viruses | |
| 1. Virus I - cDNA viral | Yellow Fever Virus |
| 2. Virus I - Protein | Yellow Fever Virus |
| 3. Virus I HAc - cDNA viral | Yellow Fever Virus |
| 4. Virus I HAc - Protein | Yellow Fever Virus |
| 5. Virus II-1 - cDNA viral | Yellow Fever Virus |
| 6. Virus II-1 - Polyprotein | Yellow Fever Virus |
| 7. Virus II-1 HAc - cDNA viral | Yellow Fever Virus |
| 8. Virus II-1 HAc - Polyprotein | Yellow Fever Virus |
| 9. Virus II-2 - cDNA viral | Yellow Fever Virus |
| 10. Virus II-2 - Polyprotein | Yellow Fever Virus |
| 11. Virus II-3 - cDNA viral | Yellow Fever Virus |
| 12. Virus II-3 - Polyprotein | Yellow Fever Virus |
| Sequences of the inserts | |
| 13. Insert I - DNA | Yellow Fever Virus |
| 14. Insert I - Protein | Yellow Fever Virus |
| 15. Insert I HAc - DNA | Yellow Fever Virus |
| 16. Insert I HAc - Protein | Yellow Fever Virus |
| 17. Insert II-1 - DNA | Yellow Fever Virus |
| 18. Insert II-1 - Protein | Yellow Fever Virus |
| 19. Insert II-1 HAc - DNA | Yellow Fever Virus |
| 20. Insert II-1 HAc - Protein | Yellow Fever Virus |
| 21. Insert II-2 - DNA | Yellow Fever Virus |
| 22. Insert II-2 - Protein | Yellow Fever Virus |
| 23. Insert II-3 - DNA | Yellow Fever Virus |
| 24. Insert II-3 - Protein | Yellow Fever Virus |
| Sequences of the motifs | |
| 25. EGFP - DNA | Aequorea victoria |
| 26. EGFP - Protein | Aequorea victoria |
| 27. N-terminal NS1 - DNA | Yellow fever virus |

TABLE 4-continued

| Numbering of the sequence and description | Organism |
|---|---|
| 28. N-terminal NS1 - Protein | Yellow fever virus |
| 29. motif containing the N-glycosylation site of the G protein of the rabies virus | Rabies virus |
| 30. motif containing the N-glycosylation site of the G protein of the rabies virus - Protein | Rabies virus |
| 31. segment corresponding to the N-glycosylation site of the G protein of the rabies virus | Rabies virus |
| 32. segment corresponding to the N-glycosylation site of the G protein of the rabies virus - protein | Rabies virus |
| 33. spacer 5' of the motif containing the N-glycosylation site of the G protein of the rabies virus | Artificial sequence |
| 34. N-terminal spacer of the motif containing the N-glycosylation site of the G protein of the rabies virus - protein | Artificial sequence |
| 35. spacer 3' of the motif containing the N-glycosylation site of the G protein of the rabies virus | Artificial sequence |
| 36. C-terminal spacer of the motif containing the N-glycosylation site of the G protein of the rabies virus - protein - protein | Artificial sequence |
| 37. motif containing the N-glycosylation site of the E protein of the dengue virus type 2 - DNA | Dengue virus type 2 |
| 38. motif containing the N-glycosylation site of the E protein of the dengue virus type 2 - Protein | Dengue virus type 2 |
| 39. segment corresponding to the N-glycosylation site of the E protein of the dengue virus type 2 | Dengue virus type 2 |
| 40. segment corresponding to the N-glycosylation site of the E protein of the dengue virus type 2 - Protein | Dengue virus type 2 |
| 41. spacer 5' of the motif containing the N-glycosylation site of the E protein of the dengue virus type 2 - DNA | Artificial sequence |
| 42. N-terminal spacer of the motif containing the N-glycosylation site of the E protein of the dengue virus type 2 - Protein | Artificial sequence |
| 43. spacer 3' of the motif containing the N-glycosylation site of the E protein of the dengue virus type 2 - DNA | Artificial sequence |
| 44. C-terminal spacer of the motif containing the N-glycosylation site of the E protein of the dengue virus type 2 - Protein | Artificial sequence |
| 45. Motif containing the furin cleavage site of the von Willebrand human factor - DNA | Homo sapiens |
| 46. Motif containing the furin cleavage site of the von Willebrand human factor - Protein | Homo sapiens |
| 47. segment corresponding to the furin cleavage site of the von Willebrand human factor - DNA | Homo sapiens |
| 48. segment corresponding to the furin cleavage site of the von Willebrand human factor - Protein | Homo sapiens |
| 49. spacer 5' of the motif containing the furin cleavage site of the von Willebrand human factor - DNA | Artificial sequence |
| 50. N-terminal spacer of the motif containing the furin cleavage site of the von Willebrand human factor - Protein | Artificial sequence |
| 51. spacer 3' of the motif containing the furin cleavage site of the von Willebrand human factor - DNA | Artificial sequence |
| 52. C-terminal spacer of the motif containing the furin cleavage site of the von Willebrand human factor - Protein | Artificial sequence |
| 53. Motif containing the furin cleavage site of the prM Protein - TBE virus - DNA | Tick-Borne Encephalitis Virus |
| 54. Motif containing the furin cleavage site of the prM Protein - TBE virus - Protein | Tick-Borne Encephalitis Virus |
| 55. segment corresponding to the furin cleavage site of the prM Protein - TBE virus - DNA | Tick-Borne Encephalitis Virus |
| 56. segment corresponding to the furin cleavage site of the prM Protein - TBE virus - Protein | Tick-Borne Encephalitis Virus |
| 57. spacer 5' of the motif containing the furin cleavage site of the prM Protein - TBE virus - DNA | Artificial sequence |
| 58. N-terminal of the motif containing the furin cleavage site of the prM Protein - TBE virus - Protein | Artificial sequence |
| 59. Spacer 3' of the motif containing the furin cleavage site of the prM Protein - TBE virus | Artificial sequence |
| 60. C-terminal spacer of the motif containing the furin cleavage site of the prM Protein - TBE virus | Artificial sequence |

TABLE 4-continued

| Numbering of the sequence and description | Organism |
|---|---|
| 61. C-terminal spacer of the motif containing the furin cleavage site of the prM Protein - TBE virus | Artificial sequence |
| 62. Motif containing the 2A peptide of the aphthous fever virus | Foot-and-mouth disease virus |
| 63. Motif containing the 2A peptide of the aphthous fever virus | Foot-and-mouth disease virus |
| 64. segment corresponding to the 2A peptide of the aphthous fever virus | Foot-and-mouth disease virus |
| 65. segment corresponding to the 2A peptide of the aphthous fever virus | Foot-and-mouth disease virus |
| 66. spacer 5' of the motif containing the 2A peptide of the aphthous fever virus | Artificial sequence |
| 67. N-terminal spacer of the motif containing the 2A peptide of the aphthous fever virus | Artificial sequence |
| 68. spacer 3' of the motif containing the 2A peptide of the aphthous fever virus - DNA | Artificial sequence |
| 69. C-terminal spacer of the motif containing the 2A peptide of the aphthous fever virus | Dengue virus type 4 |
| 70. Truncated stem-anchor domain of the E protein of the dengue virus type 4 | Dengue virus type 4 |
| 71. Truncated stem-anchor domain of the E protein of the dengue virus type 4 | Dengue virus type 4 |
| 72. Truncated stem-anchor domain of the E protein of the dengue virus type 4 | Dengue virus type 4 |

BIBLIOGRAPHICAL REFERENCES

1. Theiler, M. and H. Smith, *The use of yellow fever virus modified by in vitro cultivation for human immunization.* J. Exp. Med., 1937. 65: p. 767-786.
2. Theiler, M. and H. Smith, *The effect of prolonged cultivation in vitro upon the pathogenicity of yellow fever virus.* J. Exp. Med., 1937. 65: p. 787-800.
3. Galler, R., et al., *Genetic variability among yellow fever virus 17D substrains.* Vaccine, 1998. 16(9-10): p. 1024-8.
4. Ishikawa, T., A. Yamanaka, and E. Konishi, *A review of successful flavivirus vaccines and the problems with those flaviviruses for which vaccines are not yet available.* Vaccine, 2014. 32(12): p. 1326-37.
5. Monath, T., *Yellow fever vaccine*, in Vaccines, W. Plotkin SAO, Editor. 2004, WB Saunders: Philadelphia. p. 1095-1176.
6. Poland, J., et al., *Persistence of neutralizing antibody 30-35 years after immunization with 17D yellow fever vaccine.* Bull World Health Organ, 1981. 59(6): p. 895-900.
7. Jonker, E. F., L. G. Visser, and A. H. Roukens, *Advances and controversies in yellow fever vaccination.* Ther Adv Vaccines, 2013. 1(4): p. 144-52.
8. Pulendran, B., *Learning immunology from the yellow fever vaccine: innate immunity to systems vaccinology.* Nat Rev Immunol, 2009. 9(10): p. 741-7.
9. Pulendran, B., et al., *Immunity to viruses: learning from successful human vaccines.* Immunol Rev, 2013. 255(1): p. 243-55.
10. Franco, D., et al., *Evaluation of yellow fever virus 17D strain as a new vector for HIV-1 vaccine development.* Vaccine, 2010. 28(35): p. 5676-85.
11. Miller, J., et al., *Human effector and memory CD8+ T cell responses to smallpox and yellow fever vaccines.* Immunity, 2008. 28(5): p. 710-22.
12. Reinhardt, B., et al., *Development of viremia and humoral and cellular parameters of immune activation after vaccination with yellow fever virus strain 17D: a model of human flavivirus infection.* J Med Virol, 1998. 56(2): p. 159-67.
13. Cao, W., et al., *Toll-like receptor-mediated induction of type I interferon in plasmacytoid dendritic cells requires the rapamycin-sensitive PI(3)K-mTOR-p70S6K pathway.* Nat Immunol, 2008. 9(10): p. 1157-64.
14. Querec, T., et al., *Yellow fever vaccine YF-17D activates multiple dendritic cell subsets via TLR2, 7, 8, and 9 to stimulate polyvalent immunity.* J Exp Med, 2006. 203(2): p. 413-24.
15. Gaucher, D., et al., *Yellow fever vaccine induces integrated multilineage and polyfunctional immune responses.* J Exp Med, 2008. 205(13): p. 3119-31.
16. Neves, P. C., et al., *Early IFN-gamma production after YF 17D vaccine virus immunization in mice and its association with adaptive immune responses.* PLoS One, 2013. 8(12): p. e81953.
17. Neves, P. C., et al., *CD8+ gamma-delta TCR+ and CD4+ T cells produce IFN-gamma at 5-7 days after yellow fever vaccination in Indian rhesus macaques, before the induction of classical antigen-specific T cell responses.* Vaccine, 2010. 28(51): p. 8183-8.
18. Silva, M. L., et al., *Characterization of main cytokine sources from the innate and adaptive immune responses following primary 17DD yellow fever vaccination in adults.* Vaccine, 2011. 29(3): p. 583-92.
19. Bassi, M. R., et al., *CD8+ T cells complement antibodies in protecting against yellow fever virus.* J Immunol, 2015. 194(3): p. 1141-53.
20. Blom, K., et al., *Temporal dynamics of the primary human T cell response to yellow fever virus 17D as it matures from an effector-to a memory-type response.* J Immunol, 2013. 190(5): p. 2150-8.
21. Co, M., et al., *Human cytotoxic T lymphocyte responses to live attenuated 17D yellow fever vaccine: identification of HLA-B35-restricted CTL epitopes on nonstructural proteins NS1, NS2b, NS3, and the structural protein E.* Virology, 2002. 293(1): p. 151-63.
22. Mudd, P. A., et al., *The live-attenuated yellow fever vaccine 17D induces broad and potent T cell responses against several viral proteins in Indian rhesus macaques—implications for recombinant vaccine design.* Immunogenetics, 2010. 62(9): p. 593-600.
23. van der Most, R. G., et al., *Yellow fever virus 17D envelope and NS3 proteins are major targets of the antiviral T cell response in mice.* Virology, 2002. 296(1): p. 117-24.
24. James, E. A., et al., *Yellow fever vaccination elicits broad functional CD4+ T cell responses that recognize structural and nonstructural proteins.* J Virol, 2013. 87(23): p. 12794-804.
25. Bonaldo, M. C., P. C. Sequeira, and R. Galler, *The yellow fever 17D virus as a platform for new live attenuated vaccines.* Hum Vaccin Immunother, 2014. 10(5): p. 1256-65.
26. Rice, C. M., et al., *Transcription of infectious yellow fever RNA from full-length cDNA templates produced by in vitro ligation.* New Biol, 1989. 1(3): p. 285-96.
27. Bonaldo, M., et al., *Surface expression of an immunodominant malaria protein B cell epitope by yellow fever virus.* J Mol Biol, 2002. 315(4): p. 873-85.
28. Bonaldo, M., et al., *Attenuation of recombinant yellow fever 17D viruses expressing foreign protein epitopes at the surface.* J Virol, 2005. 79(13): p. 8602-13.
29. Chambers, T. J., et al., *Yellow fever/Japanese encephalitis chimeric viruses: construction and biological properties.* J Virol, 1999. 73(4): p. 3095-101.

30. Caufour, P. S., et al., *Construction, characterization and immunogenicity of recombinant yellow fever 17D-dengue type 2 viruses*. Virus Res, 2001. 79(1-2): p. 1-14.
31. Guirakhoo, F., et al., *Construction, safety, and immunogenicity in nonhuman primates of a chimeric yellow fever-dengue virus tetravalent vaccine*. J Virol, 2001. 75(16): p. 7290-304.
32. Arroyo, J., et al., *ChimeriVax-West Nile virus live-attenuated vaccine: preclinical evaluation of safety, immunogenicity, and efficacy*. J Virol, 2004. 78(22): p. 12497-507.
33. Capeding, R. Z., et al., *Live-attenuated, tetravalent dengue vaccine in children, adolescents and adults in a dengue endemic country: randomized controlled phase I trial in the Philippines*. Vaccine, 2011. 29(22): p. 3863-72.
34. Villar, L. A., et al., *Safety and immunogenicity of a recombinant tetravalent dengue vaccine in 9-16 year olds: a randomized, controlled, phase II trial in Latin America*. Pediatr Infect Dis J, 2013. 32(10): p. 1102-9.
35. Schaack, J., *Adenovirus vectors deleted for genes essential for viral DNA replication*. Front Biosci, 2005. 10: p. 1146-55.
36. McAllister, A., et al., *Recombinant yellow fever viruses are effective therapeutic vaccines for treatment of murine experimental solid tumors and pulmonary metastases*. J Virol, 2000. 74(19): p. 9197-205.
37. Barba-Spaeth, G., et al., *Live attenuated yellow fever 17D infects human DCs and allows for presentation of endogenous and recombinant T cell epitopes*. J Exp Med, 2005. 202(9): p. 1179-84.
38. Nogueira, R. T., et al., *Biological and immunological characterization of recombinant Yellow Fever 17D viruses expressing a Trypanosoma cruzi Amastigote Surface Protein-2 CD8+ T cell epitope at two distinct regions of the genome*. Virol J, 2011. 8: p. 127.
39. Bonaldo, M. C. and R. Galler, *Method for the Production of Recombinant Virus, DNA Constructs, Recombinant Virus and Vaccine Compositions* 2005, Fundação Oswaldo Cruz: BRAZIL. p. 93
40. Bonaldo, M. C., et al., *Surface expression of an immunodominant malaria protein B cell epitope by yellow fever virus*. J Mol Biol, 2002. 315(4): p. 873-85.
41. Bonaldo, M. C., et al., *Expression of foreign protein epitopes at the surface of recombinant yellow fever 17D viruses based on three-dimensional modeling of its envelope protein*. Cell Biochem Biophys, 2006. 44(3): p. 313-24.
42. Allison, S. L., et al., *Mapping of functional elements in the stem-anchor region of tick-borne encephalitis virus envelope protein E*. J Virol, 1999. 73(7): p. 5605-12.
43. Bonaldo, M., et al., *Construction and characterization of recombinant flaviviruses bearing insertions between E and NS1 genes*. Virol J, 2007. 4: p. 115.
44. Bonaldo, M., et al., *Recombinant yellow fever vaccine virus 17D expressing simian immunodeficiency virus SIVmac239 gag induces SIV-specific CD8+T-cell responses in rhesus macaques*. J Virol, 2010. 84(7): p. 3699-706.
45. Nogueira, R. T., et al., *Recombinant yellow fever viruses eliciCD8+T T cell responses and protective immunity against Trypanosoma cruzi*. PLoS One, 2013. 8(3): p. e59347.
46. Gillespie, L. K., et al., *The endoplasmic reticulum provides the membrane platform for biogenesis of the flavivirus replication complex*. J Virol, 2010. 84(20): p. 10438-47.
47. Mackenzie, J. M., M. K. Jones, and P. R. Young, *Immunolocalization of the dengue virus nonstructural glycoprotein NS1 suggests a role in viral RNA replication*. Virology, 1996. 220(1): p. 232-40.
48. Welsch, S., et al., *Composition and three-dimensional architecture of the dengue virus replication and assembly sites*. Cell Host Microbe, 2009. 5(4): p. 365-75.
49. Op De Beeck, A., et al., *The transmembrane domains of the prM and E proteins of yellow fever virus are endoplasmic reticulum localization signals*. J Virol, 2004. 78(22): p. 12591-602.
50. Lorenz, I. C., et al., *Intracellular assembly and secretion of recombinant subviral particles from tick-borne encephalitis virus*. J Virol, 2003. 77(7): p. 4370-82.
51. Ciczora, Y., et al., *Identification of a dominant endoplasmic reticulum-retention signal in yellow fever virus pre-membrane protein*. J Gen Virol, 2010. 91(Pt 2): p. 404-14.
52. Hsieh, S. C., W. Y. Tsai, and W. K. Wang, *The length of and nonhydrophobic residues in the transmembrane domain of dengue virus envelope protein are critical for its retention and assembly in the endoplasmic reticulum*. J Virol, 2010. 84(9): p. 4782-97.
53. Szczesna-Skorupa, E. and B. Kemper, *Endoplasmic reticulum retention determinants in the transmembrane and linker domains of cytochrome P450 2C1*. J Biol Chem, 2000. 275(25): p. 19409-15.
54. Yang, M., et al., *The transmembrane domain of a carboxyl-terminal anchored protein determines localization to the endoplasmic reticulum*. J Biol Chem, 1997. 272(3): p. 1970-5.
55. Mukhopadhyay, S., R. J. Kuhn, and M. G. Rossmann, *A structural perspective of the flavivirus life cycle*. Nat Rev Microbiol, 2005. 3(1): p. 13-22.
56. Lefeuvre, A., et al., *Host-cell interaction of attenuated and wild-type strains of yellow fever virus can be differentiated at early stages of hepatocyte infection*. Microbes Infect, 2006. 8(6): p. 1530-8.
57. Mackenzie, J. M. and E. G. Westaway, *Assembly and maturation of the flavivirus Kunjin virus appear to occur in the rough endoplasmic reticulum and along the secretory pathway, respectively*. J Virol, 2001. 75(22): p. 10787-99.
58. Yu, C. Y., et al., *Flavivirus infection activates the XBP1 pathway of the unfolded protein response to cope with endoplasmic reticulum stress*. J Virol, 2006. 80(23): p. 11868-80.
59. Ryan, M. D., A. M. King, and G. P. Thomas, *Cleavage of foot-and-mouth disease virus polyprotein is mediated by residues located within a 19 amino acid sequence*. J Gen Virol, 1991. 72 (Pt 11): p. 2727-32.
60. Duckert, P., S. Brunak, and N. Blom, *Prediction of proprotein convertase cleavage sites*. Protein Eng Des Sel, 2004. 17(1): p. 107-12.
61. Tian, S., et al., *FurinDB: A database of 20-residue furin cleavage site motifs, substrates and their associated drugs*. Int J Mol Sci, 2011. 12(2): p. 1060-5.
62. Hallenberger, S., et al., *The role of eukaryotic subtilisin-like endoproteases for the activation of human immunodeficiency virus glycoproteins in natural host cells*. J Virol, 1997. 71(2): p. 1036-45.
63. Stieneke-Grober, A., et al., *Influenza virus hemagglutinin with multibasic cleavage site is activated by furin, a subtilisin-like endoprotease*. EMBO J, 1992. 11(7): p. 2407-14.

64. Li, L., et al., *The flavivirus precursor membrane-envelope protein complex: structure and maturation*. Science, 2008. 319(5871): p. 1830-4.
65. Yu, I. M., et al., *Structure of the immature dengue virus at low pH primes proteolytic maturation*. Science, 2008. 319(5871): p. 1834-7.
66. Kim, J. H., et al., *High cleavage efficiency of a 2A peptide derived from porcine teschovirus-1 in human cell lines, zebrafish and mice*. PLoS One, 2011. 6(4): p. e18556.
67. Helenius, A. and M. Aebi, *Intracellular functions of N-linked glycans*. Science, 2001. 291(5512): p. 2364-9.
68. Molinari, M., *N-glycan structure dictates extension of protein folding or onset of disposal*. Nat Chem Biol, 2007. 3(6): p. 313-20.
69. Aebi, M., et al., *N-glycan structures: recognition and processing in the ER*. Trends Biochem Sci, 2010. 35(2): p. 74-82.
70. Benyair, R., N. Ogen-Shtern, and G. Z. Lederkremer, *Glycan regulation of ER-associated degradation through compartmentalization*. Semin Cell Dev Biol, 2014.
71. Cherepanova, N. A., S. Shrimal, and R. Gilmore, *Oxidoreductase activity is necessary for N-glycosylation of cysteine-proximal acceptor sites in glycoproteins*. J Cell Biol, 2014. 206(4): p. 525-39.
72. Bonaldo, M. C. G., R, *Method for the production of recombinant virus, DNA constructs, recombinant virus and vaccine compositions in United States Patent Office*, U.S.P. Office, Editor. 2014, Fiocruz: USA.
73. Oliveira, M. F., *Aprimoramento da platform de expressão na região intergênica E/NS1 do virus da febre amrela 17D*, in *Michelli Faria de Oliveira*. 2008, Fiocruz: Pós-Graduação em Biologic Parasitária.
74. Burger, S. R., et al., *Stable expression of rabies virus glycoprotein in Chinese hamster ovary cells*. J Gen Virol, 1991. 72 (Pt 2): p. 359-67.
75. Wojczyk, B. S., et al., *N-glycosylation at one rabies virus glycoprotein sequon influences N-glycan processing at a distant sequon on the same molecule*. Glycobiology, 2005. 15(6): p. 655-66.
76. Bonaldo, M. C., et al., *Construction and characterization of recombinant flaviviruses bearing insertions between E and NS1 genes*. Virol J, 2007. 4: p. 115.

The invention claimed is:

1. An expression cassette for heterologous proteins in an intergenic E protein/NS1 protein (E/NS1) region of a yellow fever 17D vaccine virus, wherein said expression cassette comprises:
   an insertion sequence comprising:
      a first functional domain, and
      a second functional domain, wherein said first functional domain comprises a) a spacer sequence coding for a furin cellular protease cleavage motif, or b) a spacer sequence coding for a Picornaviridae 2A factor, wherein said second functional domain comprises a spacer sequence coding for a N-glycosylation motif, and wherein the spacer sequence coding for a N-glycosylation motif is inserted into the expression cassette between a sequence coding for a NS1 N-terminal motif and a sequence coding for the heterologous protein.

2. The expression cassette of claim 1, wherein said Picornaviridae 2A factor sequence is inserted into the expression cassette before a sequence encoding a stem and an anchor domain of the E protein.

3. The expression cassette of claim 2 wherein, said Picornaviridae 2A factor sequence comprises an auto-cleavage motif, wherein the motif comprises SEQ ID 61, SEQ ID 62, SEQ ID 63, SEQ ID 64, SEQ ID 65, SEQ ID 66, SEQ ID 67, or SEQ ID 68.

4. The expression cassette of claim 1, wherein the spacer sequence coding for the N-glycosylation motif is selected from target sequences of the E protein of a Dengue type 2 virus and a G glycoprotein of a rabies virus.

5. The expression cassette of claim 1, wherein the first coding sequence for the furin cellular protease cleavage motif is at least one of, a von Willebrand human coagulation factor (vWF), or a furin cleavage motif of the prM protein of the encephalitis virus transmitted by ticks.

6. The expression cassette of claim 1, wherein said second coding sequence for the N-glycosylation motif is a glycan acceptor motif.

7. The expression cassette of claim 6, wherein the glycan acceptor motif comprises N-X-S/T, wherein N is an asparagine amino acid, and wherein -X comprises any amino acid, with the exception of proline, and -S/T comprises serine or threonine.

8. The expression cassette of claim 7, wherein said N-glycosylation motif allows for any heterologous protein expressed by the yellow fever virus to comprise an N-glycosylation motif not present in its native amino acid sequence, but present in said expression cassette.

9. A DNA construct of a modified recombinant vector virus, said construct comprising:
a nucleotide sequence, wherein the nucleotide sequence comprises:
a first sequence coding for at least one heterologous protein or a fragment thereof; wherein the first sequence is inserted into an intergenic E/NS1 region;
a second sequence coding for an NS1 protein; and
a third sequence coding for an E protein of a flavivirus, wherein the nucleotides present in the 5'-terminal of the NS1 protein and all or part of the E protein stem and anchor domains are present at both ends of the heterologous protein sequence; and wherein the expressed and processed heterologous protein induces an immune response in a host cell, and wherein a Picornaviridae 2A factor sequence motif is inserted into the intergenic E/NS1 region and before a sequence encoding a stem and an anchor domain of the E protein.

10. The DNA construct of claim 9, where a glycan acceptor motif is inserted after the domain in the 5'-terminal of the NS1 gene.

11. The DNA construct of claim 9, wherein the glycan acceptor motif comprises N-X-S/T, wherein N is an asparagine amino acid, and wherein -X comprises any amino acid, with the exception of proline, and -S/T comprises serine or threonine.

12. The DNA construct of claim 9, wherein the construct comprises SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

13. A vaccine composition for immunization against Flavivirus and/or other pathogens comprising the DNA construct of claim 9.

14. The expression cassette of claim 2, wherein said Picornaviridae 2A factor sequence produces said heterologous protein by interruption of the viral RNA translation of ribosomes in the anterior region of the carboxy terminus of a fragment of the heterologous protein.

15. The expression cassette of claim 1, wherein said furin cellular protease cleavage motif produces said heterologous protein through cleavage by a furin cellular protease.

16. The expression cassette of claim 1, wherein the E protein comprises transmembrane segments, wherein said first functional domain comprising a spacer sequence is inserted into the expression cassette before a sequence encoding for a transmembrane segments domain of the E protein; and wherein said first functional domain comprising a spacer sequence provides for proteolytic cleavage of said heterologous protein from said transmembrane segments, thereby providing for releasing said heterologous protein from said transmembrane segments.

17. A DNA construct of a modified recombinant vector virus, said construct comprising:
a nucleotide sequence, wherein the nucleotide sequence comprises:
a first sequence coding for at least one heterologous protein or a fragment thereof; wherein the first sequence is inserted into an intergenic E/NS1 region;
a second sequence coding for an NS1 protein; and
a third sequence coding for an E protein of a flavivirus, wherein the nucleotides present in the 5'-terminal of the NS1 protein and all or part of the E protein stem and anchor domains are present at both ends of the heterologous protein sequence; and wherein the expressed and processed heterologous protein induces an immune response in a host cell, and wherein a spacer sequence coding for a Furin cellular protease cleavage motif is inserted into the intergenic E/NS1 region before a sequence encoding a stem and an anchor domain of the E protein.

18. A vaccine composition for immunization against Flavivirus and/or other pathogens comprising the DNA construct of claim 17.

19. A vaccine composition for immunization against Flavivirus and/or other pathogens according to claim 18, wherein said construct comprises a sequence, and wherein the sequence is selected from the group consisting of SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

* * * * *